US009354175B2

(12) United States Patent
Auldridge et al.

(10) Patent No.: US 9,354,175 B2
(45) Date of Patent: May 31, 2016

(54) LUCIGEN YELLOW (LUCY), A YELLOW FLUORESCENT PROTEIN

(71) Applicant: Lucigen Corporation, Middleton, WI (US)

(72) Inventors: Michele E. Auldridge, Madison, WI (US); Laura P. Franz, Madison, WI (US); David Mead, Middleton, WI (US); Saurabh Sen, Madison, WI (US); Eric J. Steinmetz, Madison, WI (US)

(73) Assignee: Lucigen Corporation, Madison, WI (US)

(*) Notice: Subject to any disclaimer, the term of this patent is extended or adjusted under 35 U.S.C. 154(b) by 2 days.

(21) Appl. No.: 14/151,993

(22) Filed: Jan. 10, 2014

(65) Prior Publication Data
US 2015/0198533 A1    Jul. 16, 2015

(51) Int. Cl.
G06F 19/18    (2011.01)
G01N 21/64    (2006.01)
C07K 14/00    (2006.01)
C12N 9/04    (2006.01)
C12N 15/82    (2006.01)
C12N 9/02    (2006.01)

(52) U.S. Cl.
CPC ............ G01N 21/6486 (2013.01); C07K 14/00 (2013.01); C12N 9/001 (2013.01); C12N 9/0006 (2013.01); C12N 15/8212 (2013.01); C07K 2319/00 (2013.01); C07K 2319/60 (2013.01)

(58) Field of Classification Search
CPC combination set(s) only.
See application file for complete search history.

(56) References Cited

FOREIGN PATENT DOCUMENTS

WO    01/11054 A1    2/2001

OTHER PUBLICATIONS

Auldridge, Michele E., et al., "LucY: A Versatile New Fluorescent Reporter Protein," PLOS One, vol. 10, No. 4, Apr. 23, 2015.
Bracha-Droro, K., et al., "Detection of Protein-Protein Interactions in Plants Using Biomolecular Fluorescence Complementation,", The Plant Journal, Blackwell Scientific Publications, vol. 40, No. 3, Nov. 1, 2004.
Fan, et al., "Split mCherry as a new red biomolecular fluorescence complementation system for visualizing protein-protein interactions in living cells," Biochemical and Biophysical Research Communications, Academic Press Inc., vol. 367, No. 1, Dec. 26, 2007.
Nagai, T., et al., "A variant of yellow fluorescent protein with fast and efficient maturation for cell-biological applications," Nature Biotechnology, Nature Publishing Group, US, vol. 20, No. 1, Jan. 1, 2002, pp. 87-90.
Sarver, Ronald W., et al., "Determination of ligand-MurB interactions by isothermal denaturation: Application as a secondary assay to completement high throughput screening," Journal of Biomolecular Screening, vol. 7, No. 1, Feb. 2002, pp. 21-28.
Yang, Y, et al., "3,5-Dioxopyrazolidines, Novel Inhibitors of UDP-N-Acetylenolpyruvylglucosamine Reductase (MurB) with Activity against Gram-Positive Bacteria," Antimicrobial Agents and Chemotherapy, vol. 50, No. 2, Feb. 1, 2006, pp. 556-564.
Database UniProt [Online], May 29, 2013, UniProt: M5P2X5 Database accession No. M5P2X5 sequence.
Database UniProt [Online], Sep. 21, 2011, UniProt: F8IH59 Database accession No. F8IH59 sequence.
Database UniProt [Online], May 5, 2009, UniProt: C0QUP5 Database accession No. C0QUP5 sequence.
Database UniProt [Online], Apr. 20, 2010, UniProt: D3T3U7 Database accession No. D3T3U7 sequence.
Database UniProt [Online], Aug. 10, 2010, UniProt: D7AQA4 Database accession No. D7AQA4.
Altschul, S.F., Gish, W., Miller, W., Myers, E.W. & Lipman, D.J. Basic local alignment search tool. J. Mol. Biol. 215:403-410 (1990).
Baird, G.S., Zacharias, D.A. & Tsien, R.Y. Circular permutation and receptor insertion within green fluorescent proteins. Proc Natl Acad Sci U S A 96, 11241-11246 (1999).
Benson, T.E., Filman, D.J., Walsh, C.T. & Hogle, J.M. An enzyme-substrate complex involved in bacterial cell wall biosynthesis. Nat Struct Biol 2, 644-653 (1995).
Caffrey M. Crystallizing membrane proteins for structure determination: use of lipidic mesophases. Annu Rev Biophys 38, 29-51 (Jun. 2009).
Chen J, Zheng XF, Brown EJ, Schreiber SL (1995) Identification of an 11-kDa FKBP12-rapamycin-binding domain within the 289-kDa FKBP12-rapamycin-associated protein and characterization of a critical serine residue. Proc Natl Acad Sci U S A. 92:4947-4951.
Day, R.N. & Davidson, M.W. The fluorescent protein palette: tools for cellular imaging. Chem Soc Rev 38, 2887-2921 (2009).
El Zoeiby, A., Sanschagrin, F. & Levesque, R.C. Structure and function of the Mur enzymes: development of novel inhibitors. Mol Microbiol 47, 1-12 (2003).
Farrar MA, Alberol-Ila J, Perlmutter RM (1996) Activation of the Raf-1 kinase cascade by coumermycin-induced dimerization. Nature. 383:178-181.
Ghosh, I., Hamilton, A. & Regan, L. Antiparallel leucine zipper-directed protein reassembly: Application to the green fluorescent protein. J. Am. Chem. Soc. 122, 5658-5659 (2000).

(Continued)

Primary Examiner — Kagnew H Gebreyesus
(74) Attorney, Agent, or Firm — Daniel A. Blasiole; Joseph T. Leone, Esq.; DeWitt Ross & Stevens SC

(57) ABSTRACT

Described herein are isolated polynucleotides that encode a fluorescent protein which is at least 80% sequence identical to a protein selected from the group consisting of SEQ. ID. NOS: 2, 4, 6, 10, 14, 18, 22, 26, 30, 34, 38, 42, 46, 50, 54, 58, 62, 66, 70, and 74. Also described are expression constructs containing the polynucleotides, transformed host cells containing the expression constructions, the encoded fluorescent proteins themselves, and methods of using the nucleotides and encoded fluorescent proteins for bioanalytical research.

8 Claims, 27 Drawing Sheets

(56) References Cited

OTHER PUBLICATIONS

Gilbert EJ, Maxwell A (1994) The 24 kDa N-terminal sub-domain of the DNA gyrase B protein binds coumarin drugs. *Mol Microbiol.* 12:365-373.

Johnsson, N. & Varshavsky, A. Split ubiquitin as a sensor of protein interactions in vivo. *Proc Natl Acad Sci U S A* 91, 10340-10344 (1994).

Munro, A.W. & Noble, M.A. Fluorescence analysis of flavoproteins. *Methods Mol Biol* 131, 25-48 (1999).

Paulmurugan, R. & Gambhir, S.S. Monitoring protein-protein interactions using split synthetic renilla luciferase protein-fragment-assisted complementation. *Anal Chem* 75, 1584-1589 (2003).

Roblda AM, Kerppola TK (2009) Bimolecular fluorescence complementation analysis of inducible protein interactions: effects of factors affecting protein folding on fluorescent protein fragment association. *J Mol Biol.* 394:391-409.

Rollins CT, Rivera VM, Woolfson DN, Keenan T, Hatada M, Adams SE, Andrade LJ, Yaeger D, Van Schravendijk MR, Holt DA, Gilman M, Clackson T (2000) A ligand-reversible dimerization system for controlling protein-protein interactions. *Proc Natl Acad Sci U S A.* 97:7096-8101.

Tsien, R.Y. The green fluorescent protein. *Annu Rev Biochem* 67, 509-544 (1998).

Yu, Y. & Lutz, S. Circular permutation: a different way to engineer enzyme structure and function. *Trends Biotechnol* 29, 18-25 (2011).

Zhao HF, Boyd J, Jolicoeur N, Shen SH (2003) A coumermycin/novobiocin-regulated gene expression system. *Hum Gene Ther.* 14:1619-1629.

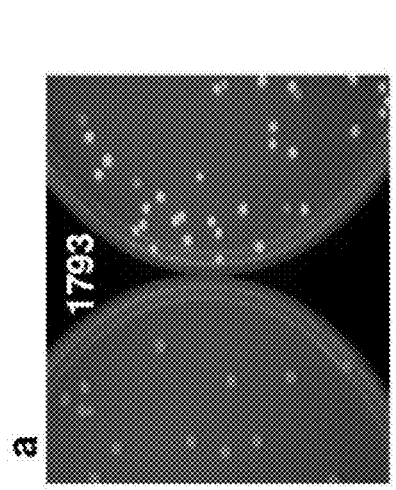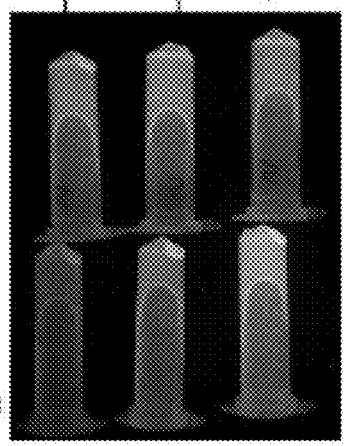

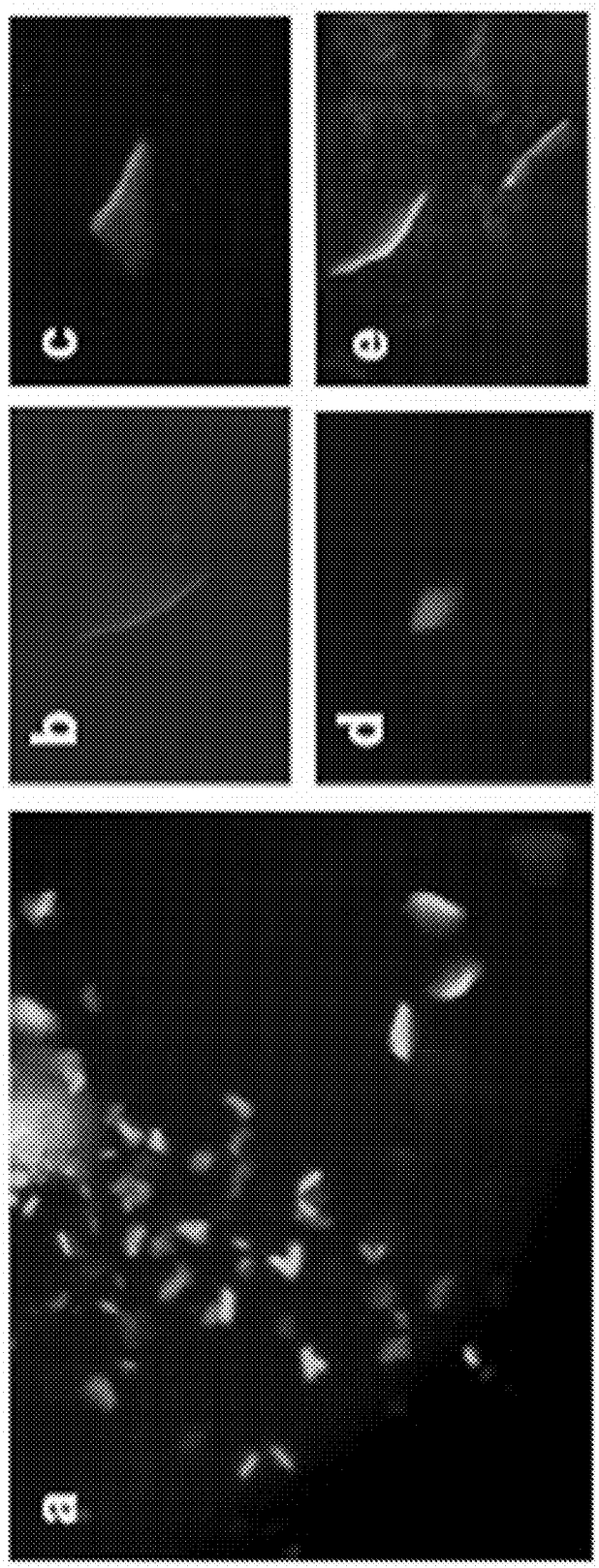

LUCIGEN YELLOW (LUCY), A YELLOW FLUORESCENT PROTEIN

BACKGROUND

Fluorescent proteins (FPs) make it possible to visualize biological processes through in vivo imaging and in vitro fluorescence labeling. Processes like protein expression, localization, degradation, and interaction can be observed through fusion of a protein of interest with a FP. Green Fluorescent Protein (GFP) from *Aequorea victoria* and its varied derivatives constitute a multi-colored toolbox ranging from blue to yellow, with red-shifted FPs (RFPs) originating mostly from the sea anemone *Discosoma striata* (Day and Davidson, 2009). Following the discovery and subsequent explosion of available FPs, came the development of their use in techniques like Fluorescence or Förster Resonance Energy Transfer (FRET), Bioluminescence Resonance Energy Transfer (BRET), and Bimolecular Fluorescence Complementation (BiFC), all of which capitalize on the variety of choices in excitation and emission maxima characteristic to each FP.

In GFP-like and RFP-like fluorophores, fluorescence emanates from a chromophore developed by the formation of an imidazolinone ring system between two centrally located residues. However, complete maturation of the chromophore requires oxidation of an adjacent tyrosine residue, making molecular oxygen a strict requirement for these systems (Tsien, 1998). For example, the chromophore of GFP itself is formed by the cyclization of the tripeptide Ser65-Tyr66-Gly67.

Bacterial MurB enzymes are a family of flavoproteins that non-covalently bind flavin adenine dinucleotide (FAD). The MurB enzyme family catalyzes a step in peptidoglycan biosynthesis. Because peptidoglycans are cell wall components, enzymes in this pathway have been targets for developing antimicrobial compounds. In a physiological setting, MurB flavoprotein enzymes catalyze a hydride transfer from NADPH to the substrate through FAD to produce the final reduced product, UDP-N-acetylmuramic acid (El Zoelby et al., 2003). A byproduct of FAD binding is fluorescence due to FAD's intrinsic fluorescent properties. Free FAD fluorescence is rather weak ($\Phi_F$=0.032) due the quenching effects of the adenine moiety. However, sequestration within a protein environment can enhance its fluorescence (Munro and Noble, 1999).

SUMMARY OF THE INVENTION

Disclosed and claimed herein is a novel fluorescent protein (FP) initially identified in and isolated from a metagenomic library. The FP has been cloned and expressed in a variety of hosts. Nucleotides encoding the novel FP and variations thereof are also disclosed herein. The FP has been given the name "LucY" for Lucigen Yellow. LucY can be used in the same methods that employ conventional FPs. For example, the LucY protein and its derivatives are useful as fluorescent markers in the many ways that such markers are already in use by those of ordinary skill in the art. Such uses include determining subcellular localization and coupling the FP to antibodies, nucleic acids or other receptors for use in detection assays (for example immunoassays or hybridization assays). Further, LucY can be used to track the movement of proteins in cells by expressing the FP in an expression vector. For another example, the FP can be useful in systems to detect induction of transcription. The FP's described herein are also useful as a visualization tool to judge solubility of fusion proteins.

Additionally, LucY and its derivatives can be used in a novel method to facilitate positive identification of membrane protein crystals grown in lipidic cubic phase.

Additionally, LucY has been developed into a split-fluorescence system by which protein-protein interactions can be determined. Due to the non-covalent binding of the FAD molecule, LucY fluorescence is reversible, distinguishing it from other available FPs. This reversibility may allow the LucY split-fluorescent system disclosed herein to be used in drug-screening platforms when looking for inhibitors of protein-protein interaction. To evaluate the reversibility of the split-LucY system, the dissociation of split-LucY fragments can be experimentally controlled through a well characterized chemically reversible dimerization strategy. Inducible dimerization of the FK506 binding protein (FKBP) has been used to evaluate BiFC complex formation and signal development (Robida and Kerppola 2009). Typically FKBP and a truncated version of its binding partner, FRB, are used in a chemically induced dimerization strategy in which a ligand promotes dimerization (Chen et al., 1995). FKBP variants ($F_M$) have since been developed that form constitutive homodimers which dissociate upon addition of drug, thus providing a reversible protein interaction model (Rollins et al., 2000). Although ligand-reversible $F_M$ dimerization has been used successfully, it is theoretically possible that FKBP specific ligands may interfere with LucY reassembly or fluorescence. If necessary an alternative drug-inducible dimerization/dissociation system may be used. The gyrase B N-terminal domain (GyrB NTD) contains binding sites for coumermycin and novobiocin (Gilbert et al., 1994). Coumermycin is a bivalent drug that binds simultaneously to two GyrB NTD monomers and promotes formation of parallel homodimers, while novobiocin is a monovalent analog that can displace coumermycin and thereby drive dimer dissociation. Fusions to the GyrB NTD have been used for demonstration of dimerization-dependent activation of Raf1 kinase activity (Farrar et al., 1996), and as a part of a dimerization-dependent transcriptional activation strategy for controlled gene expression (Zhao et al., 2003).

Nucleotides that encode LucY and its variants are also described herein. The FP may be introduced into a host cell by direct delivery or may be expressed by the host cell, e.g., by a vector. In addition, the FP expressed in bacterial, eukaryotic, insect, mammalian and in vitro systems can be used directly to monitor the interactions with fused partners in cell lysates, at the extracellular spaces, or in tissue samples. The FP's disclosed herein are very useful for high-throughput screening in drug discovery and identification procedures, and for new target validations of diseases.

Also disclosed herein are kits containing one or more compositions comprising the fluorescent proteins, which can be a portion of a fusion protein, or one or more polynucleotides that encode the fluorescent proteins. The kits may also can contain one or more recombinant nucleic acid molecules, which encode, in part, fluorescent proteins, which can be the same or different, and may further include, for example, an operatively linked second polynucleotide containing or encoding a restriction endonuclease recognition site or a recombinase recognition site, or any polypeptide of interest.

Thus, specifically disclosed herein is an isolated polynucleotide comprising a nucleotide sequence encoding a fluorescent protein which is at least 80%, 85%, 90%, 95%, and/or 97% sequence identical to a protein selected from the group consisting of SEQ. ID. NOS: 2, 4, 6, 10, 14, 18, 22, 26, 30, 34, 38, 42, 46, 50, 54, 58, 62, 66, 70, and 74, as well as circular permutations thereof. Also disclosed are these same polynucleotides further comprising an in-frame subsequence encoding a poly-His sequence at a terminus of the encoded fluorescent protein. These His-tagged polynucleotides include polynucleotides selected from the group consisting of SEQ. ID NOS: 7, 11, 15, 19, 23, 27, 31, 35, 39, 43, 47, 51, 55, 59, 63, 67, 71, and 75, and polynucleotides having at least 80% 85%, 90%, 95%, and/or 97% sequence identity to them, as well as circular permutations thereof, exclusive of the poly-His subsequence.

Also disclosed are isolated polynucleotides as described in the immediately preceding paragraph, wherein the encoded fluorescent protein has absorbance maxima at about 274 nm, about 376 nm and about 460 nm, and an emission maxima at about 530 nm. Preferably, although not required, the isolated polynucleotide as described herein encodes between 279 and 347 amino acid residues. The polynucleotide sequence may optionally further encode at least one additional polypeptide of interest in-frame with the encoded fluorescent protein.

Also disclosed herein is an expression construct comprising any of the isolated polynucleotides as described herein. Also disclosed is a host cell comprising such an expression construct. Any and all suitable host cells are within the scope of the present disclosure. The host cell, for example, may be selected from the group consisting of unicellular prokaryote cells, unicellular eukaryote cells, insect cells, and mammalian cells. Also disclosed herein is a method for making a fluorescent protein comprising cultivating the transformed host cell.

Also encompassed by the present disclosure are novel fluorescent proteins having at least 80%, 85%, 90%, 95%, and/or 97% sequence identity to a protein selected from the group consisting of SEQ. ID. NOS: 2, 4, 6, 10, 14, 18, 22, 26, 30, 34, 38, 42, 46, 50, 54, 58, 62, 66, 70, and 74, as well as circular permutations thereof. Also disclosed herein are proteins comprising a polypeptide of interest operationally linked to fluorescent protein which is at least 80%, 85%, 90%, 95%, and/or 97% sequence identity to a protein selected from the group consisting of SEQ. ID. NOS: 2, 4, 6, 10, 14, 18, 22, 26, 30, 34, 38, 42, 46, 50, 54, 58, 62, 66, 70, and 74, or circular permutations thereof.

Also disclosed herein are methods for detecting molecular interactions. One such method comprises fragmenting a fluorescent protein which is at least 80% sequence identical to a protein selected from the group consisting of SEQ. ID. NOS: 2, 4, 6, 10, 14, 18, 22, 26, 30, 34, 38, 42, 46, 50, 54, 58, 62, 66, 70, and 74, or a fluorescent circular permutation thereof, so that the fragmentation results in two or more non-fluorescent protein fragments and a reversible loss of protein fluorescence. The non-fluorescent protein fragments are separately fused or attached to other molecules. The non-fluorescent protein fragments are then re-associated through interactions of the molecules that are fused or attached to the non-fluorescent protein fragments. A resulting fluorescent signal is then detected. In the preferred version of this invention, the fluorescent protein is fragmented into two non-fluorescent protein fragments.

As noted previously, the fluorescent protein may optionally comprise a poly-His sequence at a terminus of the protein. The fluorescent protein may optionally comprise between 279 and 347 amino acid residues.

Another method for detecting molecular interactions disclosed herein comprises providing a first reagent comprising a first compound of interest linked to a first non-fluorescent protein fragment; and providing a second reagent comprising a second compound of interest linked to a second non-fluorescent protein fragment. Here, the first and second non-fluorescent protein fragments comprise complementary fragments of a fluorescent protein which is at least 80% sequence identical to a protein selected from the group consisting of SEQ. ID. NOS: 2, 4, 6, 10, 14, 18, 22, 26, 30, 34, 38, 42, 46, 50, 54, 58, 62, 66, 70, and 74, or a fluorescent circular permutation thereof, and wherein the first and second non-fluorescent protein fragments generate a fluorescent detectable signal when associated. "Complementary" when used in this context means "serving to fill out or complete" or to be "complements" in the sense of "something that completes something else." See "Merriam-Webster"® Online Dictionary (http://www.merriam-webster.com, © 2014, Merriam-Webster, Inc., Springfield, Mass., USA). The first and second non-fluorescent protein fragments are associated through interactions of the first and second compounds of interest, and any resulting fluorescent signal is detected. The first compound of interest, the second compound of interest, or both the first and second compounds of interest may comprise polypeptides.

Also disclosed herein are kits. A first kit comprises, in combination, a first non-fluorescent protein fragment in a first container; and a second non-fluorescent protein fragment in a second container. The first and second non-fluorescent protein fragments comprise complementary fragments of a fluorescent protein which is at least 80% sequence identical to a protein selected from the group consisting of SEQ. ID. NOS: 2, 4, 6, 10, 14, 18, 22, 26, 30, 34, 38, 42, 46, 50, 54, 58, 62, 66, 70, and 74, or a fluorescent circular permutation thereof, and wherein the first and second non-fluorescent protein fragments generate a fluorescent detectable signal when associated.

Another kit disclosed herein comprises, in combination, a first isolated polynucleotide that encodes a first non-fluorescent protein fragment in a first container; and a second isolated polynucleotide that encodes a second non-fluorescent protein fragment in a second container; and wherein the first and second isolated polynucleotides encode complementary, non-fluorescent protein fragments of a fluorescent protein which is at least 80% sequence identical to a protein selected from the group consisting of SEQ. ID. NOS: 2, 4, 6, 10, 14, 18, 22, 26, 30, 34, 38, 42, 46, 50, 54, 58, 62, 66, 70, and 74, or a fluorescent circular permutation thereof, and wherein the encoded first and second non-fluorescent protein fragments generate a fluorescent detectable signal when associated.

Also disclosed herein is a method of increasing the aqueous solubility of a protein of interest. The method comprises fusing or attaching to the protein of interest a protein which is at least 80% sequence identical to a protein selected from the group consisting of SEQ. ID. NOS: 2, 4, 6, 10, 14, 18, 22, 26, 30, 34, 38, 42, 46, 50, 54, 58, 62, 66, 70, and 74, or a circular permutation thereof.

BRIEF DESCRIPTION OF THE DRAWINGS

FIG. 1A depicts cell pellets (1 OD) from cultures expressing LucY from the rhaP$_{BAD}$ promoter in response to rhamnose at the indicated concentrations. FIG. 1B is a graph depicting fluorescence response to rhamnose induction measured with a plate reader using excitation at 485 nm and emission at 528 nm. FIG. 1C is a photograph depicting induction of LucY expression in *E. coli* on a plate containing 0.2% rhamnose. FIG. 1D is a photograph depicting expression of LucY in the mammalian cells COS-7. FIG. 1E is a photograph depicting expression of LucY in the mammalian cells CHO-K1. FIG. 1F is a photograph depicting expression of LucY in the mammalian cells HeLa. All mammalian transfections were carried out with "TransIT-2020"-brand transfection-reagent (Minis Bio LLC, Madison, Wis.) and imaged 24 h post-transfection with an inverted fluorescence microscope fitted with a GFP excitation/emission filter.

In FIG. 4A: Sye=*Sulfurihydrogenibium yellowstonense*; Y4.1 MC1=*Geobacillus* sp. ((strain Y4.1MC1); Dtu=*Dictyoglomus turgidum*; Rma=*Rhodothermus marinus*; Aae=*Aquifex aeolicus*; Aac=*Alicyclobacillus acidocaldarius*; Acel=*Acidothermus cellulolyticus*; Tma=*Thermotoga maritima*; Chy=*Calsicellulosiruptor hydrothermalis*; Tye=*Thermodesulfovibrio yellowstonii*. In FIG. 4B, Pma=*Persephonella marina*; Saz=*Sulfurihydrogenibium azorense*; Hth=*Hydrogenobacter thermophilus*; SspY=*Sulfurihydrogenibium* sp. (strain YO3AOP1); Tit=*Thermoanaerobacter italicus*; Tal=*Thermocrinis albus*; Hspl=*Hydrogenivirga* sp. 128-5-R1-1.

FIG. 5A is a photograph depicting *E. coli* cell pellets following illumination with UV light showing expression of LucY fused to the membrane GPCR protein, Ala, with growth at 25° C. and at 30° C. LSP=low-speed pellet; HSP=high-speed pellet. FIG. 5B depicts LucY fused to ATPb following induction with IPTG or arabinose.

FIG. 7A illustrates replacement of the GPCR intracellular loop positions 245-271 with LucY. FIG. 7B shows replacement of the GPCR intracellular loop positions 245-271 with LucY and GSG linker sequence. FIG. 7C illustrates replacement of the GPCR intracellular loop positions 245-274 with LucY and GSG linker sequence. FIG. 7D illustrates replacement of the GPCR intracellular loop positions 245-276 with LucY and GSG linker sequence. GSG linker sequence lies between LucY C-terminus and the GPCR.

FIGS. 10A, 10B, and 10C together demonstrate the utility of LucY as an indicator of protein expression and solubility. FIG. 10A is a photograph depicting Fisuc_1793-LucY expression on plates containing 0.2% rhamnose, with (right) or without (left) an amino-terminal SUMO tag. FIG. 10B is a photograph depicting cleared lysates from ~5 ml cultures of cells expressing the indicated Fibrobacter genes as LucY fusions, with (right) or without (left) a SUMO tag. FIG. 10C is a series of Coomassie blue-stained polyacrylamide gels showing expression of LucY fusion proteins in total cell lysate (T), soluble fraction (S), and pellet fraction (P) after centrifugation at 12,000×G for 5 minutes. The asterisks indicate the induced fusion protein. No band was detected corresponding to the 1793-LucY protein without the SUMO tag.

FIG. 11A is a photograph depicting weak fluorescence due to expression of SUMO-ABV-LucY fusion protein from rhaP$_{BAD}$. Plates contained no rhamnose (left), or 0.2% rhamnose (right). FIG. 11B depicts gel analysis of ABV-LucY protein expressed from rhaP$_{BAD}$, with or without an amino-terminal SUMO tag. FIG. 11C depicts gel analysis of 4110-LucY protein expressed from rhaP$_{BAD}$, with or without a SUMO solubility tag. The right and left portions of FIG. 11C are from the same gel. In FIGS. 11B and 11C, T represents total cell lysate; S represents the soluble fraction after centrifugation of the lysate; and P represents the insoluble pellet fraction after centrifugation.

FIG. 12A is a photograph of a section of a primary selection plate containing 0.2% rhamnose. Several fluorescent colonies are indicated by arrows. FIG. 12B is a photograph of individual fluorescent colonies from the initial library screen depicted in FIG. 12A, re-streaked onto a plate containing 0.2% rhamnose.

FIG. 13A is a gel analysis of soluble expression of *Geobacillus*-4110-LucY library clone 11. The Control sample is 4110-LucY with no amino-terminal fusion. T represents total cell lysate; S represents the soluble fraction after centrifugation of the lysate;

and P represents the insoluble pellet fraction after centrifugation. FIG. 13B is a photograph depicting increased partitioning of yellow fluorescence to the soluble fraction with *Geobacillus* library clone 11.

FIG. 15A is a schematic depicting conventional bimolecular fluorescence complementation (BiFC). Here, a reporter protein is split into two sub-fragments, each of which is fused to a different protein. The two proteins (Protein X and Protein Y in the figure) have the potential to interact. Only after a positive interaction of Protein X and Protein Y is achieved will the two fragments combine and elicit a signal. FIG. 15B is a schematic diagram showing the three distinct domains (colored red, blue, and green) of LucY. A five-residue loop connects domains 1 and 2 and an approximately 18-residue loop connects domains 2 and 3. Five points within each of these loops were chosen as Split Points (SP), as indicated by underlined residues. FIG. 15C is a schematic diagram showing synthetic antiparallel leucine zippers (light green), which were used as protein interaction models to test reconstitution of split LucY fragments (right) and were compared to whole LucY fusions (left). LucY fused at the N-terminus of the leucine zipper is designated NZ; LucY fused at the C-terminus of the leucine zipper is designated CZ. Split LucY fragments fused to the N-terminus and C-terminus of the leucine zippers are referred to as SPNZ and SPCZ, respectively.

FIG. 16A: Five split points between domains 1 and 2, referred to as SPa1-5, were made and their fusions with leucine zippers were coexpressed. FIG. 16B: The same conditions as in FIG. 16A, except the five split points were between domains 2 and 3 and are referred to as SPb1-5. FIG. 16C: SPbNZ5 paired with other split points to determine the pair with highest fluorescence. FIG. 16D: SPbNZ5 paired with either SPbCZ1 or SPbCZ5 was tested for fluorescence independently and without the leucine zipper (ΔZip).

FIG. 17A shows expression of NZ, CZ, and SPa1-5, corresponding to the data in FIG. 16A. FIG. 17B shows expression of NZ, CZ, and SPb1-5, corresponding to the data in FIG. 16B. FIG. 17C shows expression of SPbNZ5 and SPbCZ5 paired with a non-continuous CZ or NZ partner in whole cells, corresponding to the data in FIG. 16C. FIG. 17D shows expression of SPbNZ5, SPbCZ1 or 5 alone, in combination, or with their leucine zippers removed in whole cells, corresponding to data in FIG. 16D.

FIG. 18A shows insoluble (P) and soluble (S) fractions of SPbNZ5 and SPbCZ4, alone, coexpressed, with leucine zippers, and without leucine zippers. FIG. 18B shows expression of the C-terminal fragments of LucY without leucine zipper, uninduced (UI), and induced (I).

In FIGS. 19B and 19C, fluorescence is represented as a percentage of wild-type LucY and CZ, respectively. The image above each histogram is a photograph of the whole cell pellets of the corresponding sample under UV light. Error bars represent standard deviation from the mean (n=3).

FIG. 20A is a gel showing expression of each circular permutation, designated BP-1 through BP-10. The gel shown in FIG. 20A corresponds to the data presented in FIG. 19B. FIG. 20B is a gel showing split point trials derived from circularly permuted LucY. The gel shown in FIG. 20B corresponds to the data in FIG. 19C.

FIG. 21A is a photograph of NZ-transformed cells viewed with a band pass filter. FIG. 21B is a photograph of CZ-transformed cells viewed with a band pass filter. FIG. 21C is a photograph of SPbNZ5-transformed cells viewed with a band pass filter. FIG. 21D is a photograph of SPbCZ4-transformed cells viewed with a band pass filter. FIG. 21E is a photograph of SPbNZ5+SPbCZ4-transformed cells viewed with a band pass filter. FIG. 21F is a photograph of NZ-transformed cells viewed with bright field and band pass filters merged. FIG. 21G is a photograph of CZ-transformed cells viewed with bright field and band pass filters merged. FIG. 21H is a photograph of SPbNZ5-transformed cells viewed with bright field and band pass filters merged. FIG. 21I is a photograph of SPbCZ4-transformed cells viewed with bright field and band pass filters merged. FIG. 21J is a photograph of SPbNZ5+SPbCZ4-transformed cells viewed with bright field and band pass filters merged.

FIGS. 22A-22E are a series of fluorescent photomicrographs demonstrating the use of LucY to visualize protein crystals. FIG. 22A is a photomicrograph of LucY crystals visualized under UV light. FIG. 22B, FIG. 22C, FIG. 22D, and FIG. 22E are photomicrographs of putative crystals of a β1-AR-IL3-LucY fusion proteins in lipidic cubic phase (LCP) visualized under UV light.

DETAILED DESCRIPTION

Abbreviations and Definitions

Figures 1A, 1B, 1C:
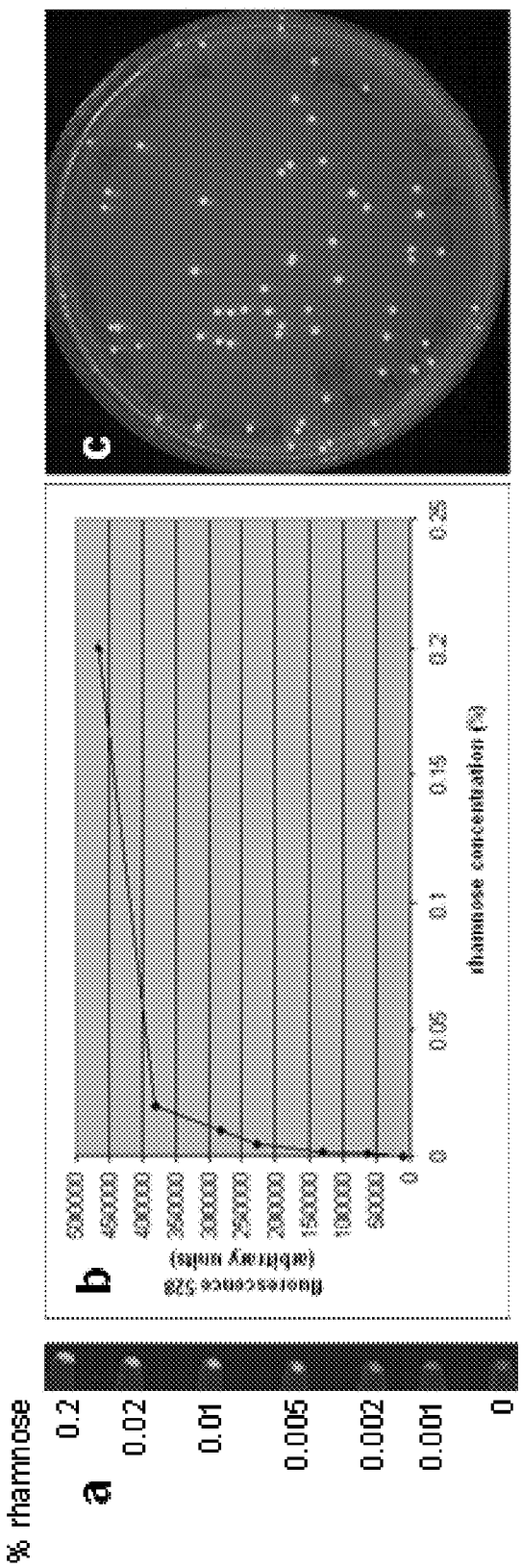
FIGS. 1A-1F. LucY expression.
Figure 1F:
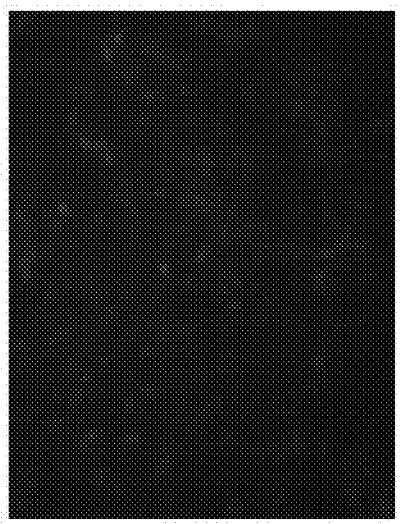
Figure 1E:
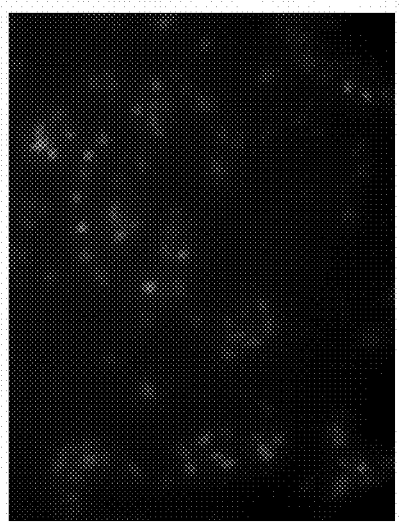

ABV=Acidianus bottle-shaped virus. ATPb=ATP synthase (part of the Fo complex; subunit a). β1-AR-IL3=cardiac β1-adrenergic receptor+interleukin 3 fusion. BiFC=bimolecular fluorescence complementation. DNAP=DNA polymerase. FP=fluorescent protein. GFP=green fluorescent protein. GPCR=G protein-coupled receptor. HA tag=human influenza hemagglutinin tag. IPTG=isopropyl β-D-1-thiogalactopyranoside. LRRK2=leucine-rich repeat kinase 2. Ni-NTA=nickel-nitrilotriacetic acid resin. PCR=polymerase chain reaction (see U.S. Pat. Nos. 4,683,195 and 4,683,202). RFP=red-shifted fluorescent protein. SDS-PAGE=sodium dodecyl sulfate polyacrylamide gel electrophoresis. SUMO=small ubiquitin-like modifier protein.

Unless specifically indicated otherwise, all technical and scientific terms used herein have the same meaning as commonly understood by those of ordinary skill in biochemistry and genetic engineering. For purposes of the present disclosure, the following terms are specifically defined.

The term "nucleic acid molecule" or "polynucleotide" refers to a deoxyribonucleotide or ribonucleotide polymer in either single-stranded or double-stranded form, and, unless specifically indicated otherwise, encompasses polynucleotides containing known analogs of naturally occurring nucleotides that can function in a similar manner as naturally occurring nucleotides. For example, this term can refer to single and double stranded forms of DNA and/or RNA.

The term "recombinant nucleic acid molecule" refers to a non-naturally occurring polynucleotide containing two or more linked polynucleotide sequences. A recombinant nucleic acid molecule can be produced by recombination methods, particularly genetic engineering techniques, or can be produced by a chemical synthesis method. A recombinant nucleic acid molecule can encode a fusion protein, for example, a fluorescent protein as disclosed herein linked to a polypeptide of interest. The term "recombinant host cell" refers to a cell that contains or can express a recombinant nucleic acid molecule.

The term "encoding" when referring to a polypeptide or protein (the terms are used synonymously herein) refers to the transcription of a corresponding polynucleotide and translation of the mRNA produced therefrom to yield the polypeptide. The encoding polynucleotide is considered to include both the coding strand, whose nucleotide sequence can be identical to an mRNA, as well as its complementary strand. Encoding polynucleotides explicitly include degenerate codons which encode the same amino acid residues or functionally equivalent amino acid residues. Nucleotide sequences encoding a polypeptide or protein can include polynucleotides containing introns and exons.

The term "expression construct" refers to a polynucleotide molecule containing at least one sub-sequence encoding a protein of interest which is operationally linked to one or more regulatory sub-sequences which drive expression of the encoded protein when the construct is transformed into a suitable host cell. Such constructs may also contain sub-sequences encoding proteins for selecting host cells transformed to contain the construct, such as sub-sequences which confer antibiotic resistance or dietary limitations to transformed cells. An expression construct may also include one or more of the FP's disclosed herein.

The terms "control sequences (or sub-sequences)," "regulatory sequences (or sub-sequences)," and the like refer to polynucleotide sequences that are necessary to effect the expression of coding and non-coding sequences in a host cell. Such control sequences can include promoters, ribosomal binding sites, transcription termination sequences, and the like. These terms are used synonymously herein and include, at a minimum, components whose presence can influence expression and also include additional components whose presence is advantageous, such as leader sequences. Fusion partner sequences may sometimes also be control sequences.

The term "operationally linked" when referring to joined polynucleotide sequences denotes that the sequences are in the same reading frame and upstream regulatory sequences will perform as such in relation to downstream structural sequences. Polynucleotide sequences which are operationally linked are not necessarily physically linked directly to one another but may be separated by intervening nucleotides which do not interfere with the operational relationship of the linked sequences. Similarly, when referring to joined polypeptide sequences, operationally linked means that the functionality of the individual joined segments are substantially identical as compared to their functionality prior to being operationally linked. For example, a fluorescent protein can be fused to a polypeptide of interest and in the fused state retain its fluorescence, while the fused polypeptide of interest also retains its original biological activity.

As used herein, the term "brightness," with reference to a fluorescent protein, is measured as the product of the extinction coefficient (c) at a given wavelength and the fluorescence quantum yield ($\Phi_F$).

The term "probe" refers to a substance that specifically binds to another substance (a "target"). Probes include, for example, antibodies, polynucleotides, receptors and their ligands, and may (or may not) be labeled so as to provide a means to identify or isolate a molecule to which the probe has specifically bound.

The term "label" refers to a composition that is detectable with or without instrumentation, for example, by visual inspection, spectroscopy, or a photochemical, biochemical, immunochemical or chemical reaction. Exemplary labels (non-limiting) include $^{32}P$, fluorescent dyes and proteins, electron-dense reagents, enzymes (such as those commonly used in an ELISA), and binding labels or tags, such as biotin, digoxigenin, or other haptens or peptides for an antiserum or antibody. For example, a label can generate a measurable signal such as fluorescent light in a sample.

The terms "polypeptide" and "protein" refer to a polymer of two or more amino acid residues. For purposes of this disclosure, the two terms are synonymous. "Polypeptides" and "proteins" are polymers of amino acid residues that are connected through amide bonds. As defined herein, the term "amino acid" includes natural α-amino acids and unnatural α-amino acids (e.g. beta-alanine, phenylglycine, homoarginine, N-alkyl α-amino acids and the like). All optical isomers are included within the definition of "amino acid."

The term "isolated" or "purified" refers to a material that is substantially or essentially free from components that normally accompany the material in its native state in nature. Purity generally can be determined using analytical chemistry techniques such as polyacrylamide gel electrophoresis, high performance liquid chromatography, and the like. A polynucleotide or a polypeptide is considered to be isolated when it is the most predominant species present in a preparation.

The term "naturally occurring" refers to a protein, nucleic acid molecule, cell, or other material that exists in nature. A naturally occurring material can be in its "native" form, that is as it exists in nature. Naturally-occurring materials may also be modified by human intervention so that they are in an isolated or purified form.

Two or more amino acid sequences or two or more nucleotide sequences are considered to be "substantially identical" or "substantially similar" if the amino acid sequences or the nucleotide sequences share at least 80% sequence identity with one another, or with a reference sequence over a given comparison window. Thus, substantially similar sequences include those having, for example, at least 80%, 85%, 90%, 95%, 97%, or 99% sequence identity. The terms "sequence identity" or "sequence identical" are defined to mean sequence identity as measured using the cluster database at high identity with tolerance method (i.e., CD-HIT). In simplified terms, terminal gaps are ignored and identity is calculated from the remaining aligned columns. An "identity" or "match" is a column having the same amino acid residues or nucleotide bases; a "mismatch" is a column with two different amino acid residues or nucleotide bases. An "indel" is a consecutive series of gaps in one sequence. Percent identity is then calculated by dividing the number of matches by the length of the shorter of the two sequences being compared. CD-HIT is well known in the field and will not be discussed in any detail herein. For a full description, see "Cd-hit: a fast program for clustering and comparing large sets of protein or nucleotide sequences," Weizhong Li & Adam Godzik *Bioinformatics*, (2006) 22:1658-9; and Limin Fu, Beifang Niu, Zhengwei Zhu, Sitao Wu and Weizhong Li, "CD-HIT: accelerated for clustering the next generation sequencing data," *Bioinformatics*, (2012), 28(23):3150-3152.

Additionally, two or more amino acid sequences or two or more nucleotide sequences are considered to be "substantially identical" or "substantially similar" if the amino acid sequences or the nucleotide sequences are circular permutations of each other. Not all sequence-based algorithms for determining percent sequence identity will detect circular permutations. However, several well known programs that require an input consisting only of a linear sequence of amino acids or nucleotides will detect circular permutations of the protein (or encoded protein in the case of nucleotides). Such programs include SHEBA (Jung, J.; Lee, B. (2001). "Circularly permuted proteins in the protein structure database," *Protein Science* 10(9):1881-1886); Multiprot (Shatsky, M.; Nussinov, R.; Wolfson, H. J. (2004). "A method for simultaneous alignment of multiple protein structures," *Proteins: Structure, Function, and Bioinformatics* 56(1):143-156); RASPODOM (Weiner, J.; Thomas, G.; Bornberg-Bauer, E. (2005). "Rapid motif-based prediction of circular permutations in multi-domain proteins," *Bioinformatics* 21(7):932-937); CPSARST (Lo, W. C.; Lyu, P. C. (2008). "CPSARST: An efficient circular permutation search tool applied to the detection of novel protein structural relationships," *Genome Biology* 9(1):R11); GANGSTA+(Schmidt-Goenner, T.; Guerler, A.; Kolbeck, B.; Knapp, E. W. (2010). "Circular permuted proteins in the universe of protein folds," *Proteins: Structure, Function, and Bioinformatics* 78(7):1618-1630.); SANA (Wang, L.; Wu, L. Y.; Wang, Y.; Zhang, X. S.; Chen, L. (2010). "SANA: An algorithm for sequential and non-sequential protein structure alignment," *Amino Acids* 39(2):417-425); and CE-CP (Prlic, A.; Bliven, S.; Rose, P. W.; Bluhm, W. F.; Bizon, C.; Godzik, A.; Bourne, P. E. (2010). "Pre-calculated protein structure alignments at the RCSB PDB website," *Bioinformatics* 26(23):2983-2985).

The term "fluorescent properties" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy.

The term "fluorescent protein" refers to any protein capable of light emission when excited with an appropriate electromagnetic energy. Fluorescent proteins include proteins having amino acid sequences that are either natural or engineered, such as the fluorescent proteins derived from *Aequorea victoria* fluorescent proteins.

The term "mutant" or "variant" also is used herein in reference to a fluorescent protein that contains a mutation with respect to a corresponding wild-type fluorescent protein. In addition, reference is made herein to a "spectral variant" or "spectral mutant" of a fluorescent protein to indicate a mutant fluorescent protein that has a different fluorescence characteristic with respect to the corresponding wild-type fluorescent protein. Similarly, thermo-tolerant mutants or variants are fluorescent protein that display fluorescent characteristics at elevated temperatures as compared to the corresponding wild-type.

The recombinant polynucleotides described herein are incorporated into a suitable host cell. The host cell may be any host cell now known or developed in the future which is amenable to transformation, including, but not limited to prokaryotic and eukaryotic unicellar host cells, e.g., bacteria, yeast, and the like, such as unicellular microbes of the genera *Saccharomyces, Bacillus, Aspergillus, Pichia, Kluyveromyces, Escherichia* and the like, or isolated, high-order cells from multi-cellular organisms, such as insect and mammalian host cells.

Many of the steps noted below for the manipulation of polynucleotides and proteins, including digesting with restriction endonucleases, amplifying by PCR, hybridizing, ligating, separating and isolating by gel electrophoresis, transforming cells with heterologous DNA, selecting successful transformants, and the like, are well known and widely practiced by those skilled in the art and are not extensively elaborated upon herein. Unless otherwise noted, the standard protocols utilized herein are described extensively in Michael R. Green & Joseph Sambrook, "Molecular Cloning: A Laboratory Manual (Fourth Edition)," © 2012, Cold Spring Harbor Laboratory Press: New York, N.Y., ISBN 978-1-936113-42-2.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth.

All references to singular characteristics or limitations described herein shall include the corresponding plural characteristic or limitation, and vice-versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods, compositions, and kits described herein can comprise, consist of, or consist essentially of the essential elements and limitations described herein, as well as any additional or optional ingredients, components, preparatory steps, subsequence steps, or limitations described herein or otherwise useful or desired.

Overview:

Disclosed herein are nucleic acid sequences and amino acid sequences of a novel yellow fluorescent protein designated LucY. The nucleic acid sequences and amino acid sequences encoding the FP are useful for monitoring and visualizing physiological processes, such as protein localization, expression of genes, solubility of protein, etc. The LucY protein, its sequence variants, and homologues, have broad applicability in characterizing cells and organisms and in detecting or measuring various cellular parameters, notably in thermo-tolerant organisms.

LucY, its sequence variants, and homologs may also be used to identify protein binding peptide partners (such as protein-protein or protein-peptide interactions) at the cellular level. More particularly, the split-protein approach described below can be used to determine peptide partners, even if previously unknown, in bacteria and eukaryotes and can be used to visualize cellular and sub-cellular protein localization in multicellular organisms. The FP also can be used to monitor signaling processes and molecular interactions in conjunction with other fluorescent entities such as other fluorescent proteins via FRET. LucY, its sequence variants, and homologues can be used in these protocols, as well as in other conventional protocols that use fluorescent markers.

Thus, LucY, its sequence variants, and homologues can be used for coupling fluorescent protein variants to antibodies, polynucleotides or other receptors for use in detection assays such as immunoassays or hybridization assays, or to track the movement of proteins in cells. For intracellular tracking studies, a first polynucleotide encoding LucY, a LucY sequence variant, or a LucY homologue is fused to at least a second polynucleotide encoding a protein of interest. The construct, if desired, can be inserted into an expression vector. Upon expression inside a heterologous host cell, the protein of interest can be localized based on fluorescence.

LucY, its sequence variants, and its homologs are also useful in systems to detect induction of transcription. For example, a nucleotide sequence encoding a non-fluorescent protein can be fused to nucleotide sequence encoding LucY, and further linked to a promoter or other expression control sequence of interest, which can be contained in an expression vector. The construct is then transfected into a host cell.

Induction of the promoter (or other regulatory element) is then measured by detecting the presence or amount of fluorescence, thereby enabling the responsiveness of a signaling pathway to be evaluated. These and other methods of using the LucY protein and its corresponding polynucleotide are described in greater detail below.

Kits:

A kit for use in transfecting host cells may be assembled using the nucleic acid molecules encoding the FPs, or for labeling target polypeptides with the FP. Host cell transfection kits may comprise at least one container containing one or more of the nucleic acid molecules encoding a FP (or a composition comprising one or more of the nucleic acid molecules or plasmids described herein), which nucleic acid molecule preferably comprises plasmid. These kits optionally may comprise at least one additional container that may contain, for example, a reagent for delivering the FP nucleic acid molecule into a host cell.

Further, kits may contain chemical reagents (e.g., polypeptides or polynucleotides) as well as other components. For example, kits may include apparatus and reagents for sample collection and/or purification, apparatus and reagents for product collection and/or purification, reagents for host cell transformation, reagents for eukaryotic cell transfection, previously transformed or transfected host cells, sample tubes, holders, trays, racks, dishes, plates, instructions to the kit user, solutions, buffers or other chemical reagents, suitable samples to be used for standardization, normalization, and/or control samples. Kits may also be packaged for convenient storage and safe shipping. In some versions, the kits might include a FP as disclosed herein, a polynucleotide vector (e.g., a plasmid) encoding a FP as disclosed herein, bacterial cell strains suitable for propagating the vector, reagents for purifying the expressed fusion proteins, and the like. The FPs and kits using such proteins and/or their corresponding nucleotides may be configured or optimized to carry out one or more of the analytical methods described herein.

Samples Useful with LucY:

The samples that can be assayed or analyzed using LucY, its sequence variants, and its homologues include biological samples, environmental samples, or any other samples for which it is desired to determine whether a particular molecule is present therein. With some embodiments, the sample can include a cell or a cell extract from any source, without limitation (prokaryotic, eukaryotic, single-celled, multicelled, etc.).

Further, the cells may be obtained from a culture of such cells, for example, a cell line, tissue line, or can be isolated from an organism. As such, the cell can be contained in a tissue sample, which can be obtained from an organism by any means commonly used to obtain a tissue sample, for example, by biopsy of a human or other organism. Where the method is performed using an intact living cell or a freshly isolated tissue or organ sample, the presence of a molecule of interest in living cells can be identified, thus providing a means to determine, for example, the intracellular compartmentalization of the molecule.

Measuring Fluorescence:

Methods for detecting the FP or of a cell expressing a FP may comprise, for example, illuminating the FP or cell expressing the FP with an illumination source such that the FP or cell expressing the FP emits radiation. Such detection methods may use an illumination source such as an incandescent light source, a fluorescent light source, a halogen light source, a laser light source, sunlight, and other equivalent sources. When illuminated by such an illumination source, the FP will emit fluorescent light that may be detected by unaided observation or by other qualitative or quantitative methods. Suitable methods for measuring fluorescence of samples are known and understood by those with ordinary skill in the art. Alternatively, the fluorescence signal and absorbance may be measured directly from the FP. The native LucY protein has strong absorbance maxima at 247, 376, and 460 nm. Thus the absorption at any of these wavelengths may be used to detect the FP via absorption spectroscopy. Further, the native LucY protein may be detected directly from a fluorescence emission at 530 nm.

Suitable methods for measuring fluorescence of samples are known and understood by those with ordinary skill in the art. They will not be described in any detail herein. Representative known methods of performing assays on fluorescent materials are described in, e.g., Lakowicz, J. R., Principles of Fluorescence Spectroscopy, (Plenum Press 1983); Herman, B., Resonance Energy Transfer Microscopy, Fluorescence Microscopy of Living Cells in Culture, Part B, Methods in Cell Biology, vol. 30, pp. 219-243 (ed. Taylor, D. L. & Wang, Y.-L., Academic Press 1989); Turro, N. J., Modern Molecular Photochemistry, pp. 296-361 (Benjamin/Cummings Publishing, Inc. 1978). There are numerous commercial suppliers of suitable fluorimeter, fluorescence spectroscopy, fluorescence microscopy, and confocal laser scanning microscopy equipment, such as Agilent Technologies (Santa Clara, Calif., USA; maker of Cary Eclipse-branded instruments) and PerkinElmer, Inc. (Waltham, Mass., USA).

One method for measuring fluorescence in samples is through the use of fluorimeters. Radiation is passed through the sample under controlled conditions. As the radiation passes through the sample at an excitation wavelength, the FP in the sample emits radiation at distinct wavelength(s), which then are captured as data by the fluorimeter. Both excitation and emission spectra are taken to determine the excitation and emission maxima for optimal fluorescence signals under any given set of conditions. The data is saved on a computer and or it can be further analyzed by computer. The scanned data is typically compared to control samples, such as calibration samples, negative and positive controls, and the like. The analyte concentration may be determined by extrapolating the fluorescence of the sample with a calibration curve.

LucY Identification and Isolation:

A 10 g sample of corn stalks collected from a field outside Middleton, Wis. in the fall of 2007 was added to YTP-2 medium containing (per liter) 2.0 g yeast extract, 2.0 g tryptone, 2.0 g sodium pyruvate, 1.0 g KCl, 2.0 g $KNO_3$, 2.0 g $Na_2HPO_4.7H_2O$, 0.1 g $MgSO_4$, 0.03 g $CaCl_2$, and 2.0 ml clarified tomato juice. (See Gao et al. (2011) *Biotechnol Biofuels* 4:5.) The sample was grown at 55° C. and 200 rpm in a 2 L flask containing 1 L of medium. After 2 weeks the media was filtered through a Miraclothbrand filter (EMD Millipore, Philadelphia, Pa.; pore size: 22-25 µm) and the remaining material was centrifuged to pellet the microbial cells. The cells from the enrichment culture were resuspended in lysis buffer and high molecular weight genomic DNA was purified using the Qiagen (Valencia, Calif.) Genomic-tip kit. The DNA was randomly fragmented to 3-6 kb using a Hydroshear Apparatus (Digilab, Marlborough, Mass.). The ends of the DNA were made blunt using the DNATerminator kit (Lucigen, Middleton, Wis.). The sheared, end-repaired DNA was gel purified and ligated to the pEZSeq vector (Lucigen, Middleton, Wis.). The ligation reaction was transformed into *E. coli* 10 G cells (Lucigen, Middleton, Wis.). The cells were plated on LB media containing 30 µg/ml kanamycin and grown overnight at 37° C. The plates containing several hundred colonies each were moved to a dark room and checked for fluorescence using a 365 nm long wavelength hand-held UV lamp (UVP, Upland, Calif.). A single colony out of approximately 1000 was a fluorescent yellow color under the UV lamp. The single yellow colony was grown overnight in terrific broth. The plasmid DNA was purified using standard procedures and the nucleotide sequence of the entire 3684 bp recombinant insert was determined by Sanger sequencing biochemistry on an Applied Biosystems 3100 Genetic Analyzer (Foster City, Calif.).

The DNA sequence of the yellow fluorescent recombinant insert was compared to the GenBank database using BLASTN (Altschul, et al., 1990) and close homology (83% sequence identity) was found to a segment of the *Bacillus licheniformis* ATCC 14580 genome. Analysis of the cloned region revealed that it contains homologues of bacterial murG and murB genes and portions of the spoVE and divlB genes. The murB gene encodes UDP-N-acetylenolpyruvoylglucosamine reductase, a flavoprotein that functions in the synthesis of the peptidoglycan cell wall (El Zoelby et al., 2003). The novel metagenomic clone encodes a MurB homologue with 95% amino acid sequence identity to the uncharacterized *Bacillus licheniformis* MurB protein. A lower level of homology to the well-studied MurB proteins from *Staphylococcus aureus* (39% identity; 63% similarity) and *Escherichia coli* (26% identity; 43% similarity) was noted. Previous studies have reported that the purified MurB protein from *E. coli* exhibits a yellow color (Benson et al., 1993). Quenching of the fluorescence of the tightly bound FAD cofactor has been used as the basis for evaluating binding of compounds to *S. aureus* MurB protein (Yang et al., 2006).

To confirm that the novel MurB protein is responsible for the observed fluorescence, its coding region (SEQ. ID. NO. 1) was cloned into a bacterial expression plasmid under the control of a bacteriophage T7 promoter. When this plasmid was introduced into BL21(DE3) cells expressing bacteriophage T7 RNA polymerase, colonies exhibited bright yellow fluorescence. Accordingly, the name LucY (Lucigen Yellow) was chosen for the novel MurB homologue. The amino acid sequence of the wild-type LucY protein is given in SEQ. ID. NO. 2.

Expression in Different Hosts:

*E. coli*: LucY has been expressed in bacterial cells under the control of the IPTG-inducible T7 promoter and the rhamnose-inducible promoter. Strong fluorescence was observed for both, as evidenced by FIGS. 1A, 1B, and 1C, and FIG. 2. FIG. 1A depicts cell pellets (1 OD) from cultures expressing LucY from the rhaP$_{BAD}$ promoter in response to rhamnose at the indicated concentrations. FIG. 1B is a graph that maps fluorescence response to rhamnose induction measured with a plate reader using excitation at 485 nm and emission at 528 nm. FIG. 1C is a photograph of LucY-transformed, fluorescent *E. coli* colonies on a plate containing 0.2% rhamnose.

Figure 2:
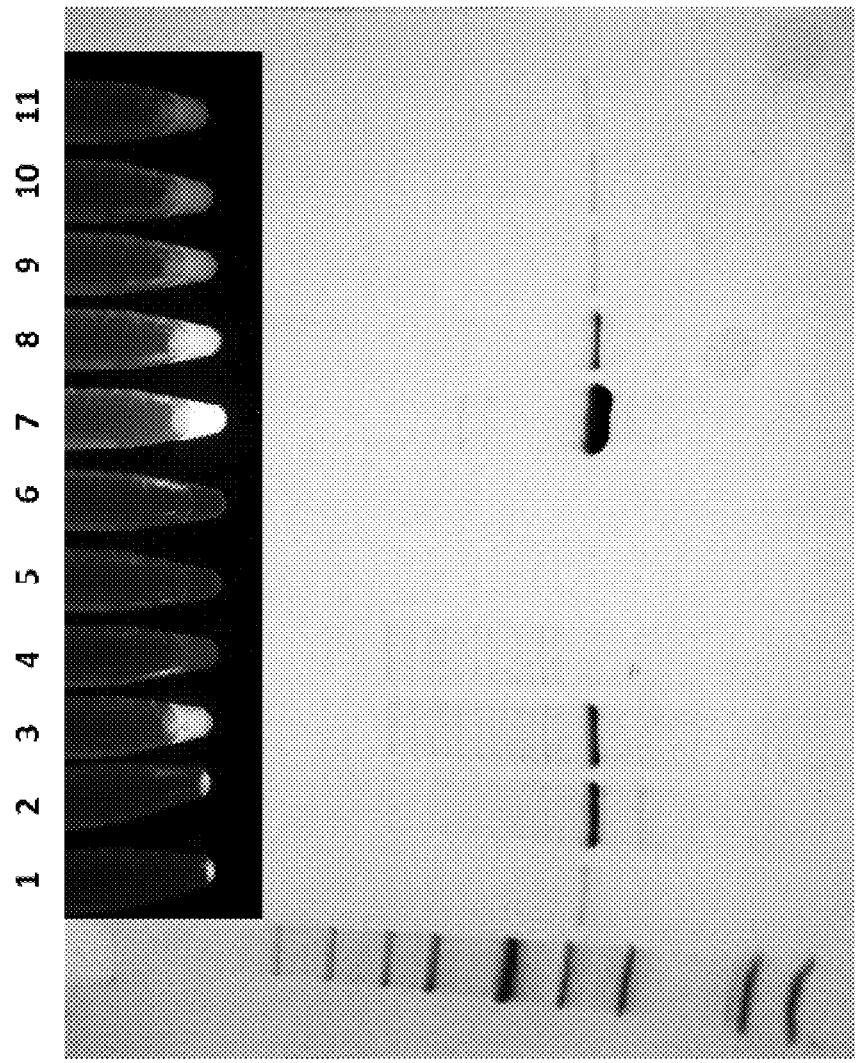
FIG. 2 is a photograph depicting the purification of LucY-His6 from *E. coli*. LucY was expressed with a carboxyl terminal His6 tag using Lucigen's Expresso™-brand T7 cloning and expression system. LucY-His6 was purified by metal affinity chromatography. Fractions from purification including whole cell pellet (lane 1), insoluble pellet after lysis (lane 2), soluble supernatant (lane 3), flowthrough (lane 4), wash (lane 5) and elution fractions (lanes 6-10) with imidazole were photographed under UV light (upper panel) and are aligned with corresponding gel lanes.

Referring to the tubes and corresponding gel lanes in FIG. 2, LucY was expressed with a carboxyl terminal His6 tag using Lucigen's Expresso™-brand T7 cloning and expression system. LucY-His6 was purified by metal affinity chromatography. Fractions from purification including whole cell pellet (lane 1), insoluble pellet after lysis (lane 2), soluble supernatant (lane 3), flow through (lane 4), wash (lane 5) and elution fractions (lanes 6-10) with imidazole were photographed under UV light (upper panel) and are aligned with the corresponding gel lanes.

HI-Control BL21(DE3) cells harboring the LucY gene under the control of the T7 promoter in Lucigen's pETite C-His vector were induced with 1 mM IPTG for 4 hours. For expression under the control of the rhamnose-inducible promoter, LucY was cloned into pRham (Lucigen), transformed into 10 G cells and expression was induced with varying percentages of rhamnose. Again see FIGS. 1A and 1B.

Figure 1D:
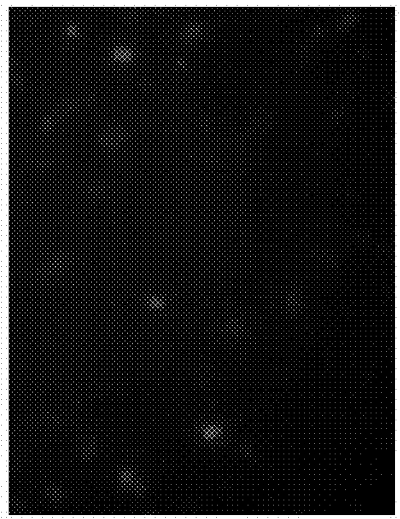

Mammalian cell culture: LucY was cloned into Lucigen's mammalian expression plasmid, pME, which contains the constitutively active cytomegalovirus (CMV) promoter. Various mammalian cell lines have been transfected with this construct, including CHO-K1, COS-7, and HeLa cell lines. Cells exhibiting strong yellow fluorescence were observed when visualized with Nikon Eclipse TE2000-S epifluorescence microscope, fitted with a Diagnostic Instruments 11.2 color camera and long pass GFP filter cube. See FIG. 1D (expression of LucY in the mammalian cells COS-7), 1E (expression of LucY in the mammalian cells CHO-K1), and 1F (expression of LucY in the mammalian cells HeLa).

LucY Purification:

LucY was expressed in HI-Control BL21(DE3) *E. coli* cells with a C-terminal 6× histidine tag and purified by nickel affinity chromatography. See FIG. 2 (described previously). Clarified lysate was loaded onto an equilibrated Ni-NTA column and then washed with 30 column volumes wash buffer final pH 8.0; 10 mM Imidazole, 1×PBS pH 7.4 (137 mM NaCl, 2.7 mM KCl, 8.1 mM Na phosphate dibasic, heptahydrate, and 1.9 mM K phosphate, monobasic) and eluted in 5 mL fractions with 5 column volumes of elution buffer final pH 8.0; 500 mM imidazole, 1×PBS pH 7.4. Fluorescent elution fractions visualized under UV light were pooled and dialyzed overnight in 2 liters 150 mM NaCl, 50 mM Tris pH 7.5 at 4° C. LucY contained minimal aggregates after dialysis and was spun for 10 minutes at 10,000 rpm (12,062×g) to clarify prior to storage at −80° C. Final protein concentration was determined to be 8 mg/mL by Bradford assay.

Figure 3:
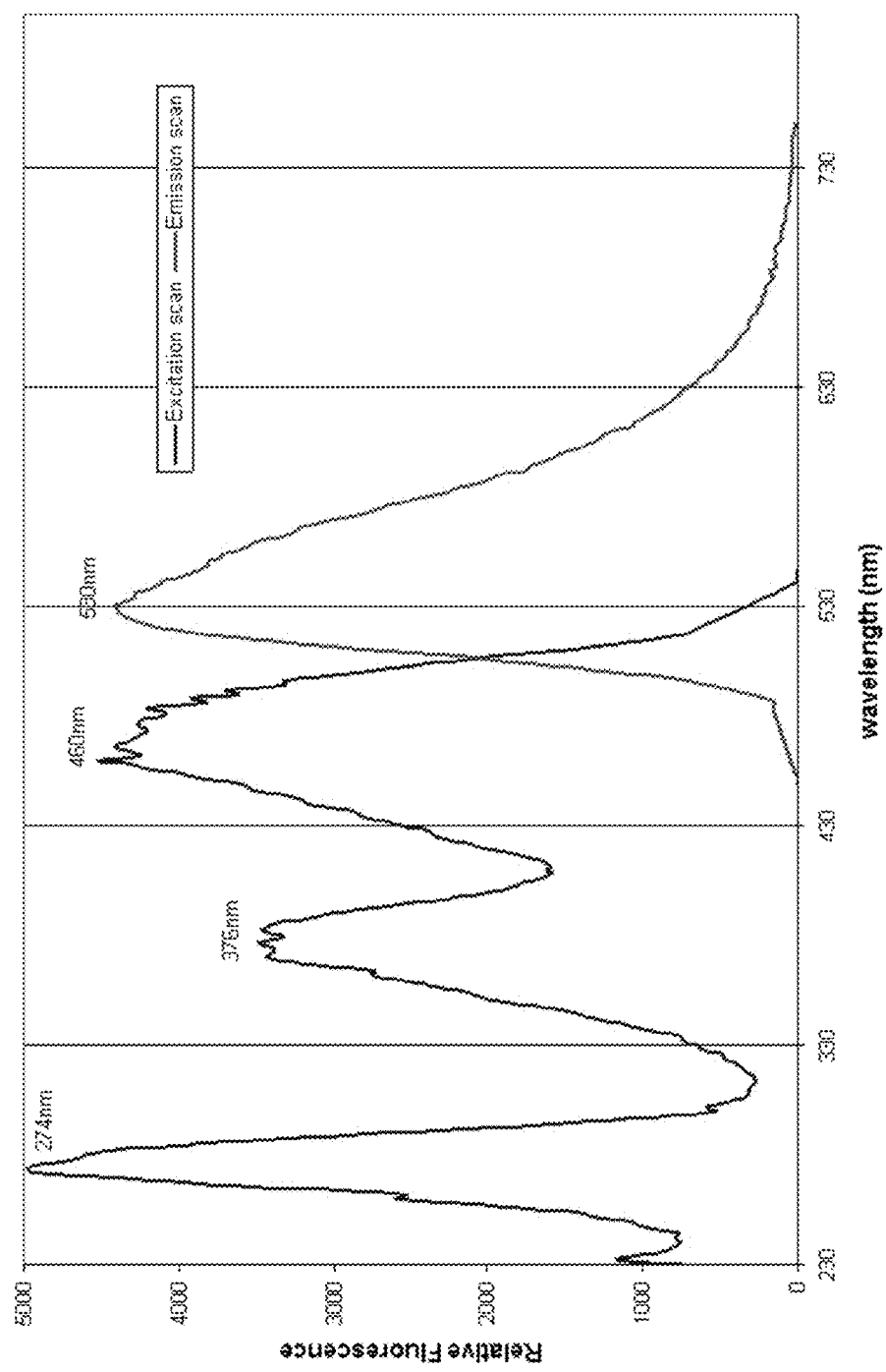
FIG. 3 is a graph depicting the superimposed excitation and emission spectra of LucY. The excitation scan (blue) was performed with emission at 528 nm and the emission scan (green) was performed with excitation at 465 nm.
Figure 4A:
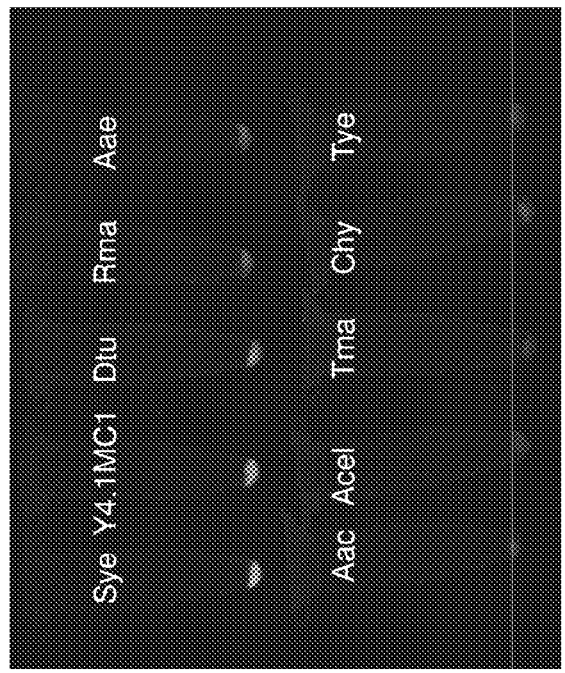
FIG. 4A and FIG. 4B are photographs depicting *E. coli* cell pellets expressing candidate thermo-tolerant homologs of LucY and visualized under a hand-held UV lamp.
Figure 4B:
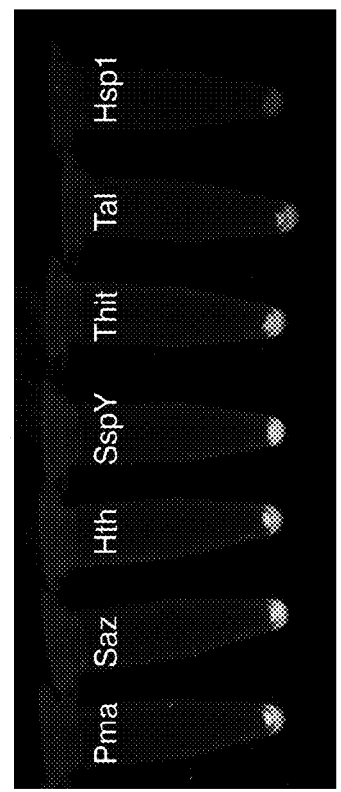
Figure 4C:
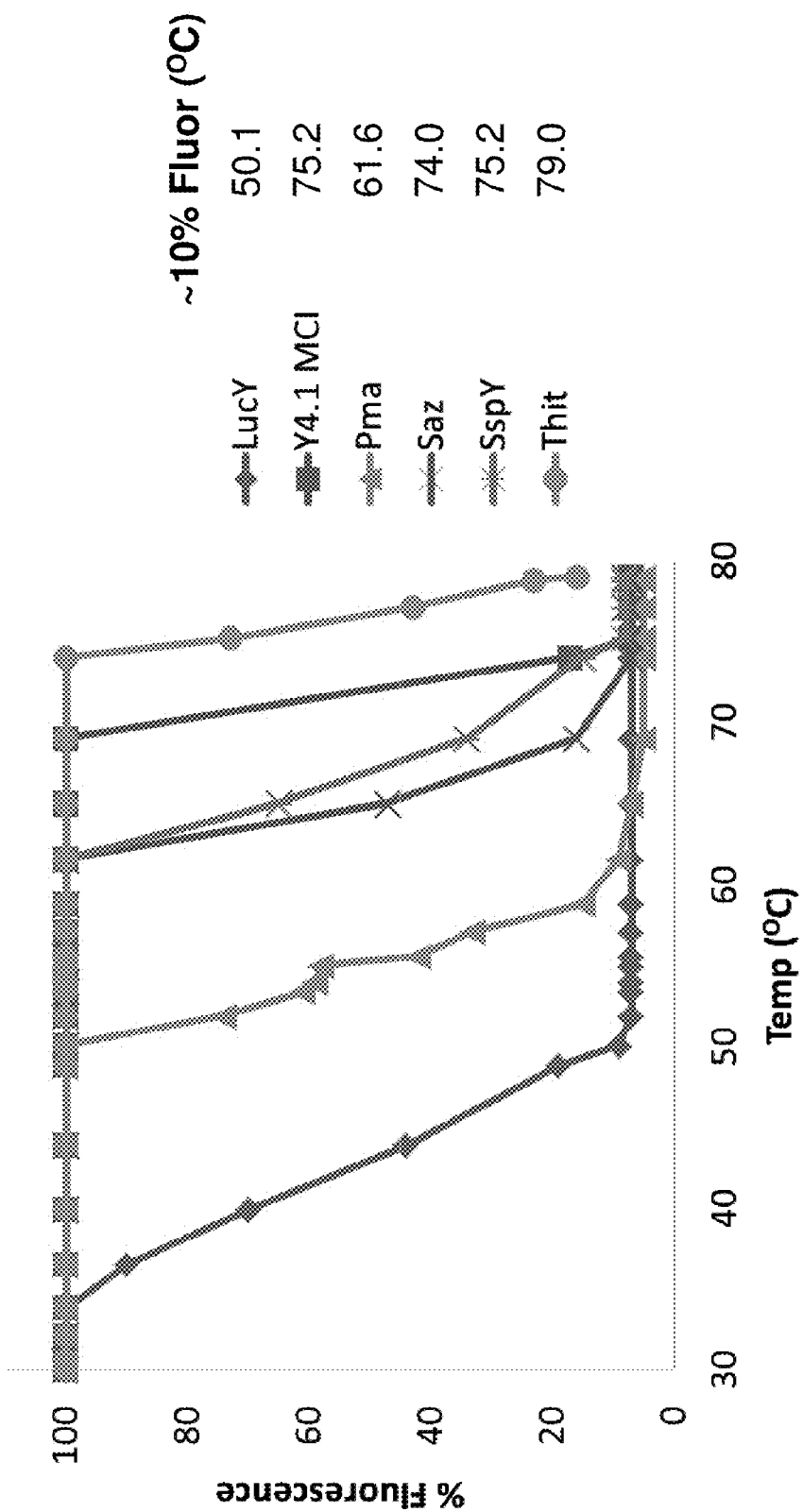
FIG. 4C is a plot of fluorescence following 45 min incubation at temperatures ranging from 30° C. to 80° C. Fluorescence is expressed as a percentage of highest fluorescence recorded across temperature range. The temperature at which fluorescence diminished to 10% is listed. The abbreviations are the same as listed for FIGS. 4A and 4B.

LucY Fluorescence Properties:

The fluorescence characteristics of LucY and related MurB proteins from *S. aureus*, *E. coli*, and *T. thermophilus* were determined through measurements on a Tecan Infinite M1000 monochromator-based plate reader (Tecan Group AG, Männedorf, Switzerland). See FIG. 3 and Table 1. Excitation scans from 230 nm to 540 nm show maximal excitation at three wavelengths, 274 nm, 376 nm, and 460 nm.

known quantities of protein at temperatures ranging from 30° C. to 80° C. and recording fluorescence every 15 minutes for 45 minutes in a Biotek Synergy 2 microplate fluorometer. LucY homologs from Y4.1MC1 and *Thermoanaerobacter italicus* (Thit) were the most thermostable LucY homologs in terms of fluorescence, with fluorescence diminishing to approximately 10% at 75.2° C. and 79.0° C. respectively. See FIG. 4B. Because Thit and Pma (*Persephonella marina*) were visually the brightest appearing homologs, quantum yield measurements were taken as stated above and are approximately, 0.485 and 0.406, respectively. FIG. 4C is a plot of percent fluorescence versus temperature following the 45 min incubation at temperatures ranging from 30° C. to 80° C. Fluorescence is expressed as a percentage of highest fluorescence recorded across temperature range.

TABLE 1

Fluorescence characteristics of LucY and other MurB homologs.

| | Excitation Max (nm) | Emission Max (nm) | $\epsilon$ $(M^{-1}cm^{-1})$ | $\Phi_F$ based on FAD | $\Phi_F$ based on FMN | Brightness (% of LucY) |
|---|---|---|---|---|---|---|
| FAD | 270/375/452 | 522 | 11,900 | — | 0.032 | 9 |
| FMN | 268/376/448 | 525 | 12,500 | 0.273 | — | 82 |
| LucY | 276/377/460 | 528 | 11,662 | 0.356 | 0.351 | 100 |
| S. aureus | 271/377/460 | 527 | 13,511 | 0.224 | 0.221 | 73 |
| E. coli | 276/369/460 | 527 | 12,008 | 0.109 | 0.108 | 32 |
| T. thermophilus | 276/375/460 | 522 | 13,745 | 0.051 | 0.051 | 17 |

$\epsilon$, extinction coefficient
$\Phi_F$, quantum yield
Published $\Phi_F$ for FAD and FMN are 0.032 and 0.27, respectively.

Quantum yield estimates for LucY and other MurB family members were ascertained via the comparative method in relation to the well characterized FAD and flavin mononucleotide (FMN) cofactors. The quantum yield ($\Phi_F$) of LucY was determined to be 0.349 and 0.357 using FAD or FMN as a reference standard, respectively. Brightness values were also ascertained by taking the product of the extinction coefficient and quantum yields for each fluorophore and are expressed as a percentage of LucY. Brightness values show that LucY enhances FAD brightness by 10-fold and that it is the brightest of the MurB homologs.

LucY Thermo-Tolerant Homologs:

Because of their extreme growth conditions, few fluorescent biological reporters are viable in thermophilic organisms. Thus, what are otherwise routine techniques using GFP are not possible in many thermophilic organisms. Enhanced thermo-tolerant fluorescent proteins also have great potential in the thermo-stabilization of GPCRs suitable for crystallization. Thus, a search was conducted for thermo-tolerant LucY homologs using the BLAST function of UniProt (www.uniprot.org). Candidate homologs that originated from thermophilic organisms were selected for further investigation. Seventeen of these genes (Table 2) were synthesized de novo with their coding sequences optimized for expression in *E. coli* (SEQ. ID. NOS: 5-76) and cloned under the control of an inducible promoter (DNA2.0-brand; DNA 2.0, Inc., Menlo Park, Calif., USA). Cultures were grown at 37° C. in LB medium and expression was induced with IPTG. Induced cells were harvested by centrifugation and cell pellets were visualized with a hand-held UV lamp. See FIG. 4A. Proteins whose expression resulted in substantial fluorescence were purified by nickel affinity chromatography. The effect of temperature on fluorescence output was evaluated by incubating

TABLE 2

Thermo-tolerant LucY homologs

| UniProt | Organism | Abbreviation |
|---|---|---|
| A0LRK5 | Acidothermus cellulolyticus | Acel |
| F8IH59 | Alicyclobacillus acidocaldarius | Aac |
| O66805 | Aquifex aeolicus | Aae |
| E4Q8N4 | Caldicellulosiruptor hydrothermalis | Chy |
| B8E323 | Dictyoglomus turgidum | Dtu |
| E3IC15 | Geobacillus strain Y4.1MC1 | Y4.1MC1 |
| G2SID5 | SG0.5JP17-172 | Rma |
| C4FHX3 | Sulfurihydrogenibium yellowstonense SS-5 | Sye |
| B5YFT2 | Thermodesulfovibrio yellowstonii strain ATCC 51303 | Tye |
| Q9X239 | Thermotoga maritima strain ATCC 43589 | Tma |
| B2V7Y9 | Sulfurihydrogenibium sp. (strain YO3AOP1) | SspY |
| C1DVM7 | Sulfurihydrogenibium azorense | Saz |
| C0QUP5 | Persephonella marina | Pma |
| A8UZI2 | Hydrogenivirga sp. 128-5-R1-1 | Hsp1 |
| D3DK91 | Hydrogenobacter thermophilus | Hth |
| D3SPD6 | Thermocrinis albus | Tal |
| D3T3U7 | Thermoanaerobacter italicus | Thit |
| B4U6R2 | Hydrogenobaculum sp. (strain Y04AAS1) | HspY |

LucY as a Fluorescent Protein Fusion Partner and as an Indicator of Protein Expression:

LucY has been used successfully as a reporter of protein expression. Fusing the LucY nucleotide sequence (and its variants and homologs) to various proteins of interest at different junction points have resulted in bright fluorescence.

Figure 5A:
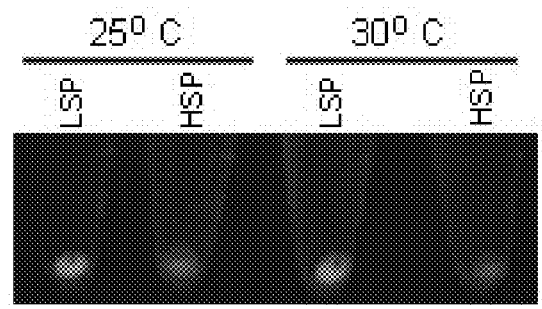
FIGS. 5A and 5B are photographs depicting subcellular localization via LucY fluorescence.
Figure 5B:
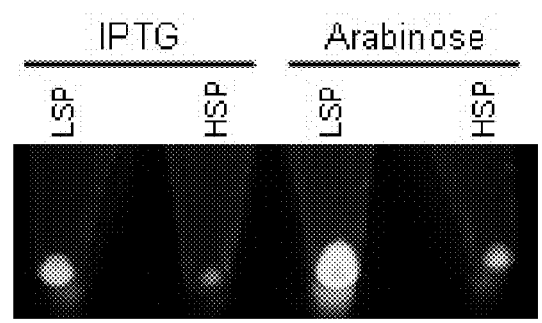
Figure 5C:
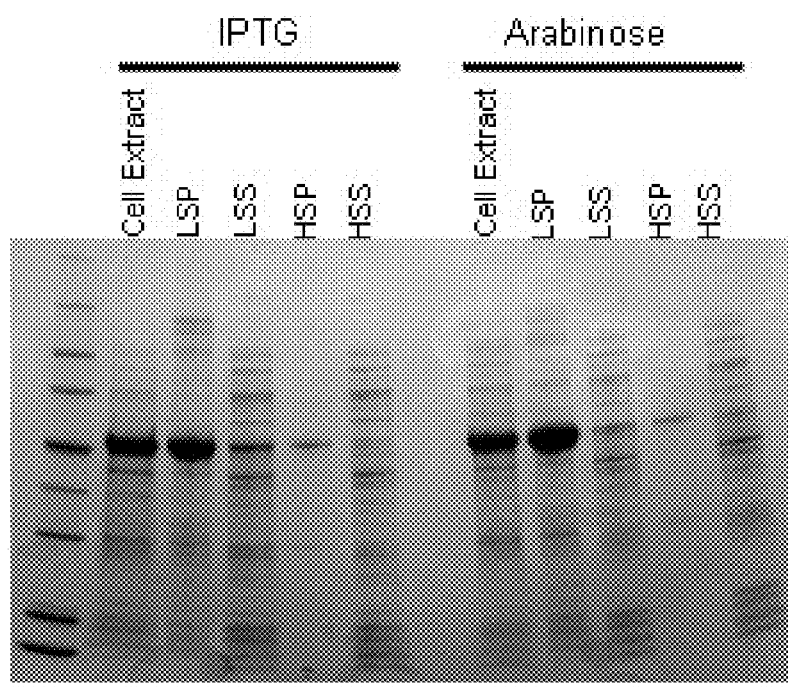
FIG. 5C is a coomassie stained SDS-PAGE of fractions from *E. coli* expressing the LucY-ATPb fusion shown in FIG. 5B. GPCR-containing extracellular membranes separate with the high-speed pellet (HSP). ATPb separates with intracellular membranes in the low-speed pellet (LSP). HSS=high-speed supernatant; LSS=low-speed supernatant.
Figure 6:
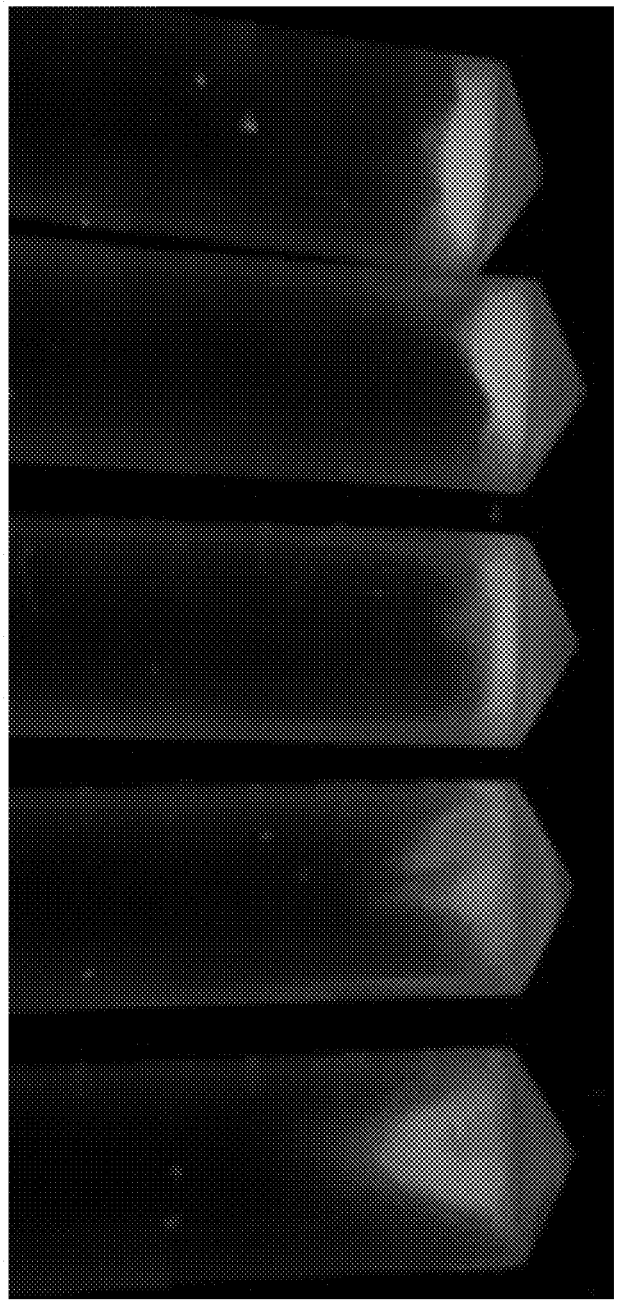
FIG. 6 is a photograph depicting expression of the COR-kinase domain of the LRRK2 enzyme as a C-terminal fusion with LucY from *E. coli*. Five different clones are shown. Each clone is yellow fluorescent, indicating positive fusion protein expression.

Expression in bacterial cells: C-terminal fusions to G-protein coupled receptor (GPCR), specifically A1a, have been visualized by bright yellow fluorescence at both 25° C. and 30° C. See FIG. 5A. In the figure, LSP=low-speed pellet; HSP=high-speed pellet. FIG. 5B corresponds to FIG. 5A and depicts LucY fused to ATPb following induction with IPTG or arabinose. FIG. 5C is a coomassie stained SDS-PAGE of fractions from *E. coli* expressing the LucY-ATPb fusion shown in FIG. 5B. GPCR-containing extracellular membranes separate with the high-speed pellet (HSP). ATPb separates with intracellular membranes in the low-speed pellet (LSP). HSS=high-speed supernatant; LSS=low-speed supernatant. Similar data have been obtained when LucY was fused to the COR-kinase domain of the Parkinson's disease related protein LRRK2. See FIG. 6, which is a photograph under UV light of the *E. coli* host cells transformed to contain and express the COR-kinase-LucY fusion protein.

Figure 7:
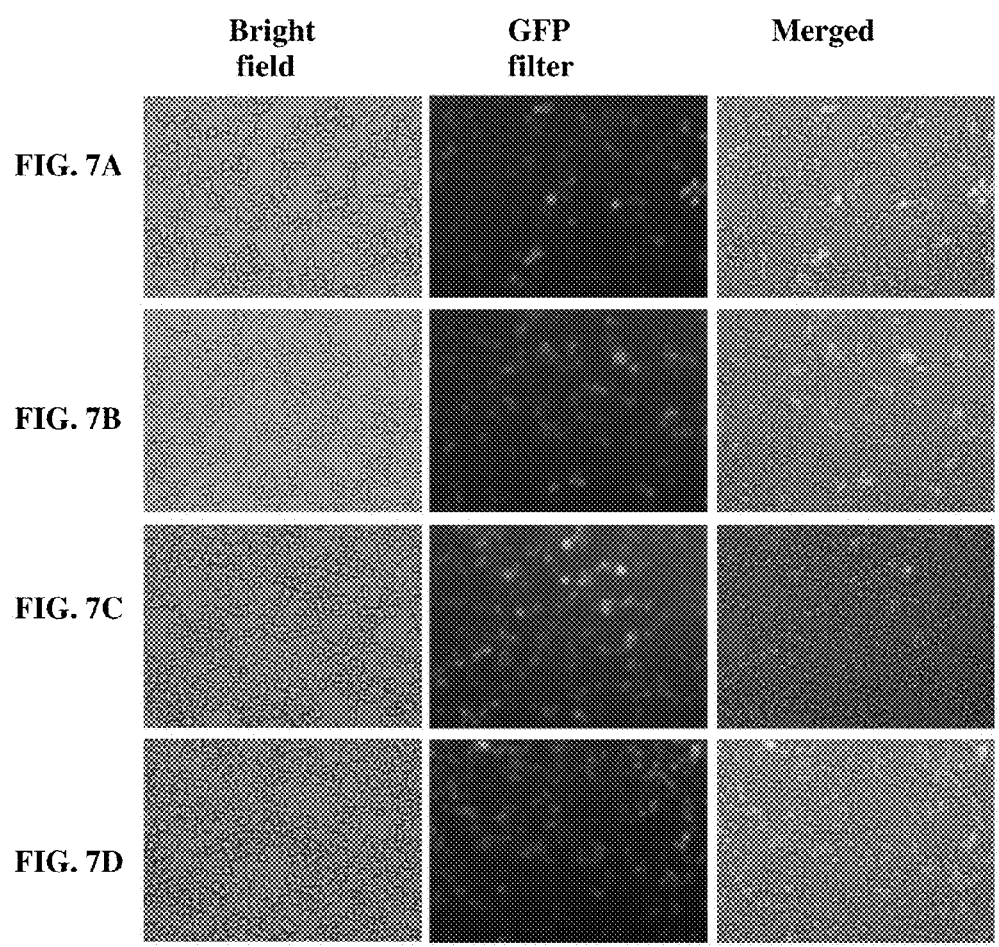
FIGS. 7A, 7B, 7C, and 7D are three-part photographs depicting expression of LucY as an intracellular loop fusion in mammalian cells. Each three-part series shows the fusion illuminated with a bright field (left), using a GFP filter (middle), and a merged bright field/GFP image (right). Each set of photos represents fusion at a different site within the intracellular loop 3 of a GPCR.

Expression in mammalian cells: Turkey β1-adrenergic receptor fused to LucY in the $3^{rd}$ intracellular loop has been expressed in mammalian cells (human embryonic kidney cells; HEK-293T) under the control of the CMV promoter. The recombinant receptor is expressed as indicated by visible yellow fluorescence. Varying the junction points of insertion did not alter the fluorescence of the fusion protein. See FIGS. 7A, 7B, 7C, and 7D. Each figure is three-part photo series depicting expression of LucY as an intracellular loop fusion in mammalian cells. Each three-part series shows the fusion illuminated with a bright field (left), using a GFP filter (middle), and a merged bright field/GFP image (right). Each set of photos represents fusion at a different site within the intracellular loop 3 of a GPCR. FIG. 7A illustrates fusion at positions 244-272; FIG. 7B at positions 244-GSG-272; FIG. 7C at positions 244-GSG-275; and FIG. 7D at positions 244-GSG-278. GSG is the linker sequence between LucY C-terminus and the GPCR.

Figure 8:
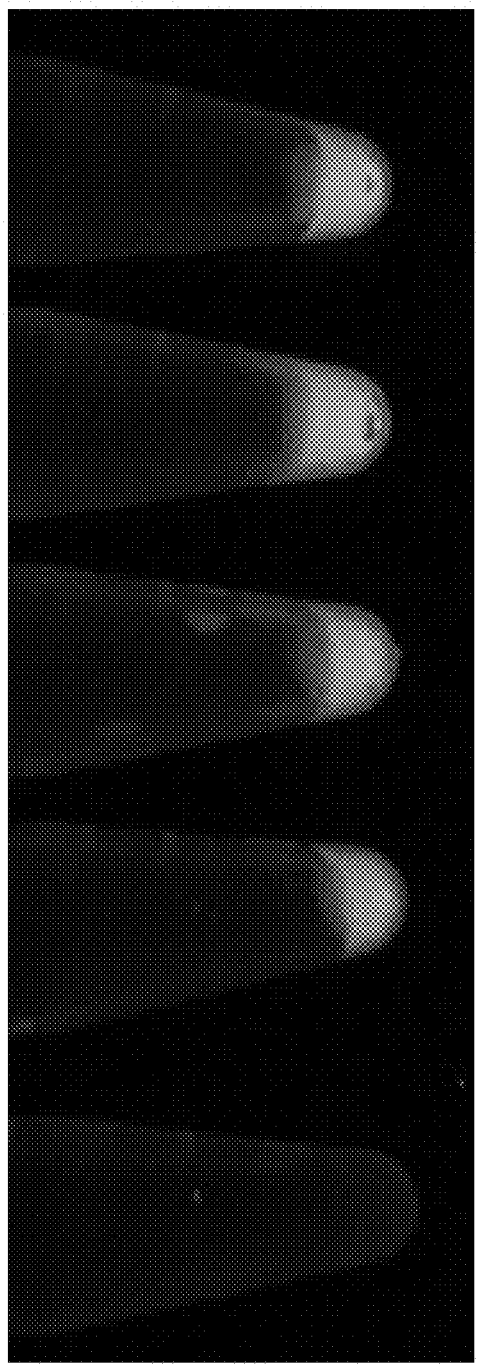
FIG. 8 is a photograph depicting insect cells ("Hi 5"-brand; Life Technologies, Carlsbad, Calif., USA; generically BTI-TN-5B1-4 cells) expressing turkey β1-adrenergic receptor-LucY fusions. The far left tube is negative control, containing only unmodified "Hi 5"-brand cells. The other four tubes contain "Hi 5"-brand cells expressing LucY fused within the intracellular loop 3 of turkey β1-adrenergic receptor at four different junction points.

Expression in insect cells: The same intracellular loop constructs used for expression in HEK-293T were also used to express LucY as a fusion protein in insect cells. When expressed in baculovirus-infected insect cells ("Hi 5"-brand cells), the cells exhibited positive protein expression as evidenced by the yellow fluorescence in the cell pellets. See FIG. 8, which is a photograph of the Hi-5 host cells transformed to express the LucY fusion protein.

LucY as a Label to Determine Subcellular Localization:

A genetically encoded fluorescent marker is extremely useful for determining cellular localization. LucY is a soluble, highly expressed protein amenable to fusion to a variety of proteins. Its fluorescence can be used to track the location of its fusion partner. The GPCR A1a protein preferentially fractionates with extracellular membranes, which can be separated by centrifugation at a low speed and visualized by fusion to LucY. See FIG. 5A, discussed earlier. Alternatively, the single-pass transmembrane protein ATPb fractionates with internal membranes following centrifugation at high speeds and can likewise be visualized by fusion to LucY. See FIGS. 5B and 5C, described previously.

Figure 9B:
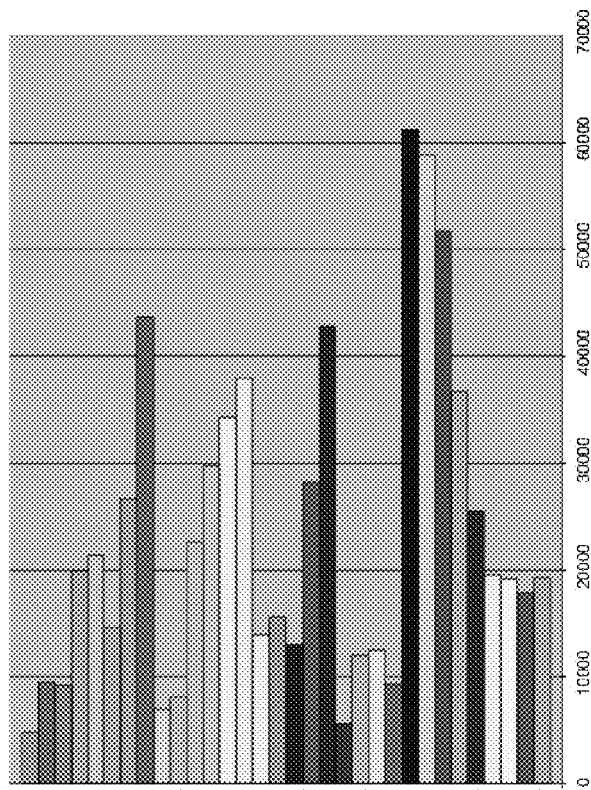
FIG. 9B is a corresponding histogram of the fluorescence exhibited by the tubes in FIG. 9A as quantified with a Biotek Synergy 2 microplate fluorometer (BioTek Instruments, Inc., Winooski, Vt., USA).
Figure 9A:
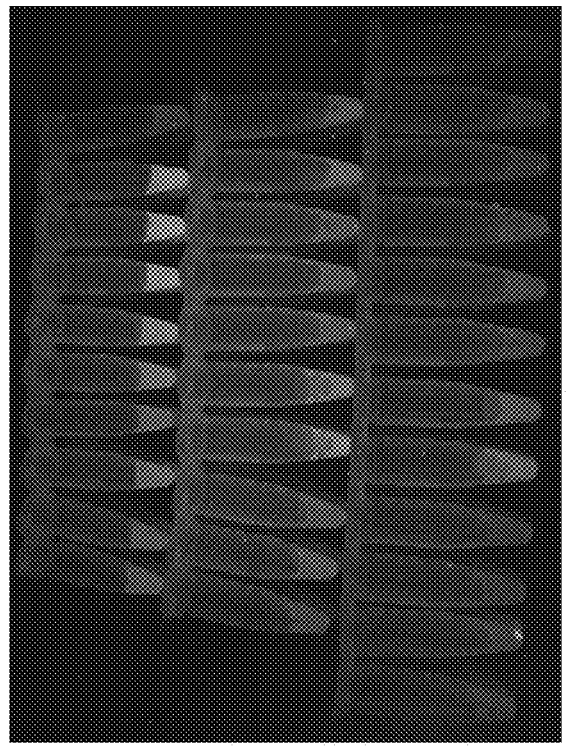
FIG. 9A is a photograph showing the utility of LucY as an indicator of detergent solubilization. ATPb was solubilized with 31 different detergents and the fluorescence was visualized by a UV light.

LucY as an Indicator of Detergent Solubilization:

Tracking the fluorescence in the soluble fraction of a detergent solubilized sample for integral membrane proteins offers an easy and quick solution for high throughput screening of different solubilization combinations. ATPb (a single-pass membrane protein) was used as a typical example of a membrane protein to demonstrate the effectiveness of different screening conditions. Thirty-one (31) different detergents belonging to various classes were tested. Solubilization was performed over night at 4° C. in an end-over rotor. The solubilized fraction was clarified with a high-speed centrifugation step and fluorescence was measured (FIG. 9A) as well as visualized (FIG. 9B) under UV light.

LucY as an Indicator of Protein Expression and Solubility.

Fluorescence enables straightforward visual evaluation of the expression and solubility of proteins fused to LucY. This visual readout can be exploited to identify expression conditions that improve protein expression, and to screen a variety of fusion partners that may promote soluble expression.

A large-scale effort to identify hydrolytic enzymes from *Fibrobacter succinogenes* identified several enzymes that were initially poorly expressed or insoluble in *E. coli* using a T7 bacteriophage polymerase expression system. Several of these recalcitrant proteins were cloned under control of the $rhaP_{BAD}$ promoter with carboxyl terminal fusions to LucY, with or without an amino terminal SUMO solubility tag. Expression of the fusion proteins was induced by inclusion of 0.2% rhamnose in plates or in liquid media. Fluorescence was monitored in colonies, in cell pellets from liquid cultures, and in soluble and insoluble fractions of induced cell lysates.

Results are shown in FIGS. 10A, 10B, and 10C for three different proteins exhibiting different expression levels. In the case of Fisuc_1793, no yellow fluorescence was observed in the absence of SUMO (FIG. 10A, left), and fusion to an amino-terminal SUMO tag led to a dramatic increase in yellow fluorescence (FIG. 10A, right). See also the top pair of tubes in FIG. 10B. A second example, Fisuc_2201, produced moderate yellow fluorescence in the absence of SUMO, but increased fluorescence with the SUMO tag (FIG. 10B, middle pair of tubes). A third case, Fisuc_2442, produced strong fluorescence that was not significantly enhanced by the SUMO tag (FIG. 10B, bottom pair of tubes).

Lysates from the induced cells were centrifuged to separate soluble and insoluble fractions, and fluorescence, when present, was found primarily in the supernatant (soluble) fraction in each case. Gel analysis of fusion protein expression by SDS-PAGE correlated well with the fluorescence results. See FIG. 10C (top panel is for 1793; middle panel for 2201; bottom panel for 2442). No detectable Fisuc_1793-LucY fusion protein was present in either the soluble or insoluble fraction when expressed without the SUMO tag, while the SUMO tagged counterpart was expressed well and in a mostly soluble form. Results with Fisuc_2201 and Fisuc_2442 similarly recapitulated the fluorescence data, with the SUMO tag enhancing the relatively weak expression of Fisucc_2201, but not significantly increasing the already strong expression of Fisuc_2442.

A potential limitation of whole cell fluorescence as an indicator of soluble expression is the possibility of false positives. Fluorescence may be observed, for example, if the proper folding of LucY is allowed despite formation of insoluble aggregates via a fusion partner. Importantly, the stable fluorescence of LucY allows the preparation and fractionation of lysates to evaluate the partitioning of fluorescence between soluble and insoluble fractions. Fluorescent fusion proteins that are found exclusively in the insoluble fraction can be eliminated from further consideration, potentially saving the time and expense of analysis by gel electrophoresis. Alternatively, the fluorescence can be used to screen for conditions that allow solubilization of the protein. For example, the use of nonionic detergents, or different buffer conditions (salt concentrations or pH) may allow dispersal of fluorescent aggregates and recovery of soluble protein.

Figure 11A:
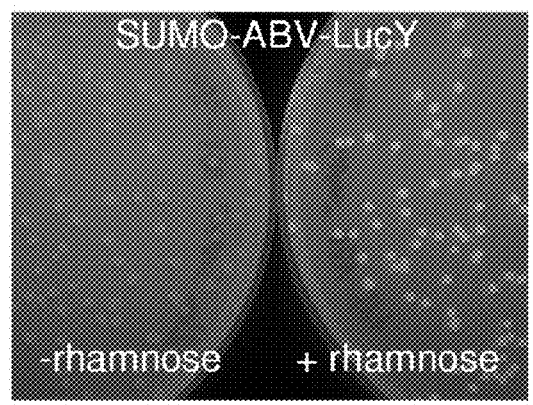
FIGS. 11A, 11B, and 11C demonstrate insoluble expression of ABV-LucY and 4110-LucY as "solubility trap" fusion proteins.
Figure 11B:
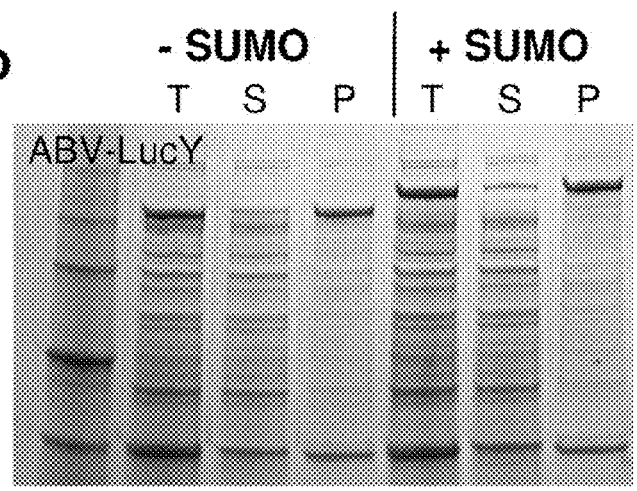
Figure 11C:
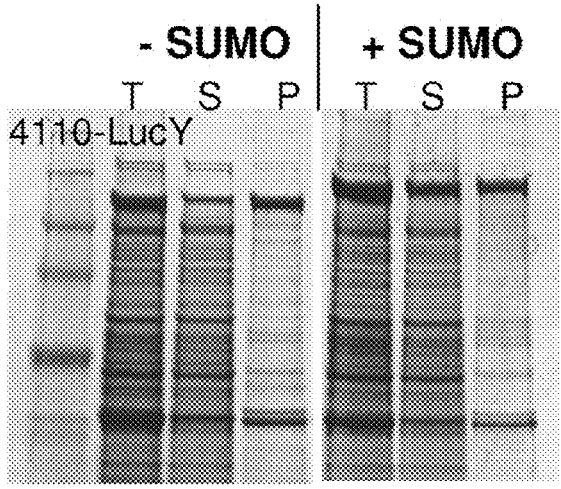

Fluorescence can also be used as the basis for a solubility "trap" screen, in which an insoluble protein fused to LucY is used to identify for novel fusion partners that impart greater levels soluble expression. Two different insoluble proteins were used to evaluate this screening strategy. In both cases LucY was fused to the C terminus of an insoluble DNA polymerase. The DNA polymerase (DNAP) genes were derived from Acidianus bottle-shaped virus (ABV DNAP), or from a screen for novel thermostable DNAPs ("4110" DNAP). These DNAP-LucY fusions were cloned under the rhaP$_{BAD}$ promoter. Fluorescence development and expression were then monitored both on plates and in liquid media with and without 0.2% rhamnose. The effect of an amino-terminal SUMO fusion on the fluorescence development and solubility of each DNAP-LucY fusion protein was also tested. The ABV-LucY fusion protein was poorly soluble, and its solubility was not enhanced by the amino-terminal SUMO tag. The low-level solubility of the SUMO-ABV-LucY fusion resulted in weak yellow fluorescence on plates containing 0.2% rhamnose. See FIG. 11A. The 4110-LucY fusion was also largely insoluble, but fusion to SUMO partially rescued solubility. Both ABV-LucY and 4110-LucY were exploited as "solubility traps" in a screen for solubility-enhancing tags. FIG. 11B depicts the gel analysis of ABV-LucY protein expressed from rhaP$_{BAD}$, with or without an amino-terminal SUMO tag. FIG. 11C depicts the gel analysis of 4110-LucY protein expressed from rhaP$_{BAD}$, with or without a SUMO solubility tag. In FIGS. 11B and 11C, T represents total cell lysate; S represents the soluble fraction after centrifugation of the lysate; and P represents the insoluble pellet fraction after centrifugation.

Figure 12B:
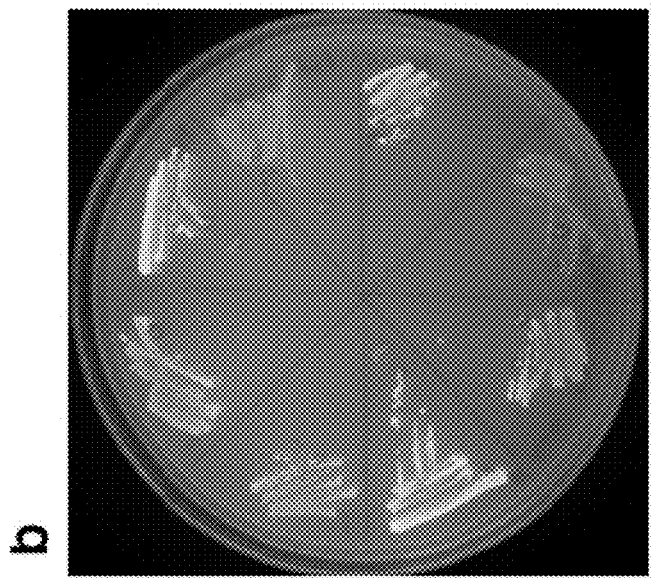
FIGS. 12A and 12B are photos demonstrating the utility of LucY to select fluorescent colonies from a random fusion library in a "solubility trap" experiment.
Figure 12A:
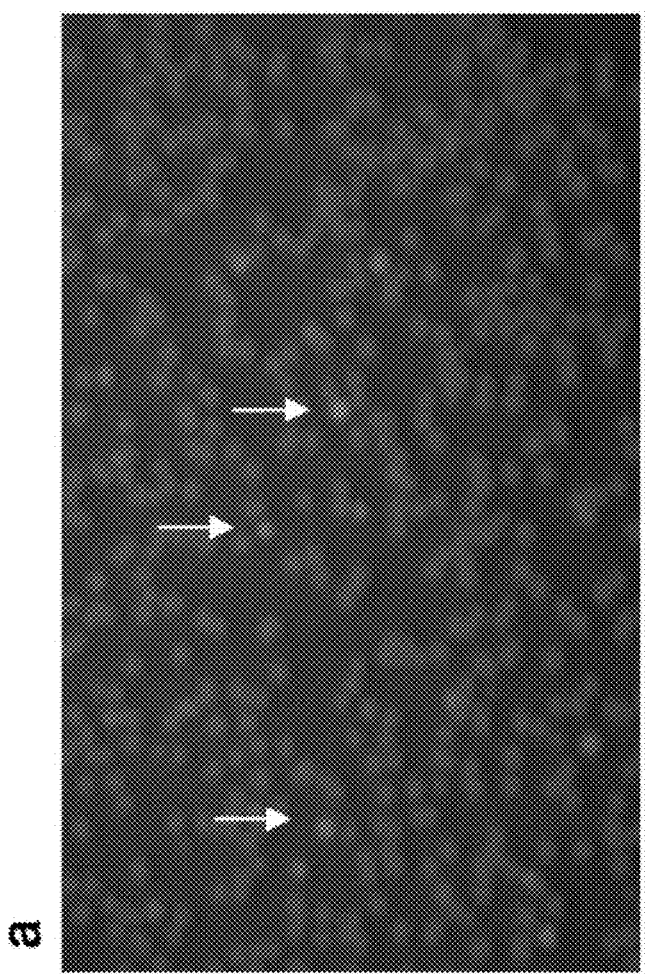

For each DNAP-LucY fusion, separate libraries were constructed using genomic fragments from several sources including *E. coli*, bacteriophage lambda, and a thermophilic *Geobacillus* species. In each case, genomic DNA was physically sheared by nebulization to generate random fragments ranging in size from ~100-700 bp. The DNA fragment ends were made blunt and phosphorylated using Lucigen's DNA terminator kit, and the fragments were cloned into the rhaP$_{BAD}$ expression vector between the ATG start codon and the second residue of the ABV-LucY or 4110-LucY solubility trap fusion. Library transformants were plated on media containing kanamycin and 0.2% rhamnose. In these small-scale test screens, approximately 5,000 to 10,000 clones were plated on each of 6 to 10 large-diameter (13 cm) plates. Plates were observed under illumination from a hand-held long-wavelength UV lamp, and colonies with varying degrees of fluorescence were detected. See FIG. 12A for an example of a primary screening plate and FIG. 12B for an example a secondary screen plate with re-streaked candidates. The 4110-LucY fusion was screened with bacteriophage λ and *Geobacillus* genomic inserts, and the ABV-LucY solubility trap was screened with *E. coli* genomic inserts.

The ABV-LucY fusion was first screened with genomic inserts from *E. coli*. In this screen, bright fluorescent colonies were observed at a frequency of <0.1%. Twenty-two (22) of these bright fluorescent colonies were chosen for further analysis. All 22 were found to have significant deletions removing large portions of the ABV sequence, re-creating an in-frame fusion that presumably resulted in expression of an ABV-LucY fragment with increased solubility. While these results illustrate the utility of LucY fusions to map soluble domains of poorly-soluble proteins, the objective of the screen is to identify novel solubility tags. These deletion clones were not analyzed further.

Figures 13A, 13B:
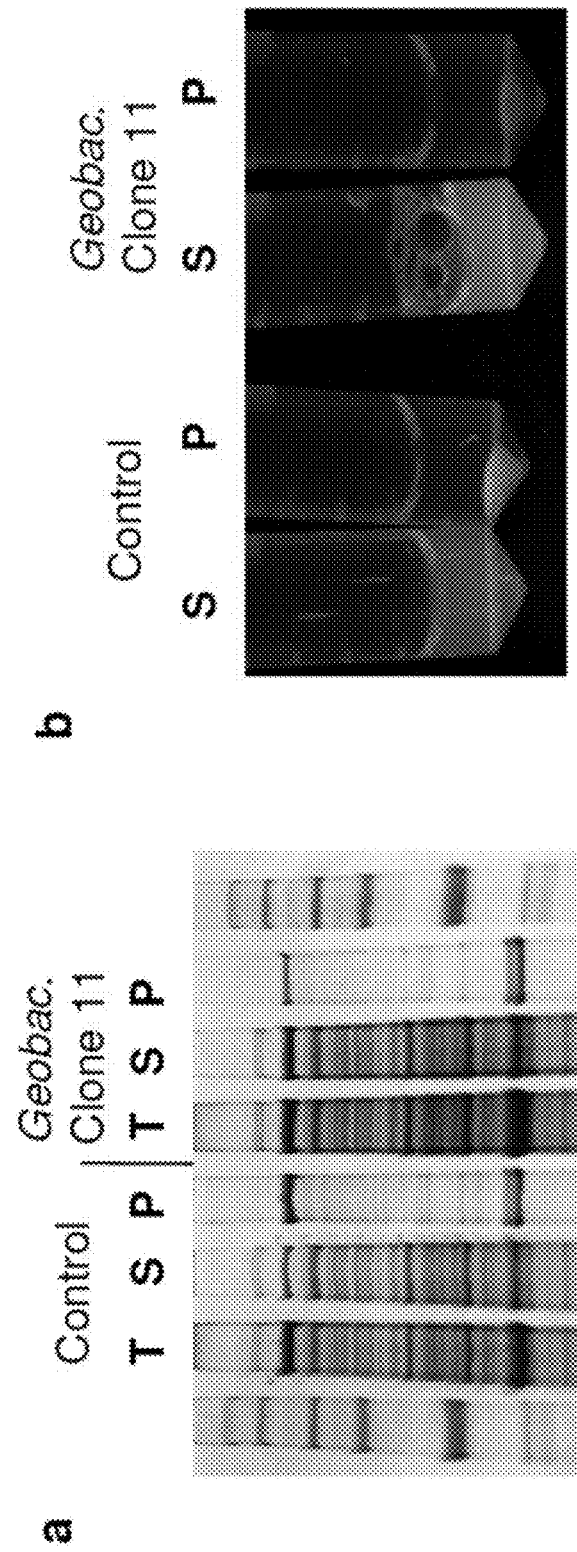
FIGS. 13A and 13B demonstrate enhanced soluble expression of 4110-LucY fusion protein with amino-terminal fusion tags derived from shotgun library screens.

Screening of the 4110-LucY solubility trap yielded several candidate solubility-enhancing tags. Small-scale screens of the 4110-LucY construct were conducted with two different genomic insert libraries derived from bacteriophage k and from a thermophilic *Geobacillus* species. Partial deletions of the 4110 DNAP coding region were obtained far less frequently than with the ABV-LucY trap construct. For the λ insert library, 24 fluorescent clones were selected for analysis. Sequences were obtained for 23 of these clones, and all 23 were found to contain inserts of λ genomic DNA. Twenty-two (22) clones were found to have fusions that restored the correct frame between the ATG initiation codon and the 4110-LucY coding region. A single clone contained a fragment that included a promoter and the amino-terminal portion of a protein coding region, fused in-frame to 4110-LucY. The genomic inserts ranged in size from 93 to 669 base-pairs, and encoded peptides of 31 to 223 residues. Interestingly, two different polypeptide regions were each represented twice by non-identical clones. The repeated isolation of these regions among only 23 clones of 100-700 base-pairs from the 48 kb lambda genome strongly suggests non-randomness in the screen results. Clones were grown in liquid LB media and induced with 0.2% rhamnose for preparation of lysates to evaluate solubility. An example of a library fusion showing a significant increase in solubility of the 4110-LucY protein is presented in FIGS. 13A and 13B. These two figures demonstrate the enhanced soluble expression of 4110-LucY fusion protein with amino-terminal fusion tags derived from the shotgun library screens. FIG. 13A is a gel analysis of soluble expression of *Geobacillus*-4110-LucY library clone 11. The Control sample is 4110-LucY with no amino-terminal fusion. T represents total cell lysate; S represents the soluble fraction after centrifugation of the lysate; and P represents the insoluble pellet fraction after centrifugation. FIG. 13B is a photograph depicting increased partitioning of yellow fluorescence to the soluble fraction with *Geobacillus* library clone 11. Again, S represents the soluble fraction after centrifugation of the lysate and P represents the insoluble pellet fraction after centrifugation.

Figure 14:
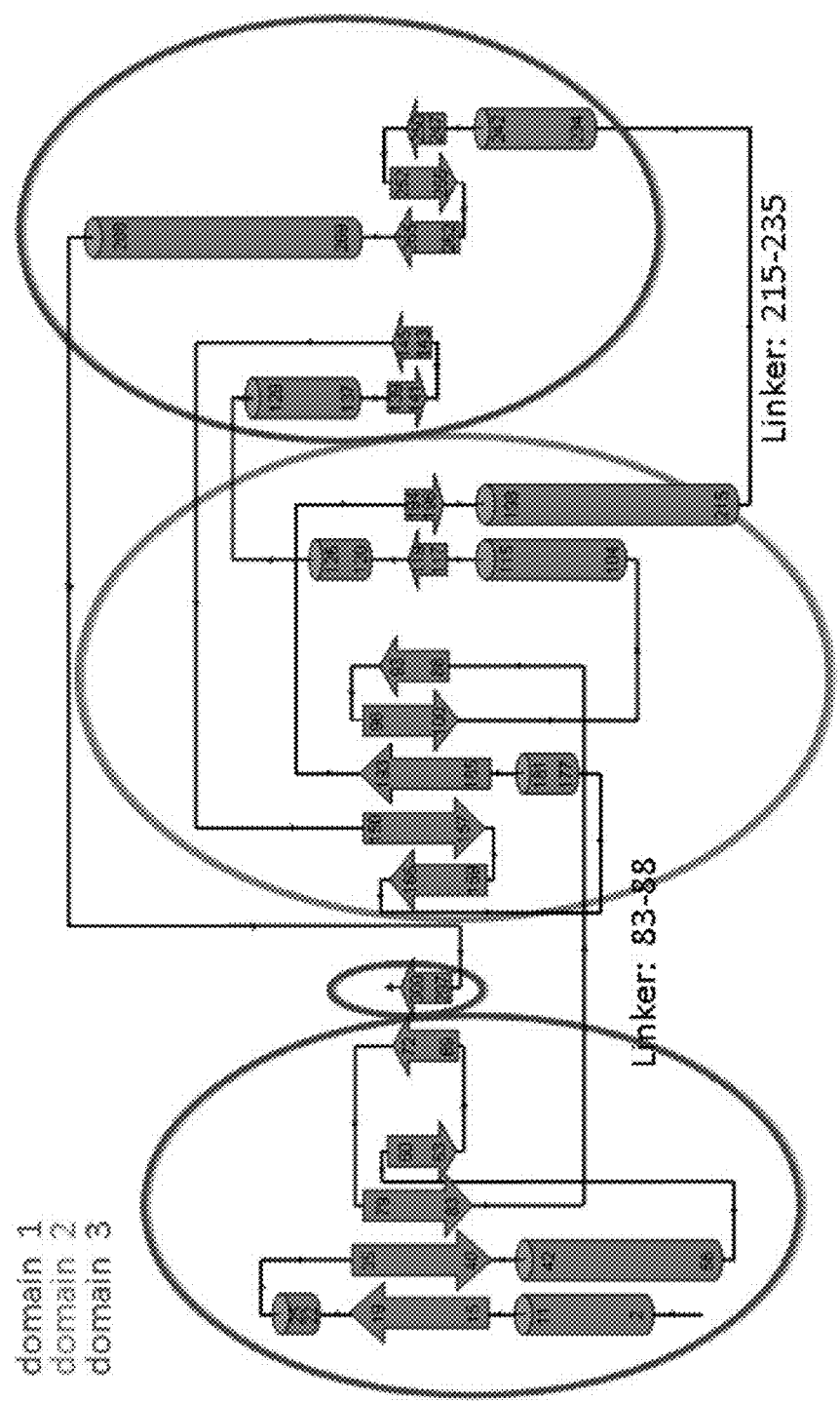
FIG. 14 is a topology diagram of LucY. LucY includes three domains as indicated by circles. Domains 1 and 2 are separated by a short loop; Domains 2 and 3 are connected by an approximately 20 amino-acid span.
Figure 15A:
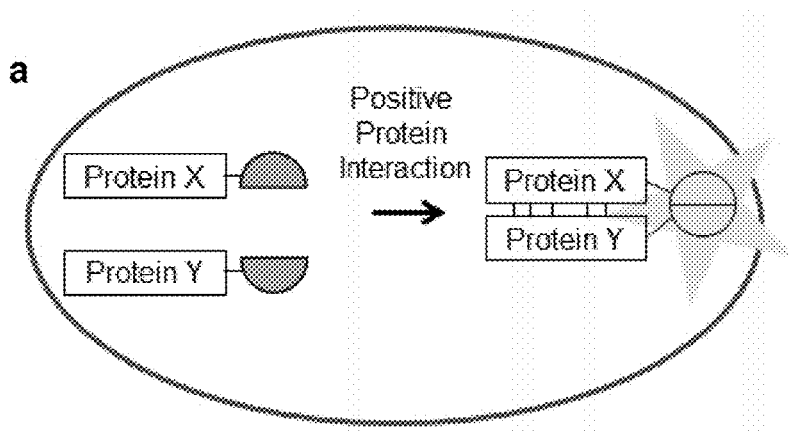
FIGS. 15A, 15B, and 15C are schematic diagrams of various split LucY systems.

The Split-LucY System for Protein-Protein Interaction Studies:

The ability of a monomeric protein to be split and reassembled was first demonstrated with ubiquitin (Johnsson and Varshavasky, 1994) and has since been adopted for use with reporter proteins like GFP (Ghosh et al., 2000) and luciferase (Paulmurugan and Gambhir, 2003). LucY is a 32.7 kDa protein made up of three discrete domains, suggesting candidate split points lie between domains. FIG. 14 presents a schematic diagram of the three domains of the native LucY. In practice, a reporter protein is split in half and each half is expressed as a translational fusion to two proteins of interest for which protein-protein interaction is a possibility and their interaction is assayed in living cells. The reporter protein provides an output signal, like fluorescence, only if its two halves are brought together in a complementary manner due to the interaction of the fusions. This is illustrated schematically in FIG. 15A. The yellow fluorescence emitted by the FAD-binding capacity of LucY is an ideal reporter of protein-protein interaction.

Figure 15B:
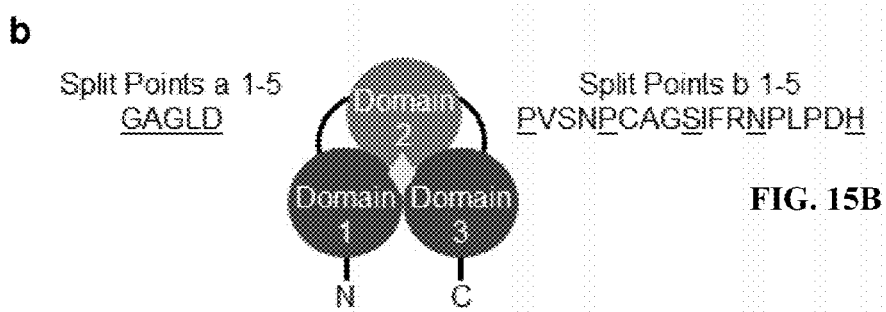
Figure 15C:
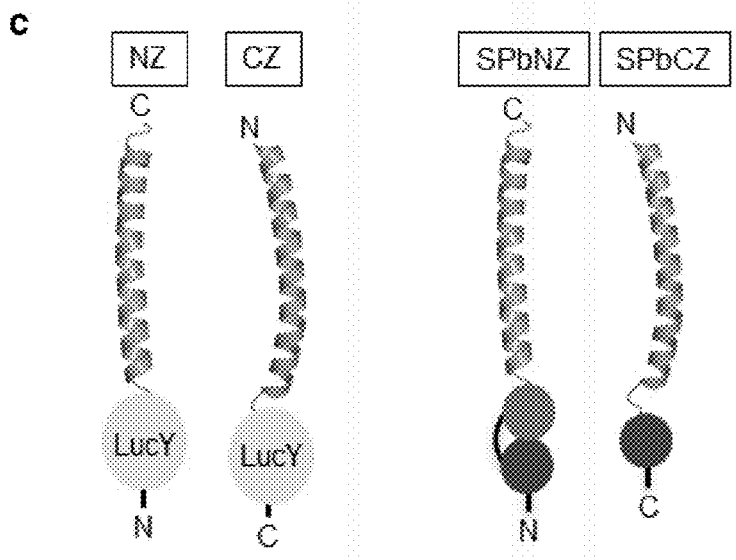

Five points were tested between the short loop between domains 1 and 2 (residues 84 to 88) and within the long loop between domains 2 and 3 (residues 217-234) of LucY. See FIG. 15B, which depicts these split points schematically. Antiparallel leucine zippers were used as an idealized model for interacting protein partners (Ghosh et al., 2000). Because these leucine zippers interact in an antiparallel fashion, one fragment of LucY was fused at the amino-terminus of a leucine zipper (Split Points SPaNZ1-5 and SPbNZ1-5) while the complementary fragment was fused to the carboxy-terminus of the partner leucine zipper (SPaCZ1-5 and SPbCZ1-5). This is depicted schematically in FIG. 15C. The letters a and b and numbers 1 through 5 indicate the location of the split; see Table 3. Matching split point numbers indicates that the CZ split point immediately follows the residue at the carboxy end of the NZ split point. Fusion pairs containing complementary LucY fragments (e.g. SPaNZ1+SPaCZ1; SPbNZ4+SPbCZ4, etc.) were tested for protein expression and for fluorescence complementation. Fluorescence produced by coexpressed fragment pairs fused to leucine zippers was compared to fluorescence of fully intact LucY fused to either the N- or C-terminus of one of the zippers (NZ and CZ). Fluorescence was determined visually in whole cell pellets and quantitatively by a fluorometer.

TABLE 3

Start and end residues for each split point (SP). NZ constructs start with a 6x-His tag. CZ constructs end with the linker sequence SLSTPPTPSTPPT, followed by an Avi-tag. Constructs destined for expression in mammalian cells instead contain an HA-tag. Split Pairs c and d were constructed from a circular permutation construct.

|        | Start | End  | includes domains: |
|--------|-------|------|-------------------|
| SPaNZ1 | D2    | G84  | 1                 |
| SPaNZ2 | D2    | A85  | 1                 |
| SPaNZ3 | D2    | G86  | 1                 |
| SPaNZ4 | D2    | L87  | 1                 |
| SPaNZ5 | D2    | D88  | 1                 |
| SPaCZ1 | A85   | R303 | 2&3               |
| SPaCZ2 | G86   | R303 | 2&3               |
| SPaCZ3 | L87   | R303 | 2&3               |
| SPaCZ4 | D88   | R303 | 2&3               |
| SPaCZ5 | H89   | R303 | 2&3               |
| SPbNZ1 | D2    | P217 | 1&2               |
| SPbNZ2 | D2    | P221 | 1&2               |
| SPbNZ3 | D2    | S225 | 1&2               |
| SPbNZ4 | D2    | N229 | 1&2               |
| SPbNZ5 | D2    | H234 | 1&2               |
| SPbCZ1 | V218  | R303 | 3                 |
| SPbCZ2 | C222  | R303 | 3                 |
| SPbCZ3 | I226  | R303 | 3                 |
| SPbCZ4 | P230  | R303 | 3                 |
| SPbCZ5 | A235  | R303 | 3                 |
| SPcNZ1 | L87   | P217 | 2                 |
| SPcCZ1 | V218  | G86  | 3&1               |
| SPcNZ2 | L87   | H234 | 2                 |
| SPcCZ2 | A235  | G86  | 3&1               |
| SPdNZ1 | P217  | G86  | 3&1               |
| SPdCZ1 | L87   | Q216 | 2                 |

Figure 16A:
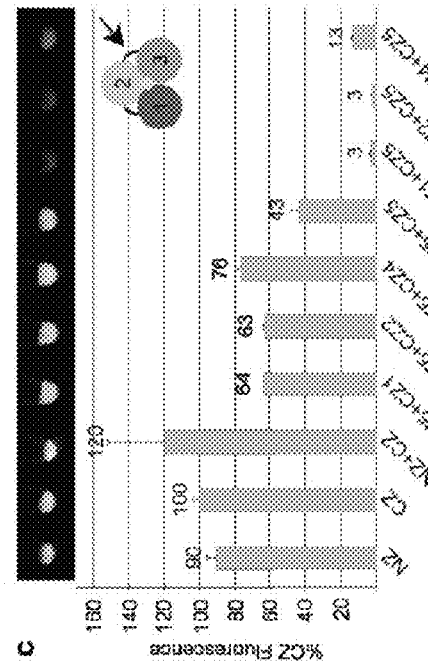
FIGS. 16A, 16B, 16C, and 16D are a series of histograms of fluorescence which demonstrate LucY reassembly. The image above each histogram shows whole cell pellets of the corresponding sample photographed under UV light. Fluorescence is represented as a percentage of CZ. Error bars represent standard deviation from the mean (n=3).
Figure 16B:
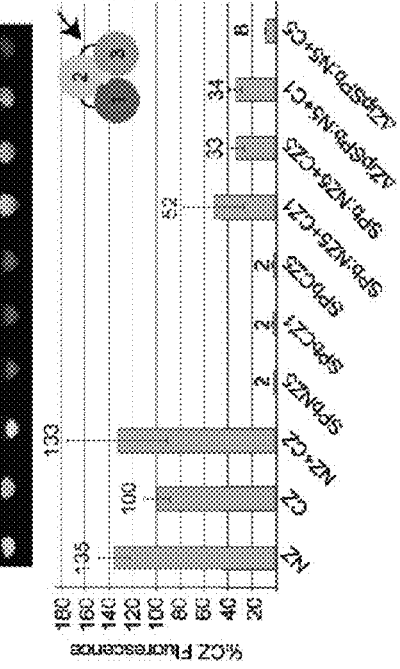
Figure 17A:
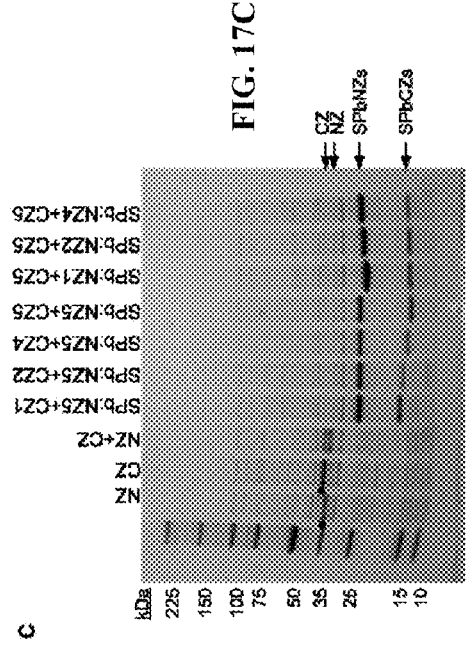
FIGS. 17A, 17B, 17C, and 17D are a series of Coomassie-stained SDS-PAGE gels depicting various split point coexpressions of LucY. In each gel, the NZ and CZ bands are adjacent to the dot.
Figure 17B:
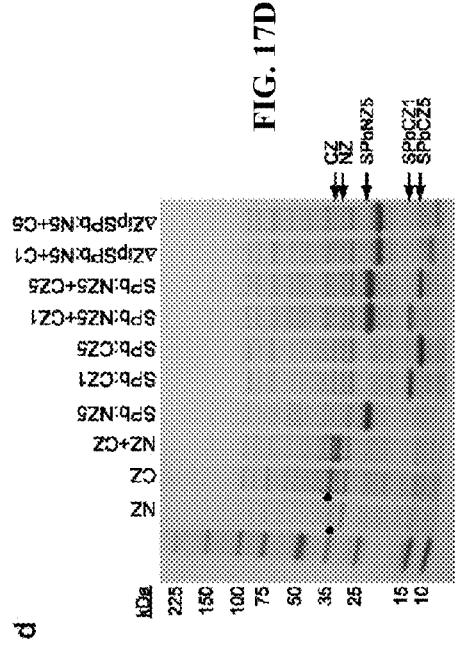

Fragmenting LucY at any of the five residues between domains 1 and 2 did not result in fluorescence when fused to leucine pairs and coexpressed (FIG. 16A). A contributing factor may have been the low expression of the CZ half of each of the split points in comparison to the complementary NZ half. See the gel shown in FIG. 17A. However, bright fluorescence was seen in four out of the five pairs split between domains 2 and 3, with highest fluorescence seen with the SPbNZ5 (ending at His 234) and SPbCZ5 partners (beginning at Ala 235). See FIG. 16B. All fusions expressed well and expression did not correlate with fluorescence. See the gel shown in FIG. 17B. Interestingly, the one split point combination between domains 2 and 3 that did not show fluorescence was at Ser 225, a residue previously shown to be important for catalysis in other MurB proteins (Benson et al., 1995).

Figure 16C:
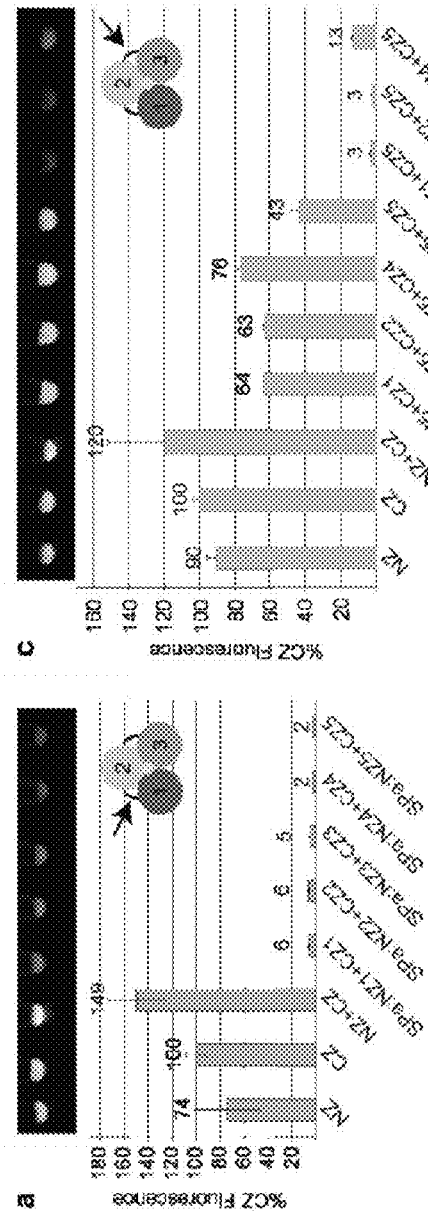
Figure 17C:
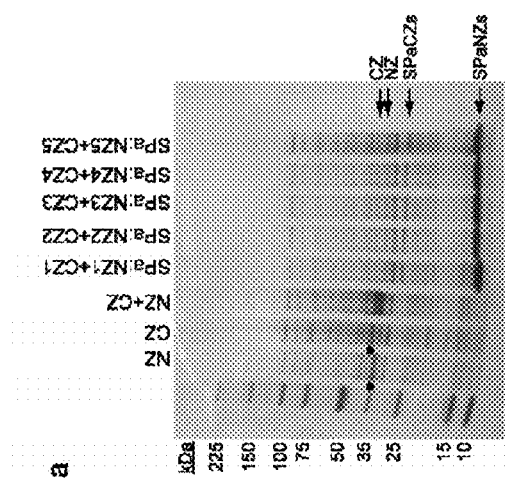

Because the SPbNZ5 and SPbCZ5 when reconstituted showed the highest fluorescence, each was tested with other split points between domains 2 and 3 to determine if overlap, or alternatively gaps, in the amino acid sequence would affect fluorescence. Pairing SPbNZ5 with SPbCZ4 was the most successful reconstituted pair and contains a four-residue overlap with SPbNZ5 ending at residue 234 and SPbCZ4 beginning at residue 230. Interestingly, the opposite pair (SPbNZ4 and SPbCZ5) did not show substantial fluorescence. See FIG. 16C. All pairs showed some level of expression. See FIG. 17C.

Figure 16D:
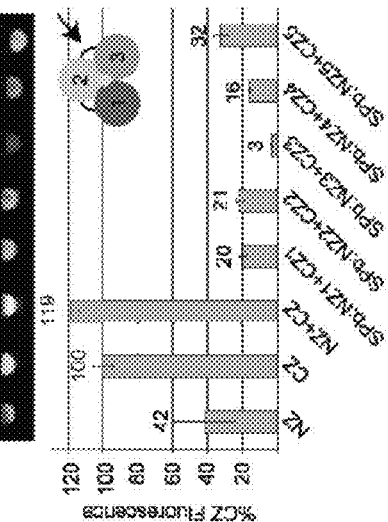
Figure 17D:
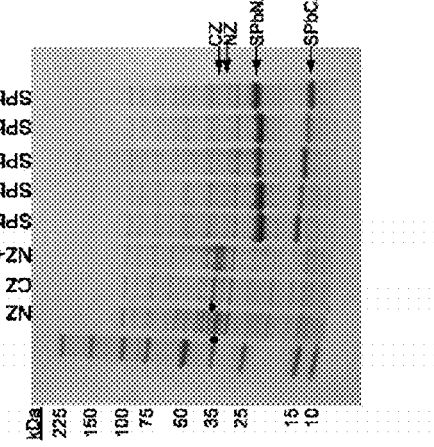
Figure 18A:
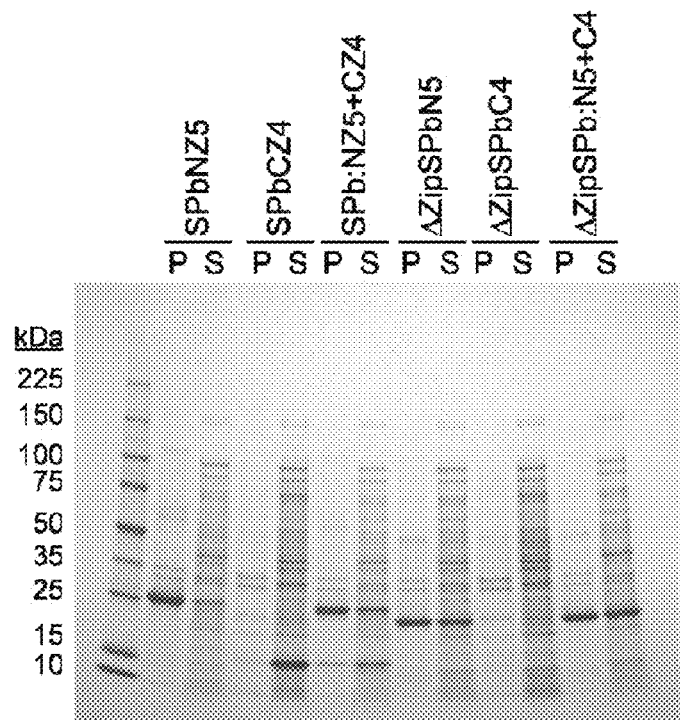
FIGS. 18A and 18B are Coomassie-stained SDS-PAGE gels depicting split point solubility and expression of LucY.
Figure 18B:
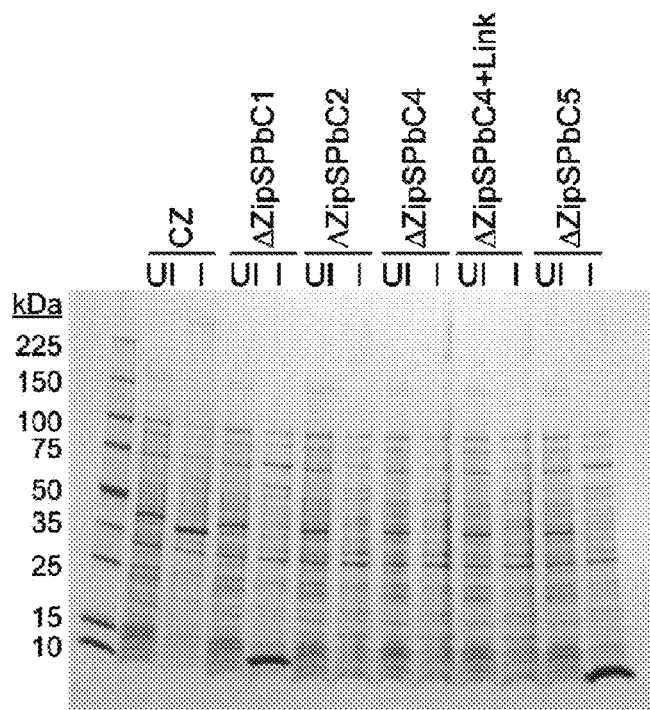

To verify that neither LucY fragment was fluorescent on its own and that the leucine zippers were driving the interaction, SPbNZ5 and SPbCZ4 were tested independently and without their leucine zipper fusions. Neither SPbNZ5 nor SPbCZ4 were fluorescent on their own. However, when expressed on its own, SPbNZ5 was less soluble than when coexpressed with SPbCZ4. Removal of the leucine zipper from SPbNZ5 did not affect expression, while removal of the leucine zipper from SPbCZ4 caused a loss of expression. See FIG. 18A. Because the zipperless SPbC4 was not expressed, it was not possible to fully obtain the background fluorescence level of the SPb:NZ5+CZ4 pair. Therefore, the fluorescence of the remaining SPbCZ fragments that exhibited fluorescence were used as a measure when coexpressed with SPbNZ5. Only SPbCZ1 and SPbCZ5 expressed when their zippers were removed. See FIG. 18B. Therefore these were chosen for further study. It was found that the SPb:NZ5+CZ5 pair possessed the highest level of fluorescence (33% of CZ control) with the least background (8% of CZ control). See FIG. 16D, and the corresponding gel showing expression in FIG. 17D.

Because LucY fluorescence is dependent on the binding of a non-covalently attached small molecule, fluorescence emission will dissipate following separation of the interacting pairs and release of the small molecule. Thus, the split-LucY system is reversible making it possible to test for inhibitors of protein interaction.

Figures 19A, 19B, 19C:
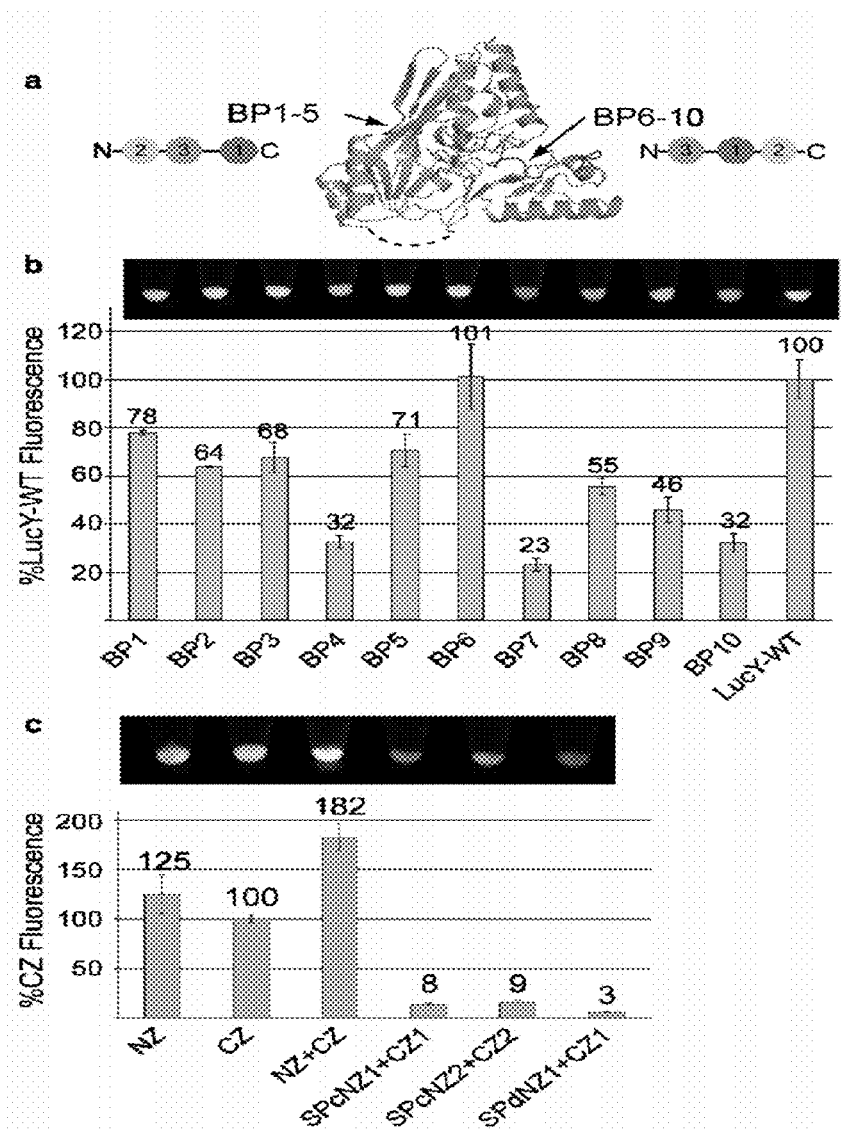
FIG. 19A is a schematic diagram illustrating circular permutation of LucY. LucY was circularly permutated such that domains 1 and 3 were connected with a small linker (dashed line) and new N and C-termini were created between domains (red loops). Break points (BP) were introduced between domains 1 and 2 (BPs1-5) or domains 2 and 3 (BPs6-10).
FIG. 19B is a histogram comparing the fluorescence of the circularized permutations to wild-type LucY.
FIG. 19C is a histogram showing fluorescence of LucY permutations in which split points were made from a circular permuted LucY such that domains 3 and 1 make up one half and domain 2 makes up the other.

Circular Permutation of LucY:

Reorganization of a polypeptide chain, called circular permutation, has been used as a means to introduce change into a protein scaffold without amino acid substitutions (Yu and Lutz, 2011) and has been successfully investigated with GFP (Baird et al., 1999). A welcome consequence to domain reorganization of LucY would be an increase in fluorescence due to increased binding affinity to FAD. Novel termini also offer variation in points of attachment to fusion partners, as well as new possibilities in split points. The wild-type LucY amino- and carboxy-termini are 16.7 Å apart and thus require a greater than four-residue linker to span the intervening space. To build a circularly permuted LucY, two tandem repeats were constructed with a 6-residue linker connecting the C-terminus of one copy to the N-terminus of the second. Deletions within this construct were performed such that new N and C termini were introduced between either domains 1 and 2 or between domains 2 and 3. This is shown schematically in FIG. 19A. The same residues used as split points above were used as breakpoints (BPs) here. Ten (10) circularly permuted LucY proteins were made. BP1-5 comprised a 2-3-1 domain arrangement, while BP6-10 comprised a 3-1-2 domain arrangement. See Table 4.

TABLE 4

N- and C-terminal residues of LucY circular permutations, with order of domain occurrence listed. Amino acid numbering is that of wild-type.

|      | N-term | C-term | Domain arrangement |
|------|--------|--------|--------------------|
| BP1  | G84    | L83    | 2-3-1              |
| BP2  | A85    | G84    | 2-3-1              |
| BP3  | G86    | A85    | 2-3-1              |
| BP4  | L87    | G86    | 2-3-1              |
| BP5  | D88    | L87    | 2-3-1              |
| BP6  | P217   | Q216   | 3-1-2              |
| BP7  | P221   | N220   | 3-1-2              |
| BP8  | S225   | G224   | 3-1-2              |
| BP9  | N229   | R228   | 3-1-2              |
| BP10 | H234   | D233   | 3-1-2              |

Figure 20A:
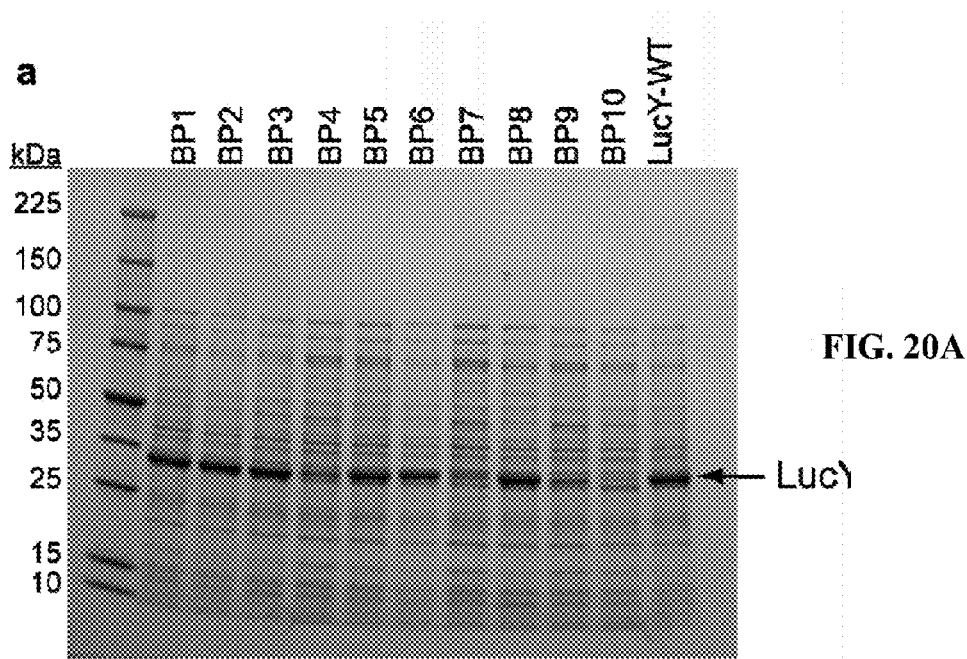
FIGS. 20A and 20B are Commassie-stained SDS-PAGE gels showing expression of circular permutations of LucY and splits made from them.
Figure 20B:
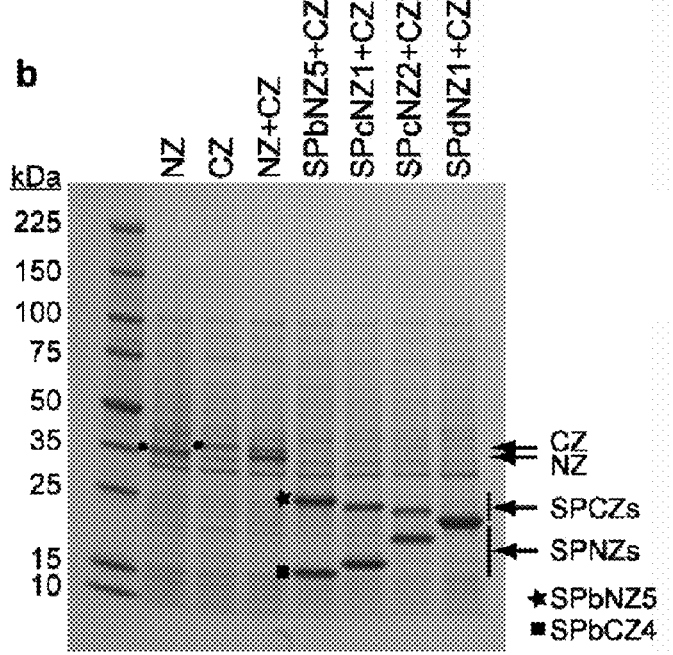

Circularly permuted LucY proteins all showed some degree of fluorescence. See the histogram of FIG. 19B. However, none of the circularly permuted LucY variations were any brighter than the wild-type. The best candidate was BP6, which has a 3-1-2 domain arrangement beginning at the long loop connecting domains 2 and 3 in wild-type. Four out of the 10 circular permutation trials (BP4, BP7, BP9 and BP10) resulted in poorly expressed variants. See the gel of FIG. 20A. New split points became available by reorganizing the domain architecture of LucY, such that domains 3 and 1 could make up one LucY fragment and domain 2 could make up the other. To determine if a split-LucY system of this type was more viable then previous trials, three (3) additional split pairs were made: SPcNZ1/CZ1, SPcNZ2/CZ2, and SPdNZ1/CZ1. SPc pairs comprise domain 2 as the SPNZ fragment and domains 3 and 1 as the SPCZ fragment, with the numbers indicating different start and end locations. SPd comprises the opposing pairing, with domains 3 and 1 as the SPNZ fragment and domain 2 as the SPCZ fragment. See Table 3. These new split pairings did not exhibit fluorescence when reconstituted despite high levels of expression. See FIG. 19C and FIG. 20B, which further show that a domain 1+2/domain 3 pair (as in SPb fusions) offers the best split-LucY system.

Figures 21A, 21B, 21C, 21D, 21E, 21F, 21G, 21H, 21I, 21J:
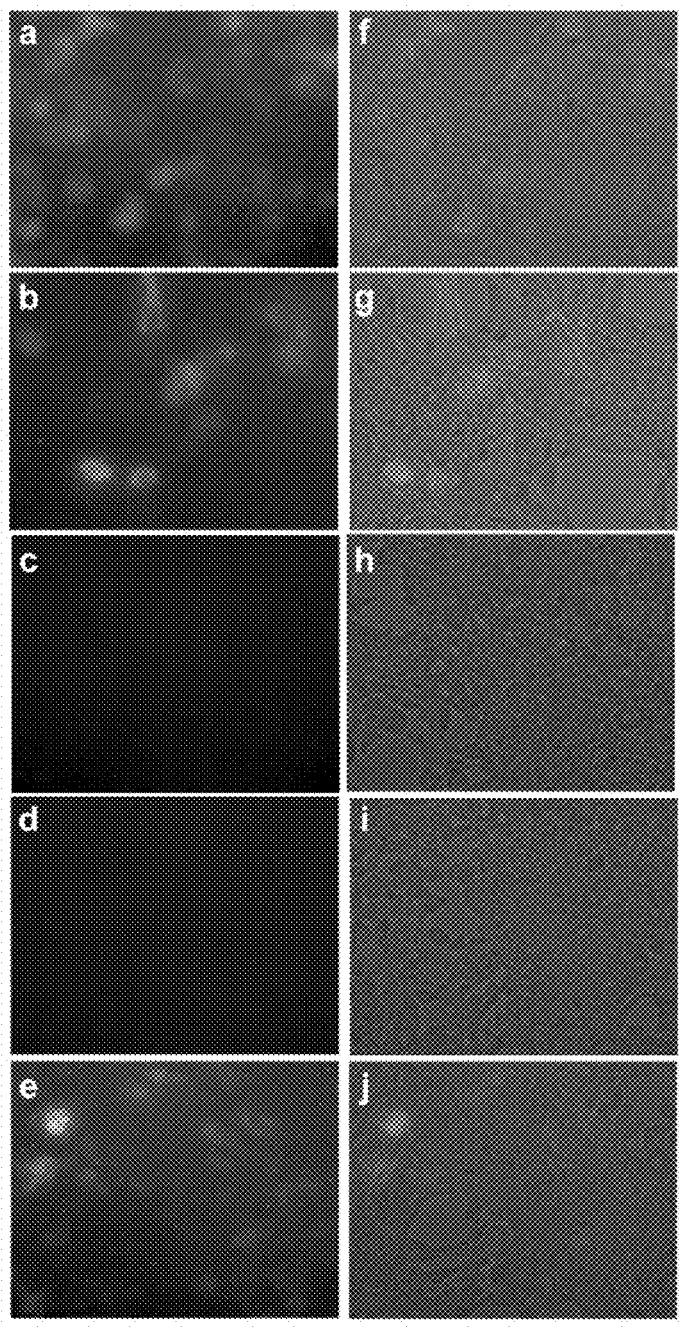
FIGS. 21A-21J make up a series of photographs showing split LucY systems expressed in HEK 293T cells.
Figure 21K:
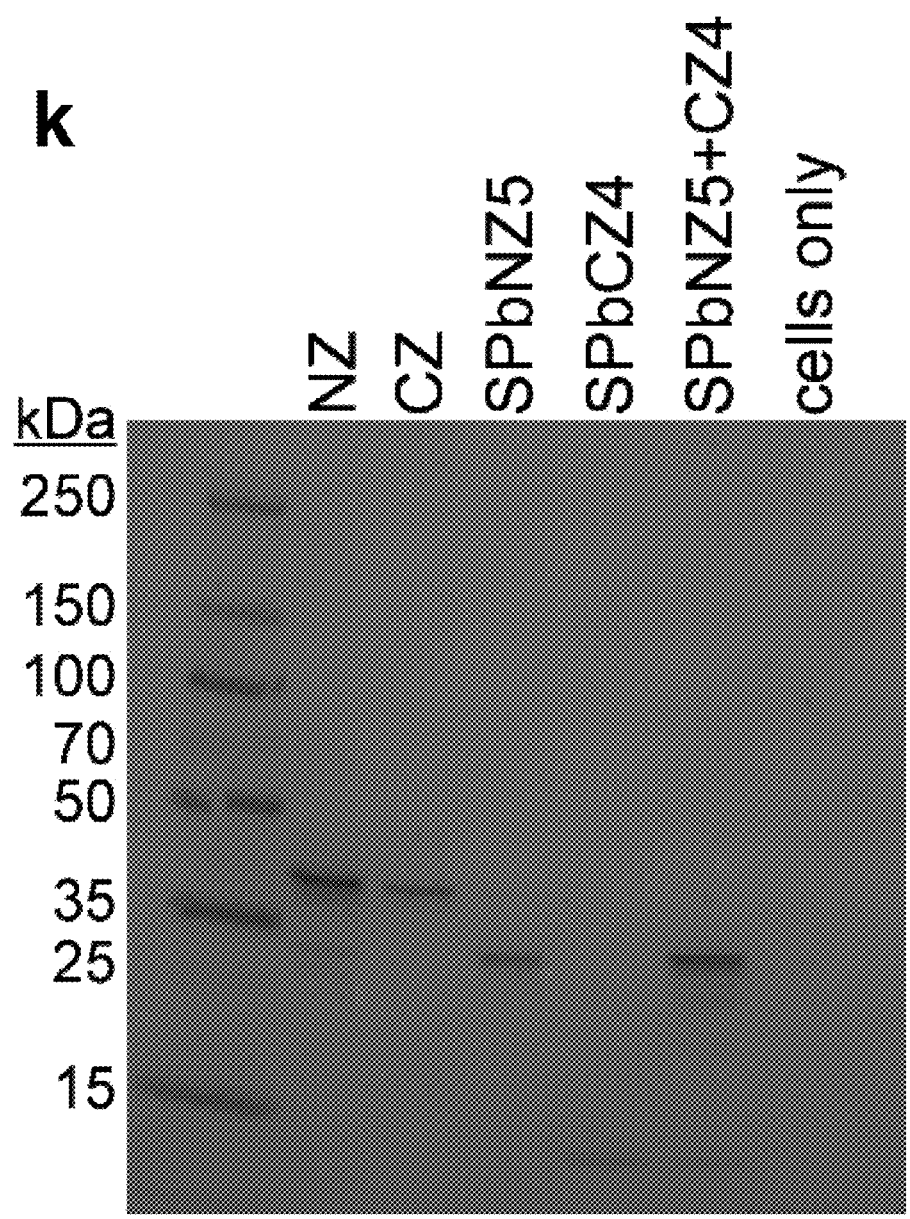
FIG. 21K is a photograph of an immunoblot gel using anti-HA to detect HA-tagged leucine zipper/LucY fusions either whole, NZ and CZ, or splits SPbNZ5 and SPbCZ4.

Protein complementation assays like BiFC are often used in higher order systems, such as mammalian cells. Therefore, the best leucine zipper split-LucY pair from the above testing (SPbNZ5+SPbCZ4) was tested in HEK 293-T cells (a mammalian host cell). Only when each fragment was present did fluorescence occur. The results are depicted in the photographic series of FIGS. 21A through 21J. FIGS. 21A, 21B, 21C, 21D, and 21E are band pass filter photos of NZ-transformed cells, CZ-transformed cells, SPbNZ5-transformed cells, SPbCZ4-transformed cells, and SPbNZ5+SPbCZ4-transformed cells, respectively. FIGS. 21F, 21G, 21H, 21I, and 21J are merged band pass and bright field filter photos of NZ-transformed cells, CZ-transformed cells, SPbNZ5-transformed cells, SPbCZ4-transformed cells, and SPbNZ5+SPbCZ4-transformed cells, respectively. FIG. 21K is a photograph of an immunoblot gel using anti-HA to detect HA-tagged leucine zipper/LucY fusions either whole, NZ and CZ, or splits SPbNZ5 and SPbCZ4.

LucY as a Visualization Tool for Crystallization:

Typically protein crystals are visualized using a standard light microscope. When LucY was crystallized for the first time, bright fluorescent yellow crystals were visualized. Observation of the fluorescent crystals opens up a new avenue for the application of LucY in which crystal detection is problematic due to small crystal size, murky mother liquor, and/or excessive precipitation. One such challenging application is growth of membrane crystals in Lipidic Cubic Phase (LCP) (Caffrey, 2009), which mimics the lipid environment in which membrane proteins are most stable. Fusion of LucY to a membrane protein of interest provides a fluorescent beacon for successful crystallization. LucY crystals themselves form within 24 hours in a variety of conditions using a conventional hanging drop method and were easily visualized using a UV light source and light microscope. FIG. 22A is an exemplary photograph. LucY was fused to the GPCR, β1-adrenergic receptor and the resulting fusion protein crystallized using LCP. Screening for crystals within a LCP matrix was visualized with Nikon Eclipse TE2000-S epifluorescence microscope, fitted with a Diagnostic Instruments 11.2 color camera and long pass GFP filter cube. Exemplary photographs of the fusion protein (LucY-β1-adrenergic receptor) in a LCP matrix are shown in FIGS. 22B, 22C, 22D, and 22E.

Figure 23A:
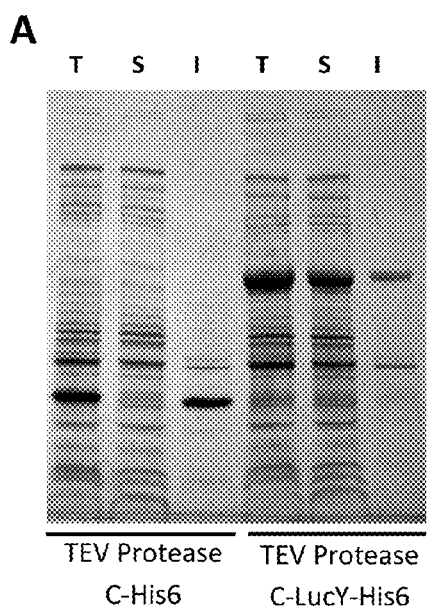
FIG. 23A is a gel depicting enhanced soluble expression of TEV protease as a fusion to C-terminal LucY. *E. coli* cultures harboring plasmids encoding TEV protease with a C-terminal His6 fusion or a C-terminal LucY-His6 fusion were grown at 37° C. and induced with 0.2% rhamnose. The induced cells were harvested and lysed by sonication, and the lysates were separated into soluble and insoluble fractions by centrifugation. Samples of the total lysate (T), soluble (S), and insoluble (I) fractions were run on SDS PAGE gel (4-20%) and proteins were stained with Coomassie blue stain.
Figure 23B:
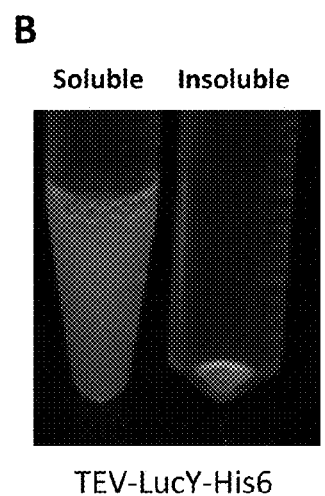
FIG. 23B depicts soluble and insoluble fractions of TEV-LucY-His6 lysate photographed under long-wavelength UV light.
Figure 23C:
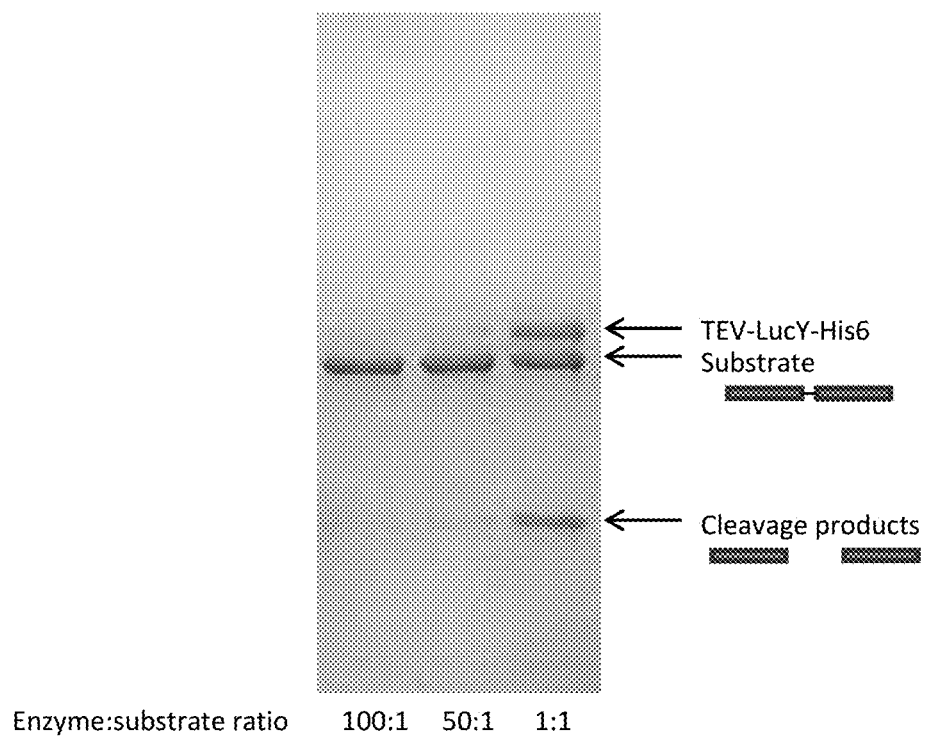
FIG. 23C is a gel depicting sequence-specific protease activity of the TEV-LucY-His6 fusion protein.

LucY as a Solubility-Enhancing Fusion Partner:

Solubility-enhancing fusion partners such as maltose binding protein (MBP), thioredoxin (TRX), small ubiquitin-like modifier (SUMO), glutathione S-transferase (GST), NusA, and others are most frequently employed as fusions to the amino terminus of the protein of interest. In this context, fusion of LucY to the carboxyl terminus of the target protein provides a useful visualization tag to evaluate solubility of the fusion protein. Examples presented above illustrate this application of LucY. In addition to functioning as a visual indicator of soluble expression, it has been found that fusion to LucY at the carboxyl terminus of a target protein can also enhance the soluble expression of the protein, regardless of fusion to an amino-terminal partner. FIGS. 23A, 23B, and 23C present an example in which the Tobacco Etch Virus (TEV) protease was expressed in $E.\ coli$ from the rhamnose-inducible rhaP$_{BAD}$ promoter. Consistent with previous studies (Kapust and Waugh 1999; van den Berg et al. 2006), TEV protease expressed with a C-terminal 6xHis tag was found almost exclusively in the insoluble (pellet) fraction after centrifugation of a cell lysate. In contrast, expression of TEV protease with LucY fused to its C-terminus resulted in expression of a large proportion of the TEV-LucY fusion protein in a soluble form. See FIGS. 23A and 23B. The proportion of TEV-LucY fusion protein found in the soluble fraction is comparable to that reported with an amino-terminal MBP-TEV fusion protein, and greater than that observed with amino-terminal GST or TRX (Kapust and Waugh 1999). Thus, LucY effectively promotes the soluble expression of TEV protease when fused to the protease as a C-terminal partner.

The TEV-LucY-His6 fusion protein was purified by nickel-affinity chromatography and assayed for sequence-specific protease activity using a purified substrate consisting of two similar-sized fluorescent proteins joined by a linker containing the TEV protease recognition sequence, ENLYFQ/G. FIG. 23C shows that incubation of the TEV-LucY-His6 fusion protein with the substrate protein results in generation of products. Thus the TEV-LucY-His6 fusion protein exhibits the sequence-specific proteolytic activity of TEV protease.

REFERENCES CITED

The following documents are incorporated herein by reference.

Altschul, S. F., Gish, W., Miller, W., Myers, E. W. & Lipman, D. J. Basic local alignment search tool. J. Mol. Biol. 215: 403-410 (1990).

Baird, G. S., Zacharias, D. A. & Tsien, R. Y. Circular permutation and receptor insertion within green fluorescent proteins. Proc Natl Acad Sci U S A 96, 11241-11246 (1999).

Benson, T. E., Filman, D. J., Walsh, C. T. & Hogle, J. M. An enzyme-substrate complex involved in bacterial cell wall biosynthesis. Nat Struct Biol 2, 644-653 (1995).

Caffrey M. Crystallizing membrane proteins for structure determination: use of lipidic mesophases. Annu Rev Biophys 38, 29-51 (June 2009).

Chen J, Zheng X F, Brown E J, Schreiber S L (1995) Identification of an 11-kDa FKBP12-rapamycin-binding domain within the 289-kDa FKBP12-rapamycin-associated protein and characterization of a critical serine residue. Proc Natl Acad Sci U S A. 92:4947-4951.

Day, R. N. & Davidson, M. W. The fluorescent protein palette: tools for cellular imaging. Chem Soc Rev 38, 2887-2921 (2009).

El Zoeiby, A., Sanschagrin, F. & Levesque, R. C. Structure and function of the Mur enzymes: development of novel inhibitors. Mol Microbiol 47, 1-12 (2003).

Farrar M A, Alberol-Ila J, Perlmutter R M (1996) Activation of the Raf-1 kinase cascade by coumermycin-induced dimerization. Nature. 383:178-181.

Ghosh, I., Hamilton, A. & Regan, L. Antiparallel leucine zipper-directed protein reassembly: Application to the green fluorescent protein. *J. Am. Chem. Soc.* 122, 5658-5659 (2000).

Gilbert E J, Maxwell A (1994) The 24 kDa N-terminal subdomain of the DNA gyrase B protein binds coumarin drugs. Mol Microbiol. 12:365-373.

Johnsson, N. & Varshaysky, A. Split ubiquitin as a sensor of protein interactions in vivo. *Proc Natl Acad Sci USA* 91, 10340-10344 (1994).

Munro, A. W. & Noble, M. A. Fluorescence analysis of flavoproteins. *Methods Mol Biol* 131, 25-48 (1999).

Paulmurugan, R. & Gambhir, S. S. Monitoring protein-protein interactions using split synthetic renilla luciferase protein-fragment-assisted complementation. *Anal Chem* 75, 1584-1589 (2003).

Robida A M, Kerppola TK (2009) Bimolecular fluorescence complementation analysis of inducible protein interactions: effects of factors affecting protein folding on fluorescent protein fragment association. J Mol Biol. 394:391-409.

Rollins C T, Rivera V M, Woolfson D N, Keenan T, Hatada M, Adams S E, Andrade L J, Yaeger D, van Schravendijk M R, Holt D A, Gilman M, Clackson T (2000) A ligand-reversible dimerization system for controlling protein-protein interactions. Proc Natl Acad Sci U S A. 97:7096-8101.

Tsien, R. Y. The green fluorescent protein. *Annu Rev Biochem* 67, 509-544 (1998).

Yu, Y. & Lutz, S. Circular permutation: a different way to engineer enzyme structure and function. *Trends Biotechnol* 29, 18-25 (2011).

Zhao H F, Boyd J, Jolicoeur N, Shen S H (2003) A coumermycin/novobiocin-regulated gene expression system. Hum Gene Ther. 14:1619-1629.

---

What is claimed is:

1. A method of assaying gene expression comprising:
cultivating a host cell comprising an expression construct, wherein the expression construct comprises a recombinant polynucleotide and the recombinant polynucleotide comprises a nucleotide sequence encoding a protein which is at least 95% sequence identical to a protein having a sequence of SEQ. ID. NO: 2.

2. A recombinant polynucleotide comprising a nucleotide sequence encoding a protein which is at least 90% sequence identical to a protein having a sequence of SEQ. ID. NO: 2, or a circular permutation thereof, or a fragment thereof, wherein the fragment comprises a portion of SEQ. ID. NO: 2 selected from the group consisting of residues 1-82, 89-214, and 236-303.

3. A recombinant polynucleotide comprising a nucleotide sequence encoding a protein which is at least 95% sequence identical to a protein having a sequence of SEQ. ID. NO: 2, or a circular permutation thereof, or a fragment thereof, wherein the fragment comprises a portion of SEQ. ID. NO: 2 selected from the group consisting of residues 1-82, 89-214, and 236-303.

4. A recombinant polynucleotide comprising a nucleotide sequence encoding a protein which is at least 95% sequence identical to a protein having a sequence of SEQ. ID. NO: 2.

5. The recombinant polynucleotide of claim 4, wherein the encoded protein is fluorescent, wherein fluorescence of the encoded protein at about 45° C. is greater than about 10% of fluorescence of the encoded protein at about 30° C.

6. The recombinant polynucleotide of claim 4, wherein the encoded protein is fluorescent and has a quantum yield greater than about 0.224 and up to about 0.357.

7. A recombinant polynucleotide comprising a nucleotide sequence encoding a protein which is at least 90% sequence identical to a protein having a sequence of SEQ. ID. NO: 2, or a circular permutation thereof, or a fragment thereof, wherein the fragment comprises a portion of SEQ. ID. NO: 2 selected from the group consisting of residues 1-82, 89-214, and 236-303, wherein the nucleotide sequence further encodes at least one additional polypeptide of interest in-frame with the encoded protein.

8. A recombinant polynucleotide comprising a nucleotide sequence encoding a protein which is at least 95% sequence identical to a protein having a sequence of SEQ. ID. NO: 2, wherein the nucleotide sequence further encodes at least one additional polypeptide of interest in-frame with the encoded protein.

* * * * *

SEQUENCE LISTING

```
<160> NUMBER OF SEQ ID NOS: 76

<210> SEQ ID NO 1
<211> LENGTH: 909
<212> TYPE: DNA
<213> ORGANISM: Unknown
<220> FEATURE:
<223> OTHER INFORMATION: Nucleotide sequence was isolated from a
      metagenomic enrichment culture of unknown microbes living on corn
      stover and grown at 55 degrees C.
<220> FEATURE:
<221> NAME/KEY: CDS
<222> LOCATION: (1)..(909)

<400> SEQUENCE: 1 atg gat aag gtg ata caa gaa tta aaa gat ctt caa gtc ggc aaa gtt      48
Met Asp Lys Val Ile Gln Glu Leu Lys Asp Leu Gln Val Gly Lys Val
1               5                   10                  15 ctg gaa aat gaa ccg ctc gca aat cat acg acg att aaa atc ggc ggc      96
Leu Glu Asn Glu Pro Leu Ala Asn His Thr Thr Ile Lys Ile Gly Gly
            20                  25                  30 cct gcc gat tgt ctc gtc att cca aag gac att cag gcc gtc cgg gat     144
Pro Ala Asp Cys Leu Val Ile Pro Lys Asp Ile Gln Ala Val Arg Asp
        35                  40                  45 acg atg gaa gtc gtg aaa aag cat ggc gtc caa tgg agg gcg atc ggc     192
Thr Met Glu Val Val Lys Lys His Gly Val Gln Trp Arg Ala Ile Gly
    50                  55                  60 aga ggc tca aac ctt ctc gtt ctt gat gaa ggc att agg ggc gtc gtc     240
Arg Gly Ser Asn Leu Leu Val Leu Asp Glu Gly Ile Arg Gly Val Val
65                  70                  75                  80 atc aag ctc gga gca ggg ctc gat cat atg gaa atc gac ggc gag cag     288
Ile Lys Leu Gly Ala Gly Leu Asp His Met Glu Ile Asp Gly Glu Gln
                85                  90                  95 gtg acg gtc ggc gga ggc tat tcc gtc gtg cgg ctg tct act ggc atc     336
Val Thr Val Gly Gly Gly Tyr Ser Val Val Arg Leu Ser Thr Gly Ile
            100                 105                 110 agc aaa aaa ggg ctt tca ggc ctt gaa ttt gca tca ggc att ccg gga     384
Ser Lys Lys Gly Leu Ser Gly Leu Glu Phe Ala Ser Gly Ile Pro Gly
        115                 120                 125 tct gtc ggg gga gcg gtg tac atg aac gcc ggc gcc cac ggc tca gat     432
Ser Val Gly Gly Ala Val Tyr Met Asn Ala Gly Ala His Gly Ser Asp
    130                 135                 140 atc agc cgg att ttg gtt aaa gct tta att ctc ttt gaa gac ggg acg     480
Ile Ser Arg Ile Leu Val Lys Ala Leu Ile Leu Phe Glu Asp Gly Thr
```

```
                    145                 150                 155                 160
atg gaa tgg ctg acg aac gaa gag atg gaa ttc agc tac cgc aca tca      528
Met Glu Trp Leu Thr Asn Glu Glu Met Glu Phe Ser Tyr Arg Thr Ser
                    165                 170                 175 atc ctg cag aac aag cgg ccg ggc att tgc ctt gaa gcg gtt ctg cag      576
Ile Leu Gln Asn Lys Arg Pro Gly Ile Cys Leu Glu Ala Val Leu Gln
                180                 185                 190 ctc gaa caa aaa gag cgc gac gcg atc gtc gca caa atg caa aaa aac      624
Leu Glu Gln Lys Glu Arg Asp Ala Ile Val Ala Gln Met Gln Lys Asn
            195                 200                 205 aaa gac tac cgg aag gaa acg cag cct gtc tca aac cct tgc gcc gga      672
Lys Asp Tyr Arg Lys Glu Thr Gln Pro Val Ser Asn Pro Cys Ala Gly
        210                 215                 220 agc atc ttc aga aat ccc ctc ccg gat cac gcc gga aga ctc gtt gaa      720
Ser Ile Phe Arg Asn Pro Leu Pro Asp His Ala Gly Arg Leu Val Glu
225                 230                 235                 240 cag gcc ggg ctg aaa ggg cat cgg atc ggc gga gca aag gtt tcc gaa      768
Gln Ala Gly Leu Lys Gly His Arg Ile Gly Gly Ala Lys Val Ser Glu
                245                 250                 255 atg cac ggc aac ttc atc gtc aac gca ggc ggc gca acc gca aaa gac      816
Met His Gly Asn Phe Ile Val Asn Ala Gly Gly Ala Thr Ala Lys Asp
            260                 265                 270 gtt ctt gat ttg att gcg ttt atc caa aaa acg att aaa gaa aaa tac      864
Val Leu Asp Leu Ile Ala Phe Ile Gln Lys Thr Ile Lys Glu Lys Tyr
        275                 280                 285 gat atc gac atg cac acg gaa gtt gaa atc gtc gga gaa aaa cgg          909
Asp Ile Asp Met His Thr Glu Val Glu Ile Val Gly Glu Lys Arg
    290                 295                 300

<210> SEQ ID NO 2
<211> LENGTH: 303
<212> TYPE: PRT
<213> ORGANISM: Unknown
<220> FEATURE:
<223> OTHER INFORMATION: Synthetic Construct

<400> SEQUENCE: 2

Met Asp Lys Val Ile Gln Glu Leu Lys Asp Leu Gln Val Gly Lys Val
1               5                   10                  15

Leu Glu Asn Glu Pro Leu Ala Asn His Thr Thr Ile Lys Ile Gly Gly
            20                  25                  30

Pro Ala Asp Cys Leu Val Ile Pro Lys Asp Ile Gln Ala Val Arg Asp
        35                  40                  45

Thr Met Glu Val Val Lys Lys His Gly Val Gln Trp Arg Ala Ile Gly
    50                  55                  60

Arg Gly Ser Asn Leu Leu Val Leu Asp Glu Gly Ile Arg Gly Val Val
65                  70                  75                  80

Ile Lys Leu Gly Ala Gly Leu Asp His Met Glu Ile Asp Gly Glu Gln
                85                  90                  95

Val Thr Val Gly Gly Gly Tyr Ser Val Val Arg Leu Ser Thr Gly Ile
            100                 105                 110

Ser Lys Lys Gly Leu Ser Gly Leu Glu Phe Ala Ser Gly Ile Pro Gly
        115                 120                 125

Ser Val Gly Gly Ala Val Tyr Met Asn Ala Gly Ala His Gly Ser Asp
    130                 135                 140

Ile Ser Arg Ile Leu Val Lys Ala Leu Ile Leu Phe Glu Asp Gly Thr
145                 150                 155                 160

Met Glu Trp Leu Thr Asn Glu Glu Met Glu Phe Ser Tyr Arg Thr Ser
```

```
                        165                 170                 175
Ile Leu Gln Asn Lys Arg Pro Gly Ile Cys Leu Glu Ala Val Leu Gln
            180                 185                 190

Leu Glu Gln Lys Glu Arg Asp Ala Ile Val Ala Gln Met Gln Lys Asn
        195                 200                 205

Lys Asp Tyr Arg Lys Glu Thr Gln Pro Val Ser Asn Pro Cys Ala Gly
    210                 215                 220

Ser Ile Phe Arg Asn Pro Leu Pro Asp His Ala Gly Arg Leu Val Glu
225                 230                 235                 240

Gln Ala Gly Leu Lys Gly His Arg Ile Gly Gly Ala Lys Val Ser Glu
                245                 250                 255

Met His Gly Asn Phe Ile Val Asn Ala Gly Gly Ala Thr Ala Lys Asp
            260                 265                 270

Val Leu Asp Leu Ile Ala Phe Ile Gln Lys Thr Ile Lys Glu Lys Tyr
        275                 280                 285

Asp Ile Asp Met His Thr Glu Val Glu Ile Val Gly Glu Lys Arg
    290                 295                 300

<210> SEQ ID NO 3
<211> LENGTH: 912
<212> TYPE: DNA
<213> ORGANISM: Artificial Sequence
<220> FEATURE:
<223> OTHER INFORMATION: Nucleotide sequence was isolated from a
      metagenomic enrichment culture of unknown microbes living on corn
      stover and grown at 55 degrees C and then optimized for expression
      in a heterologous host.
<220> FEATURE:
<221> NAME/KEY: CDS
<222> LOCATION: (1)..(912)

<400> SEQUENCE: 3 atg gat aaa gtc att caa gag ctt aag gac ctc caa gtg gga aaa gtg       48
Met Asp Lys Val Ile Gln Glu Leu Lys Asp Leu Gln Val Gly Lys Val
1               5                   10                  15 ctt gag aac gaa ccg ctc gca aac cac aca acg atc aag att ggc gga       96
Leu Glu Asn Glu Pro Leu Ala Asn His Thr Thr Ile Lys Ile Gly Gly
            20                  25                  30 ccg gct gat tgt ctc gtg atc ccc aag gac att cag gcc gtc aga gac      144
Pro Ala Asp Cys Leu Val Ile Pro Lys Asp Ile Gln Ala Val Arg Asp
        35                  40                  45 acg atg gag gtc gtg aag aag cat ggg gtc cag tgg cgc gca atc gga      192
Thr Met Glu Val Val Lys Lys His Gly Val Gln Trp Arg Ala Ile Gly
    50                  55                  60 agg ggc agc aac ttg ttg gtg ctt gac gag ggt atc cgg ggt gta gtg      240
Arg Gly Ser Asn Leu Leu Val Leu Asp Glu Gly Ile Arg Gly Val Val
65                  70                  75                  80 att aag ctg gga gct ggg ttg gat cac atg gaa atc gac ggt gag cag      288
Ile Lys Leu Gly Ala Gly Leu Asp His Met Glu Ile Asp Gly Glu Gln
                85                  90                  95 gtg acc gtg gga gga ggg tat tcc gta gta cgc ctg tca aca ggg att      336
Val Thr Val Gly Gly Gly Tyr Ser Val Val Arg Leu Ser Thr Gly Ile
            100                 105                 110 tca aag aaa ggg ttg tcg ggg ttg gag ttc gca agc ggg att cct ggt      384
Ser Lys Lys Gly Leu Ser Gly Leu Glu Phe Ala Ser Gly Ile Pro Gly
        115                 120                 125 tca gta ggt ggt gca gtg tat atg aac gcg ggt gcc cat ggg tcc gac      432
Ser Val Gly Gly Ala Val Tyr Met Asn Ala Gly Ala His Gly Ser Asp
    130                 135                 140 att tcg cgg atc ctt gtc aaa gcc ctc att ctg ttc gaa gat ggt aca      480
```

-continued

```
          Ile Ser Arg Ile Leu Val Lys Ala Leu Ile Leu Phe Glu Asp Gly Thr
          145                 150                 155                 160 atg gaa tgg ctc act aac gaa gag atg gag ttt tca tac cga acg tcg           528
Met Glu Trp Leu Thr Asn Glu Glu Met Glu Phe Ser Tyr Arg Thr Ser
                165                 170                 175 atc ctc caa aac aaa agg cca gga atc tgc ttg gaa gcg gta ttg cag           576
Ile Leu Gln Asn Lys Arg Pro Gly Ile Cys Leu Glu Ala Val Leu Gln
            180                 185                 190 ctg gaa cag aaa gag cga gat gcc atc gtg gca cag atg cag aag aac           624
Leu Glu Gln Lys Glu Arg Asp Ala Ile Val Ala Gln Met Gln Lys Asn
        195                 200                 205 aaa gac tac cgg aaa gaa acc cag ccg gtg tcg aat ccg tgc gcg ggt           672
Lys Asp Tyr Arg Lys Glu Thr Gln Pro Val Ser Asn Pro Cys Ala Gly
    210                 215                 220 agc atc ttt cgc aat ccc ctg ccc gat cat gcg gga aga ttg gtg gaa           720
Ser Ile Phe Arg Asn Pro Leu Pro Asp His Ala Gly Arg Leu Val Glu
225                 230                 235                 240 caa gcc ggc ctt aag gga cac cag atc gga ggg gcc aag gta tcg gag           768
Gln Ala Gly Leu Lys Gly His Gln Ile Gly Gly Ala Lys Val Ser Glu
                245                 250                 255 atg cac ggg aat ttc atc gtc aat gcg gga ggg gcg act gcg aag gat           816
Met His Gly Asn Phe Ile Val Asn Ala Gly Gly Ala Thr Ala Lys Asp
            260                 265                 270 gtc ctc gac ctg atc gcg ttt atc caa aag acg atc aag gag aag tac           864
Val Leu Asp Leu Ile Ala Phe Ile Gln Lys Thr Ile Lys Glu Lys Tyr
        275                 280                 285 gac att gat atg cat acc gaa gtc gag att gtc ggc gag aaa agg tga           912
Asp Ile Asp Met His Thr Glu Val Glu Ile Val Gly Glu Lys Arg
    290                 295                 300

<210> SEQ ID NO 4
<211> LENGTH: 303
<212> TYPE: PRT
<213> ORGANISM: Artificial Sequence
<220> FEATURE:
<223> OTHER INFORMATION: Synthetic Construct

<400> SEQUENCE: 4

Met Asp Lys Val Ile Gln Glu Leu Lys Asp Leu Gln Val Gly Lys Val
1               5                   10                  15

Leu Glu Asn Glu Pro Leu Ala Asn His Thr Thr Ile Lys Ile Gly Gly
            20                  25                  30

Pro Ala Asp Cys Leu Val Ile Pro Lys Asp Ile Gln Ala Val Arg Asp
        35                  40                  45

Thr Met Glu Val Val Lys Lys His Gly Val Gln Trp Arg Ala Ile Gly
    50                  55                  60

Arg Gly Ser Asn Leu Leu Val Leu Asp Glu Gly Ile Arg Gly Val Val
65                  70                  75                  80

Ile Lys Leu Gly Ala Gly Leu Asp His Met Glu Ile Asp Gly Glu Gln
                85                  90                  95

Val Thr Val Gly Gly Gly Tyr Ser Val Val Arg Leu Ser Thr Gly Ile
            100                 105                 110

Ser Lys Lys Gly Leu Ser Gly Leu Glu Phe Ala Ser Gly Ile Pro Gly
        115                 120                 125

Ser Val Gly Gly Ala Val Tyr Met Asn Ala Gly Ala His Gly Ser Asp
    130                 135                 140

Ile Ser Arg Ile Leu Val Lys Ala Leu Ile Leu Phe Glu Asp Gly Thr
145                 150                 155                 160
```

```
Met Glu Trp Leu Thr Asn Glu Glu Met Glu Phe Ser Tyr Arg Thr Ser
                165                 170                 175

Ile Leu Gln Asn Lys Arg Pro Gly Ile Cys Leu Glu Ala Val Leu Gln
            180                 185                 190

Leu Glu Gln Lys Glu Arg Asp Ala Ile Ala Gln Met Gln Lys Asn
        195                 200                 205

Lys Asp Tyr Arg Lys Glu Thr Gln Pro Val Ser Asn Pro Cys Ala Gly
    210                 215                 220

Ser Ile Phe Arg Asn Pro Leu Pro Asp His Ala Gly Arg Leu Val Glu
225                 230                 235                 240

Gln Ala Gly Leu Lys Gly His Gln Ile Gly Gly Ala Lys Val Ser Glu
                245                 250                 255

Met His Gly Asn Phe Ile Val Asn Ala Gly Gly Ala Thr Ala Lys Asp
            260                 265                 270

Val Leu Asp Leu Ile Ala Phe Ile Gln Lys Thr Ile Lys Glu Lys Tyr
        275                 280                 285

Asp Ile Asp Met His Thr Glu Val Glu Ile Val Gly Glu Lys Arg
    290                 295                 300

<210> SEQ ID NO 5
<211> LENGTH: 894
<212> TYPE: DNA
<213> ORGANISM: Aquifex aeolicus
<220> FEATURE:
<221> NAME/KEY: CDS
<222> LOCATION: (1)..(894)

<400> SEQUENCE: 5 atg ctc ttc cta aag aac gtt ccc ctt cag aac ctt acg act ata aaa    48
Met Leu Phe Leu Lys Asn Val Pro Leu Gln Asn Leu Thr Thr Ile Lys
1               5                   10                  15 ata ggg gga agg gta tcc ttt tac gca gag cct tcc gat cta aag gaa    96
Ile Gly Gly Arg Val Ser Phe Tyr Ala Glu Pro Ser Asp Leu Lys Glu
            20                  25                  30 att tcc cta tgt att gat ttt tca aaa tcc cga gac att cct ctt ttt   144
Ile Ser Leu Cys Ile Asp Phe Ser Lys Ser Arg Asp Ile Pro Leu Phe
        35                  40                  45 gtt ttg ggt aac ggt tct aat act att ttc ggt gac gta aga ggg ctc   192
Val Leu Gly Asn Gly Ser Asn Thr Ile Phe Gly Asp Val Arg Gly Leu
    50                  55                  60 gta aat tta aaa aac tta aaa ggt ttt aaa gta aaa gaa att aaa       240
Val Val Asn Leu Lys Asn Leu Lys Gly Phe Lys Val Lys Glu Ile Lys
65                  70                  75                  80 ggg aaa ttt ttt gta gaa gct ttt tcc gga acg cct tta aag gat tta   288
Gly Lys Phe Phe Val Glu Ala Phe Ser Gly Thr Pro Leu Lys Asp Leu
                85                  90                  95 ata agg ttt agt gta aag gaa aat gta aag agt ttt tac aaa ctt ctc   336
Ile Arg Phe Ser Val Lys Glu Asn Val Lys Ser Phe Tyr Lys Leu Leu
            100                 105                 110 ggt ttt ccg gca agt gtc ggg gga gcg gtt agt atg aac gcc ggg gct   384
Gly Phe Pro Ala Ser Val Gly Gly Ala Val Ser Met Asn Ala Gly Ala
        115                 120                 125 ttt ggg gtt gag ata tcg gat ttt tta aag gaa gtt tac ttc gta gat   432
Phe Gly Val Glu Ile Ser Asp Phe Leu Lys Glu Val Tyr Phe Val Asp
    130                 135                 140 tgg gag ggg aaa ctc caa aaa gca aaa agg gat gaa ctg aat ttt tct   480
Trp Glu Gly Lys Leu Gln Lys Ala Lys Arg Asp Glu Leu Asn Phe Ser
145                 150                 155                 160 tac aga aaa tcg cct ttt cca aaa ctt gga ata gtt ttc aaa gta gtt   528
```

```
Tyr Arg Lys Ser Pro Phe Pro Lys Leu Gly Ile Val Phe Lys Val Val
            165                 170                 175 ttt gag ttt gaa aga agt aaa gaa aat ata ctt ccc aag tac gaa aaa       576
Phe Glu Phe Glu Arg Ser Lys Glu Asn Ile Leu Pro Lys Tyr Glu Lys
        180                 185                 190 ata aga aga ata agg aaa gaa aag caa cct ata aac ctt cca acc agc       624
Ile Arg Arg Ile Arg Lys Glu Lys Gln Pro Ile Asn Leu Pro Thr Ser
            195                 200                 205 ggt tct acc ttc aaa aat ccg gag ggt aat ttc gcg gga aag ctt ctg       672
Gly Ser Thr Phe Lys Asn Pro Glu Gly Asn Phe Ala Gly Lys Leu Leu
        210                 215                 220 gaa aaa gca ggt tta aaa ggt ttt aga ctt aaa aac gta gga ttt tcc       720
Glu Lys Ala Gly Leu Lys Gly Phe Arg Leu Lys Asn Val Gly Phe Ser
225                 230                 235                 240 gaa aaa cac gct aac ttc ctt gta aac tac gga ggt gga act ttt tcg       768
Glu Lys His Ala Asn Phe Leu Val Asn Tyr Gly Gly Gly Thr Phe Ser
                245                 250                 255 gaa gtg gta gat tta ata aat att gca aag gaa agg gtt tac gaa aac       816
Glu Val Val Asp Leu Ile Asn Ile Ala Lys Glu Arg Val Tyr Glu Asn
            260                 265                 270 ttc ggt ata gta ttg gag gag gag gta aag ctg att gag agt agt ggt       864
Phe Gly Ile Val Leu Glu Glu Glu Val Lys Leu Ile Glu Ser Ser Gly
        275                 280                 285 tct gat ggg tgg aag gtc ctc gga gcg tga                               894
Ser Asp Gly Trp Lys Val Leu Gly Ala
    290                 295
```

<210> SEQ ID NO 6
<211> LENGTH: 297
<212> TYPE: PRT
<213> ORGANISM: Aquifex aeolicus

<400> SEQUENCE: 6

```
Met Leu Phe Leu Lys Asn Val Pro Leu Gln Asn Leu Thr Thr Ile Lys
1               5                   10                  15

Ile Gly Gly Arg Val Ser Phe Tyr Ala Glu Pro Ser Asp Leu Lys Glu
            20                  25                  30

Ile Ser Leu Cys Ile Asp Phe Ser Lys Ser Arg Asp Ile Pro Leu Phe
        35                  40                  45

Val Leu Gly Asn Gly Ser Asn Thr Ile Phe Gly Asp Val Arg Gly Leu
    50                  55                  60

Val Val Asn Leu Lys Asn Leu Lys Gly Phe Lys Val Lys Glu Ile Lys
65                  70                  75                  80

Gly Lys Phe Phe Val Glu Ala Phe Ser Gly Thr Pro Leu Lys Asp Leu
                85                  90                  95

Ile Arg Phe Ser Val Lys Glu Asn Val Lys Ser Phe Tyr Lys Leu Leu
            100                 105                 110

Gly Phe Pro Ala Ser Val Gly Gly Ala Val Ser Met Asn Ala Gly Ala
        115                 120                 125

Phe Gly Val Glu Ile Ser Asp Phe Leu Lys Glu Val Tyr Phe Val Asp
    130                 135                 140

Trp Glu Gly Lys Leu Gln Lys Ala Lys Arg Asp Glu Leu Asn Phe Ser
145                 150                 155                 160

Tyr Arg Lys Ser Pro Phe Pro Lys Leu Gly Ile Val Phe Lys Val Val
                165                 170                 175

Phe Glu Phe Glu Arg Ser Lys Glu Asn Ile Leu Pro Lys Tyr Glu Lys
            180                 185                 190
```

```
Ile Arg Arg Ile Arg Lys Glu Lys Gln Pro Ile Asn Leu Pro Thr Ser
            195                 200                 205

Gly Ser Thr Phe Lys Asn Pro Glu Gly Asn Phe Ala Gly Lys Leu Leu
    210                 215                 220

Glu Lys Ala Gly Leu Lys Gly Phe Arg Leu Lys Asn Val Gly Phe Ser
225                 230                 235                 240

Glu Lys His Ala Asn Phe Leu Val Asn Tyr Gly Gly Thr Phe Ser
                245                 250                 255

Glu Val Val Asp Leu Ile Asn Ile Ala Lys Glu Arg Val Tyr Glu Asn
                260                 265                 270

Phe Gly Ile Val Leu Glu Glu Val Lys Leu Ile Glu Ser Ser Gly
            275                 280                 285

Ser Asp Gly Trp Lys Val Leu Gly Ala
    290                 295

<210> SEQ ID NO 7
<211> LENGTH: 932
<212> TYPE: DNA
<213> ORGANISM: Aquifex aeolicus
<220> FEATURE:
<221> NAME/KEY: CDS
<222> LOCATION: (15)..(926)

<400> SEQUENCE: 7
aggagataaa acat atg ttg ttc ttg aaa aac gtt cca ttg caa aat ctg         50
               Met Leu Phe Leu Lys Asn Val Pro Leu Gln Asn Leu
                 1               5                  10 act acg atc aaa att ggt ggc cgt gtg agc ttt tat gcg gag ccg agc        98
Thr Thr Ile Lys Ile Gly Gly Arg Val Ser Phe Tyr Ala Glu Pro Ser
            15                  20                  25 gat ctg aaa gaa att agc ctg tgc atc gac ttc agc aag tct cgc gac       146
Asp Leu Lys Glu Ile Ser Leu Cys Ile Asp Phe Ser Lys Ser Arg Asp
        30                  35                  40 atc ccg ctg ttc gtg ttg ggc aat ggt agc aat acc atc ttc ggc gat       194
Ile Pro Leu Phe Val Leu Gly Asn Gly Ser Asn Thr Ile Phe Gly Asp
45                  50                  55                  60 gtg cgt ggt ctg gtt gtc aat ctg aaa aac ctg aag ggc ttc aaa gtt       242
Val Arg Gly Leu Val Val Asn Leu Lys Asn Leu Lys Gly Phe Lys Val
                65                  70                  75 aaa gag atc aag ggc aag ttc ttc gtc gaa gct ttt tcc ggt acc ccg       290
Lys Glu Ile Lys Gly Lys Phe Phe Val Glu Ala Phe Ser Gly Thr Pro
            80                  85                  90 ctg aag gat ctg atc cgt ttc agc gtg aaa gag aac gtc aag agc ttc       338
Leu Lys Asp Leu Ile Arg Phe Ser Val Lys Glu Asn Val Lys Ser Phe
        95                 100                 105 tac aag ctg ctg ggt ttt ccg gcg agc gtt ggc ggt gca gtc tcg atg       386
Tyr Lys Leu Leu Gly Phe Pro Ala Ser Val Gly Gly Ala Val Ser Met
    110                 115                 120 aac gcc ggt gcg ttt ggt gtg gag att agc gac ttt ctg aaa gag gtg       434
Asn Ala Gly Ala Phe Gly Val Glu Ile Ser Asp Phe Leu Lys Glu Val
125                 130                 135                 140 tac ttt gtc gat tgg gaa ggt aaa ctg cag aaa gcg aag cgt gac gaa       482
Tyr Phe Val Asp Trp Glu Gly Lys Leu Gln Lys Ala Lys Arg Asp Glu
                145                 150                 155 ctg aat ttc tcc tac cgt aaa agc ccg ttc ccg aaa ctg ggt att gta       530
Leu Asn Phe Ser Tyr Arg Lys Ser Pro Phe Pro Lys Leu Gly Ile Val
            160                 165                 170 ttc aag gtg gtg ttt gag ttt gag cgc tct aaa gag aac att ctg ccg       578
Phe Lys Val Val Phe Glu Phe Glu Arg Ser Lys Glu Asn Ile Leu Pro
        175                 180                 185
```

```
aaa tat gaa aag atc cgc cgt att cgt aaa gag aag cag ccg atc aat      626
Lys Tyr Glu Lys Ile Arg Arg Ile Arg Lys Glu Lys Gln Pro Ile Asn
190             195                 200 ctg cct acc agc ggc tct acg ttt aag aat ccg gaa ggc aac ttc gca      674
Leu Pro Thr Ser Gly Ser Thr Phe Lys Asn Pro Glu Gly Asn Phe Ala
205             210                 215                 220 ggc aaa ctg ctg gag aag gcc ggt ctg aag ggt ttc cgt ctg aag aac      722
Gly Lys Leu Leu Glu Lys Ala Gly Leu Lys Gly Phe Arg Leu Lys Asn
                225                 230                 235 gtg ggc ttc agc gag aaa cac gct aac ttt ctg gtc aac tac ggt ggt      770
Val Gly Phe Ser Glu Lys His Ala Asn Phe Leu Val Asn Tyr Gly Gly
            240                 245                 250 ggt acc ttt agc gag gtt gtc gac ctg att aac atc gca aaa gaa cgc      818
Gly Thr Phe Ser Glu Val Val Asp Leu Ile Asn Ile Ala Lys Glu Arg
            255                 260                 265 gtt tat gag aat ttt ggt att gtt ttg gaa gaa gaa gtt aag ctg att      866
Val Tyr Glu Asn Phe Gly Ile Val Leu Glu Glu Glu Val Lys Leu Ile
270                 275                 280 gag agc agc ggc tcc gat ggt tgg aag gtt ctg ggt gcg cat cac cac      914
Glu Ser Ser Gly Ser Asp Gly Trp Lys Val Leu Gly Ala His His His
285                 290                 295                 300 cat cac cat taa ctcgag                                               932
His His His
```

```
<210> SEQ ID NO 8
<211> LENGTH: 303
<212> TYPE: PRT
<213> ORGANISM: Aquifex aeolicus

<400> SEQUENCE: 8

Met Leu Phe Leu Lys Asn Val Pro Leu Gln Asn Leu Thr Thr Ile Lys
1               5                   10                  15

Ile Gly Gly Arg Val Ser Phe Tyr Ala Glu Pro Ser Asp Leu Lys Glu
            20                  25                  30

Ile Ser Leu Cys Ile Asp Phe Ser Lys Ser Arg Asp Ile Pro Leu Phe
        35                  40                  45

Val Leu Gly Asn Gly Ser Asn Thr Ile Phe Gly Asp Val Arg Gly Leu
    50                  55                  60

Val Val Asn Leu Lys Asn Leu Lys Gly Phe Lys Val Lys Glu Ile Lys
65                  70                  75                  80

Gly Lys Phe Phe Val Glu Ala Phe Ser Gly Thr Pro Leu Lys Asp Leu
                85                  90                  95

Ile Arg Phe Ser Val Lys Glu Asn Val Lys Ser Phe Tyr Lys Leu Leu
            100                 105                 110

Gly Phe Pro Ala Ser Val Gly Gly Ala Val Ser Met Asn Ala Gly Ala
        115                 120                 125

Phe Gly Val Glu Ile Ser Asp Phe Leu Lys Glu Val Tyr Phe Val Asp
    130                 135                 140

Trp Glu Gly Lys Leu Gln Lys Ala Lys Arg Asp Glu Leu Asn Phe Ser
145                 150                 155                 160

Tyr Arg Lys Ser Pro Phe Pro Lys Leu Gly Ile Val Phe Lys Val Val
                165                 170                 175

Phe Glu Phe Glu Arg Ser Lys Glu Asn Ile Leu Pro Lys Tyr Glu Lys
            180                 185                 190

Ile Arg Arg Ile Arg Lys Glu Lys Gln Pro Ile Asn Leu Pro Thr Ser
        195                 200                 205
```

```
Gly Ser Thr Phe Lys Asn Pro Glu Gly Asn Phe Ala Gly Lys Leu Leu
    210             215                 220

Glu Lys Ala Gly Leu Lys Gly Phe Arg Leu Lys Asn Val Gly Phe Ser
225                 230                 235                 240

Glu Lys His Ala Asn Phe Leu Val Asn Tyr Gly Gly Thr Phe Ser
            245                 250                 255

Glu Val Val Asp Leu Ile Asn Ile Ala Lys Glu Arg Val Tyr Glu Asn
                260                 265                 270

Phe Gly Ile Val Leu Glu Glu Val Lys Leu Ile Glu Ser Ser Gly
            275                 280                 285

Ser Asp Gly Trp Lys Val Leu Gly Ala His His His His His
    290                 295                 300

<210> SEQ ID NO 9
<211> LENGTH: 951
<212> TYPE: DNA
<213> ORGANISM: Alicyclobacillus acidocaldarius
<220> FEATURE:
<221> NAME/KEY: CDS
<222> LOCATION: (1)..(951)

<400> SEQUENCE: 9
```

| | | | | | | | | | | | | | | | | |
|---|---|---|---|---|---|---|---|---|---|---|---|---|---|---|---|---|
| atg | caa | gac | gat | ccg | ttg | gtg | aac | atc | ctg | atg | gag | caa | ggg | gtg | aag | 48 |
| Met | Gln | Asp | Asp | Pro | Leu | Val | Asn | Ile | Leu | Met | Glu | Gln | Gly | Val | Lys | |
| 1 | | | | 5 | | | | | 10 | | | | | 15 | | |

```
gtc atc cgg ggc gaa ccg atg aag cgg cat acg acg tgg cgg atc ggc     96
Val Ile Arg Gly Glu Pro Met Lys Arg His Thr Thr Trp Arg Ile Gly
            20                  25                  30 gga cct gcg gat tac ttt gtc gag ccg gac tcg gtg gac gcc ctg cgc    144
Gly Pro Ala Asp Tyr Phe Val Glu Pro Asp Ser Val Asp Ala Leu Arg
        35                  40                  45 gcg tgc gtt tgc gcc gcg cga gac cac ggc cta cct atc acc gtc atc    192
Ala Cys Val Cys Ala Ala Arg Asp His Gly Leu Pro Ile Thr Val Ile
    50                  55                  60 ggc cgc ggc tcc aac acc ctg gtg ttg gac ggc gga att cgc ggc ctc    240
Gly Arg Gly Ser Asn Thr Leu Val Leu Asp Gly Gly Ile Arg Gly Leu
65                  70                  75                  80 gtc atc aag ctg cac gac gcc ttc gct tcg tgc gac gtg aga gag gac    288
Val Ile Lys Leu His Asp Ala Phe Ala Ser Cys Asp Val Arg Glu Asp
                85                  90                  95 gag tgc gcg gtc tac gca atg gcg ggc cgt tcg tac gtc gcg ctg gcg    336
Glu Cys Ala Val Tyr Ala Met Ala Gly Arg Ser Tyr Val Ala Leu Ala
            100                 105                 110 aat ttg gcc atc cgc cac ggt ctc tca ggc ctc gaa ttt gcg acc ggc    384
Asn Leu Ala Ile Arg His Gly Leu Ser Gly Leu Glu Phe Ala Thr Gly
        115                 120                 125 att ccc ggg tcc gtc ggc ggc gcg gtc atg atg aac gca ggc gcg tac    432
Ile Pro Gly Ser Val Gly Gly Ala Val Met Met Asn Ala Gly Ala Tyr
    130                 135                 140 ggc cgc gag aca tgc gag gtg ctc gcg tgg gcc gag gtg atg gac gag    480
Gly Arg Glu Thr Cys Glu Val Leu Ala Trp Ala Glu Val Met Asp Glu
145                 150                 155                 160 acc gga gcc atc gcg cgg ctt tcg aac gaa gag ctg cgc ttt ggc tac    528
Thr Gly Ala Ile Ala Arg Leu Ser Asn Glu Glu Leu Arg Phe Gly Tyr
                165                 170                 175 cgc tac agc gtg ctc aag gat cgc ttc ggg att gtg aca cgg gcc aag    576
Arg Tyr Ser Val Leu Lys Asp Arg Phe Gly Ile Val Thr Arg Ala Lys
            180                 185                 190 ttt cag ctg gag cca ggc aat cgc gac gag atg cgg cgc ctc gtt cgc    624
Phe Gln Leu Glu Pro Gly Asn Arg Asp Glu Met Arg Arg Leu Val Arg
        195                 200                 205
```

```
                    195                 200                 205
gaa tgg tcc cag cgg cgc att gcg act cag cca ctc agc ttt ccg aac        672
Glu Trp Ser Gln Arg Arg Ile Ala Thr Gln Pro Leu Ser Phe Pro Asn
    210                 215                 220 tgc ggt tcc gtg ttt cga aat ccc gag ggc acc cac gcg gcc cga ctt        720
Cys Gly Ser Val Phe Arg Asn Pro Glu Gly Thr His Ala Ala Arg Leu
225                 230                 235                 240 atc gag gaa gcg ggg ctc aag gga ctg cgc cgc ggc cag gcg atg atc        768
Ile Glu Glu Ala Gly Leu Lys Gly Leu Arg Arg Gly Gln Ala Met Ile
                245                 250                 255 agc gac aag cac gcg aac ttc atc atc aac ctg ggg aac gct tcg gcg        816
Ser Asp Lys His Ala Asn Phe Ile Ile Asn Leu Gly Asn Ala Ser Ala
            260                 265                 270 agc gat gtg ctg tgg ctg att cgg cac gcg cag tcg gtg gtt cga gag        864
Ser Asp Val Leu Trp Leu Ile Arg His Ala Gln Ser Val Val Arg Glu
        275                 280                 285 cgg ttc ggc atc gcc ctc gaa acc gag gtc cgc gtg ctt ggc gaa ccc        912
Arg Phe Gly Ile Ala Leu Glu Thr Glu Val Arg Val Leu Gly Glu Pro
    290                 295                 300 ttg tcg gga ggt gcg gac gat gga att gct gcg gat tga                    951
Leu Ser Gly Gly Ala Asp Asp Gly Ile Ala Ala Asp
305                 310                 315

<210> SEQ ID NO 10
<211> LENGTH: 316
<212> TYPE: PRT
<213> ORGANISM: Alicyclobacillus acidocaldarius

<400> SEQUENCE: 10

Met Gln Asp Asp Pro Leu Val Asn Ile Leu Met Glu Gln Gly Val Lys
1               5                   10                  15

Val Ile Arg Gly Glu Pro Met Lys Arg His Thr Thr Trp Arg Ile Gly
            20                  25                  30

Gly Pro Ala Asp Tyr Phe Val Glu Pro Asp Ser Val Asp Ala Leu Arg
        35                  40                  45

Ala Cys Val Cys Ala Ala Arg Asp His Gly Leu Pro Ile Thr Val Ile
    50                  55                  60

Gly Arg Gly Ser Asn Thr Leu Val Leu Asp Gly Gly Ile Arg Gly Leu
65                  70                  75                  80

Val Ile Lys Leu His Asp Ala Phe Ala Ser Cys Asp Val Arg Glu Asp
                85                  90                  95

Glu Cys Ala Val Tyr Ala Met Ala Gly Arg Ser Tyr Val Ala Leu Ala
            100                 105                 110

Asn Leu Ala Ile Arg His Gly Leu Ser Gly Leu Glu Phe Ala Thr Gly
        115                 120                 125

Ile Pro Gly Ser Val Gly Gly Ala Val Met Met Asn Ala Gly Ala Tyr
    130                 135                 140

Gly Arg Glu Thr Cys Glu Val Leu Ala Trp Ala Glu Val Met Asp Glu
145                 150                 155                 160

Thr Gly Ala Ile Ala Arg Leu Ser Asn Glu Glu Leu Arg Phe Gly Tyr
                165                 170                 175

Arg Tyr Ser Val Leu Lys Asp Arg Phe Gly Ile Val Thr Arg Ala Lys
            180                 185                 190

Phe Gln Leu Glu Pro Gly Asn Arg Asp Glu Met Arg Arg Leu Val Arg
        195                 200                 205

Glu Trp Ser Gln Arg Arg Ile Ala Thr Gln Pro Leu Ser Phe Pro Asn
    210                 215                 220
```

```
Cys Gly Ser Val Phe Arg Asn Pro Glu Gly Thr His Ala Ala Arg Leu
225                 230                 235                 240

Ile Glu Glu Ala Gly Leu Lys Gly Leu Arg Arg Gly Gln Ala Met Ile
            245                 250                 255

Ser Asp Lys His Ala Asn Phe Ile Ile Asn Leu Gly Asn Ala Ser Ala
        260                 265                 270

Ser Asp Val Leu Trp Leu Ile Arg His Ala Gln Ser Val Val Arg Glu
    275                 280                 285

Arg Phe Gly Ile Ala Leu Glu Thr Glu Val Arg Val Leu Gly Glu Pro
290                 295                 300

Leu Ser Gly Gly Ala Asp Asp Gly Ile Ala Ala Asp
305                 310                 315

<210> SEQ ID NO 11
<211> LENGTH: 989
<212> TYPE: DNA
<213> ORGANISM: Alicyclobacillus acidocaldarius
<220> FEATURE:
<221> NAME/KEY: CDS
<222> LOCATION: (15)..(983)

<400> SEQUENCE: 11
aggagataaa acat atg caa gac gat cct ttg gta aac att ttg atg gaa      50
                Met Gln Asp Asp Pro Leu Val Asn Ile Leu Met Glu
                  1               5                  10 cag ggc gta aaa gta att cgt ggt gag ccg atg aaa cgt cac acg acc      98
Gln Gly Val Lys Val Ile Arg Gly Glu Pro Met Lys Arg His Thr Thr
         15                  20                  25 tgg cgc atc ggt ggt ccg gca gac tat ttc gtg gag ccg gat tcc gtt     146
Trp Arg Ile Gly Gly Pro Ala Asp Tyr Phe Val Glu Pro Asp Ser Val
 30                  35                  40 gat gcg ctg cgt gcg tgt gtg tgc gca gcg cgc gac cac ggc ctg cca     194
Asp Ala Leu Arg Ala Cys Val Cys Ala Ala Arg Asp His Gly Leu Pro
 45                  50                  55                  60 atc acc gtc att ggt cgc ggt agc aac act ctg gtc ctg gac ggt ggt     242
Ile Thr Val Ile Gly Arg Gly Ser Asn Thr Leu Val Leu Asp Gly Gly
                 65                  70                  75 att cgt ggt ctg gtg atc aag ctg cac gat gct ttc gcc agc tgc gac     290
Ile Arg Gly Leu Val Ile Lys Leu His Asp Ala Phe Ala Ser Cys Asp
             80                  85                  90 gtt cgc gag gat gag tgt gcg gtg tat gcg atg gcc ggt cgt agc tat     338
Val Arg Glu Asp Glu Cys Ala Val Tyr Ala Met Ala Gly Arg Ser Tyr
         95                 100                 105 gtt gct ctg gca aat ctg gcc att cgt cac ggc ctg agc ggc ctg gag     386
Val Ala Leu Ala Asn Leu Ala Ile Arg His Gly Leu Ser Gly Leu Glu
    110                 115                 120 ttt gcg acc ggc att ccg ggt agc gtg ggc ggt gcc gtt atg atg aac     434
Phe Ala Thr Gly Ile Pro Gly Ser Val Gly Gly Ala Val Met Met Asn
125                 130                 135                 140 gcc ggt gcg tac ggc cgt gaa acg tgt gag gtc ctg gcg tgg gca gaa     482
Ala Gly Ala Tyr Gly Arg Glu Thr Cys Glu Val Leu Ala Trp Ala Glu
                145                 150                 155 gtt atg gac gaa acc ggc gct atc gca cgt ctg tcg aac gaa gaa ctg     530
Val Met Asp Glu Thr Gly Ala Ile Ala Arg Leu Ser Asn Glu Glu Leu
            160                 165                 170 cgt ttc ggt tac cgt tac tct gtc ctg aaa gat cgc ttt ggc atc gtg     578
Arg Phe Gly Tyr Arg Tyr Ser Val Leu Lys Asp Arg Phe Gly Ile Val
        175                 180                 185 acc cgt gca aag ttt cag ctg gag ccg ggt aat cgt gac gag atg cgt     626
Thr Arg Ala Lys Phe Gln Leu Glu Pro Gly Asn Arg Asp Glu Met Arg
```

```
Thr Arg Ala Lys Phe Gln Leu Glu Pro Gly Asn Arg Asp Glu Met Arg
        190                 195                 200 cgt ctg gtt cgc gag tgg agc cag cgc cgc att gcg acg caa ccg ttg       674
Arg Leu Val Arg Glu Trp Ser Gln Arg Arg Ile Ala Thr Gln Pro Leu
205                 210                 215                 220 tct ttt ccg aat tgc ggt agc gtt ttc cgt aac ccg gaa ggt acg cat       722
Ser Phe Pro Asn Cys Gly Ser Val Phe Arg Asn Pro Glu Gly Thr His
                225                 230                 235 gcg gca cgt ttg atc gaa gag gcc ggt ttg aag ggt ctg cgc cgt ggc       770
Ala Ala Arg Leu Ile Glu Glu Ala Gly Leu Lys Gly Leu Arg Arg Gly
            240                 245                 250 cag gca atg atc agc gac aaa cat gcc aat ttc atc atc aac ctg ggc       818
Gln Ala Met Ile Ser Asp Lys His Ala Asn Phe Ile Ile Asn Leu Gly
        255                 260                 265 aat gcg agc gca tcc gac gtg ctg tgg ctg att cgc cat gcg caa agc       866
Asn Ala Ser Ala Ser Asp Val Leu Trp Leu Ile Arg His Ala Gln Ser
    270                 275                 280 gtc gtt cgt gaa cgt ttt ggc att gcg ctg gaa acc gag gtc cgc gtg       914
Val Val Arg Glu Arg Phe Gly Ile Ala Leu Glu Thr Glu Val Arg Val
285                 290                 295                 300 ctg ggt gag ccg ctg agc ggt ggc gcg gat gat ggt atc gct gcg gac       962
Leu Gly Glu Pro Leu Ser Gly Gly Ala Asp Asp Gly Ile Ala Ala Asp
                305                 310                 315 cat cac cac cac cat cac taa ctcgag                                     989
His His His His His His
            320

<210> SEQ ID NO 12
<211> LENGTH: 322
<212> TYPE: PRT
<213> ORGANISM: Alicyclobacillus acidocaldarius

<400> SEQUENCE: 12

Met Gln Asp Asp Pro Leu Val Asn Ile Leu Met Glu Gln Gly Val Lys
1               5                   10                  15

Val Ile Arg Gly Glu Pro Met Lys Arg His Thr Thr Trp Arg Ile Gly
            20                  25                  30

Gly Pro Ala Asp Tyr Phe Val Glu Pro Asp Ser Val Asp Ala Leu Arg
        35                  40                  45

Ala Cys Val Cys Ala Ala Arg Asp His Gly Leu Pro Ile Thr Val Ile
    50                  55                  60

Gly Arg Gly Ser Asn Thr Leu Val Leu Asp Gly Gly Ile Arg Gly Leu
65                  70                  75                  80

Val Ile Lys Leu His Asp Ala Phe Ala Ser Cys Asp Val Arg Glu Asp
                85                  90                  95

Glu Cys Ala Val Tyr Ala Met Ala Gly Arg Ser Tyr Val Ala Leu Ala
            100                 105                 110

Asn Leu Ala Ile Arg His Gly Leu Ser Gly Leu Glu Phe Ala Thr Gly
        115                 120                 125

Ile Pro Gly Ser Val Gly Gly Ala Val Met Met Asn Ala Gly Ala Tyr
    130                 135                 140

Gly Arg Glu Thr Cys Glu Val Leu Ala Trp Ala Glu Val Met Asp Glu
145                 150                 155                 160

Thr Gly Ala Ile Ala Arg Leu Ser Asn Glu Glu Leu Arg Phe Gly Tyr
                165                 170                 175

Arg Tyr Ser Val Leu Lys Asp Arg Phe Gly Ile Val Thr Arg Ala Lys
            180                 185                 190
```

```
Phe Gln Leu Glu Pro Gly Asn Arg Asp Glu Met Arg Leu Val Arg
        195                 200                 205

Glu Trp Ser Gln Arg Arg Ile Ala Thr Gln Pro Leu Ser Phe Pro Asn
    210                 215                 220

Cys Gly Ser Val Phe Arg Asn Pro Glu Gly Thr His Ala Ala Arg Leu
225                 230                 235                 240

Ile Glu Glu Ala Gly Leu Lys Gly Leu Arg Arg Gly Gln Ala Met Ile
                245                 250                 255

Ser Asp Lys His Ala Asn Phe Ile Ile Asn Leu Gly Asn Ala Ser Ala
            260                 265                 270

Ser Asp Val Leu Trp Leu Ile Arg His Ala Gln Ser Val Val Arg Glu
        275                 280                 285

Arg Phe Gly Ile Ala Leu Glu Thr Glu Val Arg Val Leu Gly Glu Pro
    290                 295                 300

Leu Ser Gly Gly Ala Asp Asp Gly Ile Ala Ala Asp His His His His
305                 310                 315                 320

His His
```

<210> SEQ ID NO 13
<211> LENGTH: 1026
<212> TYPE: DNA
<213> ORGANISM: Acidothermus cellulolyticus
<220> FEATURE:
<221> NAME/KEY: CDS
<222> LOCATION: (1)..(1026)

<400> SEQUENCE: 13

```
gtg ccc gtg ctc gac ccc ccg gtc tgc ctc gcc gag tgc acc acg ttg      48
Val Pro Val Leu Asp Pro Pro Val Cys Leu Ala Glu Cys Thr Thr Leu
1               5                   10                  15 cgt ctc ggc ggt ccg gcc gcg cgg ttc gtt gac gcc cac gac gag gcc      96
Arg Leu Gly Gly Pro Ala Ala Arg Phe Val Asp Ala His Asp Glu Ala
            20                  25                  30 gag ctg ctc gac gag atc cgc cag gcc gac gac aac ggc gag ccg ctg     144
Glu Leu Leu Asp Glu Ile Arg Gln Ala Asp Asp Asn Gly Glu Pro Leu
        35                  40                  45 ctc gtc atc ggt gcc ggc agc aac ctc gtg gtt gcc gac gcg ggc ttc     192
Leu Val Ile Gly Ala Gly Ser Asn Leu Val Val Ala Asp Ala Gly Phe
    50                  55                  60 ccg gga acc gtg ctg cgg gtc gca ttc cgc ggc atc cgc tgg tca agc     240
Pro Gly Thr Val Leu Arg Val Ala Phe Arg Gly Ile Arg Trp Ser Ser
65                  70                  75                  80 gac ggc gac cgg ctg ctg gtc gat atc gcg gcc ggt cag gtg tgg gac     288
Asp Gly Asp Arg Leu Leu Val Asp Ile Ala Ala Gly Gln Val Trp Asp
                85                  90                  95 gac gtc gtc acc gcg gcc atc gcc gaa ggg tgc gcg gga ttg gaa tgc     336
Asp Val Val Thr Ala Ala Ile Ala Glu Gly Cys Ala Gly Leu Glu Cys
            100                 105                 110 ctc tcc gga att ccc gga ctt gcc ggg gcc acg ccg gtt cag aac gtc     384
Leu Ser Gly Ile Pro Gly Leu Ala Gly Ala Thr Pro Val Gln Asn Val
        115                 120                 125 ggc gcg tac ggg gcg gaa atc gcc gat gtc tgt gtc ggc gtc cgc gtc     432
Gly Ala Tyr Gly Ala Glu Ile Ala Asp Val Cys Val Gly Val Arg Val
    130                 135                 140 tac gac cgg ctg gca cgc cgg gtg cgg tgg ttg gcc ggg tca gag tgc     480
Tyr Asp Arg Leu Ala Arg Arg Val Arg Trp Leu Ala Gly Ser Glu Cys
145                 150                 155                 160 cga ttc ggt tac cgg cac agc atc ctg aaa aac gac gac cga tac gtc     528
Arg Phe Gly Tyr Arg His Ser Ile Leu Lys Asn Asp Asp Arg Tyr Val
```

```
                165                 170                 175
gtg ctc acc gtc cgg ctt tcg ctg cgg cgc agc cgt ttg tcg acg ccg    576
Val Leu Thr Val Arg Leu Ser Leu Arg Arg Ser Arg Leu Ser Thr Pro
        180                 185                 190 atc cgc tat cag cag ctt gcc gat gcc ctc ggc gtt ccg ctg gga gac    624
Ile Arg Tyr Gln Gln Leu Ala Asp Ala Leu Gly Val Pro Leu Gly Asp
            195                 200                 205 tgc gct ccg gtg gac gcc gtc cgc aac gct gtg ctc gaa tta cgg gcc    672
Cys Ala Pro Val Asp Ala Val Arg Asn Ala Val Leu Glu Leu Arg Ala
210                 215                 220 gcc aaa gga atg ctg ctc gac ccg ggt gac ccg gac acg gtg agc gcg    720
Ala Lys Gly Met Leu Leu Asp Pro Gly Asp Pro Asp Thr Val Ser Ala
225                 230                 235                 240 gga tcg ttt ttc acc aat ccc att gtc ccg gac tcc cag gcg cct ccc    768
Gly Ser Phe Phe Thr Asn Pro Ile Val Pro Asp Ser Gln Ala Pro Pro
                245                 250                 255 gag gcg ccg cgt ttt ccg gcc cat gct ccg ggg ctg gtg aaa atc ccg    816
Glu Ala Pro Arg Phe Pro Ala His Ala Pro Gly Leu Val Lys Ile Pro
            260                 265                 270 gcc gcc tgg ctc atc gaa caa gcc ggt ttc gcc aaa gga cac cgc ttg    864
Ala Ala Trp Leu Ile Glu Gln Ala Gly Phe Ala Lys Gly His Arg Leu
        275                 280                 285 gac ggc gtc gga att tcc agc aag cac gcg ctc gcg ctg gtg aac cgc    912
Asp Gly Val Gly Ile Ser Ser Lys His Ala Leu Ala Leu Val Asn Arg
290                 295                 300 ggc gga agc acg gcg gac ctc ctg gaa ttg gcg cgc cgc atc cgg gcg    960
Gly Gly Ser Thr Ala Asp Leu Leu Glu Leu Ala Arg Arg Ile Arg Ala
305                 310                 315                 320 gcg gtt cag gag aaa ttc gga att ctg ctg gac gtc gaa ccc cgg ttg   1008
Ala Val Gln Glu Lys Phe Gly Ile Leu Leu Asp Val Glu Pro Arg Leu
                325                 330                 335 gtc ggc gtc cga ctc tga                                            1026
Val Gly Val Arg Leu
            340

<210> SEQ ID NO 14
<211> LENGTH: 341
<212> TYPE: PRT
<213> ORGANISM: Acidothermus cellulolyticus

<400> SEQUENCE: 14

Val Pro Val Leu Asp Pro Pro Val Cys Leu Ala Glu Cys Thr Thr Leu
1               5                   10                  15

Arg Leu Gly Gly Pro Ala Ala Arg Phe Val Asp Ala His Asp Glu Ala
            20                  25                  30

Glu Leu Leu Asp Glu Ile Arg Gln Ala Asp Asp Asn Gly Glu Pro Leu
        35                  40                  45

Leu Val Ile Gly Ala Gly Ser Asn Leu Val Val Ala Asp Ala Gly Phe
    50                  55                  60

Pro Gly Thr Val Leu Arg Val Ala Phe Arg Gly Ile Arg Trp Ser Ser
65                  70                  75                  80

Asp Gly Asp Arg Leu Leu Val Asp Ile Ala Ala Gly Gln Val Trp Asp
                85                  90                  95

Asp Val Val Thr Ala Ala Ile Ala Glu Gly Cys Ala Gly Leu Glu Cys
            100                 105                 110

Leu Ser Gly Ile Pro Gly Leu Ala Gly Ala Thr Pro Val Gln Asn Val
        115                 120                 125

Gly Ala Tyr Gly Ala Glu Ile Ala Asp Val Cys Val Gly Val Arg Val
```

```
                 130                 135                 140
Tyr Asp Arg Leu Ala Arg Arg Val Arg Trp Leu Ala Gly Ser Glu Cys
145                 150                 155                 160

Arg Phe Gly Tyr Arg His Ser Ile Leu Lys Asn Asp Asp Arg Tyr Val
                165                 170                 175

Val Leu Thr Val Arg Leu Ser Leu Arg Arg Ser Arg Leu Ser Thr Pro
            180                 185                 190

Ile Arg Tyr Gln Gln Leu Ala Asp Ala Leu Gly Val Pro Leu Gly Asp
        195                 200                 205

Cys Ala Pro Val Asp Ala Val Arg Asn Ala Val Leu Glu Leu Arg Ala
    210                 215                 220

Ala Lys Gly Met Leu Leu Asp Pro Gly Asp Pro Asp Thr Val Ser Ala
225                 230                 235                 240

Gly Ser Phe Phe Thr Asn Pro Ile Val Pro Asp Ser Gln Ala Pro Pro
                245                 250                 255

Glu Ala Pro Arg Phe Pro Ala His Ala Pro Gly Leu Val Lys Ile Pro
            260                 265                 270

Ala Ala Trp Leu Ile Glu Gln Ala Gly Phe Ala Lys Gly His Arg Leu
        275                 280                 285

Asp Gly Val Gly Ile Ser Ser Lys His Ala Leu Ala Leu Val Asn Arg
    290                 295                 300

Gly Gly Ser Thr Ala Asp Leu Leu Glu Leu Ala Arg Arg Ile Arg Ala
305                 310                 315                 320

Ala Val Gln Glu Lys Phe Gly Ile Leu Leu Asp Val Glu Pro Arg Leu
                325                 330                 335

Val Gly Val Arg Leu
            340

<210> SEQ ID NO 15
<211> LENGTH: 1064
<212> TYPE: DNA
<213> ORGANISM: Acidothermus cellulolyticus
<220> FEATURE:
<221> NAME/KEY: CDS
<222> LOCATION: (15)..(1058)

<400> SEQUENCE: 15
aggagataaa acat atg cca gta ctt gat cca cct gtt tgt tta gct gaa          50
               Met Pro Val Leu Asp Pro Pro Val Cys Leu Ala Glu
                 1               5                  10 tgt acg act ttg aga ttg ggc ggc ccg gca gca cgt ttt gtt gac gcg          98
Cys Thr Thr Leu Arg Leu Gly Gly Pro Ala Ala Arg Phe Val Asp Ala
         15                  20                  25 cat gac gag gcg gag ctg ctg gat gag atc cgt caa gcg gac gat aat         146
His Asp Glu Ala Glu Leu Leu Asp Glu Ile Arg Gln Ala Asp Asp Asn
     30                  35                  40 ggt gaa ccg ttg ctg gtc att ggc gca ggc agc aac ctg gtg gtc gcg         194
Gly Glu Pro Leu Leu Val Ile Gly Ala Gly Ser Asn Leu Val Val Ala
 45                  50                  55                  60 gac gcg ggt ttc ccg ggt acc gtg ctg cgc gtt gcc ttc cgt ggc att         242
Asp Ala Gly Phe Pro Gly Thr Val Leu Arg Val Ala Phe Arg Gly Ile
                 65                  70                  75 cgc tgg agc agc gat ggt gac cgc ctg ctg gtc gat att gca gcg ggt         290
Arg Trp Ser Ser Asp Gly Asp Arg Leu Leu Val Asp Ile Ala Ala Gly
         80                  85                  90 cag gtc tgg gac gat gtc gtg acg gcg gct att gct gag ggc tgc gca         338
Gln Val Trp Asp Asp Val Val Thr Ala Ala Ile Ala Glu Gly Cys Ala
     95                 100                 105
```

```
ggc ctg gag tgc ctg agc ggt atc ccg ggt ctg gcg ggt gcg acc ccg      386
Gly Leu Glu Cys Leu Ser Gly Ile Pro Gly Leu Ala Gly Ala Thr Pro
        110                 115                 120 gtt cag aac gtg ggt gcc tac ggt gcg gaa att gcc gat gtt tgc gtg      434
Val Gln Asn Val Gly Ala Tyr Gly Ala Glu Ile Ala Asp Val Cys Val
125                 130                 135                 140 ggt gtg cgt gtg tat gat cgt ctg gcg cgt cgc gtt cgc tgg ctg gcg      482
Gly Val Arg Val Tyr Asp Arg Leu Ala Arg Arg Val Arg Trp Leu Ala
                145                 150                 155 ggc tcg gag tgc cgt ttc ggt tac cgc cac tcc atc ctg aag aac gac      530
Gly Ser Glu Cys Arg Phe Gly Tyr Arg His Ser Ile Leu Lys Asn Asp
        160                 165                 170 gac cgt tat gtg gtt ctg acc gtg cgt ctg tcc ctg cgc cgt tct cgc      578
Asp Arg Tyr Val Val Leu Thr Val Arg Leu Ser Leu Arg Arg Ser Arg
        175                 180                 185 ctg agc acc ccg atc cgt tac caa cag ctg gca gac gcg ctg ggt gtt      626
Leu Ser Thr Pro Ile Arg Tyr Gln Gln Leu Ala Asp Ala Leu Gly Val
        190                 195                 200 ccg ctg ggt gac tgt gcg ccg gtg gac gct gtc cgt aat gcg gtg ttg      674
Pro Leu Gly Asp Cys Ala Pro Val Asp Ala Val Arg Asn Ala Val Leu
205                 210                 215                 220 gaa ctg cgt gcc gcc aaa ggt atg ctg ctg gac ccg ggt gat ccg gac      722
Glu Leu Arg Ala Ala Lys Gly Met Leu Leu Asp Pro Gly Asp Pro Asp
                225                 230                 235 acc gtg tct gcg ggt agc ttt ttc acg aac ccg atc gtc ccg gat agc      770
Thr Val Ser Ala Gly Ser Phe Phe Thr Asn Pro Ile Val Pro Asp Ser
        240                 245                 250 cag gct ccg cct gaa gct ccg cgt ttt ccg gca cac gca ccg ggc ctg      818
Gln Ala Pro Pro Glu Ala Pro Arg Phe Pro Ala His Ala Pro Gly Leu
        255                 260                 265 gtt aag atc ccg gca gcc tgg ctg att gaa caa gca ggc ttc gcg aaa      866
Val Lys Ile Pro Ala Ala Trp Leu Ile Glu Gln Ala Gly Phe Ala Lys
        270                 275                 280 ggc cac cgt ctg gat ggc gtc ggt atc agc agc aag cac gcg ttg gcg      914
Gly His Arg Leu Asp Gly Val Gly Ile Ser Ser Lys His Ala Leu Ala
285                 290                 295                 300 ttg gtc aat cgt ggc ggt agc acc gcc gat ctg ctg gag ctg gcc cgt      962
Leu Val Asn Arg Gly Gly Ser Thr Ala Asp Leu Leu Glu Leu Ala Arg
                305                 310                 315 cgc atc cgt gcg gca gtc caa gag aaa ttt ggc att ctg ctg gac gtt     1010
Arg Ile Arg Ala Ala Val Gln Glu Lys Phe Gly Ile Leu Leu Asp Val
        320                 325                 330 gaa ccg cgt ctg gtt ggt gtt cgc ctg cat cat cac cat cac cac taa     1058
Glu Pro Arg Leu Val Gly Val Arg Leu His His His His His His
        335                 340                 345 ctcgag                                                              1064

<210> SEQ ID NO 16
<211> LENGTH: 347
<212> TYPE: PRT
<213> ORGANISM: Acidothermus cellulolyticus

<400> SEQUENCE: 16

Met Pro Val Leu Asp Pro Pro Val Cys Leu Ala Glu Cys Thr Thr Leu
1               5                   10                  15

Arg Leu Gly Gly Pro Ala Ala Arg Phe Val Asp Ala His Asp Glu Ala
            20                  25                  30

Glu Leu Leu Asp Glu Ile Arg Gln Ala Asp Asp Asn Gly Glu Pro Leu
        35                  40                  45
```

```
Leu Val Ile Gly Ala Gly Ser Asn Leu Val Ala Asp Ala Gly Phe
         50                  55                  60

Pro Gly Thr Val Leu Arg Val Ala Phe Arg Gly Ile Arg Trp Ser Ser
 65                  70                  75                  80

Asp Gly Asp Arg Leu Leu Val Asp Ile Ala Ala Gly Gln Val Trp Asp
                 85                  90                  95

Asp Val Val Thr Ala Ala Ile Ala Glu Gly Cys Ala Gly Leu Glu Cys
            100                 105                 110

Leu Ser Gly Ile Pro Gly Leu Ala Gly Ala Thr Pro Val Gln Asn Val
        115                 120                 125

Gly Ala Tyr Gly Ala Glu Ile Ala Asp Val Cys Val Gly Val Arg Val
130                 135                 140

Tyr Asp Arg Leu Ala Arg Arg Val Arg Trp Leu Ala Gly Ser Glu Cys
145                 150                 155                 160

Arg Phe Gly Tyr Arg His Ser Ile Leu Lys Asn Asp Asp Arg Tyr Val
                165                 170                 175

Val Leu Thr Val Arg Leu Ser Leu Arg Arg Ser Arg Leu Ser Thr Pro
            180                 185                 190

Ile Arg Tyr Gln Gln Leu Ala Asp Ala Leu Gly Val Pro Leu Gly Asp
        195                 200                 205

Cys Ala Pro Val Asp Ala Val Arg Asn Ala Val Leu Glu Leu Arg Ala
210                 215                 220

Ala Lys Gly Met Leu Leu Asp Pro Gly Asp Pro Asp Thr Val Ser Ala
225                 230                 235                 240

Gly Ser Phe Phe Thr Asn Pro Ile Val Pro Asp Ser Gln Ala Pro Pro
                245                 250                 255

Glu Ala Pro Arg Phe Pro Ala His Ala Pro Gly Leu Val Lys Ile Pro
            260                 265                 270

Ala Ala Trp Leu Ile Glu Gln Ala Gly Phe Ala Lys Gly His Arg Leu
        275                 280                 285

Asp Gly Val Gly Ile Ser Ser Lys His Ala Leu Ala Leu Val Asn Arg
290                 295                 300

Gly Gly Ser Thr Ala Asp Leu Leu Glu Leu Ala Arg Arg Ile Arg Ala
305                 310                 315                 320

Ala Val Gln Glu Lys Phe Gly Ile Leu Leu Asp Val Glu Pro Arg Leu
                325                 330                 335

Val Gly Val Arg Leu His His His His His His
            340                 345

<210> SEQ ID NO 17
<211> LENGTH: 933
<212> TYPE: DNA
<213> ORGANISM: Caldicellulosiruptor hydrothermalis
<220> FEATURE:
<221> NAME/KEY: CDS
<222> LOCATION: (1)..(933)

<400> SEQUENCE: 17 atg tat tta aaa aat tca ggt att gag ttt cta aaa gac cat ccg cta    48
Met Tyr Leu Lys Asn Ser Gly Ile Glu Phe Leu Lys Asp His Pro Leu
 1               5                  10                  15 aaa gac cta aca aca ttc aag ata ggt gga aaa gca aga tat ata ata    96
Lys Asp Leu Thr Thr Phe Lys Ile Gly Gly Lys Ala Arg Tyr Ile Ile
            20                  25                  30 ttt ccc aaa agt acc gag gag ctt gtc aag gta ttg act tta gca aaa   144
Phe Pro Lys Ser Thr Glu Glu Leu Val Lys Val Leu Thr Leu Ala Lys
```

```
gat aaa gcg ata aac cac gtt gtt gtt gga aac tgc tca aat att ctt      192
Asp Lys Ala Ile Asn His Val Val Val Gly Asn Cys Ser Asn Ile Leu
 50                  55                  60 gtc tct gac aaa ggt ttt gat ggt acg ata atc gct aca gtt aag ata      240
Val Ser Asp Lys Gly Phe Asp Gly Thr Ile Ile Ala Thr Val Lys Ile
 65                  70                  75                  80 gac ttt ttt aag ata gat gga aat gtg att gaa gca gag tgt gga gct      288
Asp Phe Phe Lys Ile Asp Gly Asn Val Ile Glu Ala Glu Cys Gly Ala
                 85                  90                  95 atg ctc tct cag gtt gca aga aaa gcg tgc gaa gca ggt cta aaa ggt      336
Met Leu Ser Gln Val Ala Arg Lys Ala Cys Glu Ala Gly Leu Lys Gly
            100                 105                 110 ttt gag ttt gcg gta gga att cct ggc act gtc ggt ggt gct gtg tac      384
Phe Glu Phe Ala Val Gly Ile Pro Gly Thr Val Gly Gly Ala Val Tyr
        115                 120                 125 atg aac gct ggt gca tac gat ggc gag ata aaa gat gtt ttt gaa tgg      432
Met Asn Ala Gly Ala Tyr Asp Gly Glu Ile Lys Asp Val Phe Glu Trp
130                 135                 140 gca gag gtt ttg gat gag aac ttg aac cca gta gaa ctt ggt agg gca      480
Ala Glu Val Leu Asp Glu Asn Leu Asn Pro Val Glu Leu Gly Arg Ala
145                 150                 155                 160 gat atg agg ttt tca tac agg cac agc cga ctg aaa gaa gaa aaa atg      528
Asp Met Arg Phe Ser Tyr Arg His Ser Arg Leu Lys Glu Glu Lys Met
                165                 170                 175 gtg ctt ctc aga gca gca ttt tgc ctc aag ttt gcc gac aaa gaa gat      576
Val Leu Leu Arg Ala Ala Phe Cys Leu Lys Phe Ala Asp Lys Glu Asp
            180                 185                 190 ata tcc cct ttg caa aaa gca aat gaa ttt tca aaa cgg cga gaa         624
Ile Ser Pro Leu Gln Lys Ala Asn Glu Phe Ser Lys Arg Arg Arg Glu
        195                 200                 205 aaa cag cct ctt tct tat ccg agt gca ggt tct gtg ttt aaa aga ccg      672
Lys Gln Pro Leu Ser Tyr Pro Ser Ala Gly Ser Val Phe Lys Arg Pro
210                 215                 220 cca aac aac tat gca gga aag ctt att gaa gat gca ggc ttg aaa gga      720
Pro Asn Asn Tyr Ala Gly Lys Leu Ile Glu Asp Ala Gly Leu Lys Gly
225                 230                 235                 240 tat aga ata ggt gat gcg tgt ata tca gaa aaa cat gca ggg ttt atc      768
Tyr Arg Ile Gly Asp Ala Cys Ile Ser Glu Lys His Ala Gly Phe Ile
                245                 250                 255 ata aac tta gga gat gct aaa gct gag gat gtg aga aag ctc atc tat      816
Ile Asn Leu Gly Asp Ala Lys Ala Glu Asp Val Arg Lys Leu Ile Tyr
            260                 265                 270 ctt gct cag aag act gtg tac gaa aaa ttt gga att ttg ctt gaa cct      864
Leu Ala Gln Lys Thr Val Tyr Glu Lys Phe Gly Ile Leu Leu Glu Pro
        275                 280                 285 gag att cag ttc ata ggc gag ttt gaa aca ccg ctt ttt gtg ccc gaa      912
Glu Ile Gln Phe Ile Gly Glu Phe Glu Thr Pro Leu Phe Val Pro Glu
290                 295                 300 aat gtc caa aat aga aga tga                                          933
Asn Val Gln Asn Arg Arg
305                 310

<210> SEQ ID NO 18
<211> LENGTH: 310
<212> TYPE: PRT
<213> ORGANISM: Caldicellulosiruptor hydrothermalis

<400> SEQUENCE: 18

Met Tyr Leu Lys Asn Ser Gly Ile Glu Phe Leu Lys Asp His Pro Leu
```

```
              1               5              10              15
            Lys Asp Leu Thr Thr Phe Lys Ile Gly Gly Lys Ala Arg Tyr Ile Ile
                            20                  25                  30

Phe Pro Lys Ser Thr Glu Glu Leu Val Lys Val Leu Thr Leu Ala Lys
                            35                  40                  45

Asp Lys Ala Ile Asn His Val Val Gly Asn Cys Ser Asn Ile Leu
             50                      55                  60

Val Ser Asp Lys Gly Phe Asp Gly Thr Ile Ile Ala Thr Val Lys Ile
             65                  70                  75                  80

Asp Phe Phe Lys Ile Asp Gly Asn Val Ile Glu Ala Glu Cys Gly Ala
                                85                  90                  95

Met Leu Ser Gln Val Ala Arg Lys Ala Cys Glu Ala Gly Leu Lys Gly
                            100                 105                 110

Phe Glu Phe Ala Val Gly Ile Pro Gly Thr Val Gly Gly Ala Val Tyr
                            115                 120                 125

Met Asn Ala Gly Ala Tyr Asp Gly Glu Ile Lys Asp Val Phe Glu Trp
                    130                 135                 140

Ala Glu Val Leu Asp Glu Asn Leu Asn Pro Val Glu Leu Gly Arg Ala
            145                 150                 155                 160

Asp Met Arg Phe Ser Tyr Arg His Ser Arg Leu Lys Glu Glu Lys Met
                                165                 170                 175

Val Leu Leu Arg Ala Ala Phe Cys Leu Lys Phe Ala Asp Lys Glu Asp
                            180                 185                 190

Ile Ser Pro Leu Gln Lys Ala Asn Glu Phe Ser Lys Arg Arg Arg Glu
                            195                 200                 205

Lys Gln Pro Leu Ser Tyr Pro Ser Ala Gly Ser Val Phe Lys Arg Pro
                            210                 215                 220

Pro Asn Asn Tyr Ala Gly Lys Leu Ile Glu Asp Ala Gly Leu Lys Gly
            225                 230                 235                 240

Tyr Arg Ile Gly Asp Ala Cys Ile Ser Glu Lys His Ala Gly Phe Ile
                                245                 250                 255

Ile Asn Leu Gly Asp Ala Lys Ala Glu Asp Val Arg Lys Leu Ile Tyr
                            260                 265                 270

Leu Ala Gln Lys Thr Val Tyr Glu Lys Phe Gly Ile Leu Leu Glu Pro
                            275                 280                 285

Glu Ile Gln Phe Ile Gly Glu Phe Glu Thr Pro Leu Phe Val Pro Glu
                            290                 295                 300

Asn Val Gln Asn Arg Arg
            305                 310

<210> SEQ ID NO 19
<211> LENGTH: 971
<212> TYPE: DNA
<213> ORGANISM: Caldicellulosiruptor hydrothermalis
<220> FEATURE:
<221> NAME/KEY: CDS
<222> LOCATION: (15)..(965)

<400> SEQUENCE: 19
aggagataaa acat atg tat ttg aaa aac tct ggt att gaa ttc ttg aag         50
               Met Tyr Leu Lys Asn Ser Gly Ile Glu Phe Leu Lys
                1               5                  10 gac cac ccg ctg aaa gat ctg acc acc ttt aag atc ggc ggt aag gca         98
Asp His Pro Leu Lys Asp Leu Thr Thr Phe Lys Ile Gly Gly Lys Ala
         15                  20                  25 cgt tac atc atc ttt ccg aaa tcc acg gaa gaa ctg gtg aag gtg ctg        146
```

```
Arg Tyr Ile Ile Phe Pro Lys Ser Thr Glu Glu Leu Val Lys Val Leu
     30                  35                  40 acc ctg gcg aaa gac aag gcg atc aac cat gtc gtt gtt ggc aac tgc      194
Thr Leu Ala Lys Asp Lys Ala Ile Asn His Val Val Val Gly Asn Cys
 45                  50                  55                  60 agc aat atc ctg gtg agc gat aag ggc ttt gac ggt acc att att gca      242
Ser Asn Ile Leu Val Ser Asp Lys Gly Phe Asp Gly Thr Ile Ile Ala
                 65                  70                  75 acg gtg aaa att gat ttc ttc aaa att gac ggc aac gtt atc gag gcc      290
Thr Val Lys Ile Asp Phe Phe Lys Ile Asp Gly Asn Val Ile Glu Ala
             80                  85                  90 gaa tgc ggt gcg atg ctg agc cag gtc gcc cgt aaa gcg tgt gaa gcg      338
Glu Cys Gly Ala Met Leu Ser Gln Val Ala Arg Lys Ala Cys Glu Ala
         95                 100                 105 ggc ctg aag ggt ttt gag ttc gcg gtt ggt att ccg ggt act gtc ggc      386
Gly Leu Lys Gly Phe Glu Phe Ala Val Gly Ile Pro Gly Thr Val Gly
     110                 115                 120 ggt gcg gtt tac atg aat gca ggc gcg tat gac ggt gag att aaa gat      434
Gly Ala Val Tyr Met Asn Ala Gly Ala Tyr Asp Gly Glu Ile Lys Asp
125                 130                 135                 140 gtg ttt gaa tgg gca gag gtt ctg gat gag aat ttg aac ccg gtt gag      482
Val Phe Glu Trp Ala Glu Val Leu Asp Glu Asn Leu Asn Pro Val Glu
                145                 150                 155 ctg ggt cgt gcg gat atg cgc ttc agc tat cgc cac agc cgc ctg aaa      530
Leu Gly Arg Ala Asp Met Arg Phe Ser Tyr Arg His Ser Arg Leu Lys
            160                 165                 170 gaa gaa aag atg gtc ctg ctg cgt gcc gcc ttt tgt ttg aaa ttc gca      578
Glu Glu Lys Met Val Leu Leu Arg Ala Ala Phe Cys Leu Lys Phe Ala
        175                 180                 185 gac aaa gag gac atc tcc cca ctg caa aag gcg aat gag ttt agc aag      626
Asp Lys Glu Asp Ile Ser Pro Leu Gln Lys Ala Asn Glu Phe Ser Lys
    190                 195                 200 cgt cgc cgt gaa aaa cag ccg ctg agc tac ccg tct gca ggc agc gtt      674
Arg Arg Arg Glu Lys Gln Pro Leu Ser Tyr Pro Ser Ala Gly Ser Val
205                 210                 215                 220 ttc aag cgt ccg ccg aat aac tat gcg ggt aaa ctg atc gag gac gct      722
Phe Lys Arg Pro Pro Asn Asn Tyr Ala Gly Lys Leu Ile Glu Asp Ala
                225                 230                 235 ggt ctg aaa ggt tac cgc atc ggt gat gct tgc att agc gag aag cat      770
Gly Leu Lys Gly Tyr Arg Ile Gly Asp Ala Cys Ile Ser Glu Lys His
            240                 245                 250 gct ggc ttc atc att aat ctg ggt gac gca aag gcc gag gat gtc cgt      818
Ala Gly Phe Ile Ile Asn Leu Gly Asp Ala Lys Ala Glu Asp Val Arg
        255                 260                 265 aag ctg att tac ctg gcg caa aag acg gtg tac gag aaa ttt ggt atc      866
Lys Leu Ile Tyr Leu Ala Gln Lys Thr Val Tyr Glu Lys Phe Gly Ile
    270                 275                 280 ttg ctg gaa ccg gag att cag ttc atc ggc gag ttt gaa acc ccg ctg      914
Leu Leu Glu Pro Glu Ile Gln Phe Ile Gly Glu Phe Glu Thr Pro Leu
285                 290                 295                 300 ttc gtg cct gag aac gtc caa aat cgt cgt cat cac cac cat cac cac      962
Phe Val Pro Glu Asn Val Gln Asn Arg Arg His His His His His His
                305                 310                 315 taa ctcgag                                                            971

<210> SEQ ID NO 20
<211> LENGTH: 316
<212> TYPE: PRT
<213> ORGANISM: Caldicellulosiruptor hydrothermalis
```

<400> SEQUENCE: 20

| | | | | | | | | | | | | | | |
|---|---|---|---|---|---|---|---|---|---|---|---|---|---|---|
| Met | Tyr | Leu | Lys | Asn | Ser | Gly | Ile | Glu | Phe | Lys | Asp | His | Pro | Leu |
| 1 | | | | 5 | | | | | 10 | | | | | 15 |
| Lys | Asp | Leu | Thr | Thr | Phe | Lys | Ile | Gly | Gly | Lys | Ala | Arg | Tyr | Ile | Ile |
| | | | 20 | | | | | 25 | | | | | 30 | | |
| Phe | Pro | Lys | Ser | Thr | Glu | Glu | Leu | Val | Lys | Val | Leu | Thr | Leu | Ala | Lys |
| | | | 35 | | | | 40 | | | | | 45 | | | |
| Asp | Lys | Ala | Ile | Asn | His | Val | Val | Gly | Asn | Cys | Ser | Asn | Ile | Leu |
| 50 | | | | | 55 | | | | | 60 | | | | |
| Val | Ser | Asp | Lys | Gly | Phe | Asp | Gly | Thr | Ile | Ile | Ala | Thr | Val | Lys | Ile |
| 65 | | | | | 70 | | | | | 75 | | | | | 80 |
| Asp | Phe | Phe | Lys | Ile | Asp | Gly | Asn | Val | Ile | Glu | Ala | Glu | Cys | Gly | Ala |
| | | | | 85 | | | | | 90 | | | | | 95 | |
| Met | Leu | Ser | Gln | Val | Ala | Arg | Lys | Ala | Cys | Glu | Ala | Gly | Leu | Lys | Gly |
| | | | 100 | | | | | 105 | | | | | 110 | | |
| Phe | Glu | Phe | Ala | Val | Gly | Ile | Pro | Gly | Thr | Val | Gly | Gly | Ala | Val | Tyr |
| | | | 115 | | | | | 120 | | | | | 125 | | |
| Met | Asn | Ala | Gly | Ala | Tyr | Asp | Gly | Glu | Ile | Lys | Asp | Val | Phe | Glu | Trp |
| 130 | | | | | 135 | | | | | 140 | | | | | |
| Ala | Glu | Val | Leu | Asp | Glu | Asn | Leu | Asn | Pro | Val | Glu | Leu | Gly | Arg | Ala |
| 145 | | | | | 150 | | | | | 155 | | | | | 160 |
| Asp | Met | Arg | Phe | Ser | Tyr | Arg | His | Ser | Arg | Leu | Lys | Glu | Glu | Lys | Met |
| | | | | 165 | | | | | 170 | | | | | 175 | |
| Val | Leu | Leu | Arg | Ala | Ala | Phe | Cys | Leu | Lys | Phe | Ala | Asp | Lys | Glu | Asp |
| | | | 180 | | | | | 185 | | | | | 190 | | |
| Ile | Ser | Pro | Leu | Gln | Lys | Ala | Asn | Glu | Phe | Ser | Lys | Arg | Arg | Arg | Glu |
| | | | 195 | | | | | 200 | | | | | 205 | | |
| Lys | Gln | Pro | Leu | Ser | Tyr | Pro | Ser | Ala | Gly | Ser | Val | Phe | Lys | Arg | Pro |
| 210 | | | | | 215 | | | | | 220 | | | | | |
| Pro | Asn | Asn | Tyr | Ala | Gly | Lys | Leu | Ile | Glu | Asp | Ala | Gly | Leu | Lys | Gly |
| 225 | | | | | 230 | | | | | 235 | | | | | 240 |
| Tyr | Arg | Ile | Gly | Asp | Ala | Cys | Ile | Ser | Glu | Lys | His | Ala | Gly | Phe | Ile |
| | | | | 245 | | | | | 250 | | | | | 255 | |
| Ile | Asn | Leu | Gly | Asp | Ala | Lys | Ala | Glu | Asp | Val | Arg | Lys | Leu | Ile | Tyr |
| | | | 260 | | | | | 265 | | | | | 270 | | |
| Leu | Ala | Gln | Lys | Thr | Val | Tyr | Glu | Lys | Phe | Gly | Ile | Leu | Leu | Glu | Pro |
| | | | 275 | | | | | 280 | | | | | 285 | | |
| Glu | Ile | Gln | Phe | Ile | Gly | Glu | Phe | Glu | Thr | Pro | Leu | Phe | Val | Pro | Glu |
| 290 | | | | | 295 | | | | | 300 | | | | | |
| Asn | Val | Gln | Asn | Arg | Arg | His | His | His | His | His | | | | | |
| 305 | | | | | 310 | | | | | 315 | | | | | |

<210> SEQ ID NO 21
<211> LENGTH: 894
<212> TYPE: DNA
<213> ORGANISM: Dictyoglomus turgidum
<220> FEATURE:
<221> NAME/KEY: CDS
<222> LOCATION: (1)..(894)

<400> SEQUENCE: 21

| atg | cta | att | tgg | aat | att | ctc | aat | aaa | tat | aat | ttt | aaa | tcc | aaa | atc | 48 |
|---|---|---|---|---|---|---|---|---|---|---|---|---|---|---|---|---|
| Met | Leu | Ile | Trp | Asn | Ile | Leu | Asn | Lys | Tyr | Asn | Phe | Lys | Ser | Lys | Ile | |
| 1 | | | | 5 | | | | | 10 | | | | | 15 | | |
| tat | aaa | gat | gtg | aat | tta | tct | cat | tat | acc | tct | ttt | aag | att | ggg | gga | 96 |
| Tyr | Lys | Asp | Val | Asn | Leu | Ser | His | Tyr | Thr | Ser | Phe | Lys | Ile | Gly | Gly | |

|  |  |  |  |  |  |  |  |  |  |  |  |  |  |  |  |
|---|---|---|---|---|---|---|---|---|---|---|---|---|---|---|---|
|  |  |  | 20 |  |  |  | 25 |  |  |  | 30 |  |  |  |  |
| aaa | gta | gac | tta | ttc | att | att | cca | tat | tct | tgg | gaa | gaa | ctt | atc | tta | 144 |
| Lys | Val | Asp | Leu | Phe | Ile | Ile | Pro | Tyr | Ser | Trp | Glu | Glu | Leu | Ile | Leu |  |
|  |  | 35 |  |  |  |  | 40 |  |  |  |  | 45 |  |  |  |  |
| att | ctt | caa | att | ctt | aaa | gag | aat | aat | atc | cca | aca | aaa | gta | atg | gga | 192 |
| Ile | Leu | Gln | Ile | Leu | Lys | Glu | Asn | Asn | Ile | Pro | Thr | Lys | Val | Met | Gly |  |
| 50 |  |  |  |  | 55 |  |  |  |  | 60 |  |  |  |  |  |  |
| caa | ggt | act | aat | att | ctt | gca | cct | gat | gaa | ggg | att | aaa | gga | gca | gta | 240 |
| Gln | Gly | Thr | Asn | Ile | Leu | Ala | Pro | Asp | Glu | Gly | Ile | Lys | Gly | Ala | Val |  |
| 65 |  |  |  | 70 |  |  |  |  | 75 |  |  |  |  | 80 |  |  |
| att | aga | ttg | aat | cag | aac | ctg | ggg | aaa | atc | aat | ttt | gta | gat | aat | agc | 288 |
| Ile | Arg | Leu | Asn | Gln | Asn | Leu | Gly | Lys | Ile | Asn | Phe | Val | Asp | Asn | Ser |  |
|  |  |  |  | 85 |  |  |  |  | 90 |  |  |  |  | 95 |  |  |
| cat | ctg | gaa | gta | gaa | tcg | gga | tgc | tta | atc | tct | aaa | tta | atc | tct | ttt | 336 |
| His | Leu | Glu | Val | Glu | Ser | Gly | Cys | Leu | Ile | Ser | Lys | Leu | Ile | Ser | Phe |  |
|  |  |  | 100 |  |  |  |  | 105 |  |  |  |  | 110 |  |  |  |
| atg | gtt | gaa | aaa | aat | atg | ggt | ggg | ctt | gaa | ttt | atg | atg | ggt | att | cct | 384 |
| Met | Val | Glu | Lys | Asn | Met | Gly | Gly | Leu | Glu | Phe | Met | Met | Gly | Ile | Pro |  |
|  |  | 115 |  |  |  |  | 120 |  |  |  |  | 125 |  |  |  |  |
| gga | act | ata | gga | gga | gcg | gtg | atg | ggc | aat | gct | gga | gcc | ttt | aga | aaa | 432 |
| Gly | Thr | Ile | Gly | Gly | Ala | Val | Met | Gly | Asn | Ala | Gly | Ala | Phe | Arg | Lys |  |
| 130 |  |  |  |  | 135 |  |  |  |  | 140 |  |  |  |  |  |  |
| gct | ata | ggt | gat | ttt | gta | gag | gga | gtc | tat | gtt | tta | aat | gaa | cat | ttt | 480 |
| Ala | Ile | Gly | Asp | Phe | Val | Glu | Gly | Val | Tyr | Val | Leu | Asn | Glu | His | Phe |  |
| 145 |  |  |  | 150 |  |  |  |  | 155 |  |  |  |  | 160 |  |  |
| gag | gaa | atg | ttt | ttg | ggc | aaa | aaa | gaa | ctt | aat | ttt | aat | tat | aga | agc | 528 |
| Glu | Glu | Met | Phe | Leu | Gly | Lys | Lys | Glu | Leu | Asn | Phe | Asn | Tyr | Arg | Ser |  |
|  |  |  | 165 |  |  |  |  | 170 |  |  |  |  | 175 |  |  |  |
| tca | aac | att | cca | aaa | gac | tgg | att | att | aaa | aaa | gtg | ctg | tta | aga | tta | 576 |
| Ser | Asn | Ile | Pro | Lys | Asp | Trp | Ile | Ile | Lys | Lys | Val | Leu | Leu | Arg | Leu |  |
|  |  | 180 |  |  |  |  | 185 |  |  |  |  | 190 |  |  |  |  |
| gag | gaa | aaa | cct | aag | gaa | gaa | tct | tta | aaa | gag | att | aag | ttt | ttt | ata | 624 |
| Glu | Glu | Lys | Pro | Lys | Glu | Glu | Ser | Leu | Lys | Glu | Ile | Lys | Phe | Phe | Ile |  |
| 195 |  |  |  |  | 200 |  |  |  |  | 205 |  |  |  |  |  |  |
| aag | gaa | aga | agt | aaa | aag | ctt | cct | aaa | tat | ccg | tct | gct | ggg | agt | gta | 672 |
| Lys | Glu | Arg | Ser | Lys | Lys | Leu | Pro | Lys | Tyr | Pro | Ser | Ala | Gly | Ser | Val |  |
|  |  | 210 |  |  |  |  | 215 |  |  |  |  | 220 |  |  |  |  |
| ttt | aaa | aat | cct | aag | gaa | gga | cct | gca | gga | tat | ttt | att | gat | aac | tta | 720 |
| Phe | Lys | Asn | Pro | Lys | Glu | Gly | Pro | Ala | Gly | Tyr | Phe | Ile | Asp | Asn | Leu |  |
| 225 |  |  |  | 230 |  |  |  |  | 235 |  |  |  |  | 240 |  |  |
| ggt | ttt | aga | ggc | ttt | agg | att | gga | gat | gct | atg | gtt | tct | tat | gag | cat | 768 |
| Gly | Phe | Arg | Gly | Phe | Arg | Ile | Gly | Asp | Ala | Met | Val | Ser | Tyr | Glu | His |  |
|  |  |  |  | 245 |  |  |  |  | 250 |  |  |  |  | 255 |  |  |
| gca | aac | act | ata | ata | aat | gtt | ggc | agg | gca | aga | agt | aag | gat | gtt | tta | 816 |
| Ala | Asn | Thr | Ile | Ile | Asn | Val | Gly | Arg | Ala | Arg | Ser | Lys | Asp | Val | Leu |  |
|  |  |  | 260 |  |  |  |  | 265 |  |  |  |  | 270 |  |  |  |
| gag | att | ata | aat | att | ata | aaa | gac | aaa | gtg | aag | gag | gcc | tat | ggt | ata | 864 |
| Glu | Ile | Ile | Asn | Ile | Ile | Lys | Asp | Lys | Val | Lys | Glu | Ala | Tyr | Gly | Ile |  |
|  |  | 275 |  |  |  |  | 280 |  |  |  |  | 285 |  |  |  |  |
| gat | ttg | gag | cca | gag | att | att | att | tgg | taa |  |  |  |  |  |  | 894 |
| Asp | Leu | Glu | Pro | Glu | Ile | Ile | Ile | Trp |  |  |  |  |  |  |  |  |
|  | 290 |  |  |  |  | 295 |  |  |  |  |  |  |  |  |  |  |

<210> SEQ ID NO 22
<211> LENGTH: 297
<212> TYPE: PRT
<213> ORGANISM: Dictyoglomus turgidum

<400> SEQUENCE: 22

Met Leu Ile Trp Asn Ile Leu Asn Lys Tyr Asn Phe Lys Ser Lys Ile

```
                1               5                  10                 15
           Tyr Lys Asp Val Asn Leu Ser His Tyr Thr Ser Phe Lys Ile Gly Gly
                            20                 25                 30

Lys Val Asp Leu Phe Ile Ile Pro Tyr Ser Trp Glu Glu Leu Ile Leu
                        35                 40                 45

Ile Leu Gln Ile Leu Lys Glu Asn Asn Ile Pro Thr Lys Val Met Gly
                    50                 55                 60

Gln Gly Thr Asn Ile Leu Ala Pro Asp Glu Gly Ile Lys Gly Ala Val
            65                 70                 75                 80

Ile Arg Leu Asn Gln Asn Leu Gly Lys Ile Asn Phe Val Asp Asn Ser
                            85                 90                 95

His Leu Glu Val Glu Ser Gly Cys Leu Ile Ser Lys Leu Ile Ser Phe
                        100                105                110

Met Val Glu Lys Asn Met Gly Gly Leu Glu Phe Met Met Gly Ile Pro
                        115                120                125

Gly Thr Ile Gly Gly Ala Val Met Gly Asn Ala Gly Ala Phe Arg Lys
                    130                135                140

Ala Ile Gly Asp Phe Val Glu Gly Val Tyr Val Leu Asn Glu His Phe
           145                150                155                160

Glu Glu Met Phe Leu Gly Lys Lys Glu Leu Asn Phe Asn Tyr Arg Ser
                            165                170                175

Ser Asn Ile Pro Lys Asp Trp Ile Ile Lys Lys Val Leu Leu Arg Leu
                        180                185                190

Glu Glu Lys Pro Lys Glu Glu Ser Leu Lys Glu Ile Lys Phe Phe Ile
                        195                200                205

Lys Glu Arg Ser Lys Lys Leu Pro Lys Tyr Pro Ser Ala Gly Ser Val
                    210                215                220

Phe Lys Asn Pro Lys Glu Gly Pro Ala Gly Tyr Phe Ile Asp Asn Leu
           225                230                235                240

Gly Phe Arg Gly Phe Arg Ile Gly Asp Ala Met Val Ser Tyr Glu His
                            245                250                255

Ala Asn Thr Ile Ile Asn Val Gly Arg Ala Arg Ser Lys Asp Val Leu
                        260                265                270

Glu Ile Ile Asn Ile Ile Lys Asp Lys Val Lys Glu Ala Tyr Gly Ile
                        275                280                285

Asp Leu Glu Pro Glu Ile Ile Ile Trp
                    290                295

<210> SEQ ID NO 23
<211> LENGTH: 932
<212> TYPE: DNA
<213> ORGANISM: Dictyoglomus turgidum
<220> FEATURE:
<221> NAME/KEY: CDS
<222> LOCATION: (15)..(926)

<400> SEQUENCE: 23
aggagataaa acat atg ttg atc tgg aat att ctg aac aag tac aat ttc       50
                Met Leu Ile Trp Asn Ile Leu Asn Lys Tyr Asn Phe
                 1               5                  10 aaa agc aaa atc tat aaa gat gtg aac ctg agc cat tac acg agc ttc       98
Lys Ser Lys Ile Tyr Lys Asp Val Asn Leu Ser His Tyr Thr Ser Phe
         15                  20                  25 aaa att ggc ggt aaa gtt gac ctg ttt atc att ccg tat tct tgg gaa      146
Lys Ile Gly Gly Lys Val Asp Leu Phe Ile Ile Pro Tyr Ser Trp Glu
     30                  35                  40
```

```
gaa ctg atc ctg att ctg cag atc ttg aaa gag aac aat att ccg acc      194
Glu Leu Ile Leu Ile Leu Gln Ile Leu Lys Glu Asn Asn Ile Pro Thr
 45              50                  55                  60 aag gtg atg ggc cag ggc acg aat atc ctg gca ccg gat gaa ggc atc      242
Lys Val Met Gly Gln Gly Thr Asn Ile Leu Ala Pro Asp Glu Gly Ile
                 65                  70                  75 aag ggt gcc gtt atc cgt ctg aac caa aat ctg ggc aaa atc aat ttt      290
Lys Gly Ala Val Ile Arg Leu Asn Gln Asn Leu Gly Lys Ile Asn Phe
             80                  85                  90 gtg gac aac tcg cac ttg gaa gtc gaa tcc ggt tgc ctg atc tct aaa      338
Val Asp Asn Ser His Leu Glu Val Glu Ser Gly Cys Leu Ile Ser Lys
         95                 100                 105 ctg att agc ttc atg gtt gaa aag aac atg ggt ggc ctg gag ttt atg      386
Leu Ile Ser Phe Met Val Glu Lys Asn Met Gly Gly Leu Glu Phe Met
     110                 115                 120 atg ggc att ccg ggt acc atc ggt ggc gcg gtg atg ggt aac gct ggt      434
Met Gly Ile Pro Gly Thr Ile Gly Gly Ala Val Met Gly Asn Ala Gly
125                 130                 135                 140 gcg ttt cgc aag gct att ggt gac ttt gtc gag ggt gtt tac gtg ttg      482
Ala Phe Arg Lys Ala Ile Gly Asp Phe Val Glu Gly Val Tyr Val Leu
                 145                 150                 155 aac gag cac ttc gaa gag atg ttc ttg ggc aag aaa gag ctg aac ttc      530
Asn Glu His Phe Glu Glu Met Phe Leu Gly Lys Lys Glu Leu Asn Phe
             160                 165                 170 aat tat cgt agc agc aat att cca aag gat tgg atc atc aag aag gtg      578
Asn Tyr Arg Ser Ser Asn Ile Pro Lys Asp Trp Ile Ile Lys Lys Val
         175                 180                 185 ctg ctg cgc ctg gaa gag aaa ccg aaa gaa gag agc ctg aaa gag att      626
Leu Leu Arg Leu Glu Glu Lys Pro Lys Glu Glu Ser Leu Lys Glu Ile
     190                 195                 200 aag ttt ttc att aaa gag cgc agc aag aaa ctg ccg aag tat ccg agc      674
Lys Phe Phe Ile Lys Glu Arg Ser Lys Lys Leu Pro Lys Tyr Pro Ser
205                 210                 215                 220 gcc ggt agc gtt ttc aag aat ccg aaa gag ggt cct gcg ggc tac ttt      722
Ala Gly Ser Val Phe Lys Asn Pro Lys Glu Gly Pro Ala Gly Tyr Phe
                 225                 230                 235 att gac aat ctg ggt ttt cgt ggt ttc cgt att ggt gat gcg atg gtc      770
Ile Asp Asn Leu Gly Phe Arg Gly Phe Arg Ile Gly Asp Ala Met Val
             240                 245                 250 agc tac gag cac gca aac acc atc atc aac gtc ggc cgt gca cgt tcc      818
Ser Tyr Glu His Ala Asn Thr Ile Ile Asn Val Gly Arg Ala Arg Ser
         255                 260                 265 aag gac gtt ctg gag att atc aac atc att aag gat aag gtc aaa gag      866
Lys Asp Val Leu Glu Ile Ile Asn Ile Ile Lys Asp Lys Val Lys Glu
     270                 275                 280 gcg tac ggc att gac ctg gaa ccg gaa atc atc att tgg cac cac cat      914
Ala Tyr Gly Ile Asp Leu Glu Pro Glu Ile Ile Ile Trp His His His
285                 290                 295                 300 cac cat cat taa ctcgag                                                932
His His His <210> SEQ ID NO 24
<211> LENGTH: 303
<212> TYPE: PRT
<213> ORGANISM: Dictyoglomus turgidum

<400> SEQUENCE: 24

Met Leu Ile Trp Asn Ile Leu Asn Lys Tyr Asn Phe Lys Ser Lys Ile
1               5                   10                  15

Tyr Lys Asp Val Asn Leu Ser His Tyr Thr Ser Phe Lys Ile Gly Gly
```

```
                20                  25                  30
Lys Val Asp Leu Phe Ile Ile Pro Tyr Ser Trp Glu Glu Leu Ile Leu
            35                  40                  45

Ile Leu Gln Ile Leu Lys Glu Asn Asn Ile Pro Thr Lys Val Met Gly
    50                  55                  60

Gln Gly Thr Asn Ile Leu Ala Pro Asp Glu Gly Ile Lys Gly Ala Val
65                  70                  75                  80

Ile Arg Leu Asn Gln Asn Leu Gly Lys Ile Asn Phe Val Asp Asn Ser
                85                  90                  95

His Leu Glu Val Glu Ser Gly Cys Leu Ile Ser Lys Leu Ile Ser Phe
            100                 105                 110

Met Val Glu Lys Asn Met Gly Gly Leu Glu Phe Met Met Gly Ile Pro
        115                 120                 125

Gly Thr Ile Gly Gly Ala Val Met Gly Asn Ala Gly Ala Phe Arg Lys
    130                 135                 140

Ala Ile Gly Asp Phe Val Glu Gly Val Tyr Val Leu Asn Glu His Phe
145                 150                 155                 160

Glu Glu Met Phe Leu Gly Lys Lys Glu Leu Asn Phe Asn Tyr Arg Ser
                165                 170                 175

Ser Asn Ile Pro Lys Asp Trp Ile Ile Lys Lys Val Leu Leu Arg Leu
            180                 185                 190

Glu Glu Lys Pro Lys Glu Glu Ser Leu Lys Glu Ile Lys Phe Phe Ile
        195                 200                 205

Lys Glu Arg Ser Lys Lys Leu Pro Lys Tyr Pro Ser Ala Gly Ser Val
    210                 215                 220

Phe Lys Asn Pro Lys Glu Gly Pro Ala Gly Tyr Phe Ile Asp Asn Leu
225                 230                 235                 240

Gly Phe Arg Gly Phe Arg Ile Gly Asp Ala Met Val Ser Tyr Glu His
                245                 250                 255

Ala Asn Thr Ile Ile Asn Val Gly Arg Ala Arg Ser Lys Asp Val Leu
            260                 265                 270

Glu Ile Ile Asn Ile Ile Lys Asp Lys Val Lys Glu Ala Tyr Gly Ile
        275                 280                 285

Asp Leu Glu Pro Glu Ile Ile Trp His His His His His His
    290                 295                 300

<210> SEQ ID NO 25
<211> LENGTH: 927
<212> TYPE: DNA
<213> ORGANISM: Geobacillus strain Y4.1MC1
<220> FEATURE:
<221> NAME/KEY: CDS
<222> LOCATION: (1)..(927)

<400> SEQUENCE: 25 atg atg tac gaa aat aat gtg att tat caa gaa tta gtg cgg att tgt      48
Met Met Tyr Glu Asn Asn Val Ile Tyr Gln Glu Leu Val Arg Ile Cys
1               5                   10                  15 ggg gaa aaa aac gtg ctg cgg gac gaa ccg ttg aaa tat cat acg tta      96
Gly Glu Lys Asn Val Leu Arg Asp Glu Pro Leu Lys Tyr His Thr Leu
            20                  25                  30 gtg aaa att ggc ggc aag gcg gat ttc ctc gtc tgg ccg gaa aca tat     144
Val Lys Ile Gly Gly Lys Ala Asp Phe Leu Val Trp Pro Glu Thr Tyr
        35                  40                  45 gag cag gtg gtc gaa gtc att cga tta aag gaa aag cat cac ctc cct     192
Glu Gln Val Val Glu Val Ile Arg Leu Lys Glu Lys His His Leu Pro
    50                  55                  60
```

```
ttc acc ttg ctt ggc aac ggt tcg aac gtc atc gtg cgt gac ggc ggc      240
Phe Thr Leu Leu Gly Asn Gly Ser Asn Val Ile Val Arg Asp Gly Gly
65                  70                  75                  80 att cgc ggc att gtt gtg cag cta aag cat cta aca gaa atc aaa gtg      288
Ile Arg Gly Ile Val Val Gln Leu Lys His Leu Thr Glu Ile Lys Val
                85                  90                  95 gaa gga gaa aaa att atc gcg caa agc ggc gct gat att aaa gca gtt      336
Glu Gly Glu Lys Ile Ile Ala Gln Ser Gly Ala Asp Ile Lys Ala Val
            100                 105                 110 tct cgg gtt gca ctg gaa cac agc ttg acg ggg ctg gag ttc gcg tgc      384
Ser Arg Val Ala Leu Glu His Ser Leu Thr Gly Leu Glu Phe Ala Cys
        115                 120                 125 ggc att ccc ggc tct gtc ggg ggc gcg att atg atg aat gcg ggt gct      432
Gly Ile Pro Gly Ser Val Gly Gly Ala Ile Met Met Asn Ala Gly Ala
    130                 135                 140 tat gat ggg gaa ata aaa gac gtg att gac cat gtt aag gtc gtt aca      480
Tyr Asp Gly Glu Ile Lys Asp Val Ile Asp His Val Lys Val Val Thr
145                 150                 155                 160 caa acg gga gaa cag aaa att ttg cgc aaa gac gat ttg cag ctt ggt      528
Gln Thr Gly Glu Gln Lys Ile Leu Arg Lys Asp Asp Leu Gln Leu Gly
                165                 170                 175 tat cgc acg agc atc atc agc aag acg aac gac att gtg ctg gag gcg      576
Tyr Arg Thr Ser Ile Ile Ser Lys Thr Asn Asp Ile Val Leu Glu Ala
            180                 185                 190 gtg ttc cag ctt aaa aaa gga gat ccg caa aaa att aaa gaa aaa atg      624
Val Phe Gln Leu Lys Lys Gly Asp Pro Gln Lys Ile Lys Glu Lys Met
        195                 200                 205 gac gat ctc acc ttc cgg cgt gaa tcc aaa cag ccg ctt gaa tat cct      672
Asp Asp Leu Thr Phe Arg Arg Glu Ser Lys Gln Pro Leu Glu Tyr Pro
    210                 215                 220 tct gtc ggc agc gtg ttt aaa cgc cct cct gga tat ttt gcg ggc aag      720
Ser Val Gly Ser Val Phe Lys Arg Pro Pro Gly Tyr Phe Ala Gly Lys
225                 230                 235                 240 ctc att caa gac agc ggc ctg caa gga aaa gga gtc gga ggt gcg gaa      768
Leu Ile Gln Asp Ser Gly Leu Gln Gly Lys Gly Val Gly Gly Ala Glu
                245                 250                 255 gta tcg aca aag cac gca ggt ttt att att aat aaa aac aac gcc acc      816
Val Ser Thr Lys His Ala Gly Phe Ile Ile Asn Lys Asn Asn Ala Thr
            260                 265                 270 gcc tct gac tat att gcg acg atc gaa ctg gtg cgg aaa acg gtt aaa      864
Ala Ser Asp Tyr Ile Ala Thr Ile Glu Leu Val Arg Lys Thr Val Lys
        275                 280                 285 gaa aaa ttc ggc gtc gat ctg gaa tta gaa gtg aaa att atc ggg gag      912
Glu Lys Phe Gly Val Asp Leu Glu Leu Glu Val Lys Ile Ile Gly Glu
    290                 295                 300 gat atc aaa cag taa                                                  927
Asp Ile Lys Gln
305

<210> SEQ ID NO 26
<211> LENGTH: 308
<212> TYPE: PRT
<213> ORGANISM: Geobacillus strain Y4.1MC1

<400> SEQUENCE: 26

Met Met Tyr Glu Asn Asn Val Ile Tyr Gln Glu Leu Val Arg Ile Cys
1               5                   10                  15

Gly Glu Lys Asn Val Leu Arg Asp Glu Pro Leu Lys Tyr His Thr Leu
            20                  25                  30
```

```
Val Lys Ile Gly Gly Lys Ala Asp Phe Leu Val Trp Pro Glu Thr Tyr
         35                  40                  45

Glu Gln Val Val Glu Val Ile Arg Leu Lys Lys His His Leu Pro
 50                  55                  60

Phe Thr Leu Leu Gly Asn Gly Ser Asn Val Ile Val Arg Asp Gly Gly
 65                  70                  75                  80

Ile Arg Gly Ile Val Val Gln Leu Lys His Leu Thr Glu Ile Lys Val
                 85                  90                  95

Glu Gly Glu Lys Ile Ile Ala Gln Ser Gly Ala Asp Ile Lys Ala Val
            100                 105                 110

Ser Arg Val Ala Leu Glu His Ser Leu Thr Gly Leu Glu Phe Ala Cys
        115                 120                 125

Gly Ile Pro Gly Ser Val Gly Gly Ala Ile Met Met Asn Ala Gly Ala
130                 135                 140

Tyr Asp Gly Glu Ile Lys Asp Val Ile Asp His Val Lys Val Val Thr
145                 150                 155                 160

Gln Thr Gly Glu Gln Lys Ile Leu Arg Lys Asp Asp Leu Gln Leu Gly
                165                 170                 175

Tyr Arg Thr Ser Ile Ile Ser Lys Thr Asn Asp Ile Val Leu Glu Ala
            180                 185                 190

Val Phe Gln Leu Lys Lys Gly Asp Pro Gln Lys Ile Lys Glu Lys Met
        195                 200                 205

Asp Asp Leu Thr Phe Arg Arg Glu Ser Lys Gln Pro Leu Glu Tyr Pro
210                 215                 220

Ser Val Gly Ser Val Phe Lys Arg Pro Gly Tyr Phe Ala Gly Lys
225                 230                 235                 240

Leu Ile Gln Asp Ser Gly Leu Gln Gly Lys Gly Val Gly Gly Ala Glu
                245                 250                 255

Val Ser Thr Lys His Ala Gly Phe Ile Ile Asn Lys Asn Asn Ala Thr
            260                 265                 270

Ala Ser Asp Tyr Ile Ala Thr Ile Glu Leu Val Arg Lys Thr Val Lys
        275                 280                 285

Glu Lys Phe Gly Val Asp Leu Glu Leu Glu Val Lys Ile Ile Gly Glu
290                 295                 300

Asp Ile Lys Gln
305

<210> SEQ ID NO 27
<211> LENGTH: 965
<212> TYPE: DNA
<213> ORGANISM: Geobacillus strain Y4.1MC1
<220> FEATURE:
<221> NAME/KEY: CDS
<222> LOCATION: (15)..(959)

<400> SEQUENCE: 27
aggagataaa acat atg atg tac gaa aac aat gta atc tat caa gag ctg       50
              Met Met Tyr Glu Asn Asn Val Ile Tyr Gln Glu Leu
                1               5                  10 gtg cgt att tgt ggt gag aaa aac gtc ctg cgc gat gaa cct ctg aaa       98
Val Arg Ile Cys Gly Glu Lys Asn Val Leu Arg Asp Glu Pro Leu Lys
         15                  20                  25 tat cac acg ttg gtg aag att ggt ggc aag gcg gat ttc ctg gtt tgg      146
Tyr His Thr Leu Val Lys Ile Gly Gly Lys Ala Asp Phe Leu Val Trp
     30                  35                  40 ccg gaa acc tac gaa cag gtg gtc gag gtg atc cgt ttg aaa gag aag      194
Pro Glu Thr Tyr Glu Gln Val Val Glu Val Ile Arg Leu Lys Glu Lys
```

```
              45                  50                  55                  60
cac cac ttg ccg ttc acg ttg ctg ggt aat ggt agc aat gtc att gtt     242
His His Leu Pro Phe Thr Leu Leu Gly Asn Gly Ser Asn Val Ile Val
                     65                  70                  75 cgc gac ggt ggt atc cgt ggc atc gtg gtg caa ctg aag cat ctg act     290
Arg Asp Gly Gly Ile Arg Gly Ile Val Val Gln Leu Lys His Leu Thr
                 80                  85                  90 gag att aaa gtt gaa ggc gag aag att att gcg cag tct ggc gcc gac     338
Glu Ile Lys Val Glu Gly Glu Lys Ile Ile Ala Gln Ser Gly Ala Asp
             95                 100                 105 atc aaa gcc gtc agc cgt gtg gcg ctg gag cat tct ctg acc ggc ctg     386
Ile Lys Ala Val Ser Arg Val Ala Leu Glu His Ser Leu Thr Gly Leu
         110                 115                 120 gaa ttt gca tgc ggt att ccg ggc agc gtt ggt ggt gct att atg atg     434
Glu Phe Ala Cys Gly Ile Pro Gly Ser Val Gly Gly Ala Ile Met Met
125                 130                 135                 140 aac gct ggc gcg tac gat ggt gaa atc aaa gat gtc att gat cac gtt     482
Asn Ala Gly Ala Tyr Asp Gly Glu Ile Lys Asp Val Ile Asp His Val
                     145                 150                 155 aaa gtt gtg acc cag acc ggt gag cag aag atc ctg cgt aaa gac gat     530
Lys Val Val Thr Gln Thr Gly Glu Gln Lys Ile Leu Arg Lys Asp Asp
                 160                 165                 170 ctg cag ctg ggt tac cgt acc agc att atc agc aaa acg aat gat atc     578
Leu Gln Leu Gly Tyr Arg Thr Ser Ile Ile Ser Lys Thr Asn Asp Ile
             175                 180                 185 gtg ctg gaa gcg gtt ttt cag ttg aag aag ggt gac ccg caa aag atc     626
Val Leu Glu Ala Val Phe Gln Leu Lys Lys Gly Asp Pro Gln Lys Ile
         190                 195                 200 aaa gag aag atg gac gac ctg acc ttt cgt cgc gag tcc aaa caa ccg     674
Lys Glu Lys Met Asp Asp Leu Thr Phe Arg Arg Glu Ser Lys Gln Pro
205                 210                 215                 220 ctg gag tat ccg agc gtt ggc agc gtc ttt aag cgc cca ccg ggc tac     722
Leu Glu Tyr Pro Ser Val Gly Ser Val Phe Lys Arg Pro Pro Gly Tyr
                     225                 230                 235 ttc gcg ggc aag ctg atc cag gac agc ggt ctg caa ggt aaa ggt gtc     770
Phe Ala Gly Lys Leu Ile Gln Asp Ser Gly Leu Gln Gly Lys Gly Val
                 240                 245                 250 ggc ggt gca gag gtg agc acc aaa cat gca ggc ttc atc att aac aaa     818
Gly Gly Ala Glu Val Ser Thr Lys His Ala Gly Phe Ile Ile Asn Lys
             255                 260                 265 aac aat gcc acg gcg tcc gac tat atc gca acc att gaa ctg gtt cgt     866
Asn Asn Ala Thr Ala Ser Asp Tyr Ile Ala Thr Ile Glu Leu Val Arg
         270                 275                 280 aaa acg gtt aaa gaa aag ttc ggt gtc gat ctg gag ctg gaa gtt aag     914
Lys Thr Val Lys Glu Lys Phe Gly Val Asp Leu Glu Leu Glu Val Lys
285                 290                 295                 300 att atc ggt gag gac att aag caa cac cac cac cat cac cat taa       959
Ile Ile Gly Glu Asp Ile Lys Gln His His His His His His
                     305                 310 ctcgag                                                             965

<210> SEQ ID NO 28
<211> LENGTH: 314
<212> TYPE: PRT
<213> ORGANISM: Geobacillus strain Y4.1MC1

<400> SEQUENCE: 28

Met Met Tyr Glu Asn Asn Val Ile Tyr Gln Glu Leu Val Arg Ile Cys
1               5                   10                  15
```

-continued

Gly Glu Lys Asn Val Leu Arg Asp Glu Pro Leu Lys Tyr His Thr Leu
          20                  25                  30

Val Lys Ile Gly Gly Lys Ala Asp Phe Leu Val Trp Pro Glu Thr Tyr
              35                  40                  45

Glu Gln Val Val Glu Val Ile Arg Leu Lys Glu Lys His His Leu Pro
     50                  55                  60

Phe Thr Leu Leu Gly Asn Gly Ser Asn Val Ile Val Arg Asp Gly Gly
65                  70                  75                  80

Ile Arg Gly Ile Val Val Gln Leu Lys His Leu Thr Glu Ile Lys Val
              85                  90                  95

Glu Gly Glu Lys Ile Ile Ala Gln Ser Gly Ala Asp Ile Lys Ala Val
     100                 105                 110

Ser Arg Val Ala Leu Glu His Ser Leu Thr Gly Leu Glu Phe Ala Cys
         115                 120                 125

Gly Ile Pro Gly Ser Val Gly Gly Ala Ile Met Met Asn Ala Gly Ala
     130                 135                 140

Tyr Asp Gly Glu Ile Lys Asp Val Ile Asp His Val Lys Val Val Thr
145                 150                 155                 160

Gln Thr Gly Glu Gln Lys Ile Leu Arg Lys Asp Asp Leu Gln Leu Gly
              165                 170                 175

Tyr Arg Thr Ser Ile Ile Ser Lys Thr Asn Asp Ile Val Leu Glu Ala
              180                 185                 190

Val Phe Gln Leu Lys Lys Gly Asp Pro Gln Lys Ile Lys Glu Lys Met
         195                 200                 205

Asp Asp Leu Thr Phe Arg Arg Glu Ser Lys Gln Pro Leu Glu Tyr Pro
     210                 215                 220

Ser Val Gly Ser Val Phe Lys Arg Pro Pro Gly Tyr Phe Ala Gly Lys
225                 230                 235                 240

Leu Ile Gln Asp Ser Gly Leu Gln Gly Lys Gly Val Gly Gly Ala Glu
              245                 250                 255

Val Ser Thr Lys His Ala Gly Phe Ile Ile Asn Lys Asn Asn Ala Thr
         260                 265                 270

Ala Ser Asp Tyr Ile Ala Thr Ile Glu Leu Val Arg Lys Thr Val Lys
     275                 280                 285

Glu Lys Phe Gly Val Asp Leu Glu Leu Glu Val Lys Ile Ile Gly Glu
     290                 295                 300

Asp Ile Lys Gln His His His His His His
305                 310

<210> SEQ ID NO 29
<211> LENGTH: 1026
<212> TYPE: DNA
<213> ORGANISM: Rhodothermus marinus strain SG0.5JP17-172
<220> FEATURE:
<221> NAME/KEY: CDS
<222> LOCATION: (1)..(1026)

<400> SEQUENCE: 29 atg gca aac gag acc tct gtg att cct ccg tcg gta tat gaa gca tta       48
Met Ala Asn Glu Thr Ser Val Ile Pro Pro Ser Val Tyr Glu Ala Leu
1               5                   10                  15 gtg gcc cgg ttg ggg cct cgg cgc gtg cag cga aac gtg ccg ctg gcg       96
Val Ala Arg Leu Gly Pro Arg Arg Val Gln Arg Asn Val Pro Leu Ala
              20                  25                  30 ccg tac acg acg ttc aaa atc ggc ggg ccg gcg gat ctg ttc ttc gag      144
Pro Tyr Thr Thr Phe Lys Ile Gly Gly Pro Ala Asp Leu Phe Phe Glu
         35                  40                  45

```
gcg cac acg cgc gac gag ctg gcc gaa gcg gtg cag atc gcc cgc acg      192
Ala His Thr Arg Asp Glu Leu Ala Glu Ala Val Gln Ile Ala Arg Thr
 50                  55                  60 ctg agc atc ccc tac ttt gtg ctc ggc ctg ggc gcc aac atc cta gta      240
Leu Ser Ile Pro Tyr Phe Val Leu Gly Leu Gly Ala Asn Ile Leu Val
 65                  70                  75                  80 ggc gat cgg ggc ttt cgg gga ctg gtc att cgc aac agg gcc cgc gcc      288
Gly Asp Arg Gly Phe Arg Gly Leu Val Ile Arg Asn Arg Ala Arg Ala
                 85                  90                  95 tgc cgc ctg ctg ccc ggt cac cgg ctc tgg gcc gaa agc ggg gcg gtt      336
Cys Arg Leu Leu Pro Gly His Arg Leu Trp Ala Glu Ser Gly Ala Val
            100                 105                 110 gtc tat cct gac ctt att gaa acg gct gtc gag gcc ggc ctt tct ggc      384
Val Tyr Pro Asp Leu Ile Glu Thr Ala Val Glu Ala Gly Leu Ser Gly
            115                 120                 125 ctg gaa cat tac gtg ggc atc ccg tcc acc gta ggc ggc gcg ctc tgg      432
Leu Glu His Tyr Val Gly Ile Pro Ser Thr Val Gly Gly Ala Leu Trp
130                 135                 140 cag aac ctg cat ttt ctc tcg ccg cca ccc aag cgc gag cgt acc gtc      480
Gln Asn Leu His Phe Leu Ser Pro Pro Pro Lys Arg Glu Arg Thr Val
145                 150                 155                 160 ttt atc gaa gag gtg ctg gcc gaa gcc gaa atc ctg acg gcc gaa ggc      528
Phe Ile Glu Glu Val Leu Ala Glu Ala Glu Ile Leu Thr Ala Glu Gly
                165                 170                 175 aaa cgc cgc ctc gtt ggc cct gac tac ttc cgc ttc ggc tac gac tat      576
Lys Arg Arg Leu Val Gly Pro Asp Tyr Phe Arg Phe Gly Tyr Asp Tyr
            180                 185                 190 tcg atc ctg cat gaa cgc gac gac att gtg ctg gcc gct acg ttc cag      624
Ser Ile Leu His Glu Arg Asp Asp Ile Val Leu Ala Ala Thr Phe Gln
            195                 200                 205 cta agc ccg ggc gat cca gca cgc atg cgc gaa gtc atg gcc gcc aat      672
Leu Ser Pro Gly Asp Pro Ala Arg Met Arg Glu Val Met Ala Ala Asn
210                 215                 220 ctc gcc tgg cga cgt gaa cgc cat cca cca ctt gag acc gaa cct agt      720
Leu Ala Trp Arg Arg Glu Arg His Pro Pro Leu Glu Thr Glu Pro Ser
225                 230                 235                 240 gct ggc tcc atc ttc aaa aag atc gac ggc att ggc gct ggc cgg ctg      768
Ala Gly Ser Ile Phe Lys Lys Ile Asp Gly Ile Gly Ala Gly Arg Leu
                245                 250                 255 atc gac cag tgc ggc ctg aaa ggc acg cgc atc ggc gat gcc gag gtt      816
Ile Asp Gln Cys Gly Leu Lys Gly Thr Arg Ile Gly Asp Ala Glu Val
            260                 265                 270 tca ccg cgc cat gcc aat atc ata gtg aac cgg gga aag gca acc gct      864
Ser Pro Arg His Ala Asn Ile Ile Val Asn Arg Gly Lys Ala Thr Ala
            275                 280                 285 gcg caa gtg cgc gcg ctc atc gcc tac gtg cag cag gtg gtc gaa gcc      912
Ala Gln Val Arg Ala Leu Ile Ala Tyr Val Gln Gln Val Val Glu Ala
290                 295                 300 cgc acc ggc tat cac ctg gaa cct gaa atc cgt ttt gtc ggc gaa ttt      960
Arg Thr Gly Tyr His Leu Glu Pro Glu Ile Arg Phe Val Gly Glu Phe
305                 310                 315                 320 gat ccc cct gct gaa aac gaa ata ctt ctt ccg aac cat gcc gca atc     1008
Asp Pro Pro Ala Glu Asn Glu Ile Leu Leu Pro Asn His Ala Ala Ile
                325                 330                 335 cgc cat cca gac cgt tga                                             1026
Arg His Pro Asp Arg
            340
```

<210> SEQ ID NO 30

<211> LENGTH: 341
<212> TYPE: PRT
<213> ORGANISM: Rhodothermus marinus strain SG0.5JP17-172

<400> SEQUENCE: 30

Met Ala Asn Glu Thr Ser Val Ile Pro Pro Ser Val Tyr Glu Ala Leu
1               5                   10                  15

Val Ala Arg Leu Gly Pro Arg Val Gln Arg Asn Val Pro Leu Ala
            20                  25                  30

Pro Tyr Thr Thr Phe Lys Ile Gly Gly Pro Ala Asp Leu Phe Phe Glu
        35                  40                  45

Ala His Thr Arg Asp Glu Leu Ala Glu Ala Val Gln Ile Ala Arg Thr
    50                  55                  60

Leu Ser Ile Pro Tyr Phe Val Leu Gly Leu Gly Ala Asn Ile Leu Val
65                  70                  75                  80

Gly Asp Arg Gly Phe Arg Gly Leu Val Ile Arg Asn Arg Ala Arg Ala
                85                  90                  95

Cys Arg Leu Leu Pro Gly His Arg Leu Trp Ala Glu Ser Gly Ala Val
            100                 105                 110

Val Tyr Pro Asp Leu Ile Glu Thr Ala Val Glu Ala Gly Leu Ser Gly
        115                 120                 125

Leu Glu His Tyr Val Gly Ile Pro Ser Thr Val Gly Gly Ala Leu Trp
    130                 135                 140

Gln Asn Leu His Phe Leu Ser Pro Pro Lys Arg Glu Arg Thr Val
145                 150                 155                 160

Phe Ile Glu Glu Val Leu Ala Glu Ala Glu Ile Leu Thr Ala Glu Gly
                165                 170                 175

Lys Arg Arg Leu Val Gly Pro Asp Tyr Phe Arg Phe Gly Tyr Asp Tyr
            180                 185                 190

Ser Ile Leu His Glu Arg Asp Asp Ile Val Leu Ala Ala Thr Phe Gln
        195                 200                 205

Leu Ser Pro Gly Asp Pro Ala Arg Met Arg Glu Val Met Ala Ala Asn
    210                 215                 220

Leu Ala Trp Arg Arg Glu Arg His Pro Pro Leu Glu Thr Glu Pro Ser
225                 230                 235                 240

Ala Gly Ser Ile Phe Lys Lys Ile Asp Gly Ile Gly Ala Gly Arg Leu
                245                 250                 255

Ile Asp Gln Cys Gly Leu Lys Gly Thr Arg Ile Gly Asp Ala Glu Val
            260                 265                 270

Ser Pro Arg His Ala Asn Ile Ile Val Asn Arg Gly Lys Ala Thr Ala
        275                 280                 285

Ala Gln Val Arg Ala Leu Ile Ala Tyr Val Gln Gln Val Val Glu Ala
    290                 295                 300

Arg Thr Gly Tyr His Leu Glu Pro Glu Ile Arg Phe Val Gly Glu Phe
305                 310                 315                 320

Asp Pro Pro Ala Glu Asn Glu Ile Leu Leu Pro Asn His Ala Ala Ile
                325                 330                 335

Arg His Pro Asp Arg
            340

<210> SEQ ID NO 31
<211> LENGTH: 1064
<212> TYPE: DNA
<213> ORGANISM: Rhodothermus marinus strain SG0.5JP17-172
<220> FEATURE:
<221> NAME/KEY: CDS

<222> LOCATION: (15)..(1058)

<400> SEQUENCE: 31

```
aggagataaa acat atg gca aat gaa acg agc gta atc cca ccg tct gtg         50
               Met Ala Asn Glu Thr Ser Val Ile Pro Pro Ser Val
                 1               5                  10 tat gaa gcc ctg gtc gcc cgt ctg ggt ccg cgt cgt gtt caa cgt aat         98
Tyr Glu Ala Leu Val Ala Arg Leu Gly Pro Arg Arg Val Gln Arg Asn
             15                  20                  25 gtt ccg ttg gca ccg tac acg acc ttc aaa att ggc ggt ccg gcg gac        146
Val Pro Leu Ala Pro Tyr Thr Thr Phe Lys Ile Gly Gly Pro Ala Asp
 30                  35                  40 ctg ttt ttc gag gcg cat acc cgt gat gag ttg gcg gaa gct gtc caa        194
Leu Phe Phe Glu Ala His Thr Arg Asp Glu Leu Ala Glu Ala Val Gln
 45                  50                  55                  60 att gcc cgc acc ctg tcc atc ccg tat ttt gtc ctg ggt ctg ggc gct        242
Ile Ala Arg Thr Leu Ser Ile Pro Tyr Phe Val Leu Gly Leu Gly Ala
                 65                  70                  75 aac att ctg gtt ggc gat cgt ggt ttc cgc ggt ctg gtg att cgt aac        290
Asn Ile Leu Val Gly Asp Arg Gly Phe Arg Gly Leu Val Ile Arg Asn
             80                  85                  90 cgc gca cgt gcc tgt cgt ttg ctg cca ggc cac cgc ctg tgg gca gag        338
Arg Ala Arg Ala Cys Arg Leu Leu Pro Gly His Arg Leu Trp Ala Glu
         95                 100                 105 tct ggt gcc gtg gtg tat ccg gat ctg atc gaa acg gcg gtg gaa gcg        386
Ser Gly Ala Val Val Tyr Pro Asp Leu Ile Glu Thr Ala Val Glu Ala
    110                 115                 120 ggc ctg agc ggt ctg gag cac tac gtt ggc att ccg agc acc gtc ggc        434
Gly Leu Ser Gly Leu Glu His Tyr Val Gly Ile Pro Ser Thr Val Gly
125                 130                 135                 140 ggt gct ctg tgg cag aat ctg cat ttt ctg agc cca ccg ccg aag cgc        482
Gly Ala Leu Trp Gln Asn Leu His Phe Leu Ser Pro Pro Pro Lys Arg
                145                 150                 155 gaa cgc acg gtt ttc atc gaa gag gtt ctg gca gag gca gaa att ctg        530
Glu Arg Thr Val Phe Ile Glu Glu Val Leu Ala Glu Ala Glu Ile Leu
            160                 165                 170 acg gca gag ggt aaa cgt cgc ttg gtt ggc ccg gac tac ttt cgc ttt        578
Thr Ala Glu Gly Lys Arg Arg Leu Val Gly Pro Asp Tyr Phe Arg Phe
        175                 180                 185 ggt tac gat tac agc att ctg cac gaa cgt gac gac att gtc ctg gcg        626
Gly Tyr Asp Tyr Ser Ile Leu His Glu Arg Asp Asp Ile Val Leu Ala
    190                 195                 200 gcg acc ttc cag ctg tcc ccg ggt gac cct gcg cgc atg cgt gag gtc        674
Ala Thr Phe Gln Leu Ser Pro Gly Asp Pro Ala Arg Met Arg Glu Val
205                 210                 215                 220 atg gcg gcc aac ttg gcg tgg cgt cgc gaa cgc cat ccg ccg ctg gaa        722
Met Ala Ala Asn Leu Ala Trp Arg Arg Glu Arg His Pro Pro Leu Glu
                225                 230                 235 act gag ccg agc gcg ggt agc atc ttt aag aag atc gat ggt atc ggc        770
Thr Glu Pro Ser Ala Gly Ser Ile Phe Lys Lys Ile Asp Gly Ile Gly
            240                 245                 250 gct ggt cgc ctg atc gac caa tgc ggc ctg aaa ggt acc cgt atc ggc        818
Ala Gly Arg Leu Ile Asp Gln Cys Gly Leu Lys Gly Thr Arg Ile Gly
        255                 260                 265 gac gct gag gtg agc cct cgt cac gca aac atc att gtt aac cgt ggt        866
Asp Ala Glu Val Ser Pro Arg His Ala Asn Ile Ile Val Asn Arg Gly
    270                 275                 280 aaa gca acc gcc gca cag gtg cgt gcg ctg atc gcg tac gtg cag caa        914
Lys Ala Thr Ala Ala Gln Val Arg Ala Leu Ile Ala Tyr Val Gln Gln
285                 290                 295                 300
```

```
gtg gtt gag gcg cgt acc ggt tat cac ttg gag ccg gaa atc cgt ttc      962
Val Val Glu Ala Arg Thr Gly Tyr His Leu Glu Pro Glu Ile Arg Phe
            305                 310                 315 gtc ggt gag ttc gac cca ccg gcg gag aat gag att ctg ctg ccg aat     1010
Val Gly Glu Phe Asp Pro Pro Ala Glu Asn Glu Ile Leu Leu Pro Asn
320                 325                 330 cac gcg gcg att cgt cac ccg gat cgt cat cat cat cac cac cac taa     1058
His Ala Ala Ile Arg His Pro Asp Arg His His His His His His
        335                 340                 345 ctcgag                                                               1064

<210> SEQ ID NO 32
<211> LENGTH: 347
<212> TYPE: PRT
<213> ORGANISM: Rhodothermus marinus strain SG0.5JP17-172

<400> SEQUENCE: 32

Met Ala Asn Glu Thr Ser Val Ile Pro Pro Ser Val Tyr Glu Ala Leu
1               5                   10                  15

Val Ala Arg Leu Gly Pro Arg Val Gln Arg Asn Val Pro Leu Ala
            20                  25                  30

Pro Tyr Thr Thr Phe Lys Ile Gly Pro Ala Asp Leu Phe Phe Glu
        35                  40                  45

Ala His Thr Arg Asp Glu Leu Ala Glu Ala Val Gln Ile Ala Arg Thr
    50                  55                  60

Leu Ser Ile Pro Tyr Phe Val Leu Gly Leu Gly Ala Asn Ile Leu Val
65                  70                  75                  80

Gly Asp Arg Gly Phe Arg Gly Leu Val Ile Arg Asn Arg Ala Arg Ala
                85                  90                  95

Cys Arg Leu Leu Pro Gly His Arg Leu Trp Ala Glu Ser Gly Ala Val
                100                 105                 110

Val Tyr Pro Asp Leu Ile Glu Thr Ala Val Glu Ala Gly Leu Ser Gly
            115                 120                 125

Leu Glu His Tyr Val Gly Ile Pro Ser Thr Val Gly Gly Ala Leu Trp
    130                 135                 140

Gln Asn Leu His Phe Leu Ser Pro Pro Lys Arg Glu Arg Thr Val
145                 150                 155                 160

Phe Ile Glu Glu Val Leu Ala Glu Ala Glu Ile Leu Thr Ala Glu Gly
                165                 170                 175

Lys Arg Arg Leu Val Gly Pro Asp Tyr Phe Arg Phe Gly Tyr Asp Tyr
            180                 185                 190

Ser Ile Leu His Glu Arg Asp Asp Ile Val Leu Ala Ala Thr Phe Gln
        195                 200                 205

Leu Ser Pro Gly Asp Pro Ala Arg Met Arg Glu Val Met Ala Ala Asn
    210                 215                 220

Leu Ala Trp Arg Arg Glu Arg His Pro Pro Leu Glu Thr Glu Pro Ser
225                 230                 235                 240

Ala Gly Ser Ile Phe Lys Lys Ile Asp Gly Ile Gly Ala Gly Arg Leu
                245                 250                 255

Ile Asp Gln Cys Gly Leu Lys Gly Thr Arg Ile Gly Asp Ala Glu Val
            260                 265                 270

Ser Pro Arg His Ala Asn Ile Ile Val Asn Arg Gly Lys Ala Thr Ala
        275                 280                 285

Ala Gln Val Arg Ala Leu Ile Ala Tyr Val Gln Gln Val Val Glu Ala
    290                 295                 300
```

```
Arg Thr Gly Tyr His Leu Glu Pro Glu Ile Arg Phe Val Gly Glu Phe
305                 310                 315                 320

Asp Pro Pro Ala Glu Asn Glu Ile Leu Leu Pro Asn His Ala Ala Ile
                325                 330                 335

Arg His Pro Asp Arg His His His His His
            340                 345

<210> SEQ ID NO 33
<211> LENGTH: 867
<212> TYPE: DNA
<213> ORGANISM: Sulfurihydrogenibium,yellowstonense SS-5
<220> FEATURE:
<221> NAME/KEY: CDS
<222> LOCATION: (1)..(867)

<400> SEQUENCE: 33 atg att tta aaa acg att gaa cat caa gaa aat ata gac ctt agg aat        48
Met Ile Leu Lys Thr Ile Glu His Gln Glu Asn Ile Asp Leu Arg Asn
1               5                   10                  15 ttt tgc act ata aaa gtt ggc gaa aaa gga aag att gta tat ttt cca       96
Phe Cys Thr Ile Lys Val Gly Glu Lys Gly Lys Ile Val Tyr Phe Pro
                20                  25                  30 aaa gat tac aaa gaa atc tct att tta att aaa gag tat gat aac atc      144
Lys Asp Tyr Lys Glu Ile Ser Ile Leu Ile Lys Glu Tyr Asp Asn Ile
            35                  40                  45 tat cca ctt gga att gga agc aat cta att ttt tcc gat gga gtt gtg      192
Tyr Pro Leu Gly Ile Gly Ser Asn Leu Ile Phe Ser Asp Gly Val Val
        50                  55                  60 aat aaa gtt ttt gtc cat tct aag aat cta aaa aag tat gag ata gaa      240
Asn Lys Val Phe Val His Ser Lys Asn Leu Lys Lys Tyr Glu Ile Glu
65                  70                  75                  80 aat caa aac gat att ttt tac atc acg gca gaa gcc ggc gta agc ttt      288
Asn Gln Asn Asp Ile Phe Tyr Ile Thr Ala Glu Ala Gly Val Ser Phe
                85                  90                  95 aaa acc ata gtt tca gta gta aaa aag tac aac ctt gaa gga ttt gaa      336
Lys Thr Ile Val Ser Val Val Lys Lys Tyr Asn Leu Glu Gly Phe Glu
                100                 105                 110 aac cta tcc ggc att cct gca acc gtt ggc ggg gca act gca atg aac      384
Asn Leu Ser Gly Ile Pro Ala Thr Val Gly Gly Ala Thr Ala Met Asn
            115                 120                 125 gca gga gct tac gga agc gaa atc ttt gat tta ata gaa gag gtt tgg      432
Ala Gly Ala Tyr Gly Ser Glu Ile Phe Asp Leu Ile Glu Glu Val Trp
        130                 135                 140 tgg ata gac aga gaa gga cgg cta aat cac tca aag aag gac gag att      480
Trp Ile Asp Arg Glu Gly Arg Leu Asn His Ser Lys Lys Asp Glu Ile
145                 150                 155                 160 aaa tac tct tac aga tac tct caa ttt caa aac gaa ggt ttt gtt tat      528
Lys Tyr Ser Tyr Arg Tyr Ser Gln Phe Gln Asn Glu Gly Phe Val Tyr
                165                 170                 175 aaa gtg aag cta aaa ctt aga aaa agt gat aaa aac ata tca gag att      576
Lys Val Lys Leu Lys Leu Arg Lys Ser Asp Lys Asn Ile Ser Glu Ile
                180                 185                 190 ata aaa aac cat ctg ctt gat aga aac agt aag caa ccc ctt gat cta      624
Ile Lys Asn His Leu Leu Asp Arg Asn Ser Lys Gln Pro Leu Asp Leu
            195                 200                 205 cca aca gcc gga tca act tac aaa aat cca gcg gga aca tat gcc ggc      672
Pro Thr Ala Gly Ser Thr Tyr Lys Asn Pro Ala Gly Thr Tyr Ala Gly
        210                 215                 220 aag ctg att gaa gca gtt ggc tta aaa ggt tat aga ata aac gat ata      720
Lys Leu Ile Glu Ala Val Gly Leu Lys Gly Tyr Arg Ile Asn Asp Ile
```

```
                225                 230                 235                 240
gga ttt tct gaa aaa cat gca aac ttt ctt gta aat tat gga aat gct        768
Gly Phe Ser Glu Lys His Ala Asn Phe Leu Val Asn Tyr Gly Asn Ala
            245                 250                 255 gag ttt aaa gac cta ata aaa ctc tta gaa ctt gcc gaa aga aaa ata        816
Glu Phe Lys Asp Leu Ile Lys Leu Leu Glu Leu Ala Glu Arg Lys Ile
            260                 265                 270 tca gat gaa ttt agg ata aat ctt gaa aga gag gtt aaa atc att gat        864
Ser Asp Glu Phe Arg Ile Asn Leu Glu Arg Glu Val Lys Ile Ile Asp
            275                 280                 285 taa                                                                    867

<210> SEQ ID NO 34
<211> LENGTH: 288
<212> TYPE: PRT
<213> ORGANISM: Sulfurihydrogenibium, yellowstonense SS-5

<400> SEQUENCE: 34

Met Ile Leu Lys Thr Ile Glu His Gln Glu Asn Ile Asp Leu Arg Asn
1               5                   10                  15

Phe Cys Thr Ile Lys Val Gly Glu Lys Gly Lys Ile Val Tyr Phe Pro
            20                  25                  30

Lys Asp Tyr Lys Glu Ile Ser Ile Leu Ile Lys Glu Tyr Asp Asn Ile
            35                  40                  45

Tyr Pro Leu Gly Ile Gly Ser Asn Leu Ile Phe Ser Asp Gly Val Val
        50                  55                  60

Asn Lys Val Phe Val His Ser Lys Asn Leu Lys Lys Tyr Glu Ile Glu
65                  70                  75                  80

Asn Gln Asn Asp Ile Phe Tyr Ile Thr Ala Glu Ala Gly Val Ser Phe
                85                  90                  95

Lys Thr Ile Val Ser Val Val Lys Lys Tyr Asn Leu Glu Gly Phe Glu
            100                 105                 110

Asn Leu Ser Gly Ile Pro Ala Thr Val Gly Gly Ala Thr Ala Met Asn
            115                 120                 125

Ala Gly Ala Tyr Gly Ser Glu Ile Phe Asp Leu Ile Glu Glu Val Trp
        130                 135                 140

Trp Ile Asp Arg Glu Gly Arg Leu Asn His Ser Lys Lys Asp Glu Ile
145                 150                 155                 160

Lys Tyr Ser Tyr Arg Tyr Ser Gln Phe Gln Asn Glu Gly Phe Val Tyr
                165                 170                 175

Lys Val Lys Leu Lys Leu Arg Lys Ser Asp Lys Asn Ile Ser Glu Ile
            180                 185                 190

Ile Lys Asn His Leu Leu Asp Arg Asn Ser Lys Gln Pro Leu Asp Leu
            195                 200                 205

Pro Thr Ala Gly Ser Thr Tyr Lys Asn Pro Ala Gly Thr Tyr Ala Gly
        210                 215                 220

Lys Leu Ile Glu Ala Val Gly Leu Lys Gly Tyr Arg Ile Asn Asp Ile
225                 230                 235                 240

Gly Phe Ser Glu Lys His Ala Asn Phe Leu Val Asn Tyr Gly Asn Ala
                245                 250                 255

Glu Phe Lys Asp Leu Ile Lys Leu Leu Glu Leu Ala Glu Arg Lys Ile
            260                 265                 270

Ser Asp Glu Phe Arg Ile Asn Leu Glu Arg Glu Val Lys Ile Ile Asp
            275                 280                 285
```

<210> SEQ ID NO 35
<211> LENGTH: 905
<212> TYPE: DNA
<213> ORGANISM: Sulfurihydrogenibium yellowstonense SS-5
<220> FEATURE:
<221> NAME/KEY: CDS
<222> LOCATION: (15)..(899)

<400> SEQUENCE: 35

| | | | | | | | | | | | | |
|---|---|---|---|---|---|---|---|---|---|---|---|---|
| aggagataaa acat | atg | att | ctg | aaa | acc | att | gaa | cac | caa | gag | aac att | 50 |
| | Met | Ile | Leu | Lys | Thr | Ile | Glu | His | Gln | Glu | Asn Ile | |
| | 1 | | | 5 | | | | | 10 | | | |
| gat ttg cgt | aat | ttc | tgt | act | atc | aaa | gtc | ggt | gaa | aag | ggc aag atc | 98 |
| Asp Leu Arg | Asn | Phe | Cys | Thr | Ile | Lys | Val | Gly | Glu | Lys | Gly Lys Ile | |
| 15 | | | | 20 | | | | | 25 | | | |
| gtt tac ttt ccg | aaa | gac | tac | aaa | gaa | atc | agc | atc | ctg | att | aaa gag | 146 |
| Val Tyr Phe Pro | Lys | Asp | Tyr | Lys | Glu | Ile | Ser | Ile | Leu | Ile | Lys Glu | |
| 30 | | | 35 | | | | | 40 | | | | |
| tac gac aac att | tat | ccg | ctg | ggc | att | ggc | tcg | aat | ttg | att | ttc agc | 194 |
| Tyr Asp Asn Ile | Tyr | Pro | Leu | Gly | Ile | Gly | Ser | Asn | Leu | Ile | Phe Ser | |
| 45 | | | 50 | | | | | 55 | | | | 60 |
| gat ggc gtt gtc | aac | aag | gtt | ttc | gtt | cac | agc | aaa | aat | ctg | aag aag | 242 |
| Asp Gly Val Val | Asn | Lys | Val | Phe | Val | His | Ser | Lys | Asn | Leu | Lys Lys | |
| | | 65 | | | | | 70 | | | | | 75 |
| tat gaa att gag | aat | caa | aat | gac | atc | ttc | tat | atc | acc | gca | gag gcc | 290 |
| Tyr Glu Ile Glu | Asn | Gln | Asn | Asp | Ile | Phe | Tyr | Ile | Thr | Ala | Glu Ala | |
| | | | 80 | | | | | 85 | | | | 90 |
| ggt gtt agc ttc | aag | acg | atc | gtt | agc | gtg | gtc | aaa | aag | tac | aat ctg | 338 |
| Gly Val Ser Phe | Lys | Thr | Ile | Val | Ser | Val | Val | Lys | Lys | Tyr | Asn Leu | |
| | | 95 | | | | | 100 | | | | | 105 |
| gaa ggt ttt gaa | aac | ttg | agc | ggt | att | ccg | gct | acg | gtg | ggt | ggt gcg | 386 |
| Glu Gly Phe Glu | Asn | Leu | Ser | Gly | Ile | Pro | Ala | Thr | Val | Gly | Gly Ala | |
| | 110 | | | | | 115 | | | | | 120 | |
| acc gcc atg aat | gca | ggc | gcg | tac | ggt | tct | gaa | atc | ttt | gac | ctg att | 434 |
| Thr Ala Met Asn | Ala | Gly | Ala | Tyr | Gly | Ser | Glu | Ile | Phe | Asp | Leu Ile | |
| 125 | | | 130 | | | | | 135 | | | | 140 |
| gaa gaa gtg tgg | tgg | atc | gat | cgc | gag | ggt | cgc | ctg | aac | cac | tct aaa | 482 |
| Glu Glu Val Trp | Trp | Ile | Asp | Arg | Glu | Gly | Arg | Leu | Asn | His | Ser Lys | |
| | | | 145 | | | | | 150 | | | | 155 |
| aag gac gag atc | aaa | tac | agc | tac | cgt | tac | agc | cag | ttc | cag | aac gaa | 530 |
| Lys Asp Glu Ile | Lys | Tyr | Ser | Tyr | Arg | Tyr | Ser | Gln | Phe | Gln | Asn Glu | |
| | | | 160 | | | | 165 | | | | 170 | |
| ggc ttt gtg tat | aag | gtc | aag | ctg | aaa | ctg | cgc | aaa | agc | gac | aag aac | 578 |
| Gly Phe Val Tyr | Lys | Val | Lys | Leu | Lys | Leu | Arg | Lys | Ser | Asp | Lys Asn | |
| | 175 | | | | | 180 | | | | | 185 | |
| att tcc gag atc | atc | aaa | aat | cat | ctg | ctg | gac | cgt | aac | agc | aag cag | 626 |
| Ile Ser Glu Ile | Ile | Lys | Asn | His | Leu | Leu | Asp | Arg | Asn | Ser | Lys Gln | |
| 190 | | | | 195 | | | | | 200 | | | |
| ccg ctg gat ctg | cca | acc | gcg | ggt | agc | acg | tat | aag | aac | ccg | gct ggt | 674 |
| Pro Leu Asp Leu | Pro | Thr | Ala | Gly | Ser | Thr | Tyr | Lys | Asn | Pro | Ala Gly | |
| 205 | | | 210 | | | | | 215 | | | | 220 |
| acc tat gcg ggc | aaa | ctg | atc | gag | gcc | gtg | ggc | ctg | aag | ggt | tat cgt | 722 |
| Thr Tyr Ala Gly | Lys | Leu | Ile | Glu | Ala | Val | Gly | Leu | Lys | Gly | Tyr Arg | |
| | | | 225 | | | | | 230 | | | | 235 |
| atc aat gac att | ggt | ttc | tcc | gag | aaa | cat | gcg | aat | ttt | ctg | gtc aac | 770 |
| Ile Asn Asp Ile | Gly | Phe | Ser | Glu | Lys | His | Ala | Asn | Phe | Leu | Val Asn | |
| | | | 240 | | | | 245 | | | | 250 | |
| tac ggt aac gcg | gag | ttc | aaa | gat | ctg | att | aag | ctg | ctg | gag | ctg gca | 818 |
| Tyr Gly Asn Ala | Glu | Phe | Lys | Asp | Leu | Ile | Lys | Leu | Leu | Glu | Leu Ala | |
| | 255 | | | | | 260 | | | | | 265 | |
| gag cgt aag atc | agc | gat | gag | ttt | cgt | att | aac | ttg | gaa | cgc | gag gtg | 866 |

```
Glu Arg Lys Ile Ser Asp Glu Phe Arg Ile Asn Leu Glu Arg Glu Val
            270                 275                 280 aaa atc att gat cac cat cac cac cac taa ctcgag                        905
Lys Ile Ile Asp His His His His His
285                 290
```

<210> SEQ ID NO 36
<211> LENGTH: 294
<212> TYPE: PRT
<213> ORGANISM: Sulfurihydrogenibium yellowstonense SS-5

<400> SEQUENCE: 36

```
Met Ile Leu Lys Thr Ile Glu His Gln Glu Asn Ile Asp Leu Arg Asn
 1               5                  10                  15

Phe Cys Thr Ile Lys Val Gly Glu Lys Gly Lys Ile Val Tyr Phe Pro
            20                  25                  30

Lys Asp Tyr Lys Glu Ile Ser Ile Leu Ile Lys Glu Tyr Asp Asn Ile
        35                  40                  45

Tyr Pro Leu Gly Ile Gly Ser Asn Leu Ile Phe Ser Asp Gly Val Val
    50                  55                  60

Asn Lys Val Phe Val His Ser Lys Asn Leu Lys Lys Tyr Glu Ile Glu
65                  70                  75                  80

Asn Gln Asn Asp Ile Phe Tyr Ile Thr Ala Glu Ala Gly Val Ser Phe
                85                  90                  95

Lys Thr Ile Val Ser Val Val Lys Lys Tyr Asn Leu Glu Gly Phe Glu
            100                 105                 110

Asn Leu Ser Gly Ile Pro Ala Thr Val Gly Gly Ala Thr Ala Met Asn
        115                 120                 125

Ala Gly Ala Tyr Gly Ser Glu Ile Phe Asp Leu Ile Glu Glu Val Trp
    130                 135                 140

Trp Ile Asp Arg Glu Gly Arg Leu Asn His Ser Lys Lys Asp Glu Ile
145                 150                 155                 160

Lys Tyr Ser Tyr Arg Tyr Ser Gln Phe Gln Asn Glu Gly Phe Val Tyr
                165                 170                 175

Lys Val Lys Leu Lys Leu Arg Lys Ser Asp Lys Asn Ile Ser Glu Ile
            180                 185                 190

Ile Lys Asn His Leu Leu Asp Arg Asn Ser Lys Gln Pro Leu Asp Leu
        195                 200                 205

Pro Thr Ala Gly Ser Thr Tyr Lys Asn Pro Ala Gly Thr Tyr Ala Gly
    210                 215                 220

Lys Leu Ile Glu Ala Val Gly Leu Lys Gly Tyr Arg Ile Asn Asp Ile
225                 230                 235                 240

Gly Phe Ser Glu Lys His Ala Asn Phe Leu Val Asn Tyr Gly Asn Ala
                245                 250                 255

Glu Phe Lys Asp Leu Ile Lys Leu Leu Glu Leu Ala Glu Arg Lys Ile
            260                 265                 270

Ser Asp Glu Phe Arg Ile Asn Leu Glu Arg Glu Val Lys Ile Ile Asp
        275                 280                 285

His His His His His His
    290
```

<210> SEQ ID NO 37
<211> LENGTH: 888
<212> TYPE: DNA
<213> ORGANISM: Thermodesulfovibrio yellowstonii strain ATCC 51303
<220> FEATURE:
<221> NAME/KEY: CDS

<222> LOCATION: (1)..(888)

<400> SEQUENCE: 37

| | | | | | | | | | | | | | | | | |
|---|---|---|---|---|---|---|---|---|---|---|---|---|---|---|---|---|
| atg | aaa | aat | att | gaa | att | ttc | tta | aaa | gaa | aat | agg | ata | cct | tat | aaa | 48 |
| Met | Lys | Asn | Ile | Glu | Ile | Phe | Leu | Lys | Glu | Asn | Arg | Ile | Pro | Tyr | Lys | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| aaa | tat | gag | tct | ttg | gct | aaa | tat | aca | act | ctt | aga | att | gga | gga | tat | 96 |
| Lys | Tyr | Glu | Ser | Leu | Ala | Lys | Tyr | Thr | Thr | Leu | Arg | Ile | Gly | Gly | Tyr | |
| | | | 20 | | | | | 25 | | | | | 30 | | | |

| | | | | | | | | | | | | | | | | |
|---|---|---|---|---|---|---|---|---|---|---|---|---|---|---|---|---|
| gca | gac | ttt | gtt | gta | ttt | cca | gat | gaa | gac | tct | gtt | tta | aaa | ttg | ctt | 144 |
| Ala | Asp | Phe | Val | Val | Phe | Pro | Asp | Glu | Asp | Ser | Val | Leu | Lys | Leu | Leu | |
| | | 35 | | | | | 40 | | | | | 45 | | | | |

| | | | | | | | | | | | | | | | | |
|---|---|---|---|---|---|---|---|---|---|---|---|---|---|---|---|---|
| gaa | att | ata | aga | aat | gaa | gga | aca | gca | tac | tat | gtt | ata | gga | gga | ggc | 192 |
| Glu | Ile | Ile | Arg | Asn | Glu | Gly | Thr | Ala | Tyr | Tyr | Val | Ile | Gly | Gly | Gly | |
| | 50 | | | | | 55 | | | | | 60 | | | | | |

| | | | | | | | | | | | | | | | | |
|---|---|---|---|---|---|---|---|---|---|---|---|---|---|---|---|---|
| agt | aat | tta | gtt | gtg | cat | gat | gaa | gga | ttt | aag | gga | gtg | ata | atc | aat | 240 |
| Ser | Asn | Leu | Val | Val | His | Asp | Glu | Gly | Phe | Lys | Gly | Val | Ile | Ile | Asn | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| aca | aag | caa | atg | aag | aga | ata | aat | ctt | gaa | gga | ttt | acc | ata | agg | act | 288 |
| Thr | Lys | Gln | Met | Lys | Arg | Ile | Asn | Leu | Glu | Gly | Phe | Thr | Ile | Arg | Thr | |
| | | | | 85 | | | | | 90 | | | | | 95 | | |

| | | | | | | | | | | | | | | | | |
|---|---|---|---|---|---|---|---|---|---|---|---|---|---|---|---|---|
| tca | gct | ggc | gta | atg | ttg | cca | aga | ctt | ctt | gct | ttt | gtt | tta | aaa | ata | 336 |
| Ser | Ala | Gly | Val | Met | Leu | Pro | Arg | Leu | Leu | Ala | Phe | Val | Leu | Lys | Ile | |
| | | | 100 | | | | | 105 | | | | | 110 | | | |

| | | | | | | | | | | | | | | | | |
|---|---|---|---|---|---|---|---|---|---|---|---|---|---|---|---|---|
| aag | ctt | tca | gga | ata | gaa | ggt | ctt | att | ggt | ata | cca | gga | aca | gtt | gga | 384 |
| Lys | Leu | Ser | Gly | Ile | Glu | Gly | Leu | Ile | Gly | Ile | Pro | Gly | Thr | Val | Gly | |
| | | | 115 | | | | | 120 | | | | | 125 | | | |

| | | | | | | | | | | | | | | | | |
|---|---|---|---|---|---|---|---|---|---|---|---|---|---|---|---|---|
| ggt | gca | ata | aaa | ggc | aat | gca | ggc | tct | ttt | gga | tat | gaa | att | agt | gat | 432 |
| Gly | Ala | Ile | Lys | Gly | Asn | Ala | Gly | Ser | Phe | Gly | Tyr | Glu | Ile | Ser | Asp | |
| | 130 | | | | | 135 | | | | | 140 | | | | | |

| | | | | | | | | | | | | | | | | |
|---|---|---|---|---|---|---|---|---|---|---|---|---|---|---|---|---|
| tgc | ctt | gca | gaa | gtt | gaa | att | ata | acc | gat | aaa | ctg | gaa | act | aaa | att | 480 |
| Cys | Leu | Ala | Glu | Val | Glu | Ile | Ile | Thr | Asp | Lys | Leu | Glu | Thr | Lys | Ile | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| cta | aaa | aaa | caa | gat | att | act | ttt | caa | tat | cgt | agc | tca | aat | ttg | gtt | 528 |
| Leu | Lys | Lys | Gln | Asp | Ile | Thr | Phe | Gln | Tyr | Arg | Ser | Ser | Asn | Leu | Val | |
| | | | | 165 | | | | | 170 | | | | | 175 | | |

| | | | | | | | | | | | | | | | | |
|---|---|---|---|---|---|---|---|---|---|---|---|---|---|---|---|---|
| gaa | aca | tgg | ctt | ata | aaa | tct | gca | acc | ttt | agt | tta | aag | gaa | gat | gat | 576 |
| Glu | Thr | Trp | Leu | Ile | Lys | Ser | Ala | Thr | Phe | Ser | Leu | Lys | Glu | Asp | Asp | |
| | | | 180 | | | | | 185 | | | | | 190 | | | |

| | | | | | | | | | | | | | | | | |
|---|---|---|---|---|---|---|---|---|---|---|---|---|---|---|---|---|
| gga | gag | gct | ttt | aac | agg | atg | aaa | cag | ttt | ctc | caa | aga | aaa | aaa | cag | 624 |
| Gly | Glu | Ala | Phe | Asn | Arg | Met | Lys | Gln | Phe | Leu | Gln | Arg | Lys | Lys | Gln | |
| | | | 195 | | | | | 200 | | | | | 205 | | | |

| | | | | | | | | | | | | | | | | |
|---|---|---|---|---|---|---|---|---|---|---|---|---|---|---|---|---|
| act | caa | cct | tta | aga | gag | tat | tct | gca | gga | tgc | gta | ttt | aaa | aat | cca | 672 |
| Thr | Gln | Pro | Leu | Arg | Glu | Tyr | Ser | Ala | Gly | Cys | Val | Phe | Lys | Asn | Pro | |
| | 210 | | | | | 215 | | | | | 220 | | | | | |

| | | | | | | | | | | | | | | | | |
|---|---|---|---|---|---|---|---|---|---|---|---|---|---|---|---|---|
| gaa | gga | caa | tca | gca | ggt | tat | tta | ata | gaa | aaa | gca | gga | cta | aaa | gga | 720 |
| Glu | Gly | Gln | Ser | Ala | Gly | Tyr | Leu | Ile | Glu | Lys | Ala | Gly | Leu | Lys | Gly | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ttc | aga | gtt | gga | gat | ata | ctt | ata | agt | cat | ctc | cat | gct | aac | tat | ttc | 768 |
| Phe | Arg | Val | Gly | Asp | Ile | Leu | Ile | Ser | His | Leu | His | Ala | Asn | Tyr | Phe | |
| | | | | 245 | | | | | 250 | | | | | 255 | | |

| | | | | | | | | | | | | | | | | |
|---|---|---|---|---|---|---|---|---|---|---|---|---|---|---|---|---|
| att | aat | gtt | ggt | aaa | ggt | aag | gca | aat | gat | ttt | tta | aag | tta | atg | gat | 816 |
| Ile | Asn | Val | Gly | Lys | Gly | Lys | Ala | Asn | Asp | Phe | Leu | Lys | Leu | Met | Asp | |
| | | | 260 | | | | | 265 | | | | | 270 | | | |

| | | | | | | | | | | | | | | | | |
|---|---|---|---|---|---|---|---|---|---|---|---|---|---|---|---|---|
| att | gtt | aag | gaa | aag | gta | ttc | aag | ctt | ttt | tca | ata | gaa | ttg | gtg | cct | 864 |
| Ile | Val | Lys | Glu | Lys | Val | Phe | Lys | Leu | Phe | Ser | Ile | Glu | Leu | Val | Pro | |
| | | 275 | | | | | 280 | | | | | 285 | | | | |

| | | | | | | |
|---|---|---|---|---|---|---|
| gag | ata | aaa | att | ttg | gag | gct taa | 888 |
| Glu | Ile | Lys | Ile | Leu | Glu | Ala | |
| | 290 | | | | | 295 | |

<210> SEQ ID NO 38
<211> LENGTH: 295
<212> TYPE: PRT
<213> ORGANISM: Thermodesulfovibrio yellowstonii strain ATCC 51303

<400> SEQUENCE: 38

```
Met Lys Asn Ile Glu Ile Phe Leu Lys Glu Asn Arg Ile Pro Tyr Lys
1               5                   10                  15

Lys Tyr Glu Ser Leu Ala Lys Tyr Thr Thr Leu Arg Ile Gly Gly Tyr
            20                  25                  30

Ala Asp Phe Val Val Phe Pro Asp Glu Asp Ser Val Leu Lys Leu Leu
        35                  40                  45

Glu Ile Ile Arg Asn Glu Gly Thr Ala Tyr Tyr Val Ile Gly Gly Gly
    50                  55                  60

Ser Asn Leu Val Val His Asp Glu Gly Phe Lys Gly Val Ile Ile Asn
65                  70                  75                  80

Thr Lys Gln Met Lys Arg Ile Asn Leu Glu Gly Phe Thr Ile Arg Thr
                85                  90                  95

Ser Ala Gly Val Met Leu Pro Arg Leu Leu Ala Phe Val Leu Lys Ile
            100                 105                 110

Lys Leu Ser Gly Ile Glu Gly Leu Ile Gly Ile Pro Gly Thr Val Gly
        115                 120                 125

Gly Ala Ile Lys Gly Asn Ala Gly Ser Phe Gly Tyr Glu Ile Ser Asp
    130                 135                 140

Cys Leu Ala Glu Val Glu Ile Ile Thr Asp Lys Leu Glu Thr Lys Ile
145                 150                 155                 160

Leu Lys Lys Gln Asp Ile Thr Phe Gln Tyr Arg Ser Ser Asn Leu Val
                165                 170                 175

Glu Thr Trp Leu Ile Lys Ser Ala Thr Phe Ser Leu Lys Glu Asp Asp
            180                 185                 190

Gly Glu Ala Phe Asn Arg Met Lys Gln Phe Leu Gln Arg Lys Lys Gln
        195                 200                 205

Thr Gln Pro Leu Arg Glu Tyr Ser Ala Gly Cys Val Phe Lys Asn Pro
    210                 215                 220

Glu Gly Gln Ser Ala Gly Tyr Leu Ile Glu Lys Ala Gly Leu Lys Gly
225                 230                 235                 240

Phe Arg Val Gly Asp Ile Leu Ile Ser His Leu His Ala Asn Tyr Phe
                245                 250                 255

Ile Asn Val Gly Lys Gly Lys Ala Asn Asp Phe Leu Lys Leu Met Asp
            260                 265                 270

Ile Val Lys Glu Lys Val Phe Lys Leu Phe Ser Ile Glu Leu Val Pro
        275                 280                 285

Glu Ile Lys Ile Leu Glu Ala
    290                 295
```

<210> SEQ ID NO 39
<211> LENGTH: 926
<212> TYPE: DNA
<213> ORGANISM: Thermodesulfovibrio yellowstonii strain ATCC 51303
<220> FEATURE:
<221> NAME/KEY: CDS
<222> LOCATION: (15)..(920)

<400> SEQUENCE: 39

```
aggagataaa acat atg aag aat att gag att ttc ctg aaa gaa aac cgc      50
              Met Lys Asn Ile Glu Ile Phe Leu Lys Glu Asn Arg
```

```
            1               5                   10
atc ccg tac aag aaa tat gag agc ctg gcg aaa tac acg acc ctg cgt      98
Ile Pro Tyr Lys Lys Tyr Glu Ser Leu Ala Lys Tyr Thr Thr Leu Arg
         15                  20                  25 att ggt ggc tat gca gac ttt gtt gta ttt cca gac gag gac tcg gtg     146
Ile Gly Gly Tyr Ala Asp Phe Val Val Phe Pro Asp Glu Asp Ser Val
 30                  35                  40 ttg aag ctg ttg gag atc atc cgc aat gaa ggt acc gcg tac tat gtg    194
Leu Lys Leu Leu Glu Ile Ile Arg Asn Glu Gly Thr Ala Tyr Tyr Val
 45                  50                  55                  60 atc ggt ggc ggt tct aat ttg gtg gtt cac gac gag ggc ttc aaa ggc    242
Ile Gly Gly Gly Ser Asn Leu Val Val His Asp Glu Gly Phe Lys Gly
                 65                  70                  75 gtt atc att aac acc aag caa atg aag cgt att aac ctg gaa ggt ttc    290
Val Ile Ile Asn Thr Lys Gln Met Lys Arg Ile Asn Leu Glu Gly Phe
         80                  85                  90 acc atc cgt acc tct gca ggc gtc atg ctg ccg cgt ctg ctg gct ttt    338
Thr Ile Arg Thr Ser Ala Gly Val Met Leu Pro Arg Leu Leu Ala Phe
         95                 100                 105 gtt ctg aag att aag ctg agc ggt att gag ggt ctg att ggc att ccg    386
Val Leu Lys Ile Lys Leu Ser Gly Ile Glu Gly Leu Ile Gly Ile Pro
110                 115                 120 ggt acg gtg ggt ggc gcg atc aaa ggt aac gca ggc agc ttc ggt tat    434
Gly Thr Val Gly Gly Ala Ile Lys Gly Asn Ala Gly Ser Phe Gly Tyr
125                 130                 135                 140 gag atc agc gat tgc ctg gcg gaa gtt gaa atc atc act gat aag ttg    482
Glu Ile Ser Asp Cys Leu Ala Glu Val Glu Ile Ile Thr Asp Lys Leu
                145                 150                 155 gaa acc aaa att ctg aaa aag cag gac att acc ttc caa tac cgt tcc    530
Glu Thr Lys Ile Leu Lys Lys Gln Asp Ile Thr Phe Gln Tyr Arg Ser
                160                 165                 170 agc aat ttg gtc gaa acc tgg ctg att aag agc gca acg ttc agc ctg    578
Ser Asn Leu Val Glu Thr Trp Leu Ile Lys Ser Ala Thr Phe Ser Leu
        175                 180                 185 aaa gag gat gac ggt gag gcc ttc aat cgc atg aaa caa ttt ctg cag    626
Lys Glu Asp Asp Gly Glu Ala Phe Asn Arg Met Lys Gln Phe Leu Gln
        190                 195                 200 cgc aag aag caa acg cag ccg ctg cgt gaa tat agc gct ggt tgt gtg    674
Arg Lys Lys Gln Thr Gln Pro Leu Arg Glu Tyr Ser Ala Gly Cys Val
205                 210                 215                 220 ttc aaa aat ccg gaa ggc cag agc gcg ggt tac ctg att gag aaa gcc    722
Phe Lys Asn Pro Glu Gly Gln Ser Ala Gly Tyr Leu Ile Glu Lys Ala
                225                 230                 235 ggc ctg aag ggt ttc cgt gtc ggt gat atc ttg att agc cat ctg cat    770
Gly Leu Lys Gly Phe Arg Val Gly Asp Ile Leu Ile Ser His Leu His
        240                 245                 250 gcg aac tac ttt atc aac gtg ggt aag ggc aaa gcg aac gat ttt ctg    818
Ala Asn Tyr Phe Ile Asn Val Gly Lys Gly Lys Ala Asn Asp Phe Leu
        255                 260                 265 aaa ctg atg gat atc gtt aaa gag aaa gtc ttt aaa ctg ttt tcc atc    866
Lys Leu Met Asp Ile Val Lys Glu Lys Val Phe Lys Leu Phe Ser Ile
270                 275                 280 gag ctg gtc ccg gag att aag atc ctg gaa gcc cac cac cat cac cac    914
Glu Leu Val Pro Glu Ile Lys Ile Leu Glu Ala His His His His His
285                 290                 295                 300 cac taa ctcgag                                                     926
His
```

<210> SEQ ID NO 40

<211> LENGTH: 301
<212> TYPE: PRT
<213> ORGANISM: Thermodesulfovibrio yellowstonii strain ATCC 51303

<400> SEQUENCE: 40

```
Met Lys Asn Ile Glu Ile Phe Leu Lys Glu Asn Arg Ile Pro Tyr Lys
1               5                   10                  15
Lys Tyr Glu Ser Leu Ala Lys Tyr Thr Thr Leu Arg Ile Gly Gly Tyr
            20                  25                  30
Ala Asp Phe Val Val Phe Pro Asp Glu Asp Ser Val Leu Lys Leu Leu
        35                  40                  45
Glu Ile Ile Arg Asn Glu Gly Thr Ala Tyr Tyr Val Ile Gly Gly Gly
50                  55                  60
Ser Asn Leu Val Val His Asp Glu Gly Phe Lys Gly Val Ile Ile Asn
65                  70                  75                  80
Thr Lys Gln Met Lys Arg Ile Asn Leu Glu Gly Phe Thr Ile Arg Thr
                85                  90                  95
Ser Ala Gly Val Met Leu Pro Arg Leu Leu Ala Phe Val Leu Lys Ile
            100                 105                 110
Lys Leu Ser Gly Ile Glu Gly Leu Ile Gly Ile Pro Gly Thr Val Gly
        115                 120                 125
Gly Ala Ile Lys Gly Asn Ala Gly Ser Phe Gly Tyr Glu Ile Ser Asp
130                 135                 140
Cys Leu Ala Glu Val Glu Ile Ile Thr Asp Lys Leu Glu Thr Lys Ile
145                 150                 155                 160
Leu Lys Lys Gln Asp Ile Thr Phe Gln Tyr Arg Ser Ser Asn Leu Val
                165                 170                 175
Glu Thr Trp Leu Ile Lys Ser Ala Thr Phe Ser Leu Lys Glu Asp Asp
            180                 185                 190
Gly Glu Ala Phe Asn Arg Met Lys Gln Phe Leu Gln Arg Lys Lys Gln
        195                 200                 205
Thr Gln Pro Leu Arg Glu Tyr Ser Ala Gly Cys Val Phe Lys Asn Pro
    210                 215                 220
Glu Gly Gln Ser Ala Gly Tyr Leu Ile Glu Lys Ala Gly Leu Lys Gly
225                 230                 235                 240
Phe Arg Val Gly Asp Ile Leu Ile Ser His Leu His Ala Asn Tyr Phe
                245                 250                 255
Ile Asn Val Gly Lys Gly Lys Ala Asn Asp Phe Leu Lys Leu Met Asp
            260                 265                 270
Ile Val Lys Glu Lys Val Phe Lys Leu Phe Ser Ile Glu Leu Val Pro
        275                 280                 285
Glu Ile Lys Ile Leu Glu Ala His His His His His
    290                 295                 300
```

<210> SEQ ID NO 41
<211> LENGTH: 855
<212> TYPE: DNA
<213> ORGANISM: Thermotoga maritima strain ATCC 43589
<220> FEATURE:
<221> NAME/KEY: CDS
<222> LOCATION: (1)..(855)

<400> SEQUENCE: 41

```
atg ttc gaa aaa ctt tcc tgt cac acc agc ata aaa atc ggt gga aga       48
Met Phe Glu Lys Leu Ser Cys His Thr Ser Ile Lys Ile Gly Gly Arg
1               5                   10                  15 gtg aaa tat ctt gtt ctt cca aac gat gtt ttt tct ctg gaa cga gcc       96
```

```
                  Val Lys Tyr Leu Val Leu Pro Asn Asp Val Phe Ser Leu Glu Arg Ala
                                   20                  25                  30 atc act gtt ctg aag gat ctt ccg ttt caa ata atg gga ctt ggc acg         144
Ile Thr Val Leu Lys Asp Leu Pro Phe Gln Ile Met Gly Leu Gly Thr
             35                  40                  45 aac ctt ctg gtt caa gat gaa gat ctg gat atc gca gtg ttg aaa aca         192
Asn Leu Leu Val Gln Asp Glu Asp Leu Asp Ile Ala Val Leu Lys Thr
 50                  55                  60 gaa agg ttg aat caa att gaa ata aag gga gaa aaa gta ctg gta gaa         240
Glu Arg Leu Asn Gln Ile Glu Ile Lys Gly Glu Lys Val Leu Val Glu
 65                  70                  75                  80 agt gga act ccc ctg aag aga ctc tgt cta ttt ttg atg gaa gcg gaa         288
Ser Gly Thr Pro Leu Lys Arg Leu Cys Leu Phe Leu Met Glu Ala Glu
                 85                  90                  95 ctc ggg gga ctg gag ttc gca tac ggg ata ccg ggg agc gtg ggg gga         336
Leu Gly Gly Leu Glu Phe Ala Tyr Gly Ile Pro Gly Ser Val Gly Gly
            100                 105                 110 gcc atc tat atg aac gcg gga gcg tac gga gga gag att gga gag ttc         384
Ala Ile Tyr Met Asn Ala Gly Ala Tyr Gly Gly Glu Ile Gly Glu Phe
            115                 120                 125 gtc gaa gcg gtc gag gtt cta aga gat gga gaa aag acc tgg ctt tcg         432
Val Glu Ala Val Glu Val Leu Arg Asp Gly Glu Lys Thr Trp Leu Ser
130                 135                 140 agg aac gag att ttt ttc ggc tac aga gac agt acg ttt aaa agg gag         480
Arg Asn Glu Ile Phe Phe Gly Tyr Arg Asp Ser Thr Phe Lys Arg Glu
145                 150                 155                 160 aaa ttg atc ata aca cgt gtg atg atg agt ttc aaa aaa gaa aag aag         528
Lys Leu Ile Ile Thr Arg Val Met Met Ser Phe Lys Lys Glu Lys Lys
                165                 170                 175 gaa acc ata aaa gcg aag atg gac gat tac atg agg agg cgt ctg gaa         576
Glu Thr Ile Lys Ala Lys Met Asp Asp Tyr Met Arg Arg Arg Leu Glu
            180                 185                 190 aaa caa ccc ctt gac ctt ccg agt gcg ggt agt gtt ttc aaa agg cca         624
Lys Gln Pro Leu Asp Leu Pro Ser Ala Gly Ser Val Phe Lys Arg Pro
        195                 200                 205 aga gag gat ttc tac gtg gga aag gcc ata gaa tcc ctg ggt ctg aaa         672
Arg Glu Asp Phe Tyr Val Gly Lys Ala Ile Glu Ser Leu Gly Leu Lys
    210                 215                 220 ggt tac aga att gga ggg gct cag ata tcg gaa aaa cat gcg gga ttc         720
Gly Tyr Arg Ile Gly Gly Ala Gln Ile Ser Glu Lys His Ala Gly Phe
225                 230                 235                 240 att gtg aac gca gga agt gct act ttt gat gac gtg atg aaa ctc att         768
Ile Val Asn Ala Gly Ser Ala Thr Phe Asp Asp Val Met Lys Leu Ile
                245                 250                 255 gat ttt gtg aga aaa aag gtg aag gag aaa tac ggt gtg gag ctg gaa         816
Asp Phe Val Arg Lys Lys Val Lys Glu Lys Tyr Gly Val Glu Leu Glu
            260                 265                 270 acg gag gtt gaa atc tgg tgg aat gga aga cgg tgg tga                     855
Thr Glu Val Glu Ile Trp Trp Asn Gly Arg Arg Trp
        275                 280

<210> SEQ ID NO 42
<211> LENGTH: 284
<212> TYPE: PRT
<213> ORGANISM: Thermotoga maritima strain ATCC 43589

<400> SEQUENCE: 42

Met Phe Glu Lys Leu Ser Cys His Thr Ser Ile Lys Ile Gly Gly Arg
1               5                   10                  15

Val Lys Tyr Leu Val Leu Pro Asn Asp Val Phe Ser Leu Glu Arg Ala
```

```
                20                  25                  30
Ile Thr Val Leu Lys Asp Leu Pro Phe Gln Ile Met Gly Leu Gly Thr
                35                  40                  45

Asn Leu Leu Val Gln Asp Glu Asp Leu Asp Ile Ala Val Leu Lys Thr
             50                  55                  60

Glu Arg Leu Asn Gln Ile Glu Ile Lys Gly Lys Val Leu Val Glu
 65                  70                  75                  80

Ser Gly Thr Pro Leu Lys Arg Leu Cys Leu Phe Leu Met Glu Ala Glu
                 85                  90                  95

Leu Gly Gly Leu Glu Phe Ala Tyr Gly Ile Pro Gly Ser Val Gly Gly
                100                 105                 110

Ala Ile Tyr Met Asn Ala Gly Ala Tyr Gly Gly Glu Ile Gly Glu Phe
            115                 120                 125

Val Glu Ala Val Glu Val Leu Arg Asp Gly Glu Lys Thr Trp Leu Ser
            130                 135                 140

Arg Asn Glu Ile Phe Phe Gly Tyr Arg Asp Ser Thr Phe Lys Arg Glu
145                 150                 155                 160

Lys Leu Ile Ile Thr Arg Val Met Met Ser Phe Lys Lys Glu Lys Lys
                165                 170                 175

Glu Thr Ile Lys Ala Lys Met Asp Asp Tyr Met Arg Arg Leu Glu
                180                 185                 190

Lys Gln Pro Leu Asp Leu Pro Ser Ala Gly Ser Val Phe Lys Arg Pro
            195                 200                 205

Arg Glu Asp Phe Tyr Val Gly Lys Ala Ile Glu Ser Leu Gly Leu Lys
            210                 215                 220

Gly Tyr Arg Ile Gly Gly Ala Gln Ile Ser Glu Lys His Ala Gly Phe
225                 230                 235                 240

Ile Val Asn Ala Gly Ser Ala Thr Phe Asp Asp Val Met Lys Leu Ile
                245                 250                 255

Asp Phe Val Arg Lys Val Lys Glu Lys Tyr Gly Val Glu Leu Glu
            260                 265                 270

Thr Glu Val Glu Ile Trp Trp Asn Gly Arg Arg Trp
            275                 280

<210> SEQ ID NO 43
<211> LENGTH: 893
<212> TYPE: DNA
<213> ORGANISM: Thermotoga maritima strain ATCC 43589
<220> FEATURE:
<221> NAME/KEY: CDS
<222> LOCATION: (15)..(887)

<400> SEQUENCE: 43
aggagataaa acat atg ttc gaa aag ctc tcg tgt cat acc agc atc aaa      50
               Met Phe Glu Lys Leu Ser Cys His Thr Ser Ile Lys
                 1               5                  10 atc ggc ggt cgt gta aag tat ttg gtg ttg ccg aac gac gtg ttt agc      98
Ile Gly Gly Arg Val Lys Tyr Leu Val Leu Pro Asn Asp Val Phe Ser
        15                  20                  25 ctg gaa cgt gca att acc gtc ctg aaa gat ctg ccg ttc cag atc atg    146
Leu Glu Arg Ala Ile Thr Val Leu Lys Asp Leu Pro Phe Gln Ile Met
    30                  35                  40 ggc ctg ggt acg aat ctg ctg gtt cag gac gag gat ctg gat att gca    194
Gly Leu Gly Thr Asn Leu Leu Val Gln Asp Glu Asp Leu Asp Ile Ala
45                  50                  55                  60 gtt ctg aaa acc gaa cgc ctg aac caa atc gag att aaa ggc gaa aag    242
Val Leu Lys Thr Glu Arg Leu Asn Gln Ile Glu Ile Lys Gly Glu Lys
```

```
                        65                  70                  75
gtg ttg gtg gaa agc ggc acg ccg ctg aag cgt ctg tgc ctg ttc ctg      290
Val Leu Val Glu Ser Gly Thr Pro Leu Lys Arg Leu Cys Leu Phe Leu
            80                  85                  90 atg gaa gcc gag ctg ggt ggt ttg gag ttt gct tac ggc att ccg ggc      338
Met Glu Ala Glu Leu Gly Gly Leu Glu Phe Ala Tyr Gly Ile Pro Gly
            95                  100                 105 agc gtg ggt ggt gcg atc tac atg aac gct ggt gcg tac ggt ggt gaa      386
Ser Val Gly Gly Ala Ile Tyr Met Asn Ala Gly Ala Tyr Gly Gly Glu
            110                 115                 120 atc ggc gag ttt gtc gag gcg gtc gaa gtt ctg cgc gac ggt gag aaa      434
Ile Gly Glu Phe Val Glu Ala Val Glu Val Leu Arg Asp Gly Glu Lys
125                 130                 135                 140 acc tgg ctg tct cgt aat gag att ttc ttc ggt tac cgt gac agc acg      482
Thr Trp Leu Ser Arg Asn Glu Ile Phe Phe Gly Tyr Arg Asp Ser Thr
                    145                 150                 155 ttc aaa cgt gag aag ctg atc atc acg cgt gtc atg atg agc ttt aag      530
Phe Lys Arg Glu Lys Leu Ile Ile Thr Arg Val Met Met Ser Phe Lys
                160                 165                 170 aaa gag aag aaa gaa acc att aag gcg aag atg gat gac tat atg cgt      578
Lys Glu Lys Lys Glu Thr Ile Lys Ala Lys Met Asp Asp Tyr Met Arg
            175                 180                 185 cgt cgt ctg gag aaa cag ccg ctg gat ctg ccg agc gca ggc agc gtt      626
Arg Arg Leu Glu Lys Gln Pro Leu Asp Leu Pro Ser Ala Gly Ser Val
        190                 195                 200 ttc aag cgt cca cgc gag gac ttt tac gtc ggt aag gcg att gag tcc      674
Phe Lys Arg Pro Arg Glu Asp Phe Tyr Val Gly Lys Ala Ile Glu Ser
205                 210                 215                 220 ctg ggc ctg aaa ggc tat cgc att ggt ggt gca caa atc agc gag aaa      722
Leu Gly Leu Lys Gly Tyr Arg Ile Gly Gly Ala Gln Ile Ser Glu Lys
                    225                 230                 235 cat gcg ggt ttc atc gtg aat gcc ggc tcc gcc acc ttt gac gac gtt      770
His Ala Gly Phe Ile Val Asn Ala Gly Ser Ala Thr Phe Asp Asp Val
                240                 245                 250 atg aaa ttg att gat ttt gtt cgc aaa aag gtt aaa gag aag tat ggt      818
Met Lys Leu Ile Asp Phe Val Arg Lys Lys Val Lys Glu Lys Tyr Gly
            255                 260                 265 gtc gag ctg gaa act gaa gtg gaa att tgg tgg aac ggt cgc cgc tgg      866
Val Glu Leu Glu Thr Glu Val Glu Ile Trp Trp Asn Gly Arg Arg Trp
        270                 275                 280 cac cac cac cat cac cac taa ctcgag                                    893
His His His His His His
285                 290

<210> SEQ ID NO 44
<211> LENGTH: 290
<212> TYPE: PRT
<213> ORGANISM: Thermotoga maritima strain ATCC 43589

<400> SEQUENCE: 44

Met Phe Glu Lys Leu Ser Cys His Thr Ser Ile Lys Ile Gly Gly Arg
1               5                   10                  15

Val Lys Tyr Leu Val Leu Pro Asn Asp Val Phe Ser Leu Glu Arg Ala
            20                  25                  30

Ile Thr Val Leu Lys Asp Leu Pro Phe Gln Ile Met Gly Leu Gly Thr
        35                  40                  45

Asn Leu Leu Val Gln Asp Glu Asp Leu Asp Ile Ala Val Leu Lys Thr
    50                  55                  60

Glu Arg Leu Asn Gln Ile Glu Ile Lys Gly Glu Lys Val Leu Val Glu
```

```
                65                  70                  75                  80
Ser Gly Thr Pro Leu Lys Arg Leu Cys Leu Phe Leu Met Glu Ala Glu
                    85                  90                  95

Leu Gly Gly Leu Glu Phe Ala Tyr Gly Ile Pro Gly Ser Val Gly Gly
                100                 105                 110

Ala Ile Tyr Met Asn Ala Gly Ala Tyr Gly Gly Glu Ile Gly Glu Phe
            115                 120                 125

Val Glu Ala Val Glu Val Leu Arg Asp Gly Glu Lys Thr Trp Leu Ser
130                 135                 140

Arg Asn Glu Ile Phe Phe Gly Tyr Arg Asp Ser Thr Phe Lys Arg Glu
145                 150                 155                 160

Lys Leu Ile Ile Thr Arg Val Met Met Ser Phe Lys Glu Lys Lys
                165                 170                 175

Glu Thr Ile Lys Ala Lys Met Asp Asp Tyr Met Arg Arg Leu Glu
            180                 185                 190

Lys Gln Pro Leu Asp Leu Pro Ser Ala Gly Ser Val Phe Lys Arg Pro
            195                 200                 205

Arg Glu Asp Phe Tyr Val Gly Lys Ala Ile Glu Ser Leu Gly Leu Lys
        210                 215                 220

Gly Tyr Arg Ile Gly Gly Ala Gln Ile Ser Glu Lys His Ala Gly Phe
225                 230                 235                 240

Ile Val Asn Ala Gly Ser Ala Thr Phe Asp Asp Val Met Lys Leu Ile
                245                 250                 255

Asp Phe Val Arg Lys Val Lys Glu Lys Tyr Gly Val Glu Leu Glu
            260                 265                 270

Thr Glu Val Glu Ile Trp Trp Asn Gly Arg Arg Trp His His His
        275                 280                 285

His His
    290

<210> SEQ ID NO 45
<211> LENGTH: 867
<212> TYPE: DNA
<213> ORGANISM: Sulfurihydrogenibium sp. strain YO3AOP1
<220> FEATURE:
<221> NAME/KEY: CDS
<222> LOCATION: (1)..(867)

<400> SEQUENCE: 45 atg att tta aaa acg att gaa tat caa gaa aat ata gac ctt agg aat     48
Met Ile Leu Lys Thr Ile Glu Tyr Gln Glu Asn Ile Asp Leu Arg Asn
1               5                   10                  15 ttt tgc act ata aaa gtt ggc gga aaa gga aag att gta tat ttt cca     96
Phe Cys Thr Ile Lys Val Gly Gly Lys Gly Lys Ile Val Tyr Phe Pro
                20                  25                  30 aaa gat cac aaa gaa atc tct att tta att aaa gag tat gat aac atc    144
Lys Asp His Lys Glu Ile Ser Ile Leu Ile Lys Glu Tyr Asp Asn Ile
            35                  40                  45 tat cca ctt gga att gga agc aat cta att ttt tcc gat ggg att gtg    192
Tyr Pro Leu Gly Ile Gly Ser Asn Leu Ile Phe Ser Asp Gly Ile Val
        50                  55                  60 aat aaa gtt ttt gtc cat tct aag aat cta aaa aaa tat gaa ata gaa    240
Asn Lys Val Phe Val His Ser Lys Asn Leu Lys Lys Tyr Glu Ile Glu
65                  70                  75                  80 aat caa aac gat att ttt tac atc acg gcg gaa gcc ggc gta agc ttt    288
Asn Gln Asn Asp Ile Phe Tyr Ile Thr Ala Glu Ala Gly Val Ser Phe
                85                  90                  95
```

| | | |
|---|---|---|
| aaa acc ata gtt tca gta gta aaa aaa tac aac ctt gaa gga ttt gaa<br>Lys Thr Ile Val Ser Val Val Lys Lys Tyr Asn Leu Glu Gly Phe Glu<br>100 105 110 | | 336 |
| aac cta tcc ggc att cct gca acc gtt ggt ggg gca act gca atg aac<br>Asn Leu Ser Gly Ile Pro Ala Thr Val Gly Gly Ala Thr Ala Met Asn<br>115 120 125 | | 384 |
| gca gga gct tat gga agc gat atc ttt gat tta ata gaa gag gtt tgg<br>Ala Gly Ala Tyr Gly Ser Asp Ile Phe Asp Leu Ile Glu Glu Val Trp<br>130 135 140 | | 432 |
| tgg ata gac aga gaa gga cgg cta aat cat tca aaa aaa gaa gag att<br>Trp Ile Asp Arg Glu Gly Arg Leu Asn His Ser Lys Lys Glu Glu Ile<br>145 150 155 160 | | 480 |
| aaa tac tct tac aga tac tcc caa ttt caa aac gga ggt ttt gtt tat<br>Lys Tyr Ser Tyr Arg Tyr Ser Gln Phe Gln Asn Gly Gly Phe Val Tyr<br>165 170 175 | | 528 |
| aaa gtg aag cta aag ctt aga aaa agt gat aaa aac ata tca gag att<br>Lys Val Lys Leu Lys Leu Arg Lys Ser Asp Lys Asn Ile Ser Glu Ile<br>180 185 190 | | 576 |
| ata aaa aat cat ctg ctt gat aga aac agt aag caa ccg cta gat tta<br>Ile Lys Asn His Leu Leu Asp Arg Asn Ser Lys Gln Pro Leu Asp Leu<br>195 200 205 | | 624 |
| cca aca gcc ggg tca act tac aaa aat cca ccg gga aca tat gcc ggc<br>Pro Thr Ala Gly Ser Thr Tyr Lys Asn Pro Pro Gly Thr Tyr Ala Gly<br>210 215 220 | | 672 |
| aaa ctg att gaa gca gtt ggc tta aaa ggt tat aga ata aac gat ata<br>Lys Leu Ile Glu Ala Val Gly Leu Lys Gly Tyr Arg Ile Asn Asp Ile<br>225 230 235 240 | | 720 |
| gga ttt tct gaa aaa cat gca aac ttt ctt gta aac tat gga aat gct<br>Gly Phe Ser Glu Lys His Ala Asn Phe Leu Val Asn Tyr Gly Asn Ala<br>245 250 255 | | 768 |
| gag ttt aaa gac cta ata aaa ctc ttg gaa ctt gcc gaa aaa aaa gta<br>Glu Phe Lys Asp Leu Ile Lys Leu Leu Glu Leu Ala Glu Lys Lys Val<br>260 265 270 | | 816 |
| tta gac gaa ttt aag ata aat ctt gaa aga gag gtt aaa atc att gac<br>Leu Asp Glu Phe Lys Ile Asn Leu Glu Arg Glu Val Lys Ile Ile Asp<br>275 280 285 | | 864 |
| taa | | 867 |

<210> SEQ ID NO 46
<211> LENGTH: 288
<212> TYPE: PRT
<213> ORGANISM: Sulfurihydrogenibium sp. strain YO3AOP1

<400> SEQUENCE: 46

Met Ile Leu Lys Thr Ile Glu Tyr Gln Glu Asn Ile Asp Leu Arg Asn
1               5                   10                  15

Phe Cys Thr Ile Lys Val Gly Gly Lys Gly Lys Ile Val Tyr Phe Pro
            20                  25                  30

Lys Asp His Lys Glu Ile Ser Ile Leu Ile Lys Glu Tyr Asp Asn Ile
        35                  40                  45

Tyr Pro Leu Gly Ile Gly Ser Asn Leu Ile Phe Ser Asp Gly Ile Val
    50                  55                  60

Asn Lys Val Phe Val His Ser Lys Asn Leu Lys Lys Tyr Glu Ile Glu
65                  70                  75                  80

Asn Gln Asn Asp Ile Phe Tyr Ile Thr Ala Glu Ala Gly Val Ser Phe
                85                  90                  95

Lys Thr Ile Val Ser Val Val Lys Lys Tyr Asn Leu Glu Gly Phe Glu
            100                 105                 110

```
Asn Leu Ser Gly Ile Pro Ala Thr Val Gly Gly Ala Thr Ala Met Asn
            115                 120                 125

Ala Gly Ala Tyr Gly Ser Asp Ile Phe Asp Leu Ile Glu Glu Val Trp
        130                 135                 140

Trp Ile Asp Arg Glu Gly Arg Leu Asn His Ser Lys Lys Glu Ile
145                 150                 155                 160

Lys Tyr Ser Tyr Arg Tyr Ser Gln Phe Gln Asn Gly Gly Phe Val Tyr
                165                 170                 175

Lys Val Lys Leu Lys Leu Arg Lys Ser Asp Lys Asn Ile Ser Glu Ile
            180                 185                 190

Ile Lys Asn His Leu Leu Asp Arg Asn Ser Lys Gln Pro Leu Asp Leu
        195                 200                 205

Pro Thr Ala Gly Ser Thr Tyr Lys Asn Pro Pro Gly Thr Tyr Ala Gly
    210                 215                 220

Lys Leu Ile Glu Ala Val Gly Leu Lys Gly Tyr Arg Ile Asn Asp Ile
225                 230                 235                 240

Gly Phe Ser Glu Lys His Ala Asn Phe Leu Val Asn Tyr Gly Asn Ala
                245                 250                 255

Glu Phe Lys Asp Leu Ile Lys Leu Leu Glu Leu Ala Glu Lys Lys Val
            260                 265                 270

Leu Asp Glu Phe Lys Ile Asn Leu Glu Arg Glu Val Lys Ile Ile Asp
        275                 280                 285

<210> SEQ ID NO 47
<211> LENGTH: 905
<212> TYPE: DNA
<213> ORGANISM: Sulfurihydrogenibium sp. strain YO3AOP1
<220> FEATURE:
<221> NAME/KEY: CDS
<222> LOCATION: (15)..(899)

<400> SEQUENCE: 47
aggaggtaaa acat atg att ttg aaa act att gaa tac cag gaa aac att      50
              Met Ile Leu Lys Thr Ile Glu Tyr Gln Glu Asn Ile
                1               5                   10 gat ttg cgt aac ttt tgt act atc aag gtg ggc ggt aag ggc aag atc      98
Asp Leu Arg Asn Phe Cys Thr Ile Lys Val Gly Gly Lys Gly Lys Ile
        15                  20                  25 gtg tac ttt cca aaa gat cac aaa gaa att agc att ctg att aaa gag     146
Val Tyr Phe Pro Lys Asp His Lys Glu Ile Ser Ile Leu Ile Lys Glu
    30                  35                  40 tat gac aat atc tat ccg ctg ggt att ggt tcg aat ctg atc ttt agc     194
Tyr Asp Asn Ile Tyr Pro Leu Gly Ile Gly Ser Asn Leu Ile Phe Ser
45                  50                  55                  60 gat ggt atc gtt aac aag gtt ttc gtg cat tcc aag aac ctg aaa aag     242
Asp Gly Ile Val Asn Lys Val Phe Val His Ser Lys Asn Leu Lys Lys
                65                  70                  75 tat gaa att gag aac caa aat gac atc ttc tac atc acc gcg gaa gcc     290
Tyr Glu Ile Glu Asn Gln Asn Asp Ile Phe Tyr Ile Thr Ala Glu Ala
            80                  85                  90 ggc gtc agc ttc aaa acc att gtc agc gtt gtc aaa aag tat aat ctg     338
Gly Val Ser Phe Lys Thr Ile Val Ser Val Val Lys Lys Tyr Asn Leu
        95                  100                 105 gaa ggt ttc gag aat ttg agc ggt att ccg gca acg gtt ggt ggc gcg     386
Glu Gly Phe Glu Asn Leu Ser Gly Ile Pro Ala Thr Val Gly Gly Ala
    110                 115                 120 acc gct atg aat gcc ggt gcg tac ggc tcc gac att ttt gat ctg atc     434
Thr Ala Met Asn Ala Gly Ala Tyr Gly Ser Asp Ile Phe Asp Leu Ile
125                 130                 135                 140
```

```
gaa gaa gtt tgg tgg att gac cgt gag ggt cgc ctg aat cac agc aag      482
Glu Glu Val Trp Trp Ile Asp Arg Glu Gly Arg Leu Asn His Ser Lys
            145                 150                 155 aaa gaa gaa atc aag tac tct tac cgc tat tct cag ttt caa aac ggt      530
Lys Glu Glu Ile Lys Tyr Ser Tyr Arg Tyr Ser Gln Phe Gln Asn Gly
        160                 165                 170 ggc ttt gtg tat aag gtc aaa ctg aaa ctg cgt aaa agc gac aag aac      578
Gly Phe Val Tyr Lys Val Lys Leu Lys Leu Arg Lys Ser Asp Lys Asn
    175                 180                 185 atc agc gag att atc aaa aac cac ctg ttg gat cgt aat agc aag cag      626
Ile Ser Glu Ile Ile Lys Asn His Leu Leu Asp Arg Asn Ser Lys Gln
190                 195                 200 ccg ctg gat ctg ccg acc gcc ggt agc acc tac aaa aac ccg cct ggc      674
Pro Leu Asp Leu Pro Thr Ala Gly Ser Thr Tyr Lys Asn Pro Pro Gly
205                 210                 215                 220 acg tac gcg ggt aag ctg atc gag gcg gtg ggc ttg aaa ggt tat cgt      722
Thr Tyr Ala Gly Lys Leu Ile Glu Ala Val Gly Leu Lys Gly Tyr Arg
                225                 230                 235 atc aac gac atc ggc ttc agc gag aag cat gcg aac ttc ctg gtc aac      770
Ile Asn Asp Ile Gly Phe Ser Glu Lys His Ala Asn Phe Leu Val Asn
            240                 245                 250 tac ggt aat gca gag ttc aaa gac ctg atc aaa ctg ctg gag ctg gca      818
Tyr Gly Asn Ala Glu Phe Lys Asp Leu Ile Lys Leu Leu Glu Leu Ala
        255                 260                 265 gag aag aaa gtt ctg gac gag ttc aag atc aat ctg gag cgc gag gtg      866
Glu Lys Lys Val Leu Asp Glu Phe Lys Ile Asn Leu Glu Arg Glu Val
    270                 275                 280 aag att att gat cac cat cac cac cat cac taa ctcgag                    905
Lys Ile Ile Asp His His His His His His
285                 290
```

<210> SEQ ID NO 48
<211> LENGTH: 294
<212> TYPE: PRT
<213> ORGANISM: Sulfurihydrogenibium sp. strain YO3AOP1

<400> SEQUENCE: 48

```
Met Ile Leu Lys Thr Ile Glu Tyr Gln Glu Asn Ile Asp Leu Arg Asn
1               5                   10                  15

Phe Cys Thr Ile Lys Val Gly Lys Gly Lys Ile Val Tyr Phe Pro
            20                  25                  30

Lys Asp His Lys Glu Ile Ser Ile Leu Ile Lys Glu Tyr Asp Asn Ile
        35                  40                  45

Tyr Pro Leu Gly Ile Gly Ser Asn Leu Ile Phe Ser Asp Gly Ile Val
    50                  55                  60

Asn Lys Val Phe Val His Ser Lys Asn Leu Lys Lys Tyr Glu Ile Glu
65                  70                  75                  80

Asn Gln Asn Asp Ile Phe Tyr Ile Thr Ala Glu Ala Gly Val Ser Phe
                85                  90                  95

Lys Thr Ile Val Ser Val Val Lys Lys Tyr Asn Leu Glu Gly Phe Glu
            100                 105                 110

Asn Leu Ser Gly Ile Pro Ala Thr Val Gly Gly Ala Thr Ala Met Asn
        115                 120                 125

Ala Gly Ala Tyr Gly Ser Asp Ile Phe Asp Leu Ile Glu Glu Val Trp
    130                 135                 140

Trp Ile Asp Arg Glu Gly Arg Leu Asn His Ser Lys Lys Glu Glu Ile
145                 150                 155                 160
```

```
Lys Tyr Ser Tyr Arg Tyr Ser Gln Phe Gln Asn Gly Gly Phe Val Tyr
            165                 170                 175
Lys Val Lys Leu Lys Leu Arg Lys Ser Asp Lys Asn Ile Ser Glu Ile
        180                 185                 190
Ile Lys Asn His Leu Leu Asp Arg Asn Ser Lys Gln Pro Leu Asp Leu
        195                 200                 205
Pro Thr Ala Gly Ser Thr Tyr Lys Asn Pro Pro Gly Thr Tyr Ala Gly
    210                 215                 220
Lys Leu Ile Glu Ala Val Gly Leu Lys Gly Tyr Arg Ile Asn Asp Ile
225                 230                 235                 240
Gly Phe Ser Glu Lys His Ala Asn Phe Leu Val Asn Tyr Gly Asn Ala
                245                 250                 255
Glu Phe Lys Asp Leu Ile Lys Leu Leu Glu Leu Ala Glu Lys Lys Val
            260                 265                 270
Leu Asp Glu Phe Lys Ile Asn Leu Glu Arg Glu Val Lys Ile Ile Asp
        275                 280                 285
His His His His His His
    290

<210> SEQ ID NO 49
<211> LENGTH: 867
<212> TYPE: DNA
<213> ORGANISM: Sulfurihydrogenibium azorense
<220> FEATURE:
<221> NAME/KEY: CDS
<222> LOCATION: (1)..(867)

<400> SEQUENCE: 49 atg gat aaa ata gaa cat cta aaa aac ttt agt ctt aaa gat ttt tgc     48
Met Asp Lys Ile Glu His Leu Lys Asn Phe Ser Leu Lys Asp Phe Cys
1               5                   10                  15 act ata aaa ata ggt gga gta gga aaa gtt gtt ttt ttt cct aaa aat     96
Thr Ile Lys Ile Gly Gly Val Gly Lys Val Val Phe Phe Pro Lys Asn
            20                  25                  30 gtt gaa gaa atc tca ttt cta ata aga gag tat gga aaa gaa aat atc    144
Val Glu Glu Ile Ser Phe Leu Ile Arg Glu Tyr Gly Lys Glu Asn Ile
        35                  40                  45 ttt ccc ctt gga ata gga agt aat tta att ttt tca gat ggg ttt ata    192
Phe Pro Leu Gly Ile Gly Ser Asn Leu Ile Phe Ser Asp Gly Phe Ile
    50                  55                  60 gat aaa gtc ttt atc cac tct aaa aac tta aaa aaa tgc gag ata acc    240
Asp Lys Val Phe Ile His Ser Lys Asn Leu Lys Lys Cys Glu Ile Thr
65                  70                  75                  80 caa gaa aac gat ata ttt tac ttg acc tta gaa gca ggg gtt agt ttt    288
Gln Glu Asn Asp Ile Phe Tyr Leu Thr Leu Glu Ala Gly Val Ser Phe
                85                  90                  95 aaa act att aac aat ata gta aaa aag tac aat ctt gaa gga ttt gaa    336
Lys Thr Ile Asn Asn Ile Val Lys Lys Tyr Asn Leu Glu Gly Phe Glu
            100                 105                 110 aat ctc tct gga att cct gcc acg gtt ggt gga gct gtt gcg atg aac    384
Asn Leu Ser Gly Ile Pro Ala Thr Val Gly Gly Ala Val Ala Met Asn
        115                 120                 125 gca ggc gcc tat ggg tca gag att ttt gat att tta gaa gaa gtt tgg    432
Ala Gly Ala Tyr Gly Ser Glu Ile Phe Asp Ile Leu Glu Glu Val Trp
    130                 135                 140 tgg ata gat aaa gac ggt aat tta ata cat tca aaa aag cag gat ata    480
Trp Ile Asp Lys Asp Gly Asn Leu Ile His Ser Lys Lys Gln Asp Ile
145                 150                 155                 160 aag cac tat tac agg tac tcc cag ttt caa gaa gaa gga ttt gtt tac    528
```

```
                                                                            -continued Lys His Tyr Tyr Arg Tyr Ser Gln Phe Gln Glu Glu Gly Phe Val Tyr
            165                 170                 175 aaa gta aaa ata aag tta aaa aaa agt aat aaa gat att tcc agc atc        576
Lys Val Lys Ile Lys Leu Lys Lys Ser Asn Lys Asp Ile Ser Ser Ile
        180                 185                 190 atc aaa cag cat ctt tta gat aga aac aaa aaa caa ccc ctt gac tta        624
Ile Lys Gln His Leu Leu Asp Arg Asn Lys Lys Gln Pro Leu Asp Leu
            195                 200                 205 cca aca gca ggc tct aca tac aaa aat cca cca caa acc tat gca gga        672
Pro Thr Ala Gly Ser Thr Tyr Lys Asn Pro Pro Gln Thr Tyr Ala Gly
    210                 215                 220 aaa ctt ata gag cag gta gga cta aaa ggt tat aga ata aat gat ata        720
Lys Leu Ile Glu Gln Val Gly Leu Lys Gly Tyr Arg Ile Asn Asp Ile
225                 230                 235                 240 ggt ttt tcc tca aaa cac gca aat ttt tta gtt aac tac aaa gat gca        768
Gly Phe Ser Ser Lys His Ala Asn Phe Leu Val Asn Tyr Lys Asp Ala
                245                 250                 255 aga ttt aaa gac tta ata aat ctc ctt gaa ctt gcc gaa aag aaa gta        816
Arg Phe Lys Asp Leu Ile Asn Leu Leu Glu Leu Ala Glu Lys Lys Val
            260                 265                 270 tac gaa aaa ttt gga ata caa ctt gaa aga gag gta aag ata gtt gag        864
Tyr Glu Lys Phe Gly Ile Gln Leu Glu Arg Glu Val Lys Ile Val Glu
        275                 280                 285 taa                                                                    867

<210> SEQ ID NO 50
<211> LENGTH: 288
<212> TYPE: PRT
<213> ORGANISM: Sulfurihydrogenibium azorense

<400> SEQUENCE: 50

Met Asp Lys Ile Glu His Leu Lys Asn Phe Ser Leu Lys Asp Phe Cys
1               5                   10                  15

Thr Ile Lys Ile Gly Gly Val Gly Lys Val Val Phe Phe Pro Lys Asn
            20                  25                  30

Val Glu Glu Ile Ser Phe Leu Ile Arg Glu Tyr Gly Lys Glu Asn Ile
        35                  40                  45

Phe Pro Leu Gly Ile Gly Ser Asn Leu Ile Phe Ser Asp Gly Phe Ile
    50                  55                  60

Asp Lys Val Phe Ile His Ser Lys Asn Leu Lys Lys Cys Glu Ile Thr
65                  70                  75                  80

Gln Glu Asn Asp Ile Phe Tyr Leu Thr Leu Glu Ala Gly Val Ser Phe
                85                  90                  95

Lys Thr Ile Asn Asn Ile Val Lys Lys Tyr Asn Leu Glu Gly Phe Glu
            100                 105                 110

Asn Leu Ser Gly Ile Pro Ala Thr Val Gly Gly Ala Val Ala Met Asn
        115                 120                 125

Ala Gly Ala Tyr Gly Ser Glu Ile Phe Asp Ile Leu Glu Glu Val Trp
    130                 135                 140

Trp Ile Asp Lys Asp Gly Asn Leu Ile His Ser Lys Lys Gln Asp Ile
145                 150                 155                 160

Lys His Tyr Tyr Arg Tyr Ser Gln Phe Gln Glu Glu Gly Phe Val Tyr
                165                 170                 175

Lys Val Lys Ile Lys Leu Lys Lys Ser Asn Lys Asp Ile Ser Ser Ile
            180                 185                 190

Ile Lys Gln His Leu Leu Asp Arg Asn Lys Lys Gln Pro Leu Asp Leu
        195                 200                 205
```

```
Pro Thr Ala Gly Ser Thr Tyr Lys Asn Pro Pro Gln Thr Tyr Ala Gly
        210                 215                 220

Lys Leu Ile Glu Gln Val Gly Leu Lys Gly Tyr Arg Ile Asn Asp Ile
225                 230                 235                 240

Gly Phe Ser Ser Lys His Ala Asn Phe Leu Val Asn Tyr Lys Asp Ala
                245                 250                 255

Arg Phe Lys Asp Leu Ile Asn Leu Leu Glu Leu Ala Glu Lys Lys Val
            260                 265                 270

Tyr Glu Lys Phe Gly Ile Gln Leu Glu Arg Glu Val Lys Ile Val Glu
        275                 280                 285

<210> SEQ ID NO 51
<211> LENGTH: 905
<212> TYPE: DNA
<213> ORGANISM: Sulfurihydrogenibium azorense
<220> FEATURE:
<221> NAME/KEY: CDS
<222> LOCATION: (15)..(899)

<400> SEQUENCE: 51
aggaggtaaa acat atg gat aag att gaa cat ttg aag aac ttt agc ttg      50
               Met Asp Lys Ile Glu His Leu Lys Asn Phe Ser Leu
                1               5                   10 aaa gat ttt tgc acc att aag att ggc ggt gtc ggc aaa gtt gtg ttc      98
Lys Asp Phe Cys Thr Ile Lys Ile Gly Gly Val Gly Lys Val Val Phe
        15                  20                  25 ttt ccg aag aac gtg gaa gag att agc ttc ctg atc cgt gag tat ggt     146
Phe Pro Lys Asn Val Glu Glu Ile Ser Phe Leu Ile Arg Glu Tyr Gly
    30                  35                  40 aaa gag aat atc ttc ccg ctg ggt att ggt agc aat ctg atc ttt tcc     194
Lys Glu Asn Ile Phe Pro Leu Gly Ile Gly Ser Asn Leu Ile Phe Ser
45                  50                  55                  60 gac ggc ttc atc gat aag gtg ttc att cac agc aag aac ctg aag aaa     242
Asp Gly Phe Ile Asp Lys Val Phe Ile His Ser Lys Asn Leu Lys Lys
                65                  70                  75 tgt gag att acc caa gaa aac gac atc ttc tac ctg acc ctg gaa gcc     290
Cys Glu Ile Thr Gln Glu Asn Asp Ile Phe Tyr Leu Thr Leu Glu Ala
            80                  85                  90 ggt gtt agc ttc aaa acg atc aat aac att gtg aag aaa tac aat ctg     338
Gly Val Ser Phe Lys Thr Ile Asn Asn Ile Val Lys Lys Tyr Asn Leu
        95                  100                 105 gaa ggt ttc gag aac ctg tcc ggc atc ccg gcg acg gtt ggc ggt gca     386
Glu Gly Phe Glu Asn Leu Ser Gly Ile Pro Ala Thr Val Gly Gly Ala
    110                 115                 120 gtt gcg atg aat gct ggc gcg tac ggt agc gag att ttc gac att ctg     434
Val Ala Met Asn Ala Gly Ala Tyr Gly Ser Glu Ile Phe Asp Ile Leu
125                 130                 135                 140 gaa gag gtc tgg tgg att gac aaa gat ggc aac ctg att cat agc aag     482
Glu Glu Val Trp Trp Ile Asp Lys Asp Gly Asn Leu Ile His Ser Lys
                145                 150                 155 aag cag gac atc aag cat tac tac cgc tat agc cag ttt cag gaa gag     530
Lys Gln Asp Ile Lys His Tyr Tyr Arg Tyr Ser Gln Phe Gln Glu Glu
            160                 165                 170 ggc ttt gtt tac aaa gtg aaa atc aaa ctg aag aaa agc aac aaa gat     578
Gly Phe Val Tyr Lys Val Lys Ile Lys Leu Lys Lys Ser Asn Lys Asp
        175                 180                 185 att tcg tct att atc aaa cag cat ttg ctg gac cgt aac aag aaa caa     626
Ile Ser Ser Ile Ile Lys Gln His Leu Leu Asp Arg Asn Lys Lys Gln
    190                 195                 200
```

```
ccg ctg gat ttg ccg acc gcg ggt agc act tac aag aat cca ccg caa         674
Pro Leu Asp Leu Pro Thr Ala Gly Ser Thr Tyr Lys Asn Pro Pro Gln
205                 210                 215                 220 acg tac gca ggc aag ctg atc gaa cag gtc ggt ctg aaa ggt tat cgt         722
Thr Tyr Ala Gly Lys Leu Ile Glu Gln Val Gly Leu Lys Gly Tyr Arg
                225                 230                 235 atc aat gac att ggt ttt agc tct aag cac gcc aat ttt ctg gtt aac         770
Ile Asn Asp Ile Gly Phe Ser Ser Lys His Ala Asn Phe Leu Val Asn
            240                 245                 250 tat aaa gat gcg cgc ttc aaa gac ctg atc aat ctg ctg gag ctg gca         818
Tyr Lys Asp Ala Arg Phe Lys Asp Leu Ile Asn Leu Leu Glu Leu Ala
        255                 260                 265 gag aag aaa gtc tat gag aag ttt ggt atc caa ctg gaa cgt gaa gtc         866
Glu Lys Lys Val Tyr Glu Lys Phe Gly Ile Gln Leu Glu Arg Glu Val
    270                 275                 280 aaa atc gtg gag cac cac cac cat cac cac taa ctcgag                      905
Lys Ile Val Glu His His His His His His
285                 290

<210> SEQ ID NO 52
<211> LENGTH: 294
<212> TYPE: PRT
<213> ORGANISM: Sulfurihydrogenibium azorense

<400> SEQUENCE: 52

Met Asp Lys Ile Glu His Leu Lys Asn Phe Ser Leu Lys Asp Phe Cys
1               5                   10                  15

Thr Ile Lys Ile Gly Gly Val Gly Lys Val Val Phe Phe Pro Lys Asn
            20                  25                  30

Val Glu Glu Ile Ser Phe Leu Ile Arg Glu Tyr Gly Lys Glu Asn Ile
        35                  40                  45

Phe Pro Leu Gly Ile Gly Ser Asn Leu Ile Phe Ser Asp Gly Phe Ile
    50                  55                  60

Asp Lys Val Phe Ile His Ser Lys Asn Leu Lys Lys Cys Glu Ile Thr
65                  70                  75                  80

Gln Glu Asn Asp Ile Phe Tyr Leu Thr Leu Glu Ala Gly Val Ser Phe
                85                  90                  95

Lys Thr Ile Asn Asn Ile Val Lys Lys Tyr Asn Leu Glu Gly Phe Glu
            100                 105                 110

Asn Leu Ser Gly Ile Pro Ala Thr Val Gly Gly Ala Val Ala Met Asn
        115                 120                 125

Ala Gly Ala Tyr Gly Ser Glu Ile Phe Asp Ile Leu Glu Glu Val Trp
    130                 135                 140

Trp Ile Asp Lys Asp Gly Asn Leu Ile His Ser Lys Lys Gln Asp Ile
145                 150                 155                 160

Lys His Tyr Tyr Arg Tyr Ser Gln Phe Gln Glu Glu Gly Phe Val Tyr
                165                 170                 175

Lys Val Lys Ile Lys Leu Lys Lys Ser Asn Lys Asp Ile Ser Ser Ile
            180                 185                 190

Ile Lys Gln His Leu Leu Asp Arg Asn Lys Lys Gln Pro Leu Asp Leu
        195                 200                 205

Pro Thr Ala Gly Ser Thr Tyr Lys Asn Pro Pro Gln Thr Tyr Ala Gly
    210                 215                 220

Lys Leu Ile Glu Gln Val Gly Leu Lys Gly Tyr Arg Ile Asn Asp Ile
225                 230                 235                 240

Gly Phe Ser Ser Lys His Ala Asn Phe Leu Val Asn Tyr Lys Asp Ala
                245                 250                 255
```

```
Arg Phe Lys Asp Leu Ile Asn Leu Leu Glu Leu Ala Glu Lys Lys Val
                260                 265                 270

Tyr Glu Lys Phe Gly Ile Gln Leu Glu Arg Glu Val Lys Ile Val Glu
            275                 280                 285

His His His His His His
        290

<210> SEQ ID NO 53
<211> LENGTH: 867
<212> TYPE: DNA
<213> ORGANISM: Persephonella marina
<220> FEATURE:
<221> NAME/KEY: CDS
<222> LOCATION: (1)..(867)

<400> SEQUENCE: 53 atg ata gat tat gaa gag aat gtt gac ctg tcg aag ctg tgt act ata     48
Met Ile Asp Tyr Glu Glu Asn Val Asp Leu Ser Lys Leu Cys Thr Ile
1               5                   10                  15 aga atc ggt gga aca gct aaa agg gtt tac ttt cca aaa agt gtt gaa     96
Arg Ile Gly Gly Thr Ala Lys Arg Val Tyr Phe Pro Lys Ser Val Glu
                20                  25                  30 gat att ata cag ctt ttg aag ata tca cag gac agc gga aaa aag ata    144
Asp Ile Ile Gln Leu Leu Lys Ile Ser Gln Asp Ser Gly Lys Lys Ile
            35                  40                  45 att ccc ctt ggt gtg ggg agt aac aca gtt ttc agg gac ggc att ctt    192
Ile Pro Leu Gly Val Gly Ser Asn Thr Val Phe Arg Asp Gly Ile Leu
        50                  55                  60 gat cat ctg ttt gta tca aca tca aaa ctc aaa agg tat gag ata gaa    240
Asp His Leu Phe Val Ser Thr Ser Lys Leu Lys Arg Tyr Glu Ile Glu
65                  70                  75                  80 aga tct gaa gat cac gcc gta ata aca gct gaa gcg ggt gtc agt ttt    288
Arg Ser Glu Asp His Ala Val Ile Thr Ala Glu Ala Gly Val Ser Phe
                85                  90                  95 aaa aca ctg gtg agt ttg gtt aaa aga tac aat ctt gaa ggg ttt gag    336
Lys Thr Leu Val Ser Leu Val Lys Arg Tyr Asn Leu Glu Gly Phe Glu
                100                 105                 110 aat cta tcg gga ata cca gct tcg gta ggt ggt gct gtc gct atg aat    384
Asn Leu Ser Gly Ile Pro Ala Ser Val Gly Gly Ala Val Ala Met Asn
            115                 120                 125 gct gga gca ttt gga tct gag ata ttt gat att gtt gaa cag gtt gaa    432
Ala Gly Ala Phe Gly Ser Glu Ile Phe Asp Ile Val Glu Gln Val Glu
        130                 135                 140 tgg ata gac agt gag gga aaa ctt act gtc tca tct aaa gat gag ata    480
Trp Ile Asp Ser Glu Gly Lys Leu Thr Val Ser Ser Lys Asp Glu Ile
145                 150                 155                 160 gat tac ggg tac aga tac acc cag ttt cag aaa gag ggc ttt ata tac    528
Asp Tyr Gly Tyr Arg Tyr Thr Gln Phe Gln Lys Glu Gly Phe Ile Tyr
                165                 170                 175 aga gta aag ata aag cta aga aaa tca aaa agg aat ata cca cag atc    576
Arg Val Lys Ile Lys Leu Arg Lys Ser Lys Arg Asn Ile Pro Gln Ile
                180                 185                 190 ata aag gaa cat ctt aag gag aga aat ata aaa cag ccc ctt gat ctt    624
Ile Lys Glu His Leu Lys Glu Arg Asn Ile Lys Gln Pro Leu Asp Leu
            195                 200                 205 cca aca tca gga tcc acc ttt aaa aat cct gac ggt ata tct gca ggt    672
Pro Thr Ser Gly Ser Thr Phe Lys Asn Pro Asp Gly Ile Ser Ala Gly
        210                 215                 220 tat cta ctt gat aaa gct gga ctt aaa gga ttc aga gtg ggg gat gtt    720
Tyr Leu Leu Asp Lys Ala Gly Leu Lys Gly Phe Arg Val Gly Asp Val
```

```
                     225                 230                 235                 240 ggt  ttt  tca  gaa  aag  cat  gca  aac  ttt  aca  gta  aat  tac  ggt  cat  gga    768
Gly  Phe  Ser  Glu  Lys  His  Ala  Asn  Phe  Thr  Val  Asn  Tyr  Gly  His  Gly
                     245                 250                 255 agt  tac  gat  cag  tta  aag  aaa  ctg  ctg  gaa  act  gcc  gaa  aag  tta  gtg    816
Ser  Tyr  Asp  Gln  Leu  Lys  Lys  Leu  Leu  Glu  Thr  Ala  Glu  Lys  Leu  Val
                     260                 265                 270 gga  gaa  tat  ttt  gga  ata  aaa  ctt  gag  aag  gaa  atc  agg  att  gtt  gaa    864
Gly  Glu  Tyr  Phe  Gly  Ile  Lys  Leu  Glu  Lys  Glu  Ile  Arg  Ile  Val  Glu
                     275                 280                 285 taa                                                                                867
```

<210> SEQ ID NO 54
<211> LENGTH: 288
<212> TYPE: PRT
<213> ORGANISM: Persephonella marina

<400> SEQUENCE: 54

```
Met Ile Asp Tyr Glu Glu Asn Val Asp Leu Ser Lys Leu Cys Thr Ile
1               5                   10                  15

Arg Ile Gly Gly Thr Ala Lys Arg Val Tyr Phe Pro Lys Ser Val Glu
            20                  25                  30

Asp Ile Ile Gln Leu Leu Lys Ile Ser Gln Asp Ser Gly Lys Lys Ile
        35                  40                  45

Ile Pro Leu Gly Val Gly Ser Asn Thr Val Phe Arg Asp Gly Ile Leu
    50                  55                  60

Asp His Leu Phe Val Ser Thr Ser Lys Leu Lys Arg Tyr Glu Ile Glu
65                  70                  75                  80

Arg Ser Glu Asp His Ala Val Ile Thr Ala Glu Ala Gly Val Ser Phe
                85                  90                  95

Lys Thr Leu Val Ser Leu Val Lys Arg Tyr Asn Leu Glu Gly Phe Glu
            100                 105                 110

Asn Leu Ser Gly Ile Pro Ala Ser Val Gly Gly Ala Val Ala Met Asn
        115                 120                 125

Ala Gly Ala Phe Gly Ser Glu Ile Phe Asp Ile Val Glu Gln Val Glu
    130                 135                 140

Trp Ile Asp Ser Glu Gly Lys Leu Thr Val Ser Ser Lys Asp Glu Ile
145                 150                 155                 160

Asp Tyr Gly Tyr Arg Tyr Thr Gln Phe Gln Lys Glu Gly Phe Ile Tyr
                165                 170                 175

Arg Val Lys Ile Lys Leu Arg Lys Ser Lys Arg Asn Ile Pro Gln Ile
            180                 185                 190

Ile Lys Glu His Leu Lys Glu Arg Asn Ile Lys Gln Pro Leu Asp Leu
        195                 200                 205

Pro Thr Ser Gly Ser Thr Phe Lys Asn Pro Asp Gly Ile Ser Ala Gly
    210                 215                 220

Tyr Leu Leu Asp Lys Ala Gly Leu Lys Gly Phe Arg Val Gly Asp Val
225                 230                 235                 240

Gly Phe Ser Glu Lys His Ala Asn Phe Thr Val Asn Tyr Gly His Gly
                245                 250                 255

Ser Tyr Asp Gln Leu Lys Lys Leu Leu Glu Thr Ala Glu Lys Leu Val
            260                 265                 270

Gly Glu Tyr Phe Gly Ile Lys Leu Glu Lys Glu Ile Arg Ile Val Glu
        275                 280                 285
```

```
<210> SEQ ID NO 55
<211> LENGTH: 905
<212> TYPE: DNA
<213> ORGANISM: Persephonella marina
<220> FEATURE:
<221> NAME/KEY: CDS
<222> LOCATION: (15)..(899)

<400> SEQUENCE: 55
aggaggtaaa acat atg att gat tac gaa gaa aac gtt gac ttg agc aaa       50
              Met Ile Asp Tyr Glu Glu Asn Val Asp Leu Ser Lys
              1               5                   10 ctc tgt acg att cgc att ggt ggc acc gcg aaa cgc gtg tac ttt ccg       98
Leu Cys Thr Ile Arg Ile Gly Gly Thr Ala Lys Arg Val Tyr Phe Pro
        15                  20                  25 aag tct gtg gaa gat atc att caa ctg ctg aag atc agc cag gac agc      146
Lys Ser Val Glu Asp Ile Ile Gln Leu Leu Lys Ile Ser Gln Asp Ser
    30                  35                  40 ggt aag aag att atc ccg ctg ggt gtc ggt agc aat acc gtg ttc cgt      194
Gly Lys Lys Ile Ile Pro Leu Gly Val Gly Ser Asn Thr Val Phe Arg
45                  50                  55                  60 gac ggt atc ctg gat cac ctg ttc gtc agc acg agc aaa ctg aag cgc      242
Asp Gly Ile Leu Asp His Leu Phe Val Ser Thr Ser Lys Leu Lys Arg
                65                  70                  75 tat gag atc gag cgt agc gag gat cac gct gtc att act gca gag gcg      290
Tyr Glu Ile Glu Arg Ser Glu Asp His Ala Val Ile Thr Ala Glu Ala
            80                  85                  90 ggt gtc agc ttc aag acg ctg gtg tcc ctg gtt aaa cgc tac aat ctg      338
Gly Val Ser Phe Lys Thr Leu Val Ser Leu Val Lys Arg Tyr Asn Leu
        95                  100                 105 gaa ggt ttc gag aat ttg tcc ggt atc ccg gcc agc gta ggt ggt gcc      386
Glu Gly Phe Glu Asn Leu Ser Gly Ile Pro Ala Ser Val Gly Gly Ala
    110                 115                 120 gtt gcg atg aat gct ggc gcg ttt ggc agc gaa atc ttt gat atc gtg      434
Val Ala Met Asn Ala Gly Ala Phe Gly Ser Glu Ile Phe Asp Ile Val
125                 130                 135                 140 gaa cag gtt gaa tgg att gac agc gag ggc aaa ctg acc gtt agc agc      482
Glu Gln Val Glu Trp Ile Asp Ser Glu Gly Lys Leu Thr Val Ser Ser
                145                 150                 155 aag gac gag atc gat tac ggc tac cgt tac acg caa ttc cag aaa gag      530
Lys Asp Glu Ile Asp Tyr Gly Tyr Arg Tyr Thr Gln Phe Gln Lys Glu
            160                 165                 170 ggc ttc att tat cgt gtg aag atc aag ctg cgt aaa agc aaa cgt aac      578
Gly Phe Ile Tyr Arg Val Lys Ile Lys Leu Arg Lys Ser Lys Arg Asn
        175                 180                 185 atc cca caa atc att aaa gag cac ctg aaa gag cgt aac atc aaa caa      626
Ile Pro Gln Ile Ile Lys Glu His Leu Lys Glu Arg Asn Ile Lys Gln
    190                 195                 200 ccg ctg gat ttg ccg acc agc ggt tcg acc ttt aag aat ccg gac ggt      674
Pro Leu Asp Leu Pro Thr Ser Gly Ser Thr Phe Lys Asn Pro Asp Gly
205                 210                 215                 220 att tcc gcg ggt tat ctg ctg gac aaa gcg ggt ctg aaa ggc ttt cgc      722
Ile Ser Ala Gly Tyr Leu Leu Asp Lys Ala Gly Leu Lys Gly Phe Arg
                225                 230                 235 gtc ggt gac gtc ggc ttc tct gaa aag cat gca aac ttt acc gtt aac      770
Val Gly Asp Val Gly Phe Ser Glu Lys His Ala Asn Phe Thr Val Asn
            240                 245                 250 tac ggc cat ggc agc tat gac cag ctg aag aag ctg ttg gaa acc gca      818
Tyr Gly His Gly Ser Tyr Asp Gln Leu Lys Lys Leu Leu Glu Thr Ala
        255                 260                 265 gag aaa ctg gtg ggt gag tat ttc ggc att aag ctg gaa aaa gag att      866
Glu Lys Leu Val Gly Glu Tyr Phe Gly Ile Lys Leu Glu Lys Glu Ile
```

```
Glu Lys Leu Val Gly Glu Tyr Phe Gly Ile Lys Leu Glu Lys Glu Ile
        270                 275                 280 cgt att gtt gag cac cac cat cac cac cat taa ctcgag                905
Arg Ile Val Glu His His His His His His
285                 290
```

```
<210> SEQ ID NO 56
<211> LENGTH: 294
<212> TYPE: PRT
<213> ORGANISM: Persephonella marina

<400> SEQUENCE: 56
```

```
Met Ile Asp Tyr Glu Glu Asn Val Asp Leu Ser Lys Leu Cys Thr Ile
1               5                   10                  15

Arg Ile Gly Gly Thr Ala Lys Arg Val Tyr Phe Pro Lys Ser Val Glu
            20                  25                  30

Asp Ile Ile Gln Leu Leu Lys Ile Ser Gln Asp Ser Gly Lys Lys Ile
        35                  40                  45

Ile Pro Leu Gly Val Gly Ser Asn Thr Val Phe Arg Asp Gly Ile Leu
50                  55                  60

Asp His Leu Phe Val Ser Thr Ser Lys Leu Lys Arg Tyr Glu Ile Glu
65                  70                  75                  80

Arg Ser Glu Asp His Ala Val Ile Thr Ala Glu Ala Gly Val Ser Phe
                85                  90                  95

Lys Thr Leu Val Ser Leu Val Lys Arg Tyr Asn Leu Glu Gly Phe Glu
            100                 105                 110

Asn Leu Ser Gly Ile Pro Ala Ser Val Gly Gly Ala Val Ala Met Asn
        115                 120                 125

Ala Gly Ala Phe Gly Ser Glu Ile Phe Asp Ile Val Glu Gln Val Glu
130                 135                 140

Trp Ile Asp Ser Glu Gly Lys Leu Thr Val Ser Ser Lys Asp Glu Ile
145                 150                 155                 160

Asp Tyr Gly Tyr Arg Tyr Thr Gln Phe Gln Lys Glu Gly Phe Ile Tyr
                165                 170                 175

Arg Val Lys Ile Lys Leu Arg Lys Ser Lys Arg Asn Ile Pro Gln Ile
            180                 185                 190

Ile Lys Glu His Leu Lys Glu Arg Asn Ile Lys Gln Pro Leu Asp Leu
        195                 200                 205

Pro Thr Ser Gly Ser Thr Phe Lys Asn Pro Asp Gly Ile Ser Ala Gly
210                 215                 220

Tyr Leu Leu Asp Lys Ala Gly Leu Lys Gly Phe Arg Val Gly Asp Val
225                 230                 235                 240

Gly Phe Ser Glu Lys His Ala Asn Phe Thr Val Asn Tyr Gly His Gly
                245                 250                 255

Ser Tyr Asp Gln Leu Lys Lys Leu Leu Glu Thr Ala Glu Lys Leu Val
            260                 265                 270

Gly Glu Tyr Phe Gly Ile Lys Leu Glu Lys Glu Ile Arg Ile Val Glu
        275                 280                 285

His His His His His His
    290
```

```
<210> SEQ ID NO 57
<211> LENGTH: 849
<212> TYPE: DNA
<213> ORGANISM: Hydrogenobaculum sp. (strain Y04AAS1)
<220> FEATURE:
<221> NAME/KEY: CDS
```

<222> LOCATION: (1)..(849)

<400> SEQUENCE: 57

| | | | | | | | | | | | | | | | | |
|---|---|---|---|---|---|---|---|---|---|---|---|---|---|---|---|---|
| atg | ata | ata | aac | aaa | aat | gcg | gac | tta | aaa | gac | ttt | aca | acg | ata | aaa | 48 |
| Met | Ile | Ile | Asn | Lys | Asn | Ala | Asp | Leu | Lys | Asp | Phe | Thr | Thr | Ile | Lys | |
| 1 | | | | 5 | | | | | 10 | | | | | 15 | | |
| gta | ggc | ggt | ata | ggt | tca | tat | atg | ttt | ttt | cca | gaa | aac | gaa | aag | gag | 96 |
| Val | Gly | Gly | Ile | Gly | Ser | Tyr | Met | Phe | Phe | Pro | Glu | Asn | Glu | Lys | Glu | |
| | | | | 20 | | | | | 25 | | | | | 30 | | |
| ttc | cta | aat | ata | tat | aaa | aag | cac | aaa | aac | gat | aaa | ctc | tac | ata | ctt | 144 |
| Phe | Leu | Asn | Ile | Tyr | Lys | Lys | His | Lys | Asn | Asp | Lys | Leu | Tyr | Ile | Leu | |
| | | 35 | | | | | 40 | | | | | 45 | | | | |
| ggg | aaa | ggt | tca | aac | acc | ata | ttt | ggg | gat | ttc | aac | gga | ata | tta | ata | 192 |
| Gly | Lys | Gly | Ser | Asn | Thr | Ile | Phe | Gly | Asp | Phe | Asn | Gly | Ile | Leu | Ile | |
| | 50 | | | | | 55 | | | | | 60 | | | | | |
| aat | aca | aaa | cat | ttt | tac | gat | att | aaa | atc | tca | gaa | aca | aaa | gaa | ggt | 240 |
| Asn | Thr | Lys | His | Phe | Tyr | Asp | Ile | Lys | Ile | Ser | Glu | Thr | Lys | Glu | Gly | |
| 65 | | | | | 70 | | | | | 75 | | | | | 80 | |
| att | ttg | gta | aaa | gcc | tct | gca | gga | gta | cct | ttg | aaa | gac | tta | ata | aaa | 288 |
| Ile | Leu | Val | Lys | Ala | Ser | Ala | Gly | Val | Pro | Leu | Lys | Asp | Leu | Ile | Lys | |
| | | | | 85 | | | | | 90 | | | | | 95 | | |
| cta | tct | att | gaa | aac | aac | ata | gaa | gag | ttt | tac | aag | ttg | ata | ggt | ttt | 336 |
| Leu | Ser | Ile | Glu | Asn | Asn | Ile | Glu | Glu | Phe | Tyr | Lys | Leu | Ile | Gly | Phe | |
| | | | | 100 | | | | | 105 | | | | | 110 | | |
| cca | gca | agc | act | ggc | ggg | gca | ata | gct | atg | aat | gca | gga | gct | tat | ggt | 384 |
| Pro | Ala | Ser | Thr | Gly | Gly | Ala | Ile | Ala | Met | Asn | Ala | Gly | Ala | Tyr | Gly | |
| | | 115 | | | | | 120 | | | | | 125 | | | | |
| gtg | gaa | acc | ttt | gat | ttt | ata | aaa | ggt | gta | tgg | tgt | ata | gat | gac | gac | 432 |
| Val | Glu | Thr | Phe | Asp | Phe | Ile | Lys | Gly | Val | Trp | Cys | Ile | Asp | Asp | Asp | |
| | 130 | | | | | 135 | | | | | 140 | | | | | |
| gaa | ata | gtt | tac | aaa | cca | aaa | gaa | gag | ata | ttt | tat | tcg | tat | aga | aaa | 480 |
| Glu | Ile | Val | Tyr | Lys | Pro | Lys | Glu | Glu | Ile | Phe | Tyr | Ser | Tyr | Arg | Lys | |
| 145 | | | | | 150 | | | | | 155 | | | | | 160 | |
| acc | gag | ttt | gaa | aat | aag | cca | gtg | ttg | tac | gga | gag | ttt | tta | ttt | aaa | 528 |
| Thr | Glu | Phe | Glu | Asn | Lys | Pro | Val | Leu | Tyr | Gly | Glu | Phe | Leu | Phe | Lys | |
| | | | | 165 | | | | | 170 | | | | | 175 | | |
| aaa | agt | cat | caa | gat | ata | aaa | cct | tta | gca | caa | aat | ata | aat | caa | aaa | 576 |
| Lys | Ser | His | Gln | Asp | Ile | Lys | Pro | Leu | Ala | Gln | Asn | Ile | Asn | Gln | Lys | |
| | | | 180 | | | | | 185 | | | | | 190 | | | |
| aga | ata | gaa | gcc | cag | cca | ctt | aac | atg | ccc | act | tct | ggt | tct | aca | ttt | 624 |
| Arg | Ile | Glu | Ala | Gln | Pro | Leu | Asn | Met | Pro | Thr | Ser | Gly | Ser | Thr | Phe | |
| | 195 | | | | | 200 | | | | | 205 | | | | | |
| aaa | aat | cca | aaa | gat | cac | ttt | gcc | ggt | aag | ctt | tta | gaa | acg | gtt | ggt | 672 |
| Lys | Asn | Pro | Lys | Asp | His | Phe | Ala | Gly | Lys | Leu | Leu | Glu | Thr | Val | Gly | |
| 210 | | | | | 215 | | | | | 220 | | | | | | |
| tta | aaa | gga | tat | aga | ata | aaa | gac | ata | ggt | ttt | tca | gaa | agg | cat | gca | 720 |
| Leu | Lys | Gly | Tyr | Arg | Ile | Lys | Asp | Ile | Gly | Phe | Ser | Glu | Arg | His | Ala | |
| 225 | | | | | 230 | | | | | 235 | | | | | 240 | |
| aac | ttt | tta | ata | aat | tat | aaa | aac | gca | tct | ttt | caa | aat | gta | att | gac | 768 |
| Asn | Phe | Leu | Ile | Asn | Tyr | Lys | Asn | Ala | Ser | Phe | Gln | Asn | Val | Ile | Asp | |
| | | | | 245 | | | | | 250 | | | | | 255 | | |
| ata | tta | aac | ata | gca | aaa | gag | caa | gtt | tac | aaa | gct | ttt | aat | ata | ata | 816 |
| Ile | Leu | Asn | Ile | Ala | Lys | Glu | Gln | Val | Tyr | Lys | Ala | Phe | Asn | Ile | Ile | |
| | | | | 260 | | | | | 265 | | | | | 270 | | |
| tta | gaa | gag | gaa | ata | aaa | ctg | ata | tgc | gca | taa | | | | | | 849 |
| Leu | Glu | Glu | Glu | Ile | Lys | Leu | Ile | Cys | Ala | | | | | | | |
| | | 275 | | | | | 280 | | | | | | | | | |

<210> SEQ ID NO 58
<211> LENGTH: 282

<212> TYPE: PRT
<213> ORGANISM: Hydrogenobaculum sp. (strain Y04AAS1)

<400> SEQUENCE: 58

Met Ile Ile Asn Lys Asn Ala Asp Leu Lys Asp Phe Thr Thr Ile Lys
1               5                   10                  15

Val Gly Gly Ile Gly Ser Tyr Met Phe Pro Glu Asn Glu Lys Glu
            20                  25                  30

Phe Leu Asn Ile Tyr Lys Lys His Lys Asn Asp Lys Leu Tyr Ile Leu
        35                  40                  45

Gly Lys Gly Ser Asn Thr Ile Phe Gly Asp Phe Asn Gly Ile Leu Ile
50                  55                  60

Asn Thr Lys His Phe Tyr Asp Ile Lys Ile Ser Glu Thr Lys Glu Gly
65                  70                  75                  80

Ile Leu Val Lys Ala Ser Ala Gly Val Pro Leu Lys Asp Leu Ile Lys
                85                  90                  95

Leu Ser Ile Glu Asn Asn Ile Glu Glu Phe Tyr Lys Leu Ile Gly Phe
            100                 105                 110

Pro Ala Ser Thr Gly Gly Ala Ile Ala Met Asn Ala Gly Ala Tyr Gly
        115                 120                 125

Val Glu Thr Phe Asp Phe Ile Lys Gly Val Trp Cys Ile Asp Asp Asp
130                 135                 140

Glu Ile Val Tyr Lys Pro Lys Glu Glu Ile Phe Tyr Ser Tyr Arg Lys
145                 150                 155                 160

Thr Glu Phe Glu Asn Lys Pro Val Leu Tyr Gly Glu Phe Leu Phe Lys
                165                 170                 175

Lys Ser His Gln Asp Ile Lys Pro Leu Ala Gln Asn Ile Asn Gln Lys
            180                 185                 190

Arg Ile Glu Ala Gln Pro Leu Asn Met Pro Thr Ser Gly Ser Thr Phe
        195                 200                 205

Lys Asn Pro Lys Asp His Phe Ala Gly Lys Leu Leu Glu Thr Val Gly
210                 215                 220

Leu Lys Gly Tyr Arg Ile Lys Asp Ile Gly Phe Ser Glu Arg His Ala
225                 230                 235                 240

Asn Phe Leu Ile Asn Tyr Lys Asn Ala Ser Phe Gln Asn Val Ile Asp
                245                 250                 255

Ile Leu Asn Ile Ala Lys Glu Gln Val Tyr Lys Ala Phe Asn Ile Ile
            260                 265                 270

Leu Glu Glu Glu Ile Lys Leu Ile Cys Ala
        275                 280

<210> SEQ ID NO 59
<211> LENGTH: 887
<212> TYPE: DNA
<213> ORGANISM: Hydrogenobaculum sp. (strain Y04AAS1)
<220> FEATURE:
<221> NAME/KEY: CDS
<222> LOCATION: (15)..(881)

<400> SEQUENCE: 59
aggaggtaaa acat atg atc att aac aaa aac gcg gac ttg aaa gat ttt       50
               Met Ile Ile Asn Lys Asn Ala Asp Leu Lys Asp Phe
                 1               5                  10 acg acg att aag gta ggc ggc att ggc tcc tat atg ttc ttt ccg gag       98
Thr Thr Ile Lys Val Gly Gly Ile Gly Ser Tyr Met Phe Phe Pro Glu
        15                  20                  25 aat gag aaa gag ttc ctg aac atc tac aag aag cac aag aac gac aag      146

```
                    Asn Glu Lys Glu Phe Leu Asn Ile Tyr Lys Lys His Lys Asn Asp Lys
                         30                  35                  40 ctg tac att ctg ggc aaa ggt tcc aac acc att ttt ggt gat ttc aac        194
Leu Tyr Ile Leu Gly Lys Gly Ser Asn Thr Ile Phe Gly Asp Phe Asn
 45                  50                  55                  60 ggt att ctg att aac acc aag cac ttc tac gat atc aag atc agc gag        242
Gly Ile Leu Ile Asn Thr Lys His Phe Tyr Asp Ile Lys Ile Ser Glu
                 65                  70                  75 act aaa gaa ggt att ctg gtg aag gcg agc gca ggc gtc cct ctg aaa        290
Thr Lys Glu Gly Ile Leu Val Lys Ala Ser Ala Gly Val Pro Leu Lys
             80                  85                  90 gac ctg att aag ctg agc atc gag aac aat atc gaa gaa ttc tat aaa        338
Asp Leu Ile Lys Leu Ser Ile Glu Asn Asn Ile Glu Glu Phe Tyr Lys
         95                 100                 105 ctg att ggt ttt ccg gcc agc acg ggt ggt gcg att gca atg aat gcc        386
Leu Ile Gly Phe Pro Ala Ser Thr Gly Gly Ala Ile Ala Met Asn Ala
     110                 115                 120 ggt gcc tac ggc gtt gaa acc ttc gac ttc atc aaa ggt gtc tgg tgc        434
Gly Ala Tyr Gly Val Glu Thr Phe Asp Phe Ile Lys Gly Val Trp Cys
125                 130                 135                 140 att gac gac gat gag atc gtc tat aaa ccg aaa gaa gaa atc ttc tac        482
Ile Asp Asp Asp Glu Ile Val Tyr Lys Pro Lys Glu Glu Ile Phe Tyr
                145                 150                 155 agc tat cgt aag acc gag ttt gag aat aag ccg gtt ctg tat ggc gag        530
Ser Tyr Arg Lys Thr Glu Phe Glu Asn Lys Pro Val Leu Tyr Gly Glu
            160                 165                 170 ttc ctg ttc aaa aag agc cat cag gac atc aaa cca ctg gca caa aac        578
Phe Leu Phe Lys Lys Ser His Gln Asp Ile Lys Pro Leu Ala Gln Asn
        175                 180                 185 atc aat cag aag cgt att gaa gca caa ccg ttg aat atg ccg acc agc        626
Ile Asn Gln Lys Arg Ile Glu Ala Gln Pro Leu Asn Met Pro Thr Ser
    190                 195                 200 ggt tct acc ttc aag aat ccg aag gat cat ttt gct ggt aag ctg ctg        674
Gly Ser Thr Phe Lys Asn Pro Lys Asp His Phe Ala Gly Lys Leu Leu
205                 210                 215                 220 gaa acg gtg ggt ctg aaa ggt tac cgc att aaa gat att ggc ttt tcg        722
Glu Thr Val Gly Leu Lys Gly Tyr Arg Ile Lys Asp Ile Gly Phe Ser
                225                 230                 235 gag cgt cac gcg aac ttt ctg atc aat tac aaa aat gcg agc ttc cag        770
Glu Arg His Ala Asn Phe Leu Ile Asn Tyr Lys Asn Ala Ser Phe Gln
            240                 245                 250 aat gtt att gac atc ttg aac atc gcg aaa gag caa gtg tac aag gcg        818
Asn Val Ile Asp Ile Leu Asn Ile Ala Lys Glu Gln Val Tyr Lys Ala
        255                 260                 265 ttt aac atc atc ttg gaa gaa gag att aaa ctg atc tgt gct cat cac        866
Phe Asn Ile Ile Leu Glu Glu Glu Ile Lys Leu Ile Cys Ala His His
    270                 275                 280 cac cac cat cac taa ctcgag                                             887
His His His His
285

<210> SEQ ID NO 60
<211> LENGTH: 288
<212> TYPE: PRT
<213> ORGANISM: Hydrogenobaculum sp. (strain Y04AAS1)

<400> SEQUENCE: 60

Met Ile Ile Asn Lys Asn Ala Asp Leu Lys Asp Phe Thr Thr Ile Lys
 1               5                  10                  15

Val Gly Gly Ile Gly Ser Tyr Met Phe Phe Pro Glu Asn Glu Lys Glu
```

```
                    20                  25                  30
Phe Leu Asn Ile Tyr Lys Lys His Lys Asn Asp Lys Leu Tyr Ile Leu
                35                  40                  45

Gly Lys Gly Ser Asn Thr Ile Phe Gly Asp Phe Asn Gly Ile Leu Ile
            50                  55                  60

Asn Thr Lys His Phe Tyr Asp Ile Lys Ile Ser Glu Thr Lys Glu Gly
65                  70                  75                  80

Ile Leu Val Lys Ala Ser Ala Gly Val Pro Leu Lys Asp Leu Ile Lys
                85                  90                  95

Leu Ser Ile Glu Asn Asn Ile Glu Glu Phe Tyr Lys Leu Ile Gly Phe
            100                 105                 110

Pro Ala Ser Thr Gly Gly Ala Ile Ala Met Asn Ala Gly Ala Tyr Gly
        115                 120                 125

Val Glu Thr Phe Asp Phe Ile Lys Gly Val Trp Cys Ile Asp Asp Asp
    130                 135                 140

Glu Ile Val Tyr Lys Pro Lys Glu Glu Ile Phe Tyr Ser Tyr Arg Lys
145                 150                 155                 160

Thr Glu Phe Glu Asn Lys Pro Val Leu Tyr Gly Glu Phe Leu Phe Lys
                165                 170                 175

Lys Ser His Gln Asp Ile Lys Pro Leu Ala Gln Asn Ile Asn Gln Lys
            180                 185                 190

Arg Ile Glu Ala Gln Pro Leu Asn Met Pro Thr Ser Gly Ser Thr Phe
        195                 200                 205

Lys Asn Pro Lys Asp His Phe Ala Gly Lys Leu Leu Glu Thr Val Gly
    210                 215                 220

Leu Lys Gly Tyr Arg Ile Lys Asp Ile Gly Phe Ser Glu Arg His Ala
225                 230                 235                 240

Asn Phe Leu Ile Asn Tyr Lys Asn Ala Ser Phe Gln Asn Val Ile Asp
                245                 250                 255

Ile Leu Asn Ile Ala Lys Glu Gln Val Tyr Lys Ala Phe Asn Ile Ile
            260                 265                 270

Leu Glu Glu Glu Ile Lys Leu Ile Cys Ala His His His His His His
        275                 280                 285

<210> SEQ ID NO 61
<211> LENGTH: 864
<212> TYPE: DNA
<213> ORGANISM: Hydrogenivirga sp. 128-5R1-1
<220> FEATURE:
<221> NAME/KEY: CDS
<222> LOCATION: (1)..(864)

<400> SEQUENCE: 61 atg aaa ata tat gaa aat gta gat tta aaa aat ttt tca act ata aaa      48
Met Lys Ile Tyr Glu Asn Val Asp Leu Lys Asn Phe Ser Thr Ile Lys
1               5                   10                  15 atc gga gga aaa gct aaa aag tta tat ttt cct gaa agt ctc aac gac      96
Ile Gly Gly Lys Ala Lys Lys Leu Tyr Phe Pro Glu Ser Leu Asn Asp
                20                  25                  30 ata aaa ttc cta att aaa aaa tca aaa gac gaa gat aaa aag tta gtt     144
Ile Lys Phe Leu Ile Lys Lys Ser Lys Asp Glu Asp Lys Lys Leu Val
            35                  40                  45 ttt att gga gtt gga agt aat aca att ttt aaa gat ggg acg tta gat     192
Phe Ile Gly Val Gly Ser Asn Thr Ile Phe Lys Asp Gly Thr Leu Asp
        50                  55                  60 tac ata ttt att tca aca aaa ttt cta aaa aac ata gag ata aaa gaa     240
Tyr Ile Phe Ile Ser Thr Lys Phe Leu Lys Asn Ile Glu Ile Lys Glu
```

```
gaa aaa gac ctt ttt tat tta aat tta gaa gca gga gta agt ttt aaa      288
Glu Lys Asp Leu Phe Tyr Leu Asn Leu Glu Ala Gly Val Ser Phe Lys
                85                  90                  95 gaa att ata aat ctg gta aaa aaa ttt aat tta gaa ggt ttt gaa aat      336
Glu Ile Ile Asn Leu Val Lys Lys Phe Asn Leu Glu Gly Phe Glu Asn
            100                 105                 110 ctt tct gga ata cct gca tct tta ggt gga gct gtt gca atg aat gct      384
Leu Ser Gly Ile Pro Ala Ser Leu Gly Gly Ala Val Ala Met Asn Ala
        115                 120                 125 gga gcc ttt gga aat gaa ata ttt gat att ata gaa gat gta ctc tgg      432
Gly Ala Phe Gly Asn Glu Ile Phe Asp Ile Ile Glu Asp Val Leu Trp
    130                 135                 140 ata gat ttt gat aca aat gag cat ctt tca aaa aaa aat gaa ata aag      480
Ile Asp Phe Asp Thr Asn Glu His Leu Ser Lys Lys Asn Glu Ile Lys
145                 150                 155                 160 tac tct tac agg aca acc cag ttc caa aaa gaa ggt ttt atc tat aaa      528
Tyr Ser Tyr Arg Thr Thr Gln Phe Gln Lys Glu Gly Phe Ile Tyr Lys
                165                 170                 175 gct act ata aaa ctg aaa aaa agt aaa aaa gat ata gca aaa ata ata      576
Ala Thr Ile Lys Leu Lys Lys Ser Lys Lys Asp Ile Ala Lys Ile Ile
            180                 185                 190 aaa aac cat tta ata gaa aga aat aaa aaa cag cct tta aat tta cca      624
Lys Asn His Leu Ile Glu Arg Asn Lys Lys Gln Pro Leu Asn Leu Pro
        195                 200                 205 aca tca ggc tca aca tat aaa aat cct cca aac aat ttt gct gga aaa      672
Thr Ser Gly Ser Thr Tyr Lys Asn Pro Pro Asn Asn Phe Ala Gly Lys
    210                 215                 220 att ctg gaa gaa ata ggt tat aaa ggg aaa agg ata gga gac ata ggt      720
Ile Leu Glu Glu Ile Gly Tyr Lys Gly Lys Arg Ile Gly Asp Ile Gly
225                 230                 235                 240 ttt tca gat aaa cat gca aat ttt tta gta aat tac tca aat gca aca      768
Phe Ser Asp Lys His Ala Asn Phe Leu Val Asn Tyr Ser Asn Ala Thr
                245                 250                 255 ttc aaa gat tta atg aat tta tta gaa tct gcc gaa agg aaa gtt gaa      816
Phe Lys Asp Leu Met Asn Leu Leu Glu Ser Ala Glu Arg Lys Val Glu
            260                 265                 270 agg gtt ttt aat ata aaa ttt gaa agg gaa ata aga ata gtt gag taa      864
Arg Val Phe Asn Ile Lys Phe Glu Arg Glu Ile Arg Ile Val Glu
        275                 280                 285

<210> SEQ ID NO 62
<211> LENGTH: 287
<212> TYPE: PRT
<213> ORGANISM: Hydrogenivirga sp. 128-5R1-1

<400> SEQUENCE: 62

Met Lys Ile Tyr Glu Asn Val Asp Leu Lys Asn Phe Ser Thr Ile Lys
1               5                   10                  15

Ile Gly Gly Lys Ala Lys Lys Leu Tyr Phe Pro Glu Ser Leu Asn Asp
            20                  25                  30

Ile Lys Phe Leu Ile Lys Lys Ser Lys Asp Glu Asp Lys Lys Leu Val
        35                  40                  45

Phe Ile Gly Val Gly Ser Asn Thr Ile Phe Lys Asp Gly Thr Leu Asp
    50                  55                  60

Tyr Ile Phe Ile Ser Thr Lys Phe Leu Lys Asn Ile Glu Ile Lys Glu
65                  70                  75                  80

Glu Lys Asp Leu Phe Tyr Leu Asn Leu Glu Ala Gly Val Ser Phe Lys
                85                  90                  95
```

```
Glu Ile Ile Asn Leu Val Lys Lys Phe Asn Leu Glu Gly Phe Glu Asn
            100                 105                 110

Leu Ser Gly Ile Pro Ala Ser Leu Gly Gly Ala Val Ala Met Asn Ala
        115                 120                 125

Gly Ala Phe Gly Asn Glu Ile Phe Asp Ile Ile Glu Asp Val Leu Trp
130                 135                 140

Ile Asp Phe Asp Thr Asn Glu His Leu Ser Lys Lys Asn Glu Ile Lys
145                 150                 155                 160

Tyr Ser Tyr Arg Thr Thr Gln Phe Gln Lys Glu Gly Phe Ile Tyr Lys
                165                 170                 175

Ala Thr Ile Lys Leu Lys Lys Ser Lys Lys Asp Ile Ala Lys Ile Ile
            180                 185                 190

Lys Asn His Leu Ile Glu Arg Asn Lys Lys Gln Pro Leu Asn Leu Pro
        195                 200                 205

Thr Ser Gly Ser Thr Tyr Lys Asn Pro Pro Asn Asn Phe Ala Gly Lys
    210                 215                 220

Ile Leu Glu Glu Ile Gly Tyr Lys Gly Lys Arg Ile Gly Asp Ile Gly
225                 230                 235                 240

Phe Ser Asp Lys His Ala Asn Phe Leu Val Asn Tyr Ser Asn Ala Thr
                245                 250                 255

Phe Lys Asp Leu Met Asn Leu Leu Glu Ser Ala Glu Arg Lys Val Glu
            260                 265                 270

Arg Val Phe Asn Ile Lys Phe Glu Arg Glu Ile Arg Ile Val Glu
        275                 280                 285

<210> SEQ ID NO 63
<211> LENGTH: 902
<212> TYPE: DNA
<213> ORGANISM: Hydrogenivirga sp. 128-5R1-1
<220> FEATURE:
<221> NAME/KEY: CDS
<222> LOCATION: (15)..(896)

<400> SEQUENCE: 63
aggaggtaaa acat atg aag att tat gaa aat gta gac ttg aaa aac ttt      50
              Met Lys Ile Tyr Glu Asn Val Asp Leu Lys Asn Phe
                1               5                  10 agc acg att aag att ggc ggt aaa gcg aag aaa ctg tat ttt cca gag      98
Ser Thr Ile Lys Ile Gly Gly Lys Ala Lys Lys Leu Tyr Phe Pro Glu
        15                  20                  25 agc ctg aac gac atc aag ttt ctg att aag aag agc aaa gac gag gac     146
Ser Leu Asn Asp Ile Lys Phe Leu Ile Lys Lys Ser Lys Asp Glu Asp
    30                  35                  40 aaa aag ctg gtg ttt att ggt gtg ggt tct aac acg atc ttc aaa gac     194
Lys Lys Leu Val Phe Ile Gly Val Gly Ser Asn Thr Ile Phe Lys Asp
45                  50                  55                  60 ggt acg ttg gat tac atc ttc att agc acg aaa ttt ctg aaa aac atc     242
Gly Thr Leu Asp Tyr Ile Phe Ile Ser Thr Lys Phe Leu Lys Asn Ile
                65                  70                  75 gag atc aaa gaa gaa aaa gat ctg ttt tac ttg aat ctg gaa gcc ggt     290
Glu Ile Lys Glu Glu Lys Asp Leu Phe Tyr Leu Asn Leu Glu Ala Gly
            80                  85                  90 gtg agc ttc aaa gag atc att aac ctg gtc aag aag ttt aac ctg gaa     338
Val Ser Phe Lys Glu Ile Ile Asn Leu Val Lys Lys Phe Asn Leu Glu
        95                  100                 105 ggt ttc gag aac ctg tcg ggc att ccg gca agc ctg ggt ggc gcc gtt     386
Gly Phe Glu Asn Leu Ser Gly Ile Pro Ala Ser Leu Gly Gly Ala Val
    110                 115                 120
```

| | | | | | | | | | | | | | | | | |
|---|---|---|---|---|---|---|---|---|---|---|---|---|---|---|---|---|
| gca | atg | aat | gct | ggc | gcg | ttt | ggt | aat | gag | att | ttt | gat | atc | atc | gag | 434 |
| Ala | Met | Asn | Ala | Gly | Ala | Phe | Gly | Asn | Glu | Ile | Phe | Asp | Ile | Ile | Glu | |
| | 125 | | | | 130 | | | | | 135 | | | | | 140 | |

| | | | | | | | | | | | | | | | | |
|---|---|---|---|---|---|---|---|---|---|---|---|---|---|---|---|---|
| gat | gtc | ctg | tgg | att | gat | ttc | gat | acc | aat | gag | cac | ctg | tcc | aag | aaa | 482 |
| Asp | Val | Leu | Trp | Ile | Asp | Phe | Asp | Thr | Asn | Glu | His | Leu | Ser | Lys | Lys | |
| | | | | 145 | | | | | 150 | | | | | 155 | | |

| | | | | | | | | | | | | | | | | |
|---|---|---|---|---|---|---|---|---|---|---|---|---|---|---|---|---|
| aat | gag | atc | aag | tac | tcc | tat | cgt | acc | acc | cag | ttt | caa | aaa | gag | ggt | 530 |
| Asn | Glu | Ile | Lys | Tyr | Ser | Tyr | Arg | Thr | Thr | Gln | Phe | Gln | Lys | Glu | Gly | |
| | | 160 | | | | | 165 | | | | | 170 | | | | |

| | | | | | | | | | | | | | | | | |
|---|---|---|---|---|---|---|---|---|---|---|---|---|---|---|---|---|
| ttc | att | tac | aag | gcg | act | atc | aaa | ctg | aag | aaa | agc | aag | aag | gac | att | 578 |
| Phe | Ile | Tyr | Lys | Ala | Thr | Ile | Lys | Leu | Lys | Lys | Ser | Lys | Lys | Asp | Ile | |
| | | 175 | | | | | 180 | | | | | 185 | | | | |

| | | | | | | | | | | | | | | | | |
|---|---|---|---|---|---|---|---|---|---|---|---|---|---|---|---|---|
| gca | aaa | atc | atc | aag | aac | cat | ctg | att | gaa | cgt | aat | aag | aaa | cag | ccg | 626 |
| Ala | Lys | Ile | Ile | Lys | Asn | His | Leu | Ile | Glu | Arg | Asn | Lys | Lys | Gln | Pro | |
| 190 | | | | | 195 | | | | | 200 | | | | | | |

| | | | | | | | | | | | | | | | | |
|---|---|---|---|---|---|---|---|---|---|---|---|---|---|---|---|---|
| ctg | aat | ctg | ccg | acc | agc | ggt | agc | acc | tac | aaa | aat | ccg | ccg | aac | aac | 674 |
| Leu | Asn | Leu | Pro | Thr | Ser | Gly | Ser | Thr | Tyr | Lys | Asn | Pro | Pro | Asn | Asn | |
| 205 | | | | | 210 | | | | | 215 | | | | | 220 | |

| | | | | | | | | | | | | | | | | |
|---|---|---|---|---|---|---|---|---|---|---|---|---|---|---|---|---|
| ttc | gcg | ggc | aaa | atc | ctg | gaa | gag | atc | ggc | tat | aag | ggt | aaa | cgc | atc | 722 |
| Phe | Ala | Gly | Lys | Ile | Leu | Glu | Glu | Ile | Gly | Tyr | Lys | Gly | Lys | Arg | Ile | |
| | | | | 225 | | | | | 230 | | | | | 235 | | |

| | | | | | | | | | | | | | | | | |
|---|---|---|---|---|---|---|---|---|---|---|---|---|---|---|---|---|
| ggt | gac | att | ggc | ttc | agc | gac | aaa | cat | gcg | aat | ttc | ctg | gtt | aac | tac | 770 |
| Gly | Asp | Ile | Gly | Phe | Ser | Asp | Lys | His | Ala | Asn | Phe | Leu | Val | Asn | Tyr | |
| | | | 240 | | | | | 245 | | | | | 250 | | | |

| | | | | | | | | | | | | | | | | |
|---|---|---|---|---|---|---|---|---|---|---|---|---|---|---|---|---|
| agc | aac | gct | acc | ttc | aaa | gat | ctg | atg | aac | ctg | ttg | gaa | tct | gcg | gaa | 818 |
| Ser | Asn | Ala | Thr | Phe | Lys | Asp | Leu | Met | Asn | Leu | Leu | Glu | Ser | Ala | Glu | |
| | | | 255 | | | | | 260 | | | | | 265 | | | |

| | | | | | | | | | | | | | | | | |
|---|---|---|---|---|---|---|---|---|---|---|---|---|---|---|---|---|
| cgt | aag | gtc | gaa | cgc | gtt | ttc | aat | atc | aag | ttc | gag | cgc | gag | att | cgt | 866 |
| Arg | Lys | Val | Glu | Arg | Val | Phe | Asn | Ile | Lys | Phe | Glu | Arg | Glu | Ile | Arg | |
| | 270 | | | | | 275 | | | | | 280 | | | | | |

| | | | | | | | | | |
|---|---|---|---|---|---|---|---|---|---|
| atc | gtt | gag | cac | cat | cac | cac | cac | cac | taa ctcgag | 902 |
| Ile | Val | Glu | His | His | His | His | His | His | | |
| 285 | | | | | 290 | | | | | |

<210> SEQ ID NO 64
<211> LENGTH: 293
<212> TYPE: PRT
<213> ORGANISM: Hydrogenivirga sp. 128-5R1-1

<400> SEQUENCE: 64

Met Lys Ile Tyr Glu Asn Val Asp Leu Lys Asn Phe Ser Thr Ile Lys
1               5                   10                  15

Ile Gly Gly Lys Ala Lys Lys Leu Tyr Phe Pro Glu Ser Leu Asn Asp
            20                  25                  30

Ile Lys Phe Leu Ile Lys Lys Ser Lys Asp Glu Asp Lys Lys Leu Val
        35                  40                  45

Phe Ile Gly Val Gly Ser Asn Thr Ile Phe Lys Asp Gly Thr Leu Asp
    50                  55                  60

Tyr Ile Phe Ile Ser Thr Lys Phe Leu Lys Asn Ile Glu Ile Lys Glu
65                  70                  75                  80

Glu Lys Asp Leu Phe Tyr Leu Asn Leu Glu Ala Gly Val Ser Phe Lys
                85                  90                  95

Glu Ile Ile Asn Leu Val Lys Lys Phe Asn Leu Glu Gly Phe Glu Asn
            100                 105                 110

Leu Ser Gly Ile Pro Ala Ser Leu Gly Gly Ala Val Ala Met Asn Ala
        115                 120                 125

Gly Ala Phe Gly Asn Glu Ile Phe Asp Ile Ile Glu Asp Val Leu Trp
    130                 135                 140

```
Ile Asp Phe Asp Thr Asn Glu His Leu Ser Lys Lys Asn Glu Ile Lys
145                 150                 155                 160

Tyr Ser Tyr Arg Thr Thr Gln Phe Gln Lys Glu Gly Phe Ile Tyr Lys
                165                 170                 175

Ala Thr Ile Lys Leu Lys Lys Ser Lys Lys Asp Ile Ala Lys Ile Ile
            180                 185                 190

Lys Asn His Leu Ile Glu Arg Asn Lys Lys Gln Pro Leu Asn Leu Pro
        195                 200                 205

Thr Ser Gly Ser Thr Tyr Lys Asn Pro Pro Asn Asn Phe Ala Gly Lys
    210                 215                 220

Ile Leu Glu Glu Ile Gly Tyr Lys Gly Lys Arg Ile Gly Asp Ile Gly
225                 230                 235                 240

Phe Ser Asp Lys His Ala Asn Phe Leu Val Asn Tyr Ser Asn Ala Thr
                245                 250                 255

Phe Lys Asp Leu Met Asn Leu Leu Glu Ser Ala Glu Arg Lys Val Glu
            260                 265                 270

Arg Val Phe Asn Ile Lys Phe Glu Arg Glu Ile Arg Ile Val Glu His
            275                 280                 285

His His His His His
        290

<210> SEQ ID NO 65
<211> LENGTH: 885
<212> TYPE: DNA
<213> ORGANISM: Hydrogenobacter thermophilus
<220> FEATURE:
<221> NAME/KEY: CDS
<222> LOCATION: (1)..(885)

<400> SEQUENCE: 65 atg aag tta gag aaa aac gtg cta ctt gct cca tat acc acc ata agg      48
Met Lys Leu Glu Lys Asn Val Leu Leu Ala Pro Tyr Thr Thr Ile Arg
1               5                   10                  15 ata ggg ggt act gcg cgt ttt atg tgt ttt ccc tct gac ttt gca gag      96
Ile Gly Gly Thr Ala Arg Phe Met Cys Phe Pro Ser Asp Phe Ala Glu
            20                  25                  30 ctt tct aaa gcc ata agg tgg gca aag gag gag gga ctg cct gta ttc     144
Leu Ser Lys Ala Ile Arg Trp Ala Lys Glu Glu Gly Leu Pro Val Phe
        35                  40                  45 ttg ctg ggt agg ggt gct aac aca att ttt ggt gat tac tat ggg ctt     192
Leu Leu Gly Arg Gly Ala Asn Thr Ile Phe Gly Asp Tyr Tyr Gly Leu
    50                  55                  60 gtg ata aac acc tca aga cta aac ggt atg aag att ttc cat gca ggg     240
Val Ile Asn Thr Ser Arg Leu Asn Gly Met Lys Ile Phe His Ala Gly
65                  70                  75                  80 gaa aag gtt ctg ctg gaa gcc cag tgt ggg gtg agg ctc tcg cag gtg     288
Glu Lys Val Leu Leu Glu Ala Gln Cys Gly Val Arg Leu Ser Gln Val
                85                  90                  95 gtt aaa ctg gct ctt gag cta aac ctg gaa ggc ata tac aag ctt gcc     336
Val Lys Leu Ala Leu Glu Leu Asn Leu Glu Gly Ile Tyr Lys Leu Ala
            100                 105                 110 ggg ttt ccc gca acg gtg gga ggt gct gtg gct atg aat gca gga gct     384
Gly Phe Pro Ala Thr Val Gly Gly Ala Val Ala Met Asn Ala Gly Ala
        115                 120                 125 ttt ggc acg gaa ata tcg cat tac ctt aag agc ctt ctt gtc atg gac     432
Phe Gly Thr Glu Ile Ser His Tyr Leu Lys Ser Leu Leu Val Met Asp
    130                 135                 140 tgg gaa ggc aat gtg gag aag atc agc gcg gag gat gta aag ttt gat     480
Trp Glu Gly Asn Val Glu Lys Ile Ser Ala Glu Asp Val Lys Phe Asp
```

```
Trp Glu Gly Asn Val Glu Lys Ile Ser Ala Glu Asp Val Lys Phe Asp
145                 150                 155                 160 tac aga agc tct cct ttt ccg gat atg ggc ata gtt ctt atg gct gag    528
Tyr Arg Ser Ser Pro Phe Pro Asp Met Gly Ile Val Leu Met Ala Glu
                165                 170                 175 ctg gag cta aag aga gca gag ctt gat gtt agg cac gag cag aat ctc    576
Leu Glu Leu Lys Arg Ala Glu Leu Asp Val Arg His Glu Gln Asn Leu
            180                 185                 190 ata aag gag agg aga agg cgc aca cag ccc ata aac atg ccc aca tcc    624
Ile Lys Glu Arg Arg Arg Arg Thr Gln Pro Ile Asn Met Pro Thr Ser
        195                 200                 205 ggc tct acc ttt aag aat ccg cct ggg cag tat gcg ggc aaa ctt ctt    672
Gly Ser Thr Phe Lys Asn Pro Pro Gly Gln Tyr Ala Gly Lys Leu Leu
    210                 215                 220 gag atg gtg ggt atg aag gga tac aga gta gga gat gtg gct ttt tcc    720
Glu Met Val Gly Met Lys Gly Tyr Arg Val Gly Asp Val Ala Phe Ser
225                 230                 235                 240 cac ctt cat gct aac ttt ctt gta aac tta ggt gat ggc aga tac gaa    768
His Leu His Ala Asn Phe Leu Val Asn Leu Gly Asp Gly Arg Tyr Glu
                245                 250                 255 gat gcg ctt aaa ata ctc ttg gaa gca aaa agg aga gtt tac gag gag    816
Asp Ala Leu Lys Ile Leu Leu Glu Ala Lys Arg Arg Val Tyr Glu Glu
                260                 265                 270 ttt ggt ata tat ctt gag gag gag gta aaa gtc gtt gag agt tgt agt    864
Phe Gly Ile Tyr Leu Glu Glu Glu Val Lys Val Val Glu Ser Cys Ser
            275                 280                 285 act cat ggg ggg cag gtc tga                                        885
Thr His Gly Gly Gln Val
        290

<210> SEQ ID NO 66
<211> LENGTH: 294
<212> TYPE: PRT
<213> ORGANISM: Hydrogenobacter thermophilus

<400> SEQUENCE: 66

Met Lys Leu Glu Lys Asn Val Leu Leu Ala Pro Tyr Thr Thr Ile Arg
1               5                   10                  15

Ile Gly Gly Thr Ala Arg Phe Met Cys Phe Pro Ser Asp Phe Ala Glu
                20                  25                  30

Leu Ser Lys Ala Ile Arg Trp Ala Lys Glu Glu Gly Leu Pro Val Phe
            35                  40                  45

Leu Leu Gly Arg Gly Ala Asn Thr Ile Phe Gly Asp Tyr Tyr Gly Leu
        50                  55                  60

Val Ile Asn Thr Ser Arg Leu Asn Gly Met Lys Ile Phe His Ala Gly
65                  70                  75                  80

Glu Lys Val Leu Leu Glu Ala Gln Cys Gly Val Arg Leu Ser Gln Val
                85                  90                  95

Val Lys Leu Ala Leu Glu Leu Asn Leu Glu Gly Ile Tyr Lys Leu Ala
            100                 105                 110

Gly Phe Pro Ala Thr Val Gly Gly Ala Val Ala Met Asn Ala Gly Ala
        115                 120                 125

Phe Gly Thr Glu Ile Ser His Tyr Leu Lys Ser Leu Leu Val Met Asp
    130                 135                 140

Trp Glu Gly Asn Val Glu Lys Ile Ser Ala Glu Asp Val Lys Phe Asp
145                 150                 155                 160

Tyr Arg Ser Ser Pro Phe Pro Asp Met Gly Ile Val Leu Met Ala Glu
                165                 170                 175
```

```
Leu Glu Leu Lys Arg Ala Glu Leu Asp Val Arg His Glu Gln Asn Leu
            180                 185                 190

Ile Lys Glu Arg Arg Arg Thr Gln Pro Ile Asn Met Pro Thr Ser
        195                 200                 205

Gly Ser Thr Phe Lys Asn Pro Pro Gly Gln Tyr Ala Gly Lys Leu Leu
    210                 215                 220

Glu Met Val Gly Met Lys Gly Tyr Arg Val Gly Asp Val Ala Phe Ser
225                 230                 235                 240

His Leu His Ala Asn Phe Leu Val Asn Leu Gly Asp Gly Arg Tyr Glu
                245                 250                 255

Asp Ala Leu Lys Ile Leu Leu Glu Ala Lys Arg Arg Val Tyr Glu Glu
            260                 265                 270

Phe Gly Ile Tyr Leu Glu Glu Val Lys Val Val Glu Ser Cys Ser
        275                 280                 285

Thr His Gly Gly Gln Val
    290

<210> SEQ ID NO 67
<211> LENGTH: 923
<212> TYPE: DNA
<213> ORGANISM: Hydrogenobacter thermophilus
<220> FEATURE:
<221> NAME/KEY: CDS
<222> LOCATION: (15)..(917)

<400> SEQUENCE: 67
aggaggtaaa acat atg aag ttg gag aaa aac gta ttg ttg gca cca tat      50
              Met Lys Leu Glu Lys Asn Val Leu Leu Ala Pro Tyr
                1               5                   10 act acg att cgc atc ggt ggc acg gct cgc ttt atg tgt ttc ccg agc     98
Thr Thr Ile Arg Ile Gly Gly Thr Ala Arg Phe Met Cys Phe Pro Ser
            15                  20                  25 gat ttc gca gaa ctg tcg aaa gcg atc cgt tgg gcg aaa gaa gag ggt    146
Asp Phe Ala Glu Leu Ser Lys Ala Ile Arg Trp Ala Lys Glu Glu Gly
        30                  35                  40 ctg ccg gtt ttc ttg ctg ggt cgt ggt gcg aac acg att ttc ggt gat    194
Leu Pro Val Phe Leu Leu Gly Arg Gly Ala Asn Thr Ile Phe Gly Asp
45                  50                  55                  60 tac tat ggc ctg gtc atc aac acc agc cgt ctg aac ggc atg aag atc    242
Tyr Tyr Gly Leu Val Ile Asn Thr Ser Arg Leu Asn Gly Met Lys Ile
                65                  70                  75 ttt cac gca ggc gag aag gtc ctg ctg gaa gcc caa tgc ggc gtt cgc    290
Phe His Ala Gly Glu Lys Val Leu Leu Glu Ala Gln Cys Gly Val Arg
            80                  85                  90 ctg tct caa gtg gtt aaa ctg gcg ctg gaa ctg aat ctg gaa ggt att    338
Leu Ser Gln Val Val Lys Leu Ala Leu Glu Leu Asn Leu Glu Gly Ile
        95                  100                 105 tac aaa ctg gct ggc ttc ccg gcc acc gtt ggt ggt gcg gtg gca atg    386
Tyr Lys Leu Ala Gly Phe Pro Ala Thr Val Gly Gly Ala Val Ala Met
    110                 115                 120 aat gct ggt gcg ttt ggt acc gag atc agc cat tac ctg aag agc ctg    434
Asn Ala Gly Ala Phe Gly Thr Glu Ile Ser His Tyr Leu Lys Ser Leu
125                 130                 135                 140 ctg gtt atg gat tgg gaa ggt aat gtg gag aag att agc gca gag gac    482
Leu Val Met Asp Trp Glu Gly Asn Val Glu Lys Ile Ser Ala Glu Asp
                145                 150                 155 gtg aaa ttt gac tac cgc tcc agc ccg ttc ccg gat atg ggc att gtc    530
Val Lys Phe Asp Tyr Arg Ser Ser Pro Phe Pro Asp Met Gly Ile Val
            160                 165                 170
```

```
ctg atg gcg gaa ctg gag ctg aag cgc gca gag ctg gac gtg cgt cat      578
Leu Met Ala Glu Leu Glu Leu Lys Arg Ala Glu Leu Asp Val Arg His
        175                 180                 185 gag cag aat ctg atc aaa gag cgc cgt cgt cgt acg cag ccg att aac      626
Glu Gln Asn Leu Ile Lys Glu Arg Arg Arg Arg Thr Gln Pro Ile Asn
    190                 195                 200 atg ccg acc agc ggc agc acc ttt aag aac cca ccg ggt cag tat gcg      674
Met Pro Thr Ser Gly Ser Thr Phe Lys Asn Pro Pro Gly Gln Tyr Ala
205                 210                 215                 220 ggc aaa ctg ctg gaa atg gtt ggc atg aaa ggt tac cgt gtt ggt gac      722
Gly Lys Leu Leu Glu Met Val Gly Met Lys Gly Tyr Arg Val Gly Asp
                225                 230                 235 gtc gcc ttc tcc cac ttg cac gcc aat ttc ctg gtc aat ctg ggt gat      770
Val Ala Phe Ser His Leu His Ala Asn Phe Leu Val Asn Leu Gly Asp
            240                 245                 250 ggt cgt tat gag gac gcg ctg aag att ctg ttg gaa gcg aaa cgt cgt      818
Gly Arg Tyr Glu Asp Ala Leu Lys Ile Leu Leu Glu Ala Lys Arg Arg
        255                 260                 265 gtg tat gaa gag ttt ggc atc tac ctg gaa gaa gag gtg aag gtc gtt      866
Val Tyr Glu Glu Phe Gly Ile Tyr Leu Glu Glu Glu Val Lys Val Val
    270                 275                 280 gag agc tgc agc acc cac ggt ggc caa gtg cat cac cac cat cac cat      914
Glu Ser Cys Ser Thr His Gly Gly Gln Val His His His His His His
285                 290                 295                 300 taa ctcgag                                                            923

<210> SEQ ID NO 68
<211> LENGTH: 300
<212> TYPE: PRT
<213> ORGANISM: Hydrogenobacter thermophilus

<400> SEQUENCE: 68

Met Lys Leu Glu Lys Asn Val Leu Leu Ala Pro Tyr Thr Thr Ile Arg
1               5                   10                  15

Ile Gly Gly Thr Ala Arg Phe Met Cys Phe Pro Ser Asp Phe Ala Glu
            20                  25                  30

Leu Ser Lys Ala Ile Arg Trp Ala Lys Glu Glu Gly Leu Pro Val Phe
        35                  40                  45

Leu Leu Gly Arg Gly Ala Asn Thr Ile Phe Gly Asp Tyr Tyr Gly Leu
    50                  55                  60

Val Ile Asn Thr Ser Arg Leu Asn Gly Met Lys Ile Phe His Ala Gly
65                  70                  75                  80

Glu Lys Val Leu Leu Glu Ala Gln Cys Gly Val Arg Leu Ser Gln Val
                85                  90                  95

Val Lys Leu Ala Leu Glu Leu Asn Leu Glu Gly Ile Tyr Lys Leu Ala
            100                 105                 110

Gly Phe Pro Ala Thr Val Gly Gly Ala Val Ala Met Asn Ala Gly Ala
        115                 120                 125

Phe Gly Thr Glu Ile Ser His Tyr Leu Lys Ser Leu Leu Val Met Asp
    130                 135                 140

Trp Glu Gly Asn Val Glu Lys Ile Ser Ala Glu Asp Val Lys Phe Asp
145                 150                 155                 160

Tyr Arg Ser Ser Pro Phe Pro Asp Met Gly Ile Val Leu Met Ala Glu
                165                 170                 175

Leu Glu Leu Lys Arg Ala Glu Leu Asp Val Arg His Glu Gln Asn Leu
            180                 185                 190
```

```
Ile Lys Glu Arg Arg Arg Arg Thr Gln Pro Ile Asn Met Pro Thr Ser
        195                 200                 205

Gly Ser Thr Phe Lys Asn Pro Pro Gly Gln Tyr Ala Gly Lys Leu Leu
    210                 215                 220

Glu Met Val Gly Met Lys Gly Tyr Arg Val Gly Asp Val Ala Phe Ser
225                 230                 235                 240

His Leu His Ala Asn Phe Leu Val Asn Leu Gly Asp Gly Arg Tyr Glu
                245                 250                 255

Asp Ala Leu Lys Ile Leu Leu Glu Ala Lys Arg Arg Val Tyr Glu Glu
            260                 265                 270

Phe Gly Ile Tyr Leu Glu Glu Val Lys Val Val Glu Ser Cys Ser
        275                 280                 285

Thr His Gly Gly Gln Val His His His His His His
        290                 295                 300

<210> SEQ ID NO 69
<211> LENGTH: 888
<212> TYPE: DNA
<213> ORGANISM: Thermocrinus albus
<220> FEATURE:
<221> NAME/KEY: CDS
<222> LOCATION: (1)..(888)

<400> SEQUENCE: 69 atg cag aag gaa gag aaa gtg agc ctc tca ccc ttt aca aca ctg aag      48
Met Gln Lys Glu Glu Lys Val Ser Leu Ser Pro Phe Thr Thr Leu Lys
1               5                   10                  15 ata gga ggc gtg gct gac ctc ttc tgt agt ccg cag agg gaa gag gaa      96
Ile Gly Gly Val Ala Asp Leu Phe Cys Ser Pro Gln Arg Glu Glu Glu
                20                  25                  30 cta agg cag tgt ata cag atg gcc aag gtg aaa gac gtt cct ata ctg     144
Leu Arg Gln Cys Ile Gln Met Ala Lys Val Lys Asp Val Pro Ile Leu
            35                  40                  45 gtt atg gga agg gga gct aac ttg cta gta ggc gac gta gag ggt ctc     192
Val Met Gly Arg Gly Ala Asn Leu Leu Val Gly Asp Val Glu Gly Leu
        50                  55                  60 gtg gtg agt acc aga tat atg aga ggt atg tgg gta agg gaa gag aag     240
Val Val Ser Thr Arg Tyr Met Arg Gly Met Trp Val Arg Glu Glu Lys
65                  70                  75                  80 gat ggt ttg aag gtt aaa gtt atg gca gga gaa ccc ctg aag acc ctc     288
Asp Gly Leu Lys Val Lys Val Met Ala Gly Glu Pro Leu Lys Thr Leu
                85                  90                  95 atc cag ctg gcc ctt aag gaa aac ttg gaa ggt cta tac cgg tta gcg     336
Ile Gln Leu Ala Leu Lys Glu Asn Leu Glu Gly Leu Tyr Arg Leu Ala
            100                 105                 110 ggt ttc ccg gcc acc gtg ggt ggt gcg gta gct atg aac gcg gga gcc     384
Gly Phe Pro Ala Thr Val Gly Gly Ala Val Ala Met Asn Ala Gly Ala
        115                 120                 125 ttt ggc tac gaa ata tct cag cac ctt acc cat gtg gcc ttt ctg gac     432
Phe Gly Tyr Glu Ile Ser Gln His Leu Thr His Val Ala Phe Leu Asp
130                 135                 140 tgg gac ggt cgg ctg cac cgt gtt cct gca aag gag ata aac ttc tcg     480
Trp Asp Gly Arg Leu His Arg Val Pro Ala Lys Glu Ile Asn Phe Ser
145                 150                 155                 160 tac cgc cac tca cct ttt ccc agg tgg gga ata gtg gtg tgg gca gag     528
Tyr Arg His Ser Pro Phe Pro Arg Trp Gly Ile Val Val Trp Ala Glu
                165                 170                 175 ttc ctc ttt cca aga tcc gaa aag cca gtt tat gaa gag tat ctc cag     576
Phe Leu Phe Pro Arg Ser Glu Lys Pro Val Tyr Glu Glu Tyr Leu Gln
            180                 185                 190
```

```
ata aga gag agg agg aag aag acc caa ccc atc cac caa ccc acc tgt      624
Ile Arg Glu Arg Arg Lys Lys Thr Gln Pro Ile His Gln Pro Thr Cys
            195                 200                 205 gga tcc acc ttc aaa aac cca cct gga gat tac gct ggt cga ctc atc      672
Gly Ser Thr Phe Lys Asn Pro Pro Gly Asp Tyr Ala Gly Arg Leu Ile
    210                 215                 220 cag ctg gtg ggt ttg aaa ggc tac cga ttg ggc aga gtt gct ttt tca      720
Gln Leu Val Gly Leu Lys Gly Tyr Arg Leu Gly Arg Val Ala Phe Ser
225                 230                 235                 240 gag ata cac gcc aac ttc atc atc aac tta gga ggc gcc acc ttc caa      768
Glu Ile His Ala Asn Phe Ile Ile Asn Leu Gly Gly Ala Thr Phe Gln
                245                 250                 255 gaa gcc aca gag ctt atc cag ata gcc aaa gat aaa gtt tac aga gag      816
Glu Ala Thr Glu Leu Ile Gln Ile Ala Lys Asp Lys Val Tyr Arg Glu
            260                 265                 270 tta ggt ata acc ttg gaa gag gag gtg aga atc gtt gaa ggt cgt cgt      864
Leu Gly Ile Thr Leu Glu Glu Glu Val Arg Ile Val Glu Gly Arg Arg
        275                 280                 285 tct gat ggg tgg aag atc cta tga                                      888
Ser Asp Gly Trp Lys Ile Leu
290                 295

<210> SEQ ID NO 70
<211> LENGTH: 295
<212> TYPE: PRT
<213> ORGANISM: Thermocrinus albus

<400> SEQUENCE: 70

Met Gln Lys Glu Glu Lys Val Ser Leu Ser Pro Phe Thr Thr Leu Lys
1               5                   10                  15

Ile Gly Gly Val Ala Asp Leu Phe Cys Ser Pro Gln Arg Glu Glu Glu
            20                  25                  30

Leu Arg Gln Cys Ile Gln Met Ala Lys Val Lys Asp Val Pro Ile Leu
        35                  40                  45

Val Met Gly Arg Gly Ala Asn Leu Leu Val Gly Asp Val Glu Gly Leu
    50                  55                  60

Val Val Ser Thr Arg Tyr Met Arg Gly Met Trp Val Arg Glu Glu Lys
65                  70                  75                  80

Asp Gly Leu Lys Val Lys Val Met Ala Gly Glu Pro Leu Lys Thr Leu
                85                  90                  95

Ile Gln Leu Ala Leu Lys Glu Asn Leu Glu Gly Leu Tyr Arg Leu Ala
            100                 105                 110

Gly Phe Pro Ala Thr Val Gly Gly Ala Val Ala Met Asn Ala Gly Ala
        115                 120                 125

Phe Gly Tyr Glu Ile Ser Gln His Leu Thr His Val Ala Phe Leu Asp
    130                 135                 140

Trp Asp Gly Arg Leu His Arg Val Pro Ala Lys Glu Ile Asn Phe Ser
145                 150                 155                 160

Tyr Arg His Ser Pro Phe Pro Arg Trp Gly Ile Val Val Trp Ala Glu
                165                 170                 175

Phe Leu Phe Pro Arg Ser Glu Lys Pro Val Tyr Glu Glu Tyr Leu Gln
            180                 185                 190

Ile Arg Glu Arg Arg Lys Lys Thr Gln Pro Ile His Gln Pro Thr Cys
        195                 200                 205

Gly Ser Thr Phe Lys Asn Pro Pro Gly Asp Tyr Ala Gly Arg Leu Ile
    210                 215                 220
```

```
Gln Leu Val Gly Leu Lys Gly Tyr Arg Leu Gly Arg Val Ala Phe Ser
225                 230                 235                 240

Glu Ile His Ala Asn Phe Ile Ile Asn Leu Gly Gly Ala Thr Phe Gln
                245                 250                 255

Glu Ala Thr Glu Leu Ile Gln Ile Ala Lys Asp Lys Val Tyr Arg Glu
            260                 265                 270

Leu Gly Ile Thr Leu Glu Glu Val Arg Ile Val Glu Gly Arg Arg
        275                 280                 285

Ser Asp Gly Trp Lys Ile Leu
    290                 295

<210> SEQ ID NO 71
<211> LENGTH: 926
<212> TYPE: DNA
<213> ORGANISM: Thermocrinus albus
<220> FEATURE:
<221> NAME/KEY: CDS
<222> LOCATION: (15)..(920)

<400> SEQUENCE: 71
```

| | | | | | | | | | | | | | | |
|---|---|---|---|---|---|---|---|---|---|---|---|---|---|---|
| aggaggtaaa acat | atg | caa | aaa | gaa | gag | aaa | gta | tcc | ctg | agc | cca | ttt | | 50 |
| | Met | Gln | Lys | Glu | Glu | Lys | Val | Ser | Leu | Ser | Pro | Phe | | |
| | 1 | | | 5 | | | | | 10 | | | | | |
| acg | acc | ctg | aag | att | ggc | ggt | gta | gcg | gat | ttg | ttc | tgc | agc ccg cag | 98 |
| Thr | Thr | Leu | Lys | Ile | Gly | Gly | Val | Ala | Asp | Leu | Phe | Cys | Ser Pro Gln | |
| | 15 | | | | | 20 | | | | | 25 | | | |
| cgc | gaa | gaa | gag | ttg | cgc | cag | tgt | atc | caa | atg | gct | aag | gtg aaa gac | 146 |
| Arg | Glu | Glu | Glu | Leu | Arg | Gln | Cys | Ile | Gln | Met | Ala | Lys | Val Lys Asp | |
| | 30 | | | | 35 | | | | | 40 | | | | |
| gtt | ccg | atc | ctg | gtt | atg | ggt | cgt | ggc | gcg | aac | ctg | ttg | gtg ggt gac | 194 |
| Val | Pro | Ile | Leu | Val | Met | Gly | Arg | Gly | Ala | Asn | Leu | Leu | Val Gly Asp | |
| 45 | | | | | 50 | | | | | 55 | | | | 60 |
| gtt | gag | ggt | ctg | gtt | gtc | tcg | acc | cgt | tac | atg | cgt | ggt | atg tgg gtg | 242 |
| Val | Glu | Gly | Leu | Val | Val | Ser | Thr | Arg | Tyr | Met | Arg | Gly | Met Trp Val | |
| | | | | 65 | | | | | 70 | | | | 75 | |
| cgt | gaa | gag | aag | gac | ggc | ctg | aag | gtc | aaa | gtt | atg | gcc | ggt gaa ccg | 290 |
| Arg | Glu | Glu | Lys | Asp | Gly | Leu | Lys | Val | Lys | Val | Met | Ala | Gly Glu Pro | |
| | | 80 | | | | | 85 | | | | | 90 | | |
| ctg | aaa | acc | ttg | att | caa | ttg | gca | ctg | aaa | gaa | aat | ctg | gaa ggt ctg | 338 |
| Leu | Lys | Thr | Leu | Ile | Gln | Leu | Ala | Leu | Lys | Glu | Asn | Leu | Glu Gly Leu | |
| | | | 95 | | | | | 100 | | | | | 105 | |
| tat | cgc | ctg | gca | ggc | ttt | ccg | gcg | acc | gtc | ggt | ggc | gca | gtg gca atg | 386 |
| Tyr | Arg | Leu | Ala | Gly | Phe | Pro | Ala | Thr | Val | Gly | Gly | Ala | Val Ala Met | |
| | | 110 | | | | | 115 | | | | | 120 | | |
| aac | gcg | ggt | gcg | ttc | ggc | tac | gag | att | tct | caa | cac | ctg | acc cac gtc | 434 |
| Asn | Ala | Gly | Ala | Phe | Gly | Tyr | Glu | Ile | Ser | Gln | His | Leu | Thr His Val | |
| 125 | | | | | 130 | | | | | 135 | | | | 140 |
| gcc | ttc | ctg | gat | tgg | gac | ggt | cgt | ctg | cac | cgc | gtc | ccg | gca aaa gag | 482 |
| Ala | Phe | Leu | Asp | Trp | Asp | Gly | Arg | Leu | His | Arg | Val | Pro | Ala Lys Glu | |
| | | | | 145 | | | | | 150 | | | | | 155 |
| atc | aac | ttc | agc | tac | cgc | cat | agc | ccg | ttc | ccg | cgt | tgg | ggc atc gtc | 530 |
| Ile | Asn | Phe | Ser | Tyr | Arg | His | Ser | Pro | Phe | Pro | Arg | Trp | Gly Ile Val | |
| | | | 160 | | | | | 165 | | | | | 170 | |
| gtt | tgg | gcg | gag | ttc | ctg | ttt | ccg | cgt | agc | gag | aag | cct | gtg tat gaa | 578 |
| Val | Trp | Ala | Glu | Phe | Leu | Phe | Pro | Arg | Ser | Glu | Lys | Pro | Val Tyr Glu | |
| | | | 175 | | | | | 180 | | | | | 185 | |
| gag | tat | ctg | caa | atc | cgt | gag | cgt | cgt | aaa | aaa | acc | cag | ccg atc cac | 626 |
| Glu | Tyr | Leu | Gln | Ile | Arg | Glu | Arg | Arg | Lys | Lys | Thr | Gln | Pro Ile His | |
| | | 190 | | | | | 195 | | | | | 200 | | |
| cag | ccg | acg | tgc | ggc | agc | act | ttt | aag | aat | cca | ccg | ggc | gac tac gct | 674 |

```
Gln Pro Thr Cys Gly Ser Thr Phe Lys Asn Pro Gly Asp Tyr Ala
205                 210                 215                 220 ggt cgc ctg atc cag ctg gtt ggt ctg aaa ggt tat cgt ttg ggt cgc       722
Gly Arg Leu Ile Gln Leu Val Gly Leu Lys Gly Tyr Arg Leu Gly Arg
                225                 230                 235 gtg gcg ttt agc gag att cat gcc aac ttt atc att aat ctg ggt ggc       770
Val Ala Phe Ser Glu Ile His Ala Asn Phe Ile Ile Asn Leu Gly Gly
        240                 245                 250 gcg acg ttc cag gaa gcc acc gag ctg att cag atc gcg aaa gat aag       818
Ala Thr Phe Gln Glu Ala Thr Glu Leu Ile Gln Ile Ala Lys Asp Lys
        255                 260                 265 gtg tac cgc gag ctg ggt att acg ctg gaa gaa gag gtg cgt att gtt       866
Val Tyr Arg Glu Leu Gly Ile Thr Leu Glu Glu Glu Val Arg Ile Val
    270                 275                 280 gag ggc cgt cgt agc gat ggt tgg aag att ctg cac cac cat cac cat       914
Glu Gly Arg Arg Ser Asp Gly Trp Lys Ile Leu His His His His His
285                 290                 295                 300 cat taa ctcgag                                                        926
His
```

<210> SEQ ID NO 72
<211> LENGTH: 301
<212> TYPE: PRT
<213> ORGANISM: Thermocrinus albus

<400> SEQUENCE: 72

```
Met Gln Lys Glu Glu Lys Val Ser Leu Ser Pro Phe Thr Thr Leu Lys
1               5                   10                  15

Ile Gly Gly Val Ala Asp Leu Phe Cys Ser Pro Gln Arg Glu Glu
            20                  25                  30

Leu Arg Gln Cys Ile Gln Met Ala Lys Val Lys Asp Val Pro Ile Leu
        35                  40                  45

Val Met Gly Arg Gly Ala Asn Leu Leu Val Gly Asp Val Glu Gly Leu
    50                  55                  60

Val Val Ser Thr Arg Tyr Met Arg Gly Met Trp Val Arg Glu Glu Lys
65                  70                  75                  80

Asp Gly Leu Lys Val Lys Val Met Ala Gly Glu Pro Leu Lys Thr Leu
                85                  90                  95

Ile Gln Leu Ala Leu Lys Glu Asn Leu Glu Gly Leu Tyr Arg Leu Ala
            100                 105                 110

Gly Phe Pro Ala Thr Val Gly Ala Val Ala Met Asn Ala Gly Ala
        115                 120                 125

Phe Gly Tyr Glu Ile Ser Gln His Leu Thr His Val Ala Phe Leu Asp
    130                 135                 140

Trp Asp Gly Arg Leu His Arg Val Pro Ala Lys Glu Ile Asn Phe Ser
145                 150                 155                 160

Tyr Arg His Ser Pro Phe Pro Arg Trp Gly Ile Val Val Trp Ala Glu
                165                 170                 175

Phe Leu Phe Pro Arg Ser Glu Lys Pro Val Tyr Glu Glu Tyr Leu Gln
            180                 185                 190

Ile Arg Glu Arg Lys Lys Thr Gln Pro Ile His Gln Pro Thr Cys
        195                 200                 205

Gly Ser Thr Phe Lys Asn Pro Pro Gly Asp Tyr Ala Gly Arg Leu Ile
    210                 215                 220

Gln Leu Val Gly Leu Lys Gly Tyr Arg Leu Gly Arg Val Ala Phe Ser
225                 230                 235                 240
```

```
Glu Ile His Ala Asn Phe Ile Ile Asn Leu Gly Gly Ala Thr Phe Gln
                245                 250                 255

Glu Ala Thr Glu Leu Ile Gln Ile Ala Lys Asp Lys Val Tyr Arg Glu
            260                 265                 270

Leu Gly Ile Thr Leu Glu Glu Val Arg Ile Val Glu Gly Arg Arg
        275                 280                 285

Ser Asp Gly Trp Lys Ile Leu His His His His His
    290                 295                 300

<210> SEQ ID NO 73
<211> LENGTH: 840
<212> TYPE: DNA
<213> ORGANISM: Thermoanaerobacter italicus
<220> FEATURE:
<221> NAME/KEY: CDS
<222> LOCATION: (1)..(840)

<400> SEQUENCE: 73 atg aaa aga cac act tct ttt aaa ata ggt gga cct gca gat gtg tta      48
Met Lys Arg His Thr Ser Phe Lys Ile Gly Gly Pro Ala Asp Val Leu
1               5                  10                  15 gtt gta cca aat aat cga aaa gaa tta ttg gaa gcc ata tct ttg ttg      96
Val Val Pro Asn Asn Arg Lys Glu Leu Leu Glu Ala Ile Ser Leu Leu
            20                  25                  30 aaa cga gaa aac ata cct ttt ttt ata cta gga aat ggt act aat cta     144
Lys Arg Glu Asn Ile Pro Phe Phe Ile Leu Gly Asn Gly Thr Asn Leu
        35                  40                  45 tta gta agt gaa aaa ggc att aga gga gtt gta ata aaa tta tcc tct     192
Leu Val Ser Glu Lys Gly Ile Arg Gly Val Val Ile Lys Leu Ser Ser
    50                  55                  60 ttg agg aat gta gtt gta gaa ggt aat agg ata att gct gaa gca gga     240
Leu Arg Asn Val Val Val Glu Gly Asn Arg Ile Ile Ala Glu Ala Gly
65                  70                  75                  80 gca cct ctt tcc tat att gcc aat gtg gca ctt gta cat gaa ctt gcg     288
Ala Pro Leu Ser Tyr Ile Ala Asn Val Ala Leu Val His Glu Leu Ala
                85                  90                  95 gga ttt gaa ttt gct agc ggg att cct ggc act tta ggt gga gca ata     336
Gly Phe Glu Phe Ala Ser Gly Ile Pro Gly Thr Leu Gly Gly Ala Ile
            100                 105                 110 gtg atg aac gca ggg gct tat ggg tct gaa atg aag gac gtg ata gaa     384
Val Met Asn Ala Gly Ala Tyr Gly Ser Glu Met Lys Asp Val Ile Glu
        115                 120                 125 aaa gta gag gtt tta gat gga gaa ggc aat ata ttg att tta tca aac     432
Lys Val Glu Val Leu Asp Gly Glu Gly Asn Ile Leu Ile Leu Ser Asn
    130                 135                 140 gaa gaa atg aat ttt tcc tat aga tac agc att att cat gaa aag gat     480
Glu Glu Met Asn Phe Ser Tyr Arg Tyr Ser Ile Ile His Glu Lys Asp
145                 150                 155                 160 tgg att gtt tta aga gca tgg ctt agt ttg gca aaa ggg aaa tac gaa     528
Trp Ile Val Leu Arg Ala Trp Leu Ser Leu Ala Lys Gly Lys Tyr Glu
                165                 170                 175 gag ata aaa agc aaa atg gag gaa cta aat gca aaa aga agg gaa aaa     576
Glu Ile Lys Ser Lys Met Glu Glu Leu Asn Ala Lys Arg Arg Glu Lys
            180                 185                 190 cag cct ttg gag tat cca agt gcc gga agt act ttt aaa agg cca cct     624
Gln Pro Leu Glu Tyr Pro Ser Ala Gly Ser Thr Phe Lys Arg Pro Pro
        195                 200                 205 gga tat tat gct ggg aaa ttg att gag gaa gca gga ctt aaa ggc tat     672
Gly Tyr Tyr Ala Gly Lys Leu Ile Glu Glu Ala Gly Leu Lys Gly Tyr
    210                 215                 220
```

```
tca att gga gga gct aaa gtt tcc gaa aag cat tcg gga ttt att ata      720
Ser Ile Gly Gly Ala Lys Val Ser Glu Lys His Ser Gly Phe Ile Ile
225             230                 235                 240 aat act ggc aat gca act ttt tac gat gtt tta aat ttg att gag cat      768
Asn Thr Gly Asn Ala Thr Phe Tyr Asp Val Leu Asn Leu Ile Glu His
                245                 250                 255 ata caa aaa gta gta aaa gaa aag ttt gga gta gaa ctt gta cca gaa      816
Ile Gln Lys Val Val Lys Glu Lys Phe Gly Val Glu Leu Val Pro Glu
            260                 265                 270 ata aaa ata ata gga gag aaa tag                                      840
Ile Lys Ile Ile Gly Glu Lys
        275
```

<210> SEQ ID NO 74
<211> LENGTH: 279
<212> TYPE: PRT
<213> ORGANISM: Thermoanaerobacter italicus

<400> SEQUENCE: 74

```
Met Lys Arg His Thr Ser Phe Lys Ile Gly Gly Pro Ala Asp Val Leu
1               5                   10                  15

Val Val Pro Asn Asn Arg Lys Glu Leu Leu Glu Ala Ile Ser Leu Leu
            20                  25                  30

Lys Arg Glu Asn Ile Pro Phe Phe Ile Leu Gly Asn Gly Thr Asn Leu
        35                  40                  45

Leu Val Ser Glu Lys Gly Ile Arg Gly Val Val Ile Lys Leu Ser Ser
    50                  55                  60

Leu Arg Asn Val Val Glu Gly Asn Arg Ile Ile Ala Glu Ala Gly
65                  70                  75                  80

Ala Pro Leu Ser Tyr Ile Ala Asn Val Ala Leu Val His Glu Leu Ala
                85                  90                  95

Gly Phe Glu Phe Ala Ser Gly Ile Pro Gly Thr Leu Gly Gly Ala Ile
            100                 105                 110

Val Met Asn Ala Gly Ala Tyr Gly Ser Glu Met Lys Asp Val Ile Glu
        115                 120                 125

Lys Val Glu Val Leu Asp Gly Glu Gly Asn Ile Leu Ile Leu Ser Asn
    130                 135                 140

Glu Glu Met Asn Phe Ser Tyr Arg Tyr Ser Ile Ile His Glu Lys Asp
145                 150                 155                 160

Trp Ile Val Leu Arg Ala Trp Leu Ser Leu Ala Lys Gly Lys Tyr Glu
                165                 170                 175

Glu Ile Lys Ser Lys Met Glu Glu Leu Asn Ala Lys Arg Arg Glu Lys
            180                 185                 190

Gln Pro Leu Glu Tyr Pro Ser Ala Gly Ser Thr Phe Lys Arg Pro Pro
        195                 200                 205

Gly Tyr Tyr Ala Gly Lys Leu Ile Glu Glu Ala Gly Leu Lys Gly Tyr
    210                 215                 220

Ser Ile Gly Gly Ala Lys Val Ser Glu Lys His Ser Gly Phe Ile Ile
225                 230                 235                 240

Asn Thr Gly Asn Ala Thr Phe Tyr Asp Val Leu Asn Leu Ile Glu His
                245                 250                 255

Ile Gln Lys Val Val Lys Glu Lys Phe Gly Val Glu Leu Val Pro Glu
            260                 265                 270

Ile Lys Ile Ile Gly Glu Lys
        275
```

```
<210> SEQ ID NO 75
<211> LENGTH: 944
<212> TYPE: DNA
<213> ORGANISM: Thermoanaerobacter italicus
<220> FEATURE:
<221> NAME/KEY: CDS
<222> LOCATION: (15)..(938)

<400> SEQUENCE: 75
aggaggtaaa acat atg aat gag att att gac aaa ttg aag gac att ttg         50
               Met Asn Glu Ile Ile Asp Lys Leu Lys Asp Ile Leu
                 1               5                  10 cgt gag ggt aag ctg tat ttg aac gaa ccg atg aaa cgc cat acg agc         98
Arg Glu Gly Lys Leu Tyr Leu Asn Glu Pro Met Lys Arg His Thr Ser
         15                  20                  25 ttt aag att ggc ggt ccg gcg gat gtt ctg gtg gtg ccg aat aac cgt        146
Phe Lys Ile Gly Gly Pro Ala Asp Val Leu Val Val Pro Asn Asn Arg
     30                  35                  40 aaa gaa ctg ctg gaa gca atc agc ctg ctg aaa cgt gag aac att ccg        194
Lys Glu Leu Leu Glu Ala Ile Ser Leu Leu Lys Arg Glu Asn Ile Pro
45                  50                  55                  60 ttc ttc atc ctg ggt aac ggc act aat ctg ctg gtg agc gag aag ggt        242
Phe Phe Ile Leu Gly Asn Gly Thr Asn Leu Leu Val Ser Glu Lys Gly
                 65                  70                  75 atc cgt ggt gtc gtg att aag ttg agc agc ctg cgt aac gtc gtt gtc        290
Ile Arg Gly Val Val Ile Lys Leu Ser Ser Leu Arg Asn Val Val Val
         80                  85                  90 gaa ggc aat cgt atc att gcc gag gcg ggt gcg ccg ctg tcc tat atc        338
Glu Gly Asn Arg Ile Ile Ala Glu Ala Gly Ala Pro Leu Ser Tyr Ile
     95                 100                 105 gcg aac gtc gct ctg gtt cat gag ctg gca ggc ttt gag ttt gcc agc        386
Ala Asn Val Ala Leu Val His Glu Leu Ala Gly Phe Glu Phe Ala Ser
    110                 115                 120 ggc att ccg ggt acc ctg ggt ggc gca att gtt atg aac gcg ggt gca        434
Gly Ile Pro Gly Thr Leu Gly Gly Ala Ile Val Met Asn Ala Gly Ala
125                 130                 135                 140 tac ggt agc gag atg aaa gat gtg att gag aag gtg gaa gtg ctg gat        482
Tyr Gly Ser Glu Met Lys Asp Val Ile Glu Lys Val Glu Val Leu Asp
                145                 150                 155 ggc gaa ggc aac atc ctg atc ttg agc aat gaa gaa atg aat ttc tct        530
Gly Glu Gly Asn Ile Leu Ile Leu Ser Asn Glu Glu Met Asn Phe Ser
        160                 165                 170 tac cgt tac tcg att atc cac gag aag gac tgg atc gtg ctg cgc gcc        578
Tyr Arg Tyr Ser Ile Ile His Glu Lys Asp Trp Ile Val Leu Arg Ala
    175                 180                 185 tgg ctg agc ttg gcg aaa ggc aag tat gaa gag att aag tcc aaa atg        626
Trp Leu Ser Leu Ala Lys Gly Lys Tyr Glu Glu Ile Lys Ser Lys Met
    190                 195                 200 gaa gaa ctg aac gcg aaa cgc cgc gag aaa cag ccg ctg gag tat cca        674
Glu Glu Leu Asn Ala Lys Arg Arg Glu Lys Gln Pro Leu Glu Tyr Pro
205                 210                 215                 220 agc gcc ggt agc acc ttc aaa cgt ccg cct ggt tac tac gct ggc aag        722
Ser Ala Gly Ser Thr Phe Lys Arg Pro Pro Gly Tyr Tyr Ala Gly Lys
                225                 230                 235 ctg att gaa gag gcg ggt ctg aag ggc tat tcc atc ggc ggt gca aag        770
Leu Ile Glu Glu Ala Gly Leu Lys Gly Tyr Ser Ile Gly Gly Ala Lys
        240                 245                 250 gtt agc gaa aaa cac tct ggt ttc att atc aat acg ggt aac gcg acc        818
Val Ser Glu Lys His Ser Gly Phe Ile Ile Asn Thr Gly Asn Ala Thr
    255                 260                 265 ttt tac gac gtc ctg aat ctg atc gag cac atc caa aaa gtt gtt aaa        866
Phe Tyr Asp Val Leu Asn Leu Ile Glu His Ile Gln Lys Val Val Lys
```

```
Phe Tyr Asp Val Leu Asn Leu Ile Glu His Ile Gln Lys Val Val Lys
        270                 275                 280 gag aag ttt ggt gtt gaa ctg gtc ccg gag atc aag atc att ggt gag      914
Glu Lys Phe Gly Val Glu Leu Val Pro Glu Ile Lys Ile Ile Gly Glu
285                 290                 295                 300 aaa cat cac cac cat cac cac taa ctcgag                                944
Lys His His His His His His
                305
```

<210> SEQ ID NO 76
<211> LENGTH: 307
<212> TYPE: PRT
<213> ORGANISM: Thermoanaerobacter italicus

<400> SEQUENCE: 76

```
Met Asn Glu Ile Ile Asp Lys Leu Lys Asp Ile Leu Arg Gly Lys
1               5                   10                  15

Leu Tyr Leu Asn Glu Pro Met Lys Arg His Thr Ser Phe Lys Ile Gly
            20                  25                  30

Gly Pro Ala Asp Val Leu Val Pro Asn Asn Arg Lys Glu Leu Leu
        35                  40                  45

Glu Ala Ile Ser Leu Leu Lys Arg Glu Asn Ile Pro Phe Phe Ile Leu
50                  55                  60

Gly Asn Gly Thr Asn Leu Leu Val Ser Glu Lys Gly Ile Arg Gly Val
65                  70                  75                  80

Val Ile Lys Leu Ser Ser Leu Arg Asn Val Val Glu Gly Asn Arg
                85                  90                  95

Ile Ile Ala Glu Ala Gly Ala Pro Leu Ser Tyr Ile Ala Asn Val Ala
            100                 105                 110

Leu Val His Glu Leu Ala Gly Phe Glu Phe Ala Ser Gly Ile Pro Gly
        115                 120                 125

Thr Leu Gly Gly Ala Ile Val Met Asn Ala Gly Ala Tyr Gly Ser Glu
130                 135                 140

Met Lys Asp Val Ile Glu Lys Val Glu Val Leu Asp Gly Glu Gly Asn
145                 150                 155                 160

Ile Leu Ile Leu Ser Asn Glu Glu Met Asn Phe Ser Tyr Arg Tyr Ser
                165                 170                 175

Ile Ile His Glu Lys Asp Trp Ile Val Leu Arg Ala Trp Leu Ser Leu
            180                 185                 190

Ala Lys Gly Lys Tyr Glu Glu Ile Lys Ser Lys Met Glu Glu Leu Asn
        195                 200                 205

Ala Lys Arg Arg Glu Lys Gln Pro Leu Glu Tyr Pro Ser Ala Gly Ser
210                 215                 220

Thr Phe Lys Arg Pro Pro Gly Tyr Tyr Ala Gly Lys Leu Ile Glu Glu
225                 230                 235                 240

Ala Gly Leu Lys Gly Tyr Ser Ile Gly Gly Ala Lys Val Ser Glu Lys
                245                 250                 255

His Ser Gly Phe Ile Ile Asn Thr Gly Asn Ala Thr Phe Tyr Asp Val
            260                 265                 270

Leu Asn Leu Ile Glu His Ile Gln Lys Val Val Lys Glu Lys Phe Gly
        275                 280                 285

Val Glu Leu Val Pro Glu Ile Lys Ile Ile Gly Glu Lys His His His
290                 295                 300

His His His
305
```